United States Patent
Yoshikawa et al.

(10) Patent No.: US 7,074,798 B2
(45) Date of Patent: Jul. 11, 2006

(54) XANTHINE DERIVATIVE AND DPPIV INHIBITOR

(75) Inventors: Seiji Yoshikawa, Ibaraki (JP); Eita Emori, Ibaraki (JP); Fumiyoshi Matsuura, Ibaraki (JP); Richard Clark, Ibaraki (JP); Hironori Ikuta, Ibaraki (JP); Nobuyuki Yasuda, Ibaraki (JP); Tadashi Nagakura, Ibaraki (JP); Kazuto Yamazaki, Ibaraki (JP); Mika Aoki, Ibaraki (JP)

(73) Assignee: Eisai Co., Ltd, Tokyo (JP)

( * ) Notice: Subject to any disclaimer, the term of this patent is extended or adjusted under 35 U.S.C. 154(b) by 396 days.

(21) Appl. No.: 10/374,918

(22) Filed: Feb. 24, 2003

(65) Prior Publication Data

US 2004/0082570 A1  Apr. 29, 2004

(30) Foreign Application Priority Data

Feb. 25, 2002  (JP) ............................ 2002-047761
May 23, 2002  (JP) ............................ 2002-149557

(51) Int. Cl.
  C07D 473/06  (2006.01)
  C07D 473/08  (2006.01)
  C07D 473/04  (2006.01)
  A61K 31/522  (2006.01)
  A61P 3/10   (2006.01)

(52) U.S. Cl. .................. 514/263.2; 544/271; 544/272; 514/217.05; 540/575

(58) Field of Classification Search ............... 544/271, 544/272; 540/575; 514/263.2, 217.05
See application file for complete search history.

(56) References Cited

U.S. PATENT DOCUMENTS

| | | | |
|---|---|---|---|
| 3,896,119 A * | 7/1975 | Klingler ...................... 544/118 |
| 6,011,155 A | 1/2000 | Villhauer | |
| 6,303,661 B1 | 10/2001 | Demuth et al. | |
| 6,548,481 B1 | 4/2003 | Demuth et al. | |
| 2001/0020006 A1 | 9/2001 | Demuth et al. | |
| 2002/0161001 A1 | 10/2002 | Kanstrup et al. | |
| 2002/0198205 A1 | 12/2002 | Himmelsbach et al. | |
| 2003/0199528 A1* | 10/2003 | Kanstrup et al. ........ 514/263.2 |
| 2004/0077645 A1* | 4/2004 | Himmelsbach et al. .. 514/234.5 |
| 2004/0118328 A1 | 6/2004 | Yoshikawa et al. | |

FOREIGN PATENT DOCUMENTS

| | | |
|---|---|---|
| DE | 101 09 021 A1 | 9/2002 |
| DE | 101 17 803 A1 | 10/2002 |
| EP | 1054012 A1 | 11/2000 |
| EP | 1 308 439 A1 | 5/2003 |
| EP | 1 323 710 A1 | 7/2003 |
| EP | 1 333 025 A1 | 8/2003 |
| EP | 1 338 595 A2 | 8/2003 |
| EP | 1 338 595 A3 | 8/2003 |
| EP | 1 354 882 A1 | 10/2003 |
| WO | WO 95/29691 A1 | 11/1995 |
| WO | WO 97/40832 A1 | 11/1997 |
| WO | WO 99/61431 A1 | 12/1999 |
| WO | WO 99/67279 A1 | 12/1999 |
| WO | WO 00/34241 A1 | 6/2000 |
| WO | WO 00/56296 A2 | 9/2000 |
| WO | WO 02/02560 A2 | 1/2002 |
| WO | WO 02/14271 A1 | 2/2002 |
| WO | WO 02/30890 A1 | 4/2002 |
| WO | WO 02/38541 A1 | 5/2002 |
| WO | WO 02/051836 A1 | 7/2002 |
| WO | WO 02/062764 A1 | 8/2002 |
| WO | WO 02/68420 A1 | 9/2002 |
| WO | WO 02/076450 A1 | 10/2002 |
| WO | WO 02/083128 A1 | 10/2002 |
| WO | WO 03/004496 A1 | 1/2003 |
| WO | WO 03/104229 A1 | 12/2003 |
| WO | WO 2004/028524 A1 | 4/2004 |
| WO | WO 2004/050656 A1 | 6/2004 |

OTHER PUBLICATIONS

Balkan, et al. "Inhibition of Dipeptidyl Peptidase IV with NVP-DPP728 Increases Plasma GLP-1 (7-36 Amide) Concentrations and Improves Oral Glucose Tolerance in Obese Zucker Rats." *Diabetologia*, vol. 42, No. 11, pp. 1324-1331. Springer-Verlag. 1999.

(Continued)

*Primary Examiner*—Mark L. Berch
(74) *Attorney, Agent, or Firm*—Townsend and Townsend and Crew LLP

(57) ABSTRACT

The present invention provides novel compounds exhibiting an excellent DPPIV inhibition effect.

The compounds are represented by the formula:

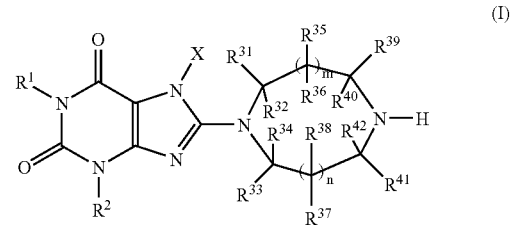

(I)

wherein, m is 0 or 1;
n is 0;
$R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ each represent a hydrogen atom;
X represents an alkynyl group, an aryl group, and such, which group may be substituted; and,
$R^1$ and $R^2$ each independently represents a hydrogen atom, an alkyl group, an alkoxyl group, or such,
or salts or hydrates thereof.

9 Claims, No Drawings

OTHER PUBLICATIONS

Bauvois, et al. "Constitutive Expression of CD26/Dipeptidylpeptidase IV on Peripheral Blood B Lymphocytes of Patients with B Chronic Lymphocytic Leukaemia." *British Journal of Cancer*, vol. 79, No. 7-8, pp. 1042-1048. 1999.

Callebaut, et al. "T Cell Activation Antigen, CD26, as a Cofactor for Entry of HIV In CD4+Cells." *Science*, vol. 262, No. 5142, pp. 2045-2050. 1993.

Gotoh, et al. "Activity of Dipeptidyl Peptidase IV and Post-Proline Cleaving Enzyme in Sera from Osteoporotic Patients." *Clinical Chemistry*, vol. 34, No. 12, pp. 2499-2501. 1988.

Hartmann, et al. "Dipeptidyl Peptidase IV Inhibition Enhances the Intestinotrophic Effect of Glucagon-Like Peptide-2 in Rats and Mice." *Endocrinology*, vol. 141, No. 11, pp. 4013-4020. 2000.

Holst, et al. "Inhibition of the Activity of Dipeptidyl-Peptidase IV as a Treatment for Type 2 Diabetes." *Diabetes*, vol. 47, No. 11, pp. 1663-1670. 1998.

Kohl, et al. "The Role of Dipeptidylpeptidase IV Positive T Cells in Wound Healing and Angiogenesis." *Agents and Actions*, vol. 32, No. 1/2, pp. 125-127. Birkhäuser Verlag, Basel. 1991.

Steinbrecher, et al. "Targeting Dipeptidyl Peptidase IV (CD26) Suppresses Autoimmune Encephalomyelitis and Up-Regulates TGF-β1 Secretion In Vivo." *The Journal of Immunology*, vol. 166, No. 3, pp. 2041-2048. 2001.

Wilson, et al. "Dipeptidylpeptidase IV Activities are Elevated in Prostate Cancers and Adjacent Benign Hyperplastic Glands." *Journal of Andrology*, vol. 21, No. 2, pp. 220-226. 2000.

Yip, et al. "Minireview: GIP Biology and Fat Metabolism." *Life Sciences*, vol. 66, No. 2, pp. 91-103. Elsevier Science Inc., USA. 2000.

Augustyns, K., et al., "The Unique Properties of Dipeptidyl-Peptidase IV (DPP IV/CD26) and the Therapeutic Potential of DPP IV Inhibitors", *Current Medicinal Chemistry* (1999) vol. 6, No. 4.

Translation of WO 03/104229.
Translation of WO 2004/050656.
Translation of WO 2004/028524.

\* cited by examiner

XANTHINE DERIVATIVE AND DPPIV INHIBITOR

FIELD OF THE INVENTION

This invention relates to novel xanthine derivatives having dipeptidyl peptidase-IV (DPPIV) inhibitory action.

BACKGROUND OF THE INVENTION

Dipeptidyl peptidase-IV (DPPIV) is a type of serine protease that specifically hydrolyzes the dipeptide —X-Pro (X may be any amino acid) from the free N terminus of a polypeptide chain.

Glucose-dependent insulin secretion-stimulating hormones, in other words incretins (GLP-1, Glucagon-Like Peptide-1, and GIP, Glucose-dependent Insulinotropic Polypeptide) which are secreted from the intestinal tract following a meal, are quickly degraded and inactivated by DPPIV. Incretin (GLP-1 and GIP) action can be enhanced by inhibiting this degradation by DPPIV, which leads to an increase in glucose-stimulated insulin secretion from pancreatic β-cells. Such inhibition has been shown to result in improved hyperglycemia following the oral glucose tolerance test (see Diabetologia 1999 November, 42(11), 1324–31). Furthermore, the involvement of GLP-1 in inhibiting the appetite and food consumption, as well as the β-cell protective action of GLP-1 based on pancreatic β-cell differentiation and proliferation-promoting action have been elucidated.

Thus, a DPPIV inhibitor is expected to be a useful therapeutic and preventive agent for diseases in which GLP-1 and GIP are involved, such as, obesity and diabetes.

Furthermore, since a relationship between dipeptidyl peptidase-IV and the various diseases indicated below has been reported, DPPIV inhibitors are expected to become therapeutic agents for such diseases.

(1) preventive and therapeutic agents for AIDS (see Science 1993, 262, 2045–2050)

(2) preventive and therapeutic agents for osteoporosis (see Clinical chemistry 1988, 34, 2499–2501)

(3) preventive and therapeutic agents for intestinal disorders (see Endocrinology 2000, 141, 4013–4020)

(4) preventive and therapeutic agents for diabetes, obesity, and hyperlipidemia (see Diabetes 1998, 47, 1663–1670; and Life Sci 2000, 66(2), 91–103)

(5) preventive and therapeutic agents for neovascularization (see Agents and Actions 1991, 32, 125–127)

(6) preventive and therapeutic agents for infertility (see International Publication Pamphlet No. 00/56296)

(7) preventive and therapeutic agents for inflammatory diseases, autoimmune diseases, and chronic rheumatoid arthritis (see The Journal of Immunology 2001, 166, 2041–2048)

(8) preventive and therapeutic agents for cancer (see Br J Cancer 1999 March, 79(7–8), 1042–8; and J Androl 2000 March–April, 21(2), 220–6)

DPPIV inhibitors are disclosed in International Publication Pamphlet Nos. 95/29691, 97/40832, 99/61431, 99/67279 and 00/34241; U.S. Pat. Nos. 6,011,155 and 6,303,661, International Publication Pamphlet Nos. 02/14271, 02/30890, 02/38541, 02/051836, 02/062764, 02/076450, 02/083128, etc.; however, they are clearly structurally different from the present invention.

International Publication Pamphlet Nos. 02/02560 and 02/068420 describe the presence of a DPPIV inhibitory action in a certain type of xanthine derivative, and the use thereof as a therapeutic agent for diabetes. However, since position 7 of most compounds cited in the Examples of International Publication Pamphlet No. 02/02560 is a benzyl group or a substituted benzyl group, and since no disclosure of inhibitory activity is made in the Examples, the structure of a xanthine derivative that can withstand practical use has not been elucidated. Furthermore, since positions 7 and 8 of most compounds cited in the Examples of International Publication Pamphlet No. 02/068420 are a 3-methyl-2-buten-1-nyl group and 3-aminopiperidine-1-yl group, respectively, the compounds are clearly different from those disclosed in the present invention.

SUMMARY OF THE INVENTION

As mentioned above, there is a strong need for a compound having a DPPIV inhibitory action that is useful as a medicament. However, a compound that (i) shows an excellent DPPIV inhibitory action, (ii) is highly useful as a medicament, and (iii) shows an effective clinical action has not yet been found. Thus, an objective of this invention is to screen for and discover a compound having a DPPIV inhibitory action that is useful as an agent for treating, preventing, or improving diabetic diseases, etc.

Hence, the present inventors conducted exhaustive studies, and discovered that a certain type of xanthine derivative has an excellent DPPIV inhibitory action and oral effectiveness. As a result, the following invention was completed.

Specifically, this invention relates to the following.

<1> A compound represented by the formula (I), or a salt or hydrate thereof (I)

wherein m and n are identical to or different from each other and denote 0 or 1;

$R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are identical to or different from each other and individually denote a hydrogen atom, hydroxyl group, cyano group, halogen atom, a substituted or unsubstituted $C_{1-6}$ alkyl group, a substituted or unsubstituted $C_{1-6}$ alkoxy group, a substituted or unsubstituted $C_{1-6}$ alkylthio group, a substituted or unsubstituted $C_{1-6}$ hydroxyalkyl group, a substituted or unsubstituted $C_{1-6}$ hydroxyalkoxy group, a substituted or unsubstituted $C_{1-6}$ hydroxyalkylthio group, a substituted or unsubstituted $C_{1-6}$ aminoalkyl group, a substituted or unsubstituted $C_{1-6}$ aminoalkoxy group, a substituted or unsubstituted $C_{1-6}$ aminoalkylthio group, a substituted or unsubstituted $C_{1-6}$ halogenated alkyl group, a substituted or unsubstituted $C_{1-6}$ halogenated alkoxy group, a substituted or unsubstituted $C_{1-6}$ halogenated alkylthio group, a substituted or unsubstituted $C_{1-6}$ alkoxy $C_{1-6}$ alkyl group, a substituted or unsubstituted $C_{1-6}$ alkoxy $C_{1-6}$ alkoxy group, a substituted or unsubstituted $C_{1-6}$ alkoxy $C_{1-6}$ alkylthio group, a substituted or unsubstituted $C_{1-6}$ alkylthio $C_{1-6}$ alkyl group, a substituted or unsubstituted $C_{3-7}$ cycloalkyl group, a substituted or unsubstituted C$_{3-7}$ cycloalkyl C$_{1-6}$ alkyl group, a substituted or unsubstituted C$_{3-7}$ cycloalkyloxy group, a substituted or unsubstituted C$_{3-7}$ cycloalkyl C$_{1-6}$ alkyloxy group, a substituted or unsubstituted C$_{3-7}$ cycloalkylthio group, a substituted or unsubstituted C$_{2-6}$ alkenyl group, a substituted or unsubstituted C$_{2-6}$ alkenyloxy group, a substituted or unsubstituted C$_{2-6}$ alkenylthio group, a substituted or unsubstituted C$_{2-6}$ alkynyl group, a substituted or unsubstituted C$_{2-6}$ alkynyloxy group, a substituted or unsubstituted C$_{2-6}$ alkynylthio group, a substituted or unsubstituted C$_{6-12}$ aryl group, a substituted or unsubstituted 5 to 14-membered heteroaryl group, a substituted or unsubstituted C$_{6-12}$ aryloxy group, a substituted or unsubstituted C$_{6-12}$ arylthio group, a substituted or unsubstituted C$_{6-12}$ aryl C$_{1-6}$ alkyl group, a substituted or unsubstituted 5 to 14-membered heteroaryl C$_{1-6}$ alkyl group, a substituted or unsubstituted C$_{6-12}$ aryl C$_{1-6}$ alkyloxy group, a substituted or unsubstituted C$_{6-12}$ aryl C$_{1-6}$ alkylthio group, a substituted or unsubstituted C$_{2-7}$ aliphatic acyl group, a substituted or unsubstituted C$_{7-19}$ aromatic acyl group, a substituted or unsubstituted C$_{2-7}$ aliphatic alkoxycarbonyl group, a substituted or unsubstituted C$_{7-19}$ aryloxycarbonyl group, a substituted or unsubstituted C$_{1-6}$ aliphatic sulfonyl group, a substituted or unsubstituted C$_{6-18}$ aromatic sulfonyl group, a substituted or unsubstituted C$_{2-7}$ cyanoalkyl group, a group represented by the formula —N(R$^3$)R$^4$, wherein R$^3$ and R$^4$ are identical to or different from each other and individually denote a hydrogen atom, cyano group, formyl group, a substituted or unsubstituted C$_{1-6}$ alkyl group, a substituted or unsubstituted C$_{2-6}$ hydroxyalkyl group, a substituted or unsubstituted C$_{2-6}$ aminoalkyl group, a substituted or unsubstituted C$_{2-6}$ halogenated alkyl group, a substituted or unsubstituted C$_{1-6}$ alkoxy C$_{1-6}$ alkyl group, a substituted or unsubstituted C$_{3-7}$ cycloalkyl group, a substituted or unsubstituted C$_{2-6}$ alkenyl group, a substituted or unsubstituted C$_{2-6}$ alkynyl group, a substituted or unsubstituted C$_{6-12}$ aryl group, a substituted or unsubstituted 5 to 14-membered heteroaryl group, a substituted or unsubstituted C$_{6-12}$ aryl C$_{1-6}$ alkyl group, a substituted or unsubstituted 5 to 14-membered heteroaryl C$_{1-6}$ alkyl group, a substituted or unsubstituted C$_{1-6}$ aliphatic sulfonyl group, or a substituted or unsubstituted C$_{6-18}$ aromatic sulfonyl group; or, R$^3$ and R$^4$ may be linked to each other to form a substituted or unsubstituted ring containing one or more heteroatoms, a group represented by the formula

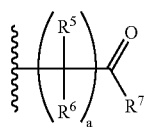

wherein a denotes 0 to 4;

R$^5$ and R$^6$ are identical to or different from each other and individually denote a hydrogen atom, hydroxyl group, cyano group, halogen atom, a substituted or unsubstituted C$_{1-6}$ alkyl group, a substituted or unsubstituted C$_{1-6}$ alkoxy group, a substituted or unsubstituted C$_{1-6}$ alkylthio group, a substituted or unsubstituted C$_{1-6}$ hydroxyalkyl group, a substituted or unsubstituted C$_{1-6}$ hydroxyalkoxy group, a substituted or unsubstituted C$_{1-6}$ hydroxyalkylthio group, a substituted or unsubstituted C$_{1-6}$ aminoalkyl group, a substituted or unsubstituted C$_{1-6}$ aminoalkoxy group, a substituted or unsubstituted C$_{1-6}$ aminoalkylthio group, a substituted or unsubstituted C$_{1-6}$ halogenated alkyl group, a substituted or unsubstituted C$_{1-6}$ halogenated alkoxy group, a substituted or unsubstituted C$_{1-6}$ halogenated alkylthio group, a substituted or unsubstituted C$_{1-6}$ alkoxy C$_{1-6}$ alkyl group, a substituted or unsubstituted C$_{1-6}$ alkoxy C$_{1-6}$ alkoxy group, a substituted or unsubstituted C$_{1-6}$ alkoxy C$_{1-6}$ alkylthio group, a substituted or unsubstituted C$_{1-6}$ alkylthio C$_{1-6}$ alkyl group, a substituted or unsubstituted C$_{3-7}$ cycloalkyl group, a substituted or unsubstituted C$_{3-7}$ cycloalkyl C$_{1-6}$ alkyl group, a substituted or unsubstituted C$_{3-7}$ cycloalkyloxy group, a substituted or unsubstituted C$_{3-7}$ cycloalkyl C$_{1-6}$ alkyloxy group, a substituted or unsubstituted C$_{3-7}$ cycloalkylthio group, a substituted or unsubstituted C$_{2-6}$ alkenyl group, a substituted or unsubstituted C$_{2-6}$ alkenyloxy group, a substituted or unsubstituted C$_{2-6}$ alkenylthio group, a substituted or unsubstituted C$_{2-6}$ alkynyl group, a substituted or unsubstituted C$_{2-6}$ alkynyloxy group, a substituted or unsubstituted C$_{2-6}$ alkynylthio group, a substituted or unsubstituted C$_{6-12}$ aryl group, a substituted or unsubstituted 5 to 14-membered heteroaryl group, a substituted or unsubstituted C$_{6-12}$ aryloxy group, a substituted or unsubstituted C$_{6-12}$ arylthio group, a substituted or unsubstituted C$_{6-12}$ aryl C$_{1-6}$ alkyl group, a substituted or unsubstituted C$_{6-12}$ aryl C$_{1-6}$ alkoxy group, a substituted or unsubstituted C$_{6-12}$ aryl C$_{1-6}$ alkylthio group, a substituted or unsubstituted 5 to 14-membered heteroaryl C$_{1-6}$ alkyl group, a substituted or unsubstituted C$_{2-7}$ aliphatic acyl group, a substituted or unsubstituted C$_{7-19}$ aromatic acyl group, a substituted or unsubstituted C$_{2-7}$ aliphatic alkoxycarbonyl group, a substituted or unsubstituted C$_{7-19}$ aryloxycarbonyl group, a substituted or unsubstituted C$_{1-6}$ aliphatic sulfonyl group, a substituted or unsubstituted C$_{6-18}$ aromatic sulfonyl group, a substituted or unsubstituted C$_{2-7}$ cyanoalkyl group, or a group represented by the formula —N(R$^3$)R$^4$, wherein R$^3$ and R$^4$ individually indicate the same groups as defined above, alternatively, R$^5$ and R$^6$ may bind to each other;

R$^7$ denotes a hydroxyl group, a substituted or unsubstituted C$_{1-6}$ alkyl group, a substituted or unsubstituted C$_{1-6}$ alkoxy group, a substituted or unsubstituted C$_{3-7}$ cycloalkyl group, a substituted or unsubstituted C$_{6-12}$ aryl group, a substituted or unsubstituted C$_{6-12}$ aryloxy group, a substituted or unsubstituted 5 to 14-membered heteroaryl group, a substituted or unsubstituted 5 to 14-membered heteroaryloxy group, or a group represented by the formula —N(R$^3$)R$^4$, wherein R$^3$ and R$^4$ individually denote the same groups as defined above, alternatively, any two of R$^{31}$, R$^{32}$, R$^{33}$, R$^{34}$, R$^{35}$, R$^{36}$, R$^{37}$, R$^{38}$, R$^{39}$, R$^{40}$, R$^{41}$, and R$^{42}$ may be linked to each other;

R$^1$ and R$^2$ are identical to or different from each other and individually denote a hydrogen atom, a substituted or unsubstituted C$_{1-6}$ alkyl group, a substituted or unsubstituted C$_{1-6}$ hydroxyalkyl group, a substituted or unsubstituted C$_{1-6}$ aminoalkyl group, a substituted or unsubstituted C$_{1-6}$ halogenated alkyl group, a substituted or unsubstituted C$_{1-6}$ alkoxy C$_{1-6}$ alkyl group, a substituted or unsubstituted C$_{1-6}$ alkylthio C$_{1-6}$ alkyl group, a substituted or unsubstituted C$_{3-7}$ cycloalkyl group, a substituted or unsubstituted $C_{3-7}$ cycloalkyl $C_{1-6}$ alkyl group, a substituted or unsubstituted $C_{3-6}$ alkenyl group, a substituted or unsubstituted $C_{3-6}$ alkynyl group, a substituted or unsubstituted $C_{6-12}$ aryl group, a substituted or unsubstituted 5 to 14-membered heteroaryl group, a substituted or unsubstituted $C_{6-12}$ aryl $C_{1-6}$ alkyl group, a substituted or unsubstituted $C_{6-12}$ aryloxy $C_{1-6}$ alkyl group, a substituted or unsubstituted 5 to 14-membered heteroaryl $C_{1-6}$ alkyl group, a substituted or unsubstituted 3 to 10-membered heterocyclic group, a substituted or unsubstituted 3 to 10-membered heterocyclic $C_{1-6}$ alkyl group, a substituted or unsubstituted $C_{1-6}$ aliphatic sulfonyl group, a substituted or unsubstituted $C_{6-18}$ aromatic sulfonyl group, a substituted or unsubstituted $C_{2-7}$ cyanoalkyl group, or a group represented by the formula

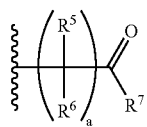

wherein a, $R^5$, $R^6$, and $R^7$ individually indicate the same groups as defined above;

X denotes a substituted or unsubstituted $C_{3-6}$ alkenyl group, a substituted or unsubstituted $C_{3-6}$ alkynyl group, a substituted or unsubstituted $C_{6-12}$ aryl group, or a substituted or unsubstituted 5 to 14-membered heteroaryl group, alternatively, X may bind to any one of $R^{31}$, $R^{32}$, $R^{33}$, and $R^{34}$ except the following compounds (1) to (16) wherein m and n both denote 0, and $R^{31}$, $R^{32}$, $R^{33}$, $R^{34}$, $R^{39}$, $R^{40}$, $R^{41}$, and $R^{42}$ individually denote a hydrogen atom in the formula (I), and in addition:

(1) X denotes a 2-propenyl group, $R^1$ denotes a methyl group, and $R^2$ denotes a methyl group;
(2) X denotes a 2-propenyl group, $R^1$ denotes a hydrogen atom, and $R^2$ denotes a methyl group;
(3) X denotes a 2-methyl-2-propenyl group, $R^1$ denotes a hydrogen atom, and $R^2$ denotes a methyl group;
(4) X denotes a 2-buten-1-yl group, $R^1$ denotes a hydrogen atom, and $R^2$ denotes a methyl group;
(5) X denotes a 3-chloro-2-buten-1-yl group, $R^1$ denotes a hydrogen atom, and $R^2$ denotes a methyl group;
(6) X denotes a 3-methyl-2-buten-1-yl group, $R^1$ denotes a methyl group, and $R^2$ denotes a methyl group;
(7) X denotes a 3-methyl-2-buten-1-yl group, $R^1$ denotes a phenethyl group, and $R^2$ denotes a methyl group;
(8) X denotes a 3-methyl-2-buten-1-yl group, $R^1$ denotes a phenacyl group, and $R^2$ denotes a methyl group;
(9) X denotes a 2,3-dimethyl-2-buten-1-yl group, $R^1$ denotes a methyl group, and $R^2$ denotes a methyl group;
(10) X denotes a (E)-2-methyl-2-buten-1-yl group, $R^1$ denotes a methyl group, and $R^2$ denotes a methyl group;
(11) X denotes a (Z)-2-methyl-2-buten-1-yl group, $R^1$ denotes a methyl group, and $R^2$ denotes a methyl group; or
(12) X denotes a 2-propynyl group, $R^1$ denotes a methyl group, and $R^2$ denotes a methyl group;
compounds wherein m stands for 0, n stands for 1, and $R^{31}$, $R^{32}$, $R^{33}$, $R^{34}$, $R^{35}$, $R^{36}$, $R^{39}$, $R^{40}$, $R^{41}$, and $R^{42}$ individually denote a hydrogen atom in the formula (I), and in addition,

(13) X denotes a 3-methyl-2-buten-1-yl group, $R^1$ denotes a methyl group, and $R^2$ denotes a methyl group;
(14) X denotes a 3-methyl-2-buten-1-yl group, $R^1$ denotes a phenethyl group, and $R^2$ denotes a methyl group;
(15) X denotes a 3-methyl-2-buten-1-yl group, $R^1$ denotes a phenacyl group, and $R^2$ denotes a methyl group;
and compounds wherein m stands for 0, n stands for 1, and $R^{31}$, $R^{32}$, $R^{33}$, $R^{34}$, $R^{39}$, $R^{40}$, $R^{41}$, and $R^{42}$ individually denote a hydrogen atom, and either one of $R^{35}$ or $R^{36}$ denotes a hydrogen atom and the other denotes an amino group in the formula (I), and in addition,
(16) X denotes a 3-methyl-2-buten-1-yl group, $R^1$ denotes a methyl group, and $R^2$ denotes a methyl group.

<2> The compound of <1>, or a salt or hydrate thereof, wherein X stands for a $C_{3-6}$ alkynyl group.
<3> The compound of <1>, or a salt or hydrate thereof, wherein X stands for a 2-butynyl group.
<4> The compound of <1>, or a salt or hydrate thereof, wherein X stands for a $C_{3-6}$ alkenyl group that may have one or more substituents.
<5> The compound of <1>, or a salt or hydrate thereof, wherein X stands for a 2-propenyl group.
<6> The compound of <1>, or a salt or hydrate thereof, wherein X stands for a 3-methyl-2-buten-1-yl group.
<7> The compound of <1>, or a salt or hydrate thereof, wherein X stands for a substituted or unsubstituted phenyl group.
<8> The compound of <1>, or a salt or hydrate thereof, wherein X stands for a phenyl group wherein position 2 may have a substituent selected from the group consisting of a hydrogen atom, hydroxyl group, fluorine atom, chlorine atom, methyl group, ethyl group, fluoromethyl group, ethenyl group, methoxy group, ethoxy group, acetyl group, cyano group, formyl group, and $C_{2-7}$ aliphatic alkoxy carbonyl group.
<9> The compound of any one of <1> to <8>, or a salt or hydrate thereof, wherein m denotes 0, n denotes 1, and all of $R^{31}$, $R^{32}$, $R^{33}$, $R^{34}$, $R^{37}$, $R^{38}$, $R^{39}$, $R^{40}$, $R^{41}$, and $R^{42}$ are hydrogen atoms.
<10> The compound of any one of <1> to <8>, or a salt or hydrate thereof, wherein m and n both denote 0, and all of $R^{31}$, $R^{32}$, $R^{33}$, $R^{34}$, $R^{39}$, $R^{40}$, $R^{41}$, and $R^{42}$ are hydrogen atoms.
<11> The compound of any one of <1> to <10>, or a salt or hydrate thereof, wherein $R^1$ and $R^2$ are identical to or different from each other and individually denote a hydrogen atom, a substituted or unsubstituted $C_{1-6}$ alkyl group, a substituted or unsubstituted $C_{1-6}$ halogenated alkyl group, a substituted or unsubstituted $C_{1-6}$ alkoxy $C_{1-6}$ alkyl group, a substituted or unsubstituted $C_{3-7}$ cycloalkyl group, a substituted or unsubstituted $C_{3-7}$ cycloalkyl $C_{1-6}$ alkyl group, a substituted or unsubstituted $C_{3-6}$ alkenyl group, a substituted or unsubstituted $C_{3-6}$ alkynyl group, a substituted or unsubstituted $C_{3-7}$ cycloalkenyl group, a substituted or unsubstituted $C_{6-12}$ aryl group, a substituted or unsubstituted 5 to 14-membered heteroaryl group, a substituted or unsubstituted 3 to 10-membered heterocyclic group, a substituted or unsubstituted $C_{6-12}$ aryl $C_{1-6}$ alkyl group, a substituted or unsubstituted $C_{6-12}$ aryloxy $C_{1-6}$ alkyl group, a substituted or unsubstituted 5 to 14-membered heteroaryl $C_{1-6}$ alkyl group, a substituted or unsubstituted 5 to 14-membered heteroaryloxy $C_{1-6}$ alkyl group, a substituted or unsubstituted 3 to 10-membered heterocyclic $C_{1-6}$ alkyl group, a substituted or unsubstituted $C_{2-7}$ cyanoalkyl group, or a group represented by the formula

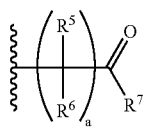

wherein, a denotes 1 to 3;

$R^5$ and $R^6$ are identical to or different from each other and individually denote a hydrogen atom, halogen atom, a substituted or unsubstituted $C_{1-6}$ alkyl group, a substituted or unsubstituted $C_{1-6}$ hydroxyalkyl group, a substituted or unsubstituted $C_{6-12}$ aryl group, a substituted or unsubstituted 5 to 14-membered heteroaryl group, a substituted or unsubstituted $C_{6-12}$ aryl $C_{1-6}$ alkyl group, a substituted or unsubstituted 5 to 14-membered heteroaryl $C_{1-6}$ alkyl group, alternatively, $R^5$ and $R^6$ may bind to each other;

$R^7$ denotes a hydroxyl group, a substituted or unsubstituted $C_{1-6}$ alkyl group, a substituted or unsubstituted $C_{1-6}$ alkoxy group, a substituted or unsubstituted $C_{6-12}$ aryl group, a substituted or unsubstituted 5 to 14-membered heteroaryl group, or a group represented by the formula —$N(R^3)R^4$, wherein, $R^3$ and $R^4$ are identical to or different from each other and individually denote a hydrogen atom, a substituted or unsubstituted $C_{1-6}$ alkyl group, a substituted or unsubstituted $C_{1-6}$ alkoxy $C_{1-6}$ alkyl group, a substituted or unsubstituted $C_{3-7}$ cycloalkyl group, a substituted or unsubstituted $C_{3-6}$ alkenyl group, a substituted or unsubstituted $C_{3-6}$ alkynyl group, a substituted or unsubstituted $C_{6-12}$ aryl group, a substituted or unsubstituted 5 to 14-membered heteroaryl group, a substituted or unsubstituted $C_{6-12}$ aryl $C_{1-6}$ alkyl group, or a substituted or unsubstituted 5 to 14-membered heteroaryl $C_{1-6}$ alkyl group, alternatively, $R^3$ and $R^4$ may be linked to each other to form a substituted or unsubstituted ring containing one or more heteroatoms.

<12> The compound of any one of <1> to <10>, or a salt or hydrate thereof, wherein $R^1$ and $R^2$ are identical to or different from each other and individually denote a hydrogen atom, a substituted or unsubstituted $C_{1-6}$ alkyl group, a substituted or unsubstituted $C_{1-6}$ alkoxy $C_{1-6}$ alkyl group, a substituted or unsubstituted $C_{3-7}$ cycloalkyl group, a substituted or unsubstituted $C_{3-6}$ alkenyl group, a substituted or unsubstituted $C_{3-6}$ alkynyl group, a substituted or unsubstituted 3 to 10-membered heterocyclic group, a substituted or unsubstituted $C_{6-12}$ aryl $C_{1-6}$ alkyl group, a substituted or unsubstituted $C_{6-12}$ aryloxy $C_{1-6}$ alkyl group, a substituted or unsubstituted 3 to 10-membered heterocyclic $C_{1-6}$ alkyl group, a substituted or unsubstituted $C_{2-7}$ cyanoalkyl group, or a group represented by the formula

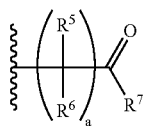

wherein, a denotes 1;

$R^5$ and $R^6$ are identical to or different from each other and individually denote a hydrogen atom, a substituted or unsubstituted $C_{1-6}$ alkyl group, or a substituted or unsubstituted $C_{6-12}$ aryl group; $R^7$ denotes a hydroxyl group, a substituted or unsubstituted $C_{1-6}$ alkyl group, a substituted or unsubstituted $C_{1-6}$ alkoxy group, a substituted or unsubstituted $C_{6-12}$ aryl group, or a group represented by the formula —$N(R^3)R^4$ wherein, $R^3$ and $R^4$ are identical to or different from each other and individually denote a hydrogen atom, a substituted or unsubstituted $C_{1-6}$ alkyl group, a substituted or unsubstituted $C_{3-7}$ cycloalkyl group, a substituted or unsubstituted $C_{3-6}$ alkynyl group, or a substituted or unsubstituted $C_{6-12}$ aryl group, alternatively, $R^3$ and $R^4$ may be linked to each other to form a substituted or unsubstituted ring containing one or more heteroatoms.

<13> The compound of any one of <1> to <12>, or a salt or hydrate thereof, wherein $R^1$ stands for a hydrogen atom, a substituted or unsubstituted $C_{1-6}$ alkyl group, a substituted or unsubstituted $C_{1-6}$ alkoxy $C_{1-6}$ alkyl group, a substituted or unsubstituted $C_{3-6}$ alkynyl group, a substituted or unsubstituted $C_{2-7}$ cyanoalkyl group, a substituted or unsubstituted $C_{6-12}$ aryl $C_{1-6}$ alkyl group, a substituted or unsubstituted $C_{6-12}$ aryloxy $C_{1-6}$ alkyl group, or a group represented by the formula

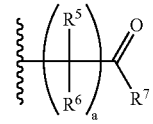

wherein, a denotes 1;

$R^5$ and $R^6$ both denote a hydrogen atom;

$R^7$ denotes a hydroxyl group, a substituted or unsubstituted $C_{1-6}$ alkoxy group, a substituted or unsubstituted phenyl group, or a group represented by the formula —$N(R^3)R^4$, wherein $R^3$ and $R^4$ are identical to or different from each other and individually denote a hydrogen atom, or a substituted or unsubstituted $C_{1-6}$ alkyl group.

<14> The compound of any one of <1> to <12>, or a salt or hydrate thereof, wherein $R^1$ stands for a hydrogen atom, $C_{1-6}$ alkyl group, $C_{3-6}$ alkynyl group, cyanomethyl group, a substituted or unsubstituted benzyl group, a substituted or unsubstituted phenethyl group, a substituted or unsubstituted phenoxyethyl group, or a group represented by the formula

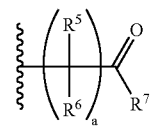

wherein a denotes 1;

$R^5$ and $R^6$ both denote a hydrogen atom;

$R^7$ denotes a hydroxyl group, $C_{1-6}$ alkoxy group, or a substituted or unsubstituted phenyl group.

<15> The compound of any one of <1> to <12>, or a salt or hydrate thereof, wherein $R^1$ stands for a hydrogen atom, methyl group, 2-propynyl group, 2-butynyl group, cyanomethyl group, phenethyl group, phenoxyethyl group, or a group represented by the formula

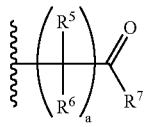

wherein a denotes 1;
$R^5$ and $R^6$ both denote a hydrogen atom;
$R^7$ denotes a hydroxyl group, $C_{1-6}$ alkoxy group, or phenyl group.

<16> The compound of any one of <1> to <15>, or a salt or hydrate thereof, wherein $R^2$ stands for a hydrogen atom, a substituted or unsubstituted $C_{1-6}$ alkyl group, a substituted or unsubstituted $C_{1-6}$ alkoxy $C_{1-6}$ alkyl group, a substituted or unsubstituted 3 to 10-membered heterocyclic $C_{1-6}$ alkyl group, a substituted or unsubstituted $C_{6-12}$ aryl $C_{1-6}$ alkyl group, a group represented by the formula

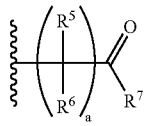

wherein,
a denotes 1;
$R^5$ and $R^6$ are identical to or different from each other and individually denote a hydrogen atom, $C_{1-6}$ alkyl group, or phenyl group;
$R^7$ denotes a hydroxyl group, $C_{1-6}$ alkyl group, $C_{1-6}$ alkoxy group, a substituted or unsubstituted phenyl group, or a group represented by —N($R^3$)$R^4$,
wherein,
$R^3$ and $R^4$ are identical to or different from each other and individually denote a hydrogen atom, $C_{1-6}$ alkyl group, $C_{3-7}$ cycloalkyl group, $C_{3-6}$ alkynyl group, or $C_{6-12}$ aryl group, alternatively,
$R^3$ and $R^4$ may be linked to each other to form a ring containing one or more heteroatoms, or a group represented by the formula

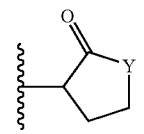

wherein Y denotes an oxygen atom, or a group represented by —$NR^8$, wherein $R^8$ denotes a hydrogen atom, or $C_{1-6}$ alkyl group.

<17> The compound of any one of <1> to <15>, or a salt or hydrate thereof, wherein $R^2$ stands for a substituted or unsubstituted $C_{1-6}$ alkoxy $C_{1-6}$ alkyl group, a substituted or unsubstituted 3 to 10-membered heterocyclic $C_{1-6}$ alkyl group, a substituted or unsubstituted $C_{6-12}$ aryl $C_{1-6}$ alkyl group, a group represented by the formula

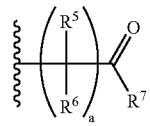

wherein,
a denotes 1;
$R^5$ and $R^6$ are identical to or different from each other and individually denote a hydrogen atom, $C_{1-6}$ alkyl group, or a phenyl group; $R^7$ denotes a hydroxyl group, $C_{1-6}$ alkyl group, $C_{1-6}$ alkoxy group, a substituted or unsubstituted phenyl group, or a group represented by the formula —N($R^3$)$R^4$,
wherein $R^3$ and $R^4$ are identical to or different from each other and individually denote a hydrogen atom, $C_{1-6}$ alkyl group, $C_{3-7}$ cycloalkyl group, $C_{3-6}$ alkynyl group, or $C_{6-12}$ aryl group, alternatively,
$R^3$ and $R^4$ may be linked to each other to form a ring containing one or more heteroatoms, or a group represented by the formula

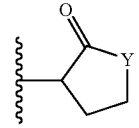

wherein Y denotes an oxygen atom, or a group represented by —$NR^8$, wherein $R^8$ denotes a hydrogen atom, or a $C_{1-6}$ alkyl group.

<18> The compound of any one of <1> to <15>, or a salt or hydrate thereof, wherein $R^2$ stands for a hydrogen atom, $C_{1-6}$ alkyl group, $C_{1-6}$ alkoxy $C_{1-6}$ alkyl group, tetrahydrofuranylmethyl group, a substituted or unsubstituted benzyl group, a group represented by the formula

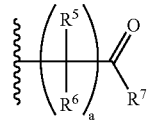

wherein,
a denotes 1;
$R^5$ and $R^6$ are identical to or different from each other and individually denote a hydrogen atom, $C_{1-6}$ alkyl group, or a phenyl group; $R^7$ denotes a hydroxyl group, $C_{1-6}$ alkyl group, $C_{1-6}$ alkoxy group, a substituted or unsubstituted phenyl group, or a group represented by the formula —N($R^3$)$R^4$,
wherein,
$R^3$ and $R^4$ are identical to or different from each other and individually denote a hydrogen atom, or a $C_{1-6}$ alkyl group, or a group represented by the formula

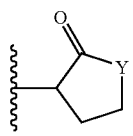

wherein Y denotes an oxygen atom, or —NR⁸, wherein $R^8$ denotes a hydrogen atom, or $C_{1-6}$ alkyl group.

<19> The compound of any one of <1> to <15>, or a salt or hydrate thereof, wherein $R^2$ stands for a $C_{1-6}$ alkoxy $C_{1-6}$ alkyl group, tetrahydrofuranylmethyl group, a substituted or unsubstituted benzyl group, a group represented by the formula

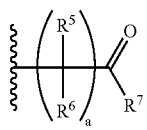

wherein,
a denotes 1;
$R^5$ and $R^6$ are identical to or different from each other and individually denote a hydrogen atom, $C_{1-6}$ alkyl group, or a phenyl group; $R^7$ denotes a hydroxyl group, $C_{1-6}$ alkyl group, $C_{1-6}$ alkoxy group, a substituted or unsubstituted phenyl group, or a group represented by the formula —N(R³)R⁴,
wherein,
$R^3$ and $R^4$ are identical to or different from each other and individually denote a hydrogen atom, or $C_{1-6}$ alkyl group, or a group represented by the formula

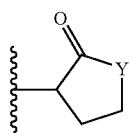

wherein Y denotes an oxygen atom, or —NR⁸, wherein $R^8$ denotes a hydrogen atom, or $C_{1-6}$ alkyl group.

<20> The compound of any one of <1> to <15>, or a salt or hydrate thereof, wherein $R^2$ stands for a hydrogen atom, $C_{1-6}$ alkyl group, ethoxyethyl group, tetrahydrofuranylmethyl group, a group represented by the formula

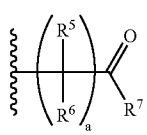

wherein,
a denotes 1;
$R^5$ and $R^6$ are identical to or different from each other and individually denote a hydrogen atom, methyl group, or phenyl group;
$R^7$ denotes a hydroxyl group, $C_{1-6}$ alkoxy group, or phenyl group, or a group represented by the formula

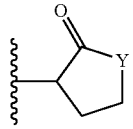

wherein Y denotes —NR⁸, wherein $R^8$ denotes a hydrogen atom.

<21> The compound of any one of <1> to <15>, or a salt or hydrate thereof, wherein $R^2$ stands for an ethoxyethyl group, tetrahydrofuranylmethyl group, a group represented by the formula

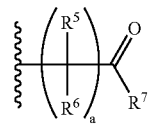

wherein,
a denotes 1;
$R^5$ and $R^6$ are identical to or different from each other and individually denote a hydrogen atom, methyl group, or phenyl group;
$R^7$ denotes a hydroxyl group, $C_{1-6}$ alkoxy group, or phenyl group, or a group represented by the formula

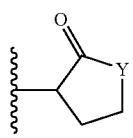

wherein Y denotes —NR⁸, wherein $R^8$ denotes a hydrogen atom.

<22> A compound selected from the group consisting of (1) to (61), a salt thereof, and a hydrate thereof:
(1) 7-(2-butynyl)-1,3-dimethyl-8-(piperazin-1-yl)-3,7-dihydropurine-2,6-dione,
(2) 7-(2-butynyl)-3-methyl-8-(piperazin-1-yl)-3,7-dihydropurine-2,6-dione,
(3) [7-(2-butynyl)-3-methyl-2,6-dioxo-8-(piperazin-1-yl)-2,3,6,7-tetrahydropurin-1-yl]acetic acid methyl ester,
(4) 7-(2-butynyl)-3-methyl-8-(piperazin-1-yl)-1-(2-propynyl)-3,7-dihydropurine-2,6-dione,
(5) 1,7-bis(2-butynyl)-3-methyl-8-(piperazin-1-yl)-3,7-dihydropurine-2,6-dione,
(6) [7-(2-butynyl)-3-methyl-2,6-dioxo-8-(piperazin-1-yl)-2,3,6,7-tetrahydropurin-1-yl]acetonitrile,
(7) 7-(2-butynyl)-3-methyl-1-(2-oxo-2-phenylethyl)-8-(piperazin-1-yl)-3,7-dihydropurine-2,6-dione,
(8) 7-(2-butynyl)-3-ethyl-1-methyl-8-(piperazin-1-yl)-3,7-dihydropurine-2,6-dione,
(9) [7-(2-butynyl)-1-methyl-2,6-dioxo-8-(piperazin-1-yl)-1,2,6,7-tetrahydropurin-3-yl]acetic acid methyl ester,

(10) 7-(2-butynyl)-3-(2-tetrahydrofuranyl)methyl-1-methyl-8-(piperazin-1-yl)-3,7-dihydropurine-2,6-dione,
(11) [7-(2-butynyl)-1-methyl-2,6-dioxo-8-(piperazin-1-yl)-1,2,6,7-tetrahydropurin-3-yl]phenyl acetic acid methyl ester,
(12) 7-(2-butynyl)-3-propyl-1-methyl-8-(piperazin-1-yl)-3,7-dihydropurine-2,6-dione,
(13) 7-(2-butynyl)-3-(2-oxo-2-phenethyl)-1-methyl-8-(piperazin-1-yl)-3,7-dihydropurine-2,6-dione,
(14) 2-[7-(2-butynyl)-1-methyl-2,6-dioxo-8-(piperazin-1-yl)-1,2,6,7-tetrahydropurin-3-yl]propionic acid ethyl ester,
(15) 7-(2-butynyl)-3-(2-ethoxyethyl)-1-methyl-8-(piperazin-1-yl)-3,7-dihydropurine-2,6-dione,
(16) 7-(2-butynyl)-3-isopropyl-1-methyl-8-(piperazin-1-yl)-3,7-dihydropurine-2,6-dione,
(17) 7-(2-butynyl)-3-(3,3-dimethyl-2-oxobutyl)-1-methyl-8-(piperazin-1-yl)-3,7-dihydropurine-2,6-dione,
(18) 7-(2-butynyl)-1-methyl-3-(2-oxopyrrolidin-3-yl)-8-(piperazin-1-yl)-3,7-dihydropurine-2,6-dione,
(19) 7-(2-butynyl)-3-(2-ethoxyethyl)-1-(2-oxo-2-phenylethyl)-8-(piperazin-1-yl)-3,7-dihydropurine-2,6-dione,
(20) [7-(2-butynyl)-2,6-dioxo-1-(2-oxo-2-phenylethyl)-8-(piperazin-1-yl)-1,2,6,7-tetrahydropurin-3-yl]acetic acid methyl ester,
(21) [7-(2-butynyl)-2,6-dioxo-1-(2-phenethyl)-8-(piperazin-1-yl)-1,2,6,7-tetrahydropurin-3-yl]acetic acid ethyl ester,
(22) [7-(2-butynyl)-2,6-dioxo-1-(2-phenethyl)-8-(piperazin-1-yl)-1,2,6,7-tetrahydropurin-3-yl]acetic acid,
(23) 7-(2-butynyl)-3-[2-oxo-2-(pyrrolidin-1-yl)ethyl]-1-(2-phenethyl)-8-(piperazin-1-yl)-3,7-dihydropurine-2,6-dione,
(24) 2-[7-(2-butynyl)-2,6-dioxo-1-(2-phenethyl)-8-(piperazin-1-yl)-1,2,6,7-tetrahydropurin-3-yl]-N-methylacetamide,
(25) 2-[7-(2-butynyl)-2,6-dioxo-1-(2-phenethyl)-8-(piperazin-1-yl)-1,2,6,7-tetrahydropurin-3-yl]-N-cyclopropylacetamide,
(26) 2-[7-(2-butynyl)-2,6-dioxo-1-(2-phenethyl)-8-(piperazin-1-yl)-1,2,6,7-tetrahydropurin-3-yl]-N-phenylacetamide,
(27) 2-[7-(2-butynyl)-2,6-dioxo-1-(2-phenethyl)-8-(piperazin-1-yl)-1,2,6,7-tetrahydropurin-3-yl]-N-(2-propynyl)acetamide,
(28) 7-(2-butynyl)-1-(2-ethoxyethyl)-3-methyl-8-(piperazin-1-yl)-3,7-dihydropurine-2,6-dione,
(29) 7-(2-butynyl)-1-ethyl-3-methyl-8-(piperazin-1-yl)-3,7-dihydropurine-2,6-dione,
(30) 7-(2-butynyl)-1-[2-(4-chlorophenyl)-2-oxoethyl]-3-methyl-8-(piperazin-1-yl)-3,7-dihydropurine-2,6-dione,
(31) 7-(2-butynyl)-3-methyl-1-(2-phenoxyethyl)-8-(piperazin-1-yl)-3,7-dihydropurine-2,6-dione,
(32) 2-[7-(2-butynyl)-3-methyl-2,6-dioxo-8-(piperazin-1-yl)-2,3,6,7-tetrahydropurin-1-ylmethyl]-benzonitrile,
(33) 4-[7-(2-butynyl)-3-methyl-2,6-dioxo-8-(piperazin-1-yl)-2,3,6,7-tetrahydropurin-1-ylmethyl]benzoic acid methyl ester,
(34) 3-[7-(2-butynyl)-3-methyl-2,6-dioxo-8-(piperazin-1-yl)-2,3,6,7-tetrahydropurin-1-ylmethyl]benzoic acid methyl ester,
(35) 7-(2-butynyl)-3-methyl-1-(2-phenylethyl)-8-(piperazin-1-yl)-3,7-dihydropurine-2,6-dione,
(36) 2-[7-(2-butynyl)-3-methyl-2,6-dioxo-8-(piperazin-1-yl)-2,3,6,7-tetrahydropurin-1-yl]-N-phenylacetamide,
(37) 7-(2-methoxyphenyl)-1,3-dimethyl-8-(piperazin-1-yl)-3,7-dihydropurine-2,6-dione,
(38) 7-(2-vinylphenyl)-1,3-dimethyl-8-(piperazin-1-yl)-3,7-dihydropurine-2,6-dione,
(39) 7-(2-chlorophenyl)-3-methyl-8-(piperazin-1-yl)-3,7-dihydropurine-2,6-dione,
(40) 7-(2-chlorophenyl)-3-methyl-1-(2-phenethyl)-8-(piperazin-1-yl)-3,7-dihydropurine-2,6-dione,
(41) 7-(2-chlorophenyl)-3-methyl-1-(2-oxo-2-phenylethyl)-8-(piperazin-1-yl)-3,7-dihydropurine-2,6-dione,
(42) 7-(2-methoxyphenyl)-3-methyl-8-(piperazin-1-yl)-3,7-dihydropurine-2,6-dione,
(43) [7-(2-methoxyphenyl)-3-methyl-2,6-dioxo-8-(piperazin-1-yl)-2,3,6,7-tetrahydropurin-1-yl]acetonitrile,
(44) 7-(2-methoxyphenyl)-3-methyl-1-(2-oxo-2-phenylethyl)-8-(piperazin-1-yl)-3,7-dihydropurine-2,6-dione,
(45) 7-(2-methoxyphenyl)-3-methyl-1-(2-phenylethyl)-8-(piperazin-1-yl)-3,7-dihydropurine-2,6-dione,
(46) 7-(2-vinylphenyl)-3-methyl-8-(piperazin-1-yl)-3,7-dihydropurine-2,6-dione,
(47) 7-(2-chlorophenyl)-3-(2-oxo-2-phenethyl)-8-(piperazin-1-yl)-3,7-dihydropurine-2,6-dione,
(48) 2-[7-(2-chlorophenyl)-2,6-dioxo-8-(piperazin-1-yl)-1,2,6,7-tetrahydropurin-3-yl]-4-hydroxybutyric acid,
(49) 2-[7-(2-chlorophenyl)-2,6-dioxo-8-(piperazin-1-yl)-1,2,6,7-tetrahydropurin-3-yl]acetamide,
(50) [7-(2-chlorophenyl)-1-methyl-2,6-dioxo-8-(piperazin-1-yl)-1,2,6,7-tetrahydropurin-3-yl]acetic acid,
(51) [7-(2-chlorophenyl)-2,6-dioxo-8-(piperazin-1-yl)-1,2,6,7-tetrahydropurin-3-yl]acetic acid,
(52) [7-(2-chlorophenyl)-2,6-dioxo-1-(2-phenethyl)-8-(piperazin-1-yl)-1,2,6,7-tetrahydropurin-3-yl]acetic acid,
(53) 2-[7-(2-chlorophenyl)-2,6-dioxo-1-(2-phenethyl)-8-(piperazin-1-yl)-1,2,6,7-tetrahydropurin-3-yl]acetamide,
(54) 7-(2-butynyl)-3-benzyl-1-methyl-8-(piperazin-1-yl)-3,7-dihydropurine-2,6-dione,
(55) 2-[7-(2-butynyl)-1-methyl-2,6-dioxo-8-(piperazin-1-yl)-1,2,6,7-tetrahydropurin-3-yl]acetamide,
(56) 7-(2-butynyl)-3-(2-oxotetrahydrofuran-3-yl)-1-methyl-8-(piperazin-1-yl)-3,7-dihydropurine-2,6-dione,
(57) 7-(2-butynyl)-3-(2-ethoxyethyl)-8-(piperazin-1-yl)-3,7-dihydropurine-2,6-dione,
(58) [7-(2-butynyl)-3-(2-ethoxyethyl)-2,6-dioxo-8-(piperazin-1-yl)-2,3,6,7-tetrahydropurin-1-yl]acetic acid methyl ester,
(59) [7-(2-butynyl)-2,6-dioxo-1-(2-phenoxyethyl)-8-(piperazin-1-yl)-1,2,6,7-tetrahydropurin-3-yl]acetic acid ethyl ester,
(60) [1-methyl-2,6-dioxo-8-(piperazin-1-yl)-7-(2-vinylphenyl)-1,2,6,7-tetrahydropurin-3-yl]acetic acid ethyl ester, and
(61) [1-methyl-2,6-dioxo-8-(piperazin-1-yl)-7-(2-vinylphenyl)-1,2,6,7-tetrahydropurin-3-yl]acetic acid.

<23> A compound selected from the group consisting of (1) to (27) a salt thereof, and a hydrate thereof:
(1) 7-(2-butynyl)-1,3-dimethyl-8-(piperazin-1-yl)-3,7-dihydropurine-2,6-dione,
(2) 7-(2-butynyl)-3-methyl-8-(piperazin-1-yl)-3,7-dihydropurine-2,6-dione,
(3) [7-(2-butynyl)-3-methyl-2,6-dioxo-8-(piperazin-1-yl)-2,3,6,7-tetrahydropurin-1-yl]acetic acid methyl ester,
(4) 7-(2-butynyl)-3-methyl-8-(piperazin-1-yl)-1-(2-propynyl)-3,7-dihydropurine-2,6-dione,
(5) 1,7-bis(2-butynyl)-3-methyl-8-(piperazin-1-yl)-3,7-dihydropurine-2,6-dione,
(6) [7-(2-butynyl)-3-methyl-2,6-dioxo-8-(piperazin-1-yl)-2,3,6,7-tetrahydropurin-1-yl]acetonitrile,
(7) 7-(2-butynyl)-3-methyl-1-(2-oxo-2-phenylethyl)-8-(piperazin-1-yl)-3,7-dihydropurine-2,6-dione, (8) 7-(2-butynyl)-3-ethyl-1-methyl-8-(piperazin-1-yl)-3,7-dihydropurine-2,6-dione,
(9) [7-(2-butynyl)-1-methyl-2,6-dioxo-8-(piperazin-1-yl)-1,2,6,7-tetrahydropurin-3-yl]acetic acid methyl ester,
(10) 7-(2-butynyl)-3-(2-tetrahydrofuranyl)methyl-1-methyl-8-(piperazin-1-yl)-3,7-dihydropurine-2,6-dione,
(11) [7-(2-butynyl)-1-methyl-2,6-dioxo-8-(piperazin-1-yl)-1,2,6,7-tetrahydropurin-3-yl]phenyl acetic acid methyl ester,
(12) 7-(2-butynyl)-3-propyl-1-methyl-8-(piperazin-1-yl)-3,7-dihydropurine-2,6-dione,
(13) 7-(2-butynyl)-3-(2-oxo-2-phenethyl)-1-methyl-8-(piperazin-1-yl)-3,7-dihydropurine-2,6-dione,
(14) 2-[7-(2-butynyl)-1-methyl-2,6-dioxo-8-(piperazin-1-yl)-1,2,6,7-tetrahydropurin-3-yl]propionic acid ethyl ester,
(15) 7-(2-butynyl)-3-(2-ethoxyethyl)-1-methyl-8-(piperazin-1-yl)-3,7-dihydropurine-2,6-dione,
(16) 7-(2-butynyl)-3-isopropyl-1-methyl-8-(piperazin-1-yl)-3,7-dihydropurine-2,6-dione,
(17) 7-(2-butynyl)-3-(3,3-dimethyl-2-oxobutyl)-1-methyl-8-(piperazin-1-yl)-3,7-dihydropurine-2,6-dione,
(18) 7-(2-butynyl)-1-methyl-3-(2-oxopyrrolidin-3-yl)-8-(piperazin-1-yl)-3,7-dihydropurine-2,6-dione,
(19) 7-(2-butynyl)-3-(2-ethoxyethyl)-1-(2-oxo-2-phenylethyl)-8-(piperazin-1-yl)-3,7-dihydropurine-2,6-dione,
(20) [7-(2-butynyl)-2,6-dioxo-1-(2-oxo-2-phenylethyl)-8-(piperazin-1-yl)-1,2,6,7-tetrahydropurin-3-yl]acetic acid methyl ester,
(21) [7-(2-butynyl)-2,6-dioxo-1-(2-phenethyl)-8-(piperazin-1-yl)-1,2,6,7-tetrahydropurin-3-yl]acetic acid ethyl ester,
(22) [7-(2-butynyl)-2,6-dioxo-1-(2-phenethyl)-8-(piperazin-1-yl)-1,2,6,7-tetrahydropurin-3-yl]acetic acid,
(23) 7-(2-butynyl)-3-[2-oxo-2-(pyrrolidin-1-yl)ethyl]-1-(2-phenethyl)-8-(piperazin-1-yl)-3,7-dihydropurine-2,6-dione,
(24) 2-[7-(2-butynyl)-2,6-dioxo-1-(2-phenethyl)-8-(piperazin-1-yl)-1,2,6,7-tetrahydropurin-3-yl]-N-methylacetamide,
(25) 2-[7-(2-butynyl)-2,6-dioxo-1-(2-phenethyl)-8-(piperazin-1-yl)-1,2,6,7-tetrahydropurin-3-yl]-N-cyclopropylacetamide,
(26) 2-[7-(2-butynyl)-2,6-dioxo-1-(2-phenethyl)-8-(piperazin-1-yl)-1,2,6,7-tetrahydropurin-3-yl]-N-phenylacetamide, and
(27) 2-[7-(2-butynyl)-2,6-dioxo-1-(2-phenethyl)-8-(piperazin-1-yl)-1,2,6,7-tetrahydropurin-3-yl]-N-(2-propynyl)acetamide.

<24> A dipeptidyl peptidase IV (DPPIV) inhibitor, comprising as the active ingredient a compound of any one of <1> to <23>, or a salt or hydrate thereof.
<25> A pharmaceutical composition comprising a compound of any one of <1> to <23>, or a salt or hydrate thereof.
<26> A preventive or therapeutic agent for a diabetic disease, comprising as the active ingredient a compound of any one of <1> to <23>, or a salt or hydrate thereof.
<27> A preventive or therapeutic agent for a disease selected from the group consisting of diabetes, obesity, hyperlipidemia, AIDS, osteoporosis, intestinal disorder, angiogenesis, infertility, inflammatory disease, allergic disease, and cancer, wherein said agent comprises as the active ingredient a compound of any one of <1> to <23>, or a salt or hydrate thereof.
<28> An immunomodulator comprising as the active ingredient a compound of any one of <1> to <23>, or a salt or hydrate thereof.
<29> A hormone regulator comprising as the active ingredient a compound of any one of <1> to <23>, or a salt or hydrate thereof.
<30> An anti-rheumatic agent comprising as the active ingredient a compound of any one of <1> to <23>, or a salt or hydrate thereof.

The present invention will be described in detail below by explaining the meaning of the terms, symbols, and such mentioned in the present description.

In the present description, the structural formula of the compounds may represent a certain isomer for convenience; however, the present invention includes all geometrical isomers, optical isomers based on asymmetric carbon, axial isomers, stereoisomers, and tautomers, and mixtures of isomers. Therefore, it is not to be construed as being limited to the representation in the formula (made only for convenience), and may be any one or a mixture of isomers. Thus, an optically active substance and a racemic substance having an asymmetric carbon atom in the molecule may exist; however, according to the present invention, there are no particular limitations and both of them are included. Furthermore, crystal polymorphism may exist; but similarly there are no limitations and the crystal form may be any one form or may be a mixture and may be either an anhydride or a hydrate.

The "$C_{1-6}$ alkyl group" according to the present description means a straight or branched chain alkyl group containing 1 to 6 carbons, and is a monovalent group derived by removing one arbitrary hydrogen atom from an aliphatic hydrocarbon having 1 to 6 carbons. Specific examples include a methyl group, ethyl group, n-propyl group, i-propyl group, n-butyl group, i-butyl group, sec-butyl group, t-butyl group, n-pentyl group, i-pentyl group, sec-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, and 1-ethyl-2-methylpropyl group, and is preferably a methyl group, ethyl group, n-propyl group, i-propyl group, n-butyl group, i-butyl group, sec-butyl group, or t-butyl group.

The "$C_{1-6}$ alkylene group" in the present description means a divalent group derived by removing one more arbitrary hydrogen atom from the "$C_{1-6}$ alkyl group" as defined above. A specific example includes a methylene group, ethylene group, methylethylene group, propylene group, ethylethylene group, 1,1-dimethylethylene group, 1,2-dimethylethylene group, tetramethylene group, pentamethylene group, and hexamethylene group, and is preferably a methylene group or ethylene group.

The "$C_{1-6}$ alkoxy group" in the present description means an oxy group to which the "$C_{1-6}$ alkyl group" defined above is bound. A specific example includes a methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group, and 1-ethyl-2-methylpropoxy group, and is preferably a methoxy group, ethoxy group, n-propoxy group, i-propoxy group, n-butoxy group, i-butoxy group, sec-butoxy group, or t-butoxy group.

The "$C_{1-6}$ alkylthio group" in the present description means a thio group to which the "$C_{1-6}$ alkyl group" defined above is bound. A specific example includes a methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, neopentylthio group, 1-methylbutylthio group, 2-methylbutylthio group, 1,1-dimethylpropylthio group, 1,2-dimethylpropylthio group, n-hexylthio group, i-hexylthio group, 1-methylpentylthio group, 2-methylpentylthio group, 3-methylpentylthio group, 1,1-dimethylbutylthio group, 1,2-dimethylbutylthio group, 2,2-dimethylbutylthio group, 1,3-dimethylbutylthio group, 2,3-dimethylbutylthio group, 3,3-dimethylbutylthio group, 1-ethylbutylthio group, 2-ethylbutylthio group, 1,1,2-trimethylpropylthio group, 1,2,2-trimethylpropylthio group, 1-ethyl-1-methylpropylthio group, and 1-ethyl-2-methylpropylthio group, and is preferably a methylthio group, ethylthio group, n-propylthio group, i-propylthio group, n-butylthio group, i-butylthio group, sec-butylthio group, or t-butylthio group.

The "$C_{1-6}$ hydroxyalkyl group" in the present description refers to a group in which a substitutable site of the "$C_{1-6}$ alkyl group" defined above is substituted with a hydroxyl group. A specific example includes a hydroxymethyl group, 2-hydroxyethyl group, or 1-hydroxyethyl group.

The "$C_{1-6}$ hydroxyalkoxy group" in the present description refers to a group in which a substitutable site of the "$C_{1-6}$ alkoxy group" defined above is substituted with a hydroxyl group. A specific example includes a hydroxymethoxy group, 2-hydroxyethoxy group, or 1-hydroxyethoxy group.

The "$C_{1-6}$ hydroxyalkylthio group" in the present description refers to a group in which a substitutable site of the "$C_{1-6}$ alkylthio group" defined above is substituted with a hydroxyl group. A specific example includes a hydroxymethylthio group, a 2-hydroxyethylthio group, and a 1-hydroxyethylthio group.

The "$C_{1-6}$ aminoalkyl group" in the present description refers to a group in which a substitutable site of the "$C_{1-6}$ alkyl group" defined above is substituted with an amino group. A specific example includes an amino methyl group, 2-aminoethyl group, or 1-aminoethyl group.

The "$C_{1-6}$ aminoalkoxy group" in the present description refers to a group in which a substitutable site of the "$C_{1-6}$ alkoxy group" defined above is substituted with an amino group. A specific example includes a 2-aminoethoxy group, 2-aminopropoxy group, or 3-aminopropoxy group.

The "$C_{1-6}$ aminoalkylthio group" in the present description refers to a group in which a substitutable site of the "$C_{1-6}$ alkylthio group" defined above is substituted with an amino group. A specific example includes an aminomethylthio group, 2-aminoethylthio group, or 1-aminoethylthio group.

The "halogen atom" in the present description means a fluorine atom, chlorine atom, bromine atom or iodine atom; it is preferably a fluorine atom, chlorine atom, or bromine atom.

The "$C_{1-6}$ halogenated alkyl group" in the present description refers to a group in which a substitutable site of the "$C_{1-6}$ alkyl group" defined above is substituted with one or more halogen atoms. A specific example includes a fluoromethyl group, trifluoromethyl group, 2-fluoroethyl group, or 1-fluoroethyl group.

The "$C_{1-6}$ halogenated alkoxy group" in the present description refers to a group in which a substitutable site of the "$C_{1-6}$ alkoxy group" defined above is substituted with one or more halogen atoms. A specific example includes a fluoromethoxy group, trifluoromethoxy group, 2-fluoroethoxy group, or 1-fluoroethoxy group.

The "$C_{1-6}$ halogenated alkylthio group" in the present description refers to a group in which a substitutable site of the "$C_{1-6}$ alkylthio group" defined above is substituted with one or more halogenatoms. A specific example includes a fluoromethylthio group, trifluoromethylthio group, 2-fluoroethylthio group, or 1-fluoroethylthio group.

The "$C_{1-6}$ alkoxy $C_{1-6}$ alkyl group" in the present description refers to a group in which a substitutable site of "$C_{1-6}$ alkyl group" defined above is substituted with the "$C_{1-6}$ alkoxy group" defined above. A specific example includes a methoxymethyl group, ethoxymethyl group, 1-methoxyethyl group, 2-methoxyethyl group, 1-ethoxyethyl group, or 2-ethoxyethyl group.

The "$C_{1-6}$ alkoxy $C_{1-6}$ alkoxy group" in the present description refers to a group in which a substitutable site of the "$C_{1-6}$ alkoxy group" defined above is substituted with "$C_{1-6}$ alkoxy group" defined above. A specific example includes a methoxymethoxy group, ethoxymethoxy group, 1-methoxyethoxy group, 2-methoxyethoxy group, 1-ethoxyethoxy group, and 2-ethoxyethoxy group.

The "$C_{1-6}$ alkoxy $C_{1-6}$ alkylthio group" in the present description refers to a group in which a substitutable site of the "$C_{1-6}$ alkylthio group" defined above is substituted with "$C_{1-6}$ alkoxy group" defined above. A specific example includes a methoxymethylthio group, ethoxymethylthio group, 1-methoxyethylthio group, 2-methoxyethylthio group, 1-ethoxyethylthio group, or 2-ethoxyethylthio group.

The "$C_{1-6}$ alkylthio $C_{1-6}$ alkyl group" in the present description refers to a group in which a substitutable site of the "$C_{1-6}$ alkyl group" defined above is substituted with "$C_{1-6}$ alkylthio group" defined above. A specific example includes a methylthiomethyl group, ethylthiomethyl group, 1-methylthioethyl group, 2-methylthioethyl group, 1-ethylthioethyl group, or 2-ethylthioethyl group.

The "$C_{2-6}$ alkenyl group" in the present description means a straight or branched chain alkenyl group that may contain 1 to 2 double bonds, wherein the number of carbons ranges from 2 to 6. A specific example includes an ethenyl group, 1-propenyl group, 2-propenyl group, 1-butenyl group, 2-butenyl group, 3-butenyl group, 2-methyl-1-propenyl group, pentenyl group, hexenyl group, and hexanedienyl group, and is preferably an ethenyl group, 1-propenyl group, 2-propenyl group, 1-butenyl group, 2-butenyl group, 3-butenyl group, or 2-methyl-1-propenyl group.

The "$C_{3-6}$ alkenyl group" in the present description means a straight or branched chain alkenyl group that may contain 1 to 2 double bonds, wherein the number of carbon ranges from 3 to 6. A specific example includes a 1-propenyl group, 2-propenyl group, 1-butenyl group, 2-butenyl group, 3-butenyl group, 2-methyl-1-propenyl group, pentenyl group, hexenyl group, and hexanedienyl group, and is preferably a 1-propenyl group, 2-propenyl group, 1-butenyl group, 2-butenyl group, 3-butenyl group, or 2-methyl-1-propenyl group.

The "$C_{2-6}$ alkenyloxy group" of the present description means an oxy group to which the "$C_{2-6}$ alkenyl group" defined above is bound. A specific example includes an ethenyloxy group, 1-propenyloxy group, 2-propenyloxy group, 1-butenyloxy group, 2-butenyloxy group, 3-butenyloxy group, 2-methyl-1-propenyloxy group, pentenyloxy group, hexenyloxy group, and hexanedienyloxy group, and is preferably an ethenyloxy group, 1-propenyloxy group, 2-propenyloxy group, 1-butenyloxy group, 2-butenyloxy group, 3-butenyloxy group, or 2-methyl-1-propenyloxy group.

The "$C_{2-6}$ alkenylthio group" of the present description means a thio group to which the "$C_{2-6}$ alkenyl group" defined above is bound. A specific example includes an ethenylthio group, 1-propenylthio group, 2-propenylthio group, 1-butenylthio group, 2-butenylthio group, 3-butenylthio group, 2-methyl-1-propenylthio group, pentenylthio group, hexenylthio group, and hexanedienylthio group, and is preferably an ethenylthio group, 1-propenylthio group, 2-propenylthio group, 1-butenylthio group, 2-butenylthio group, 3-butenylthio group, or 2-methyl-1-propenylthio group.

The "$C_{2-6}$ alkynyl group" in the present description means a straight or branched chain alkynyl group that may contain 1 to 2 triple bonds, wherein the number of carbon ranges from 2 to 6. A specific example includes an ethynyl group, 1-propynyl group, 2-propynyl group, 1-butynyl group, 2-butynyl group, 3-butynyl group, pentynyl group, hexynyl group, and hexanediynyl group, and is preferably an ethynyl group, 1-propynyl group, 2-propynyl group, 1-butynyl group, 2-butynyl group, or 3-butynyl group.

The "$C_{3-6}$ alkynyl group" in the present description means a straight or branched chain alkynyl group that may contain 1 to 2 triple bonds, wherein the number of carbon ranges from 3 to 6. A specific example includes a 1-propynyl group, 2-propynyl group, 1-butynyl group, 2-butynyl group, 3-butynyl group, pentynyl group, hexynyl group, and hexanediynyl group, and is preferably a 1-propynyl group, 2-propynyl group, 1-butynyl group, 2-butynyl group, or 3-butynyl group.

The "$C_{2-6}$ alkynyloxy group" of the present description means an oxy group to which the "$C_{2-6}$ alkynyl group" defined above is bound. A specific example includes an ethynyloxy group, 1-propynyloxy group, 2-propynyloxy group, 1-butynyloxy group, 2-butynyloxy group, 3-butynyloxy group, pentynyloxy group, hexynyloxy group, and hexanediynyloxy group, and is preferably an ethynyloxy group, 1-propynyloxy group, 2-propynyloxy group, 1-butynyloxy group, 2-butynyloxy group, or 3-butynyloxy group.

The "$C_{2-6}$ alkynylthio group" of the present description means a thio group to which the "$C_{2-6}$ alkynyl group" defined above is bound. A specific example includes an ethynylthio group, 1-propynylthio group, 2-propynylthio group, 1-butynylthio group, 2-butynylthio group, 3-butynylthio group, pentynylthio group, hexynylthio group, and hexanediynylthio group, and is preferably an ethynylthio group, 1-propynylthio group, 2-propynylthio group, 1-butynylthio group, 2-butynylthio group, or 3-butynylthio group.

The "$C_{3-7}$ cycloalkyl group" in the present description means a cyclic saturated aliphatic hydrocarbon group, wherein the number of carbon ranges from 3 to 7. A specific example includes a cyclopropyl group, cyclobutyl group, cyclopentyl group, cyclohexyl group, and cycloheptyl group, and is preferably a cyclopropyl group, cyclobutyl group, cyclopentyl group, or cyclohexyl group.

The "$C_{3-7}$ cycloalkyl $C_{1-6}$ alkyl group" in the present description refers to a group in which a substitutable site of the "$C_{1-6}$ alkyl group" defined above is substituted with "$C_{3-7}$ cycloalkyl group" defined above. A specific example includes a cyclopropylmethyl group, cyclobutylmethyl group, cyclopentylmethyl group, cyclohexylmethyl group, cycloheptylmethyl group, cyclopropylethyl group, cyclobutylethyl group, cyclopentylethyl group, cyclohexylethyl group, and cycloheptylethyl group.

The "$C_{3-7}$ cycloalkyloxy group" of the present description means an oxy group to which "$C_{3-7}$ cycloalkyl group" defined above is bound. A specific example includes a cyclopropyloxy group, cyclobutyloxy group, cyclopentyloxy group, cyclohexyloxy group, or cycloheptyloxy group.

The "$C_{3-7}$ cycloalkyl $C_{1-6}$ alkyloxy group" of the present description means an oxy group to which the "$C_{3-7}$ cycloalkyl $C_{1-6}$ alkyl group" defined above is bound. A specific example includes a cyclopropylmethoxy group, cyclopropylethoxy group, cyclopropyl-n-propoxy group, cyclopropyl-i-propoxy group, cyclopropyl-n-butoxy group, cyclopropyl-i-butoxy group, cyclopropyl-sec-butoxy group, and cyclopropyl-t-butoxy group, and is preferably a cyclopropylmethoxy group, cyclopropylethoxy group, cyclopropyl-n-propoxy group, or cyclopropyl-i-propoxy group.

The "$C_{3-7}$ cycloalkylthio group" of the present description means a thio group to which "$C_{3-7}$ cycloalkyl group" defined above is bound. A specific example includes a cyclopropylthio group, cyclobutylthio group, cyclopentylthio group, cyclohexylthio group, or cycloheptylthio group.

The "$C_{3-7}$ cycloalkenyl group" in the present description means a cyclic unsaturated aliphatic hydrocarbon group, wherein the number of carbon ranges from 3 to 7. A specific example includes a cyclopropenyl group, cyclobutenyl group, cyclopentenyl group, cyclohexenyl group, and cycloheptenyl group, and is preferably a cyclopropenyl group, cyclobutenyl group, cyclopentenyl group, or cyclohexenyl group.

The "$C_{6-12}$ aryl group" in the present description means an aromatic cyclic hydrocarbon group, wherein the number of carbon ranges from 6 to 12. A specific example includes a phenyl group, 1-naphthyl group, 2-naphthyl group, indenyl group, azulenyl group, and heptalenyl group, and is preferably a phenyl group, 1-naphthyl group, or 2-naphthyl group.

The "$C_{6-12}$ aryloxy group" of the present description means an oxy group to which the "$C_{6-12}$ aryl group" defined above is bound. A specific example includes a phenoxy group, 1-naphthyloxy group, 2-naphthyloxy group, indenyloxy group, azulenyloxy group, and heptalenyloxy group, and is preferably a phenoxy group, 1-naphthyloxy group, or 2-naphthyloxy group.

The "$C_{6-12}$ arylthio group" of the present description means a thio group to which the "$C_{6-12}$ aryl group" defined above is bound. A specific example includes a phenylthio group, 1-naphthylthio group, 2-naphthylthio group, indenylthio group, azulenylthio group, and heptalenylthio group, and is preferably a phenylthio group, 1-naphthylthio group, or 2-naphthylthio group.

The "$C_{6-12}$ aryl $C_{1-6}$ alkyl group" in the present description refers to a group in which a substitutable site of the "$C_{1-6}$ alkyl group" defined above is substituted with the "$C_{6-12}$ aryl group" defined above. A specific example includes a benzyl group, phenethyl group, 3-phenylpropyl group, 1-naphthylmethyl group, 2-naphthylmethyl group, 1-naphthylethyl group, and 2-naphthylethyl group, and is preferably a benzyl group, or phenethyl group.

The "$C_{6-12}$ aryl $C_{1-6}$ alkyloxy group" of the present description means an oxy group to which the "$C_{6-12}$ aryl $C_{1-6}$ alkyl group" defined above is bound. A specific example includes a benzyloxy group, phenethyloxy group, 3-phenylpropyloxy group, 1-naphthylmethyloxy group, 2-naphthylmethyloxy group, 1-naphthylethyloxy group, and 2-naphthylethyloxy group, and is preferably a benzyloxy group, or phenethyloxy group.

The "$C_{6-12}$ aryl $C_{1-6}$ alkylthio group" of the present description means a thio group to which the "$C_{6-12}$ aryl $C_{1-6}$ alkyl group" defined above is bound. A specific example includes a benzylthio group, phenethylthio group, 3-phenylpropylthio group, 1-naphthylmethylthio group, 2-naphthylmethylthio group, 1-naphthylethylthio group, and 2-naphthylethylthio group, and is preferably a benzylthio group, or phenethylthio group.

The "$C_{6-12}$ aryloxy $C_{1-6}$ alkyl group" in the present description refers to a group in which a substitutable site of the "$C_{1-6}$ alkyl group" defined above is substituted with the "$C_{6-12}$ aryloxy group" defined above. A specific example includes a phenoxymethyl group, 1-naphthyloxymethyl group, 2-naphthyloxymethyl group, indenyloxymethyl group, azulenyloxymethyl group, heptalenyloxymethyl group, phenoxyethyl group, 1-naphthyloxyethyl group, 2-naphthyloxyethyl group, indenyloxyethyl group, azulenyloxyethyl group, and heptalenyloxyethyl group, and is preferably a phenoxyethyl group, 1-naphthyloxyethyl group, or 2-naphthyloxyethyl group.

The "hetero atom" in the present description means a nitrogen atom, a sulfur atom, or an oxygen atom.

The "5 to 14-membered heteroaryl group" in the present description means an aromatic cyclic group containing one or more heteroatoms among the atoms constituting the ring, wherein the number of atoms constituting the ring ranges from 5 to 14. A specific example includes a furyl group, thienyl group, pyrrolyl group, pyridyl group, quinolyl group, isoquinolyl group, cinnolyl group, quinazolyl group, quinoxalyl group, indolyl group, indazolyl group, oxazolyl group, isoxazolyl group, thiazolyl group, isothiazolyl group, imidazolyl group, pyrazolyl group, furazanyl group, pyridazinyl group, pyrimidyl group, pyrazyl group, benzofuryl group, and benzothienyl group, and is preferably a furyl group, thienyl group, benzothienyl group, or quinolyl group.

The "5 to 14-membered heteroaryloxy group" of the present description means an oxy group to which the "5 to 14-membered heteroaryl group" defined above is bound. A specific example includes a furyloxy group, thienyloxy group, pyrrolyloxy group, pyridyloxy group, quinolyloxy group, isoquinolyloxy group, cinnolyloxy group, quinazolyloxy group, quinoxalyloxy group, indolyloxy group, indazolyloxy group, oxazolyloxy group, isoxazolyloxy group, thiazolyloxy group, isothiazolyloxy group, imidazolyloxy group, pyrazolyloxy group, furazanyloxy group, pyridazinyloxy group, pyrimidyloxy group, pyrazyloxy group, benzofuryloxy group, or benzothienyloxy group.

The "5 to 14-membered heteroaryl $C_{1-6}$ alkyl group" in the present description refers to a group in which a substitutable site of the "$C_{1-6}$ alkyl group" defined above is substituted with the "5 to 14-membered heteroaryl group" defined above. A specific example includes a furylmethyl group, thienylmethyl group, pyrrolylmethyl group, pyridylmethyl group, quinolylmethyl group, benzofurylmethyl group, benzothienylmethyl group, furylethyl group, thienylethyl group, pyrrolylethyl group, pyridylethyl group, quinolylethyl group, benzofurylethyl group, and benzothienylethyl group, and is preferably a thienylmethyl group, pyridylmethyl group, or pyrrolylethyl group.

The "5 to 14-membered heteroaryloxy $C_{1-6}$ alkyl group" in the present description refers to a group in which a substitutable site of the "$C_{1-6}$ alkyl group" defined above is substituted with the "5 to 14-membered heteroaryloxy group" defined above. A specific example includes a furyloxymethyl group, thienyloxymethyl group, pyrrolyloxymethyl group, pyridyloxymethyl group, quinolyloxymethyl group, benzofuryloxymethyl group, benzothienyloxymethyl group, furyloxyethyl group, thienyloxyethyl group, pyrrolyloxyethyl group, pyridyloxyethyl group, quinolyloxyethyl group, benzofuryloxyethyl group, and benzothienyloxyethyl group, and is preferably a thienyloxymethyl group, pyridyloxymethyl group, or pyrrolyloxyethyl group.

The "aliphatic $C_{2-7}$ acyl group" in the present description corresponds to a group in which a carbonyl group is bound to the end of the "$C_{1-6}$ alkyl group", the "$C_{2-6}$ alkenyl group", or the "$C_{2-6}$ alkynyl group" defined above. A specific example includes an acetyl group, propionyl group, butyryl group, isobutyryl group, valeryl group, isovaleryl group, pivaloyl group, hexanoyl group, octanoyl group, acryloyl group, methacryloyl group, and crotonyl group. An acetyl group, propionyl group, butyryl group, isobutyryl group, valeryl group, isovaleryl group, pivaloyl group, hexanoyl group, octanoyl group, acryloyl group, methacryloyl group, or crotonyl group is preferable, an acetyl group, propionyl group, butyryl group, isobutyryl group, valeryl group, isovaleryl group, pivaloyl group, hexanoyl group, or octanoyl group is more preferable, an acetyl group, propionyl group, butyryl group, or isobutyryl group is even more preferable, and an acetyl group, or propionyl group is most preferable.

The "aromatic $C_{7-19}$ acyl group" in the present description corresponds to a group in which a carbonyl group or a group derived by removing one more hydrogen atom from the "aliphatic $C_{2-7}$ acyl group" defined above is bound to the end of the "$C_{6-12}$ aryl group" defined above. A specific example includes a benzoyl group, cinnamoyl group, 1-naphthoyl group, and 2-naphthoyl group, and is preferably a benzoyl group, or cinnamoyl group, and more preferably a benzoyl group.

The "aliphatic $C_{2-7}$ alkoxycarbonyl group" in the present description corresponds to a group in which a carbonyl group is bound to the end of the "$C_{1-6}$ alkoxy group", the "$C_{2-6}$ alkenyloxy group", or the "$C_{2-6}$ alkynyloxy group" defined above. A specific example includes a methoxycarbonyl group, ethoxycarbonyl group, n-propyloxycarbonyl group, i-propyloxycarbonyl group, n-butoxycarbonyl group, i-butoxycarbonyl group, t-butoxycarbonyl group, pentyloxycarbonyl group, hexyloxycarbonyl group, allyloxycarbonyl group, methallyloxycarbonyl group, and crotyloxycarbonyl group. A methoxycarbonyl group, ethoxycarbonyl group, n-propyloxycarbonyl group, i-propyloxycarbonyl group, n-butoxycarbonyl group, i-butoxycarbonyl group, or t-butoxycarbonyl group is preferable, and methoxycarbonyl group, ethoxycarbonyl group, or n-propyloxycarbonyl group is more preferable.

The "$C_{7-19}$ aryloxycarbonyl group" in the present description corresponds to a group in which a carbonyl group or a group derived by removing one more hydrogen atom from the "aliphatic $C_{2-7}$ alkoxycarbonyl group" defined above is bound to the end of the "$C_{6-12}$ aryloxy group" defined above. A specific example includes a phenoxycarbonyl group, 1-naphthyloxycarbonyl group, and 2-naphthyloxycarbonyl group, and is preferably a phenoxycarbonyl group.

The "aliphatic $C_{1-6}$ sulfonyl group" in the present description corresponds to a group in which a sulfonyl group is bound to the end of the "$C_{1-6}$ alkyl group", the "$C_{2-6}$ alkenyl group", the "$C_{2-6}$ alkynyl group", or the "$C_{3-7}$ cycloalkyl group" defined above. A specific example includes a methanesulfonyl group, ethanesulfonyl group, propanesulfonyl group, isopropylsulfonyl group, butanesulfonyl group, cyclopropanesulfonyl group, cyclobutanesulfonyl group, cyclopentanesulfonyl group, and cyclohexanesulfonyl group. A methanesulfonyl group, ethanesulfonyl group, propanesulfonyl group, cyclopropanesulfonyl group, cyclobutanesulfonyl group, or cyclopentanesulfonyl group is preferable, and a methanesulfonyl group, or ethanesulfonyl group is more preferable.

The "aromatic $C_{6-18}$ sulfonyl group" in the present description corresponds to a group in which a sulfonyl group or a group derived by removing one more hydrogen atom from the "aliphatic $C_{1-6}$ sulfonyl group" defined above is bound to the end of the "$C_{6-12}$ aryl group" defined above. A specific example includes a benzenesulfonyl group, p-toluenesulfonyl group, m-toluenesulfonyl group, p-fluorobenzenesulfonyl group, 1-naphthalenesulfonyl group, and 2-naphthalenesulfonyl group. Preferable is a benzenesulfonyl group, or p-toluenesulfonyl group, and more preferable is a benzenesulfonyl group.

The "$C_{2-7}$ cyanoalkyl group" in the present description corresponds to a group in which a cyano group is bound to a substitutable site of the "$C_{1-6}$ alkyl group" defined above. A specific example includes a cyanomethyl group, 1-cyanoethyl group, 2-cyanoethyl group, 1-methyl-1-cyanoethyl group, 1,1-dimethyl-1-cyanoethyl group, 1-cyanopropyl group, 2-cyanopropyl group, 3-cyanopropyl group, and cyanobutyl group, and is preferably a cyanomethyl group, 1-cyanoethyl group, or 2-cyanoethyl group.

The "3 to 10-membered heterocycle" in the present description means a non-aromatic ring, wherein
(1) the number of atoms constituting the ring ranges from 3 to 10,
(2) the atoms constituting the ring include 1 to 2 heteroatoms,
(3) the ring may contain 1 to 2 double bonds,
(4) the ring may contain 1 to 3 carbonyl groups, and
(5) the ring is monocyclic or bicyclic.

A specific example includes an aziridine ring, azetidine ring, pyrrolidine ring, piperidine ring, homopiperidine ring, piperazine ring, homopiperazine ring, morpholine ring, thiomorpholine ring, pyridone ring, phthalimide ring, succinimide ring, tetrahydrofuran ring, tetrahydropyran ring, γ-butyrolactone ring, γ-valerolactone ring, pyrrolidone ring, and piperidone ring; is preferably a pyrrolidine ring, piperidine ring, piperazine ring, tetrahydrofuran ring, butyrolactone ring, or pyrrolidone ring.

The "3 to 10-membered heterocyclic group" in the present description means a monovalent group derived by removing one hydrogen atom from an arbitrary position in "3 to 10-membered heterocycle" defined above.

The "3 to 10-membered heterocyclic $C_{1-6}$ alkyl group" in the present description refers to a group in which a substitutable site of "$C_{1-6}$ alkyl group" defined above is substituted with "3 to 10-membered heterocycle" defined above.

"Substituted or unsubstituted" in the present description means that "the substitutable site may have an arbitrary combination of one or more substituents". Specifically, the substituents are, for example,
(1) halogen atom,
(2) hydroxyl group,
(3) thiol group,
(4) nitro group,
(5) cyano group,
(6) azido group,
(7) formyl group,
(8) carboxyl group,
(9) amino group, or

(10) a group represented by the formula $-T^1-T^2-T^3$ (wherein $T^1$ denotes a single bond or $C_{1-6}$ alkylene group; $T^2$ denotes a single bond, $C_{1-6}$ alkylene group, oxygen atom, sulfur atom, sulfinyl group, sulfonyl group, carbonyl group, or a group represented by the formula —O—CO—, the formula —CO—O—, the formula —$NR^{T1}$—, the formula —CO—$NR^{T1}$—, the formula —$NR^{T1}$—CO—, the formula —$SO_2$—$NR^{T1}$—, or the formula —$NR^{T1}$—$SO_2$—, $T^3$ denotes a hydrogen atom, $C_{1-6}$ alkyl group, $C_{2-6}$ alkenyl group, $C_{2-6}$ alkynyl group, $C_{3-7}$ cycloalkyl group, $C_{6-12}$ aryl group, 5 to 14-membered heteroaryl group, 3 to 10-membered heterocyclic group, or a group represented by the formula —$N(R^{T2})(R^{T3})$; $R^{T1}$, $R^{T2}$, and $R^{T3}$ individually denote a hydrogen atom, or $C_{1-6}$ alkyl group. However, in $T^3$, the $C_{1-6}$ alkyl group, the $C_{2-6}$ alkenyl group, the $C_{2-6}$ alkynyl group, the $C_{3-7}$ cycloalkyl group, the $C_{6-12}$ aryl group, the 5 to 14-membered heteroaryl group, and the 3 to 10-membered heterocyclic group may individually have 1 to 3 substituents selected from the group consisting of the following substituents.

<Group of Substituents> halogen atom, hydroxyl group, thiol group, nitro group, cyano group, $C_{1-6}$ alkyl group, $C_{3-7}$ cycloalkyl group, $C_{2-6}$ alkenyl group, $C_{2-6}$ alkynyl group, $C_{6-12}$ aryl group, 5 to 14-membered heteroaryl group, 3 to 10-membered heterocyclic group, $C_{1-6}$ alkoxy group, and $C_{1-6}$ alkylthio group).

"$R^3$ and $R^4$ may bind to each other to form a substituted or unsubstituted ring containing one or more heteroatoms" as used in the present description means that, the ring containing one or more heteroatoms includes an aziridine ring, azetidine ring, pyrrolidine ring, piperidine ring, piperazine ring, homopiperazine ring, morpholine ring, and thiomorpholine ring. An azetidine ring, pyrrolidine ring, piperidine ring, piperazine ring, homopiperazine ring, or morpholine ring is preferable, and a pyrrolidine ring, piperidine ring, or piperazine ring is more preferable.

"$R^5$ and $R^6$ may form a bond to each other" as used in the present description means that $R^5$ and $R^6$ together form a ring such as cyclopropane, cyclobutane, cyclopentane, and cyclohexane.

"Any two of $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ may be bound" as used in the present description means that any two of $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ form together a ring structure, and refers to compounds represented by the following formulae:

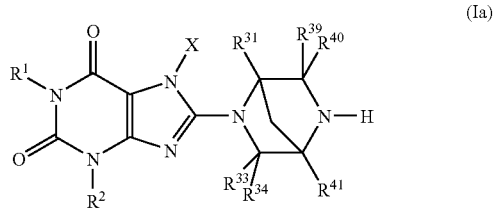

(Ia)

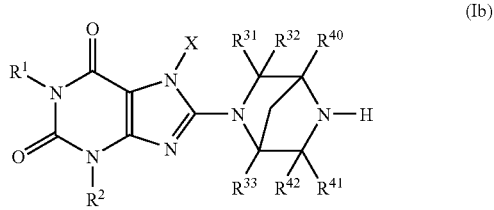

(Ib)

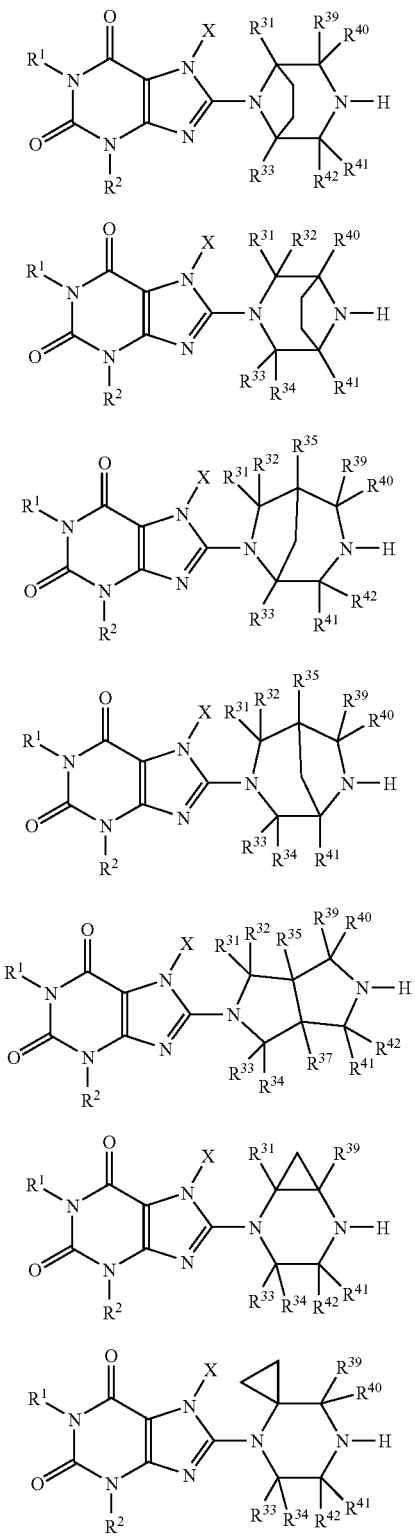

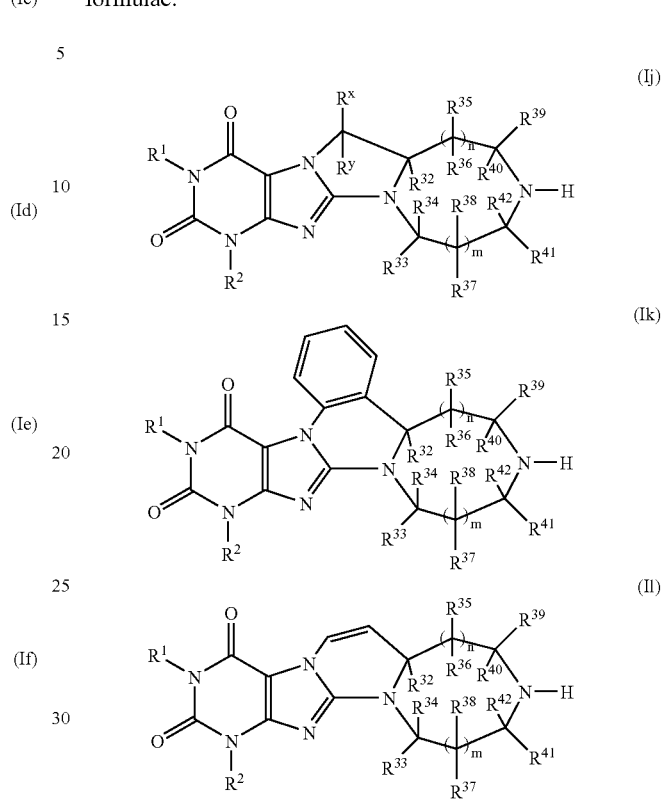

(wherein the symbols have the same meaning as defined above).

"X may form a bond with any one of $R^{31}$, $R^{32}$, $R^{33}$, and $R^{34}$" as used in the present description means that X together with any one of $R^{31}$, $R^{32}$, $R^{33}$, and $R^{34}$ forms a ring structure, and refers to compounds represented by the following formulae:

(wherein the symbols have the same meaning as defined above).

Examples of "salt" as used in the present description include a salt formed with an inorganic acid, a salt formed with an organic acid, a salt formed with an inorganic base, a salt formed with an organic base, and a salt formed with an acidic or basic amino acid. Especially preferable is a pharmaceutically acceptable salt. An acid or a base forms a salt at the appropriate ratio of 0.1 to 5 molecules per molecule of the compound.

Examples of a preferable salt formed with an inorganic acid include salts formed with hydrochloric acid, hydrobromic acid, sulfuric acid, nitric acid, and phosphoric acid. Examples of a preferable salt formed with an organic acid include salts formed with acetic acid, succinic acid, fumaric acid, maleic acid, tartaric acid, citric acid, lactic acid, stearic acid, benzoic acid, methanesulfonic acid, and p-toluenesulfonic acid.

Examples of a preferable salt formed with an inorganic base include salts formed with alkali metals such as sodium salt or potassium salt, with alkaline earth metals such as calcium salt or magnesium salt, and aluminum salt, and ammonium salt. Examples of a preferable salt formed with an organic base include salts formed with diethylamine, diethanolamine, meglumine, and N,N'-dibenzylethylenediamine.

Examples of a preferable salt formed with an acidic amino acid include salts with aspartic acid, and glutamic acid. Examples of a preferable salt formed with a basic amino acid include salts with arginine, lysine, and ornithine.

Examples of "formulation adjuvant" as used in the present description include fillers, binders, disintegrators, lubricants, coloring agents, corrigents, stabilizers, emulsifiers, absorption enhancers, surfactants, pH regulators, preservatives, and antioxidants.

DETAILED DESCRIPTION OF THE INVENTION

Various methods can be used to produce the compounds of the present invention. Representative methods are exemplified below.

[General Synthesis Method]

In general, compounds represented by formula (I) are synthesized by the methods described below.

The symbols used in the following descriptions of the production methods are:

$R^1$, $R^2$, $R^{31}$–$R^{42}$, m, n, and X have the same definitions as defined above;

Pro1, Pro2, and Pro3 independently denote a group to protect the —NH group, such as pivalyloxymethyl and trimethylsilylethoxymethyl;

$U^1$ and Ha1 independently denote a leaving group such as chlorine, bromine, iodine, a methanesulfonyloxy, or p-toluenesulfonyloxy;

$U^2$ denotes chlorine, bromine, iodine, methanesulfonyloxy, p-toluenesulfonyloxy, —B(OH)$_2$, 4,4,5,5-tetramethyl-1,3,2-dioxaboran-2-yl, or formula —Sn($R^Z$)$_3$ (wherein $R^Z$ denotes $C_{1-6}$ alkyl);

$R^{51}$–$R^{57}$ independently denote hydrogen, $C_{1-6}$ alkyl, or $C_{6-12}$ aryl; and $R_x$, $R_y$, and $R_z$ independently denote $C_{1-6}$ alkyl or $C_{6-12}$ aryl.

Production Method A

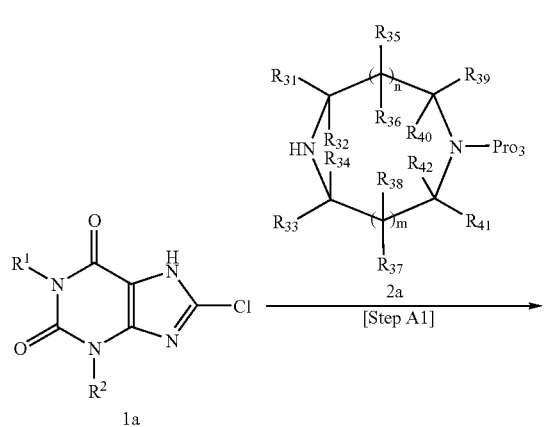

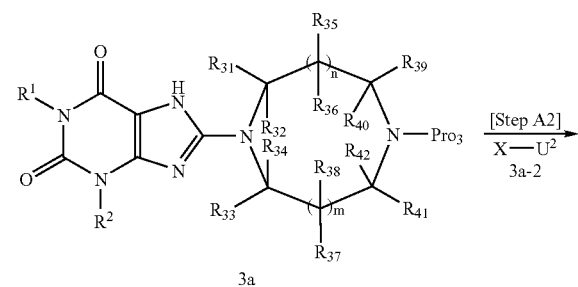

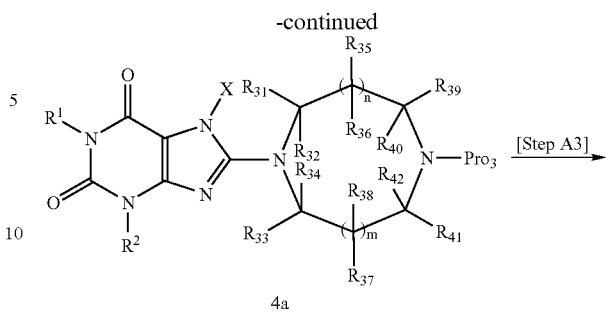

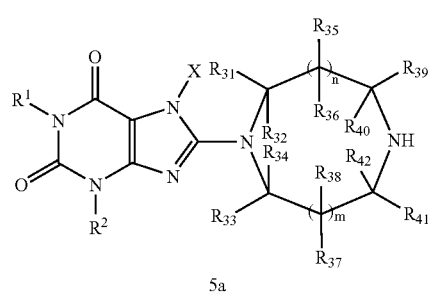

[Step A1]

The step of reacting compound (1a) with compound (2a) to give compound (3a):

There are no particular limitations on the reaction conditions. For example, the reaction may be performed by mixing compounds (1a) and (2a) in a solvent such as N,N-dimethylformamide, N-methylpyrrolidone, methanol, ethanol, 1,4-dioxane, toluene, or xylene, or in the absence of a solvent at a temperature from 0° C. to 150° C.

[Step A2]

The step of introducing a substituent into the —NH group at position 7 of compound (3a) to give compound (4a) by substituting compound (3a) with compound (3a-2):

Specifically, for example, an alkyl halide such as iodomethane, iodoethane, iodopropane or benzylbromide, an alkenyl halide such as aryl bromide or 1-bromo-3-methyl-2-butene, or an alkynyl halide such as propargyl bromide or 1-bromo-2-butyne may be used as compound (3a-2).

There is no particular limitation on the conditions for the substitution reaction. For example, the reaction may be performed in a solvent such as dimethyl sulfoxide, N,N-dimethylformamide, N-methylpyrrolidone, dioxane, tetrahydrofuran, or toluene; in the presence of bases such as lithium hydroxide, sodium hydroxide, potassium hydroxide, lithium carbonate, sodium carbonate, potassium carbonate, cesium carbonate, lithium hydride, sodium hydride, potassium hydride, butyl lithium, methyl lithium, lithium bis (trimethylsilyl)amide, sodium bis (trimethylsilyl)amide, or potassium bis(trimethylsilyl)amide; and at a temperature from 0° C. to 150° C.

When X to be introduced is a $C_{6-12}$ aryl group that may have a substituent or a 5 to 14-membered heteroaryl group that may have a substituent, the reaction may be performed using, specifically, for example, arylboronic acid or heteroarylboronic acid as compound (3a-2).

In this instance, the reaction may be performed in a solvent such as dichloromethane, chloroform, 1,4-dioxane, tetrahydrofuran, toluene, pyridine, N,N-dimethylformamide or N-methylpyrrolidone; in the presence of bases such as triethylamine, N,N-diisopropylamine, pyridine, and N,N-dimethylaminopyridine; and in the presence of a copper catalyst such as copper acetate (III), copper trifluoroacetate (II), copper chloride (II), or copper iodide (II), at a temperature from 0° C. to 150° C.

[Step A3]

The step of removing Pro3 of compound (4a) to give compound (5a):

The conditions for the removal of Pro3 vary with protection group used. For example, when t-butoxycarbonyl is used, Pro3 may be deprotected with anhydrous hydrogen chloride in a methanol solution, anhydrous hydrogen chloride in an ethanol solution, anhydrous hydrogen chloride in a dioxane solution, trifluoroacetic acid, formic acid, etc.

Production Method B

[Step B1]

The step of introducing a substituent into the —NH group at position 7 of compound (1b) to give compound (2b) by substituting compound (1b) with compound (1b-2):

The reaction conditions for the substitution are the same as those set forth in [Step A2] of the production method A.

[Step B2]

The step of reacting compound (2b) with a halogenating agent to give compound (3b):

Specifically, halogenating agents include N-chlorosuccinimide, N-bromosuccinimide, and N-iodosuccinimide.

There is no particular limitation on the reaction conditions for the halogenation. The reaction may be performed in a solvent such as acetonitrile, N,N-dimethylformamide, N-methylpyrrolidone, 1,4-dioxane, tetrahydrofuran, or dimethoxyethane, and at a temperature from 0° C. to 150° C.

[Step B3]

The step of removing Pro3 to give compound (5b) after reacting compound (3b) with compound (4b):

The reaction conditions for the coupling are the same as those set forth in [Step A1] of production method A.

The reaction conditions for the removal of Pro3 are the same as those set forth in [Step A3] of production method A.

Production Method C

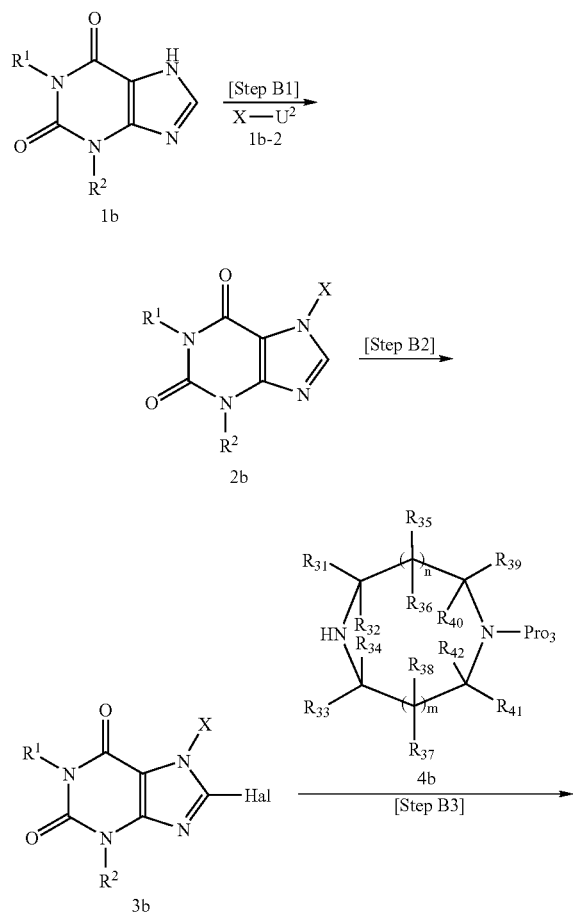

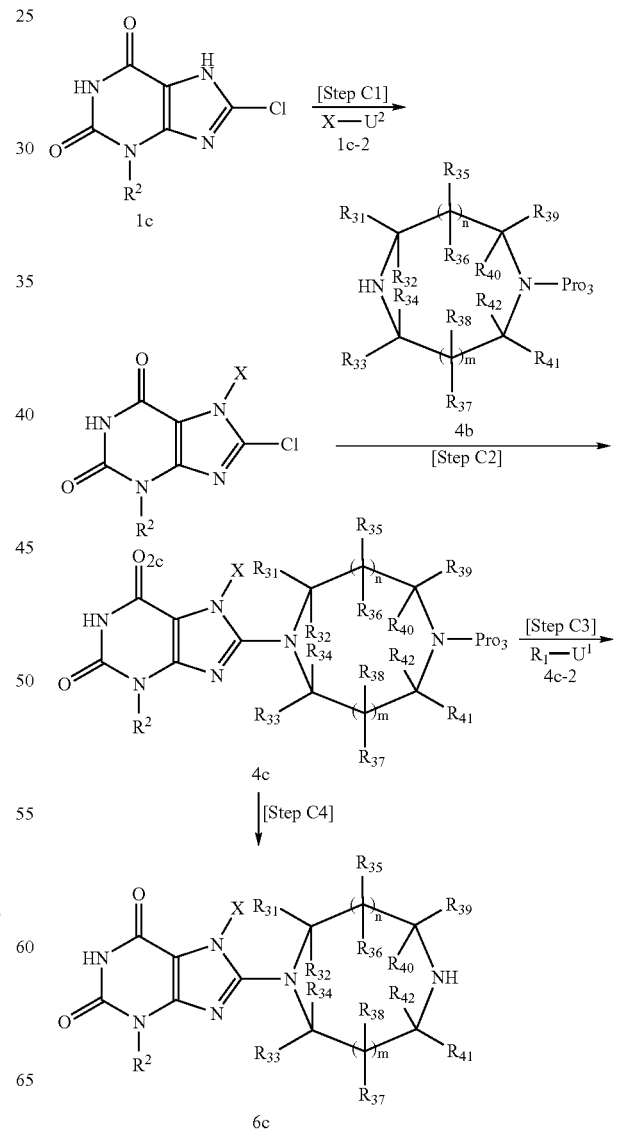

-continued

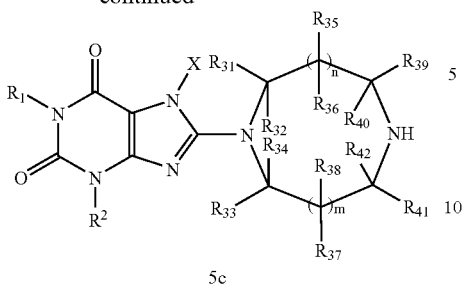

5c

[Step C1]

The step of introducing a substituent into the —NH group at position 7 of compound (1c) to give compound (2c) by substituting compound (1c) with compound (1c-2):

The reaction conditions for the substitution are the same as those set forth in [Step A2] of production method A.

[Step C2]

The step of reacting compound (2c) with compound (3c) to give compound (4c):

The reaction conditions are the same as those set forth in [Step A1] of production method A.

[Step C3]

The step of introducing a substituent into the nitrogen at position 1 of compound (4c) to give compound (5c) by substituting compound (4c) with compound (4c-2) followed by the removal of Pro3:

Compound (4c-2) is an electrophilic reagent such as an alkyl halide represented by formula $R^1$—$U^1$ (wherein $R^1$ and $U^1$ have the same definitions as defined above). Specifically, preferred examples of this compound include alkyl halides such as iodomethane, iodoethane, iodopropane, and benzylbromide; alkenyl halides such as allyl bromide or 1-bromo-3-methyl-2-butene; and alkynyl halides such as propargyl bromide and 1-bromo-2-butyne.

There is no particular limitation on the conditions for the substitution reaction. For example, the reaction may be performed in a solvent such as dimethyl sulfoxide, N,N-dimethylformamide, N-methylpyrrolidone, dioxane, tetrahydrofuran, or toluene; in the presence of bases such as lithium hydroxide, sodium hydroxide, potassium hydroxide, lithium carbonate, sodium carbonate, potassium carbonate, cesium carbonate, lithium hydride, sodium hydride, potassium hydride, butyl lithium, methyl lithium, lithium bis (trimethylsilyl)amide, sodium bis(trimethylsilyl)amide, and potassium bis(trimethylsilyl)amide; and at a temperature from 0° C. to 150° C.

The reaction conditions for the removal of Pro3 are the same as those set forth in [Step A3] of production method A.

[Step C4]

The step of removing Pro3 of compound (4c) to give compound (6c):

The reaction conditions for the removal of Pro3 are the same as those set forth in [Step A3] of production method A.

Production Method D

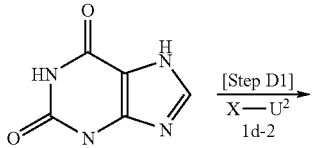

1d

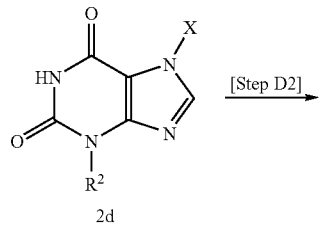

2d

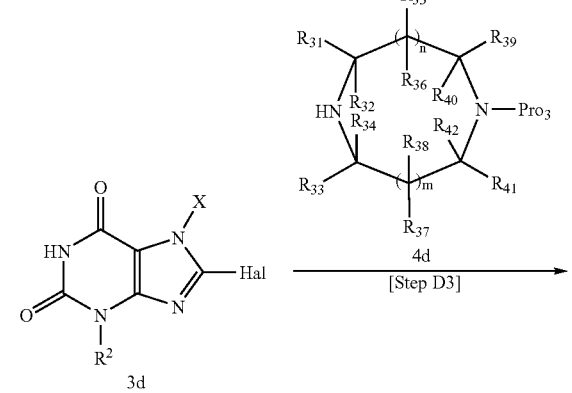

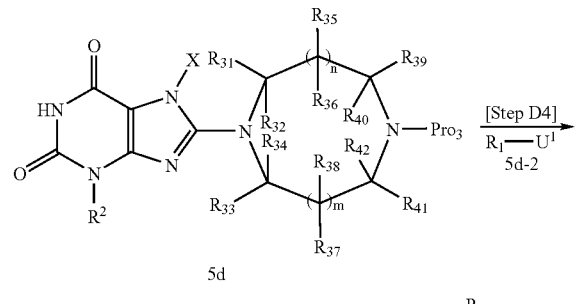

5d

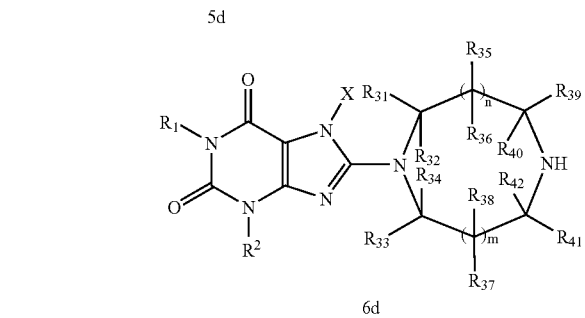

6d

[Step D1]

The step of introducing a substituent into the —NH group at position 7 of compound (1d) to give compound (2d) by substituting compound (1d) with compound (1d-2):

The reaction conditions for the substitution are the same as those set forth in [Step A2] of production method A.

33

[Step D2]

The step of reacting compound (2d) with a halogenating agent to give compound (3d):

The reaction conditions for the halogenation are the same as those set forth in [Step B2] of production method B.

[Step D3]

The step of reacting compound (3d) with compound (4d) to give compound (5d):

The reaction conditions are the same as those set forth in [Step A1] of production method A.

[Step D4]

The step of removing Pro3 to give compound (6d) after alkylation of compound (5d) at position 1:

The reaction conditions for the alkylation are the same as those set forth in [Step C3] of production method C.

The reaction conditions for the removal of Pro3 are the same as those set forth in [Step A3] of production method A.

Production Method E

34 wherein each symbol represents a group as defined above, s denotes 1 to 4, and Alkyl denotes $C_{1-6}$ alkyl.

[Step E1]

The step of alkylation of compound (1e) at position 1, then hydrolyzing the resulting intermediate to give (2e):

There is no particular limitation on the reaction conditions for the alkylation. For example, the reaction may be performed by reacting a compound represented by formula (1e-2), such as methyl bromoacetate or ethyl bromoacetate; in a solvent such as dimethyl sulfoxide, N,N-dimethylformamide, N-methylpyrrolidone, dioxane, tetrahydrofuran, or toluene; in the presence of bases such as lithium hydroxide sodium hydroxide, potassium hydroxide, lithium carbonate, sodium carbonate, potassium carbonate, cesium carbonate, lithium hydride, sodium hydride, potassium hydride, butyl lithium, methyl lithium, lithium bis(trimethylsilyl)amide, sodium bis(trimethylsilyl)amide, or potassium bis(trimethylsilyl)amide; and at a temperature from 0° C. to 150° C.

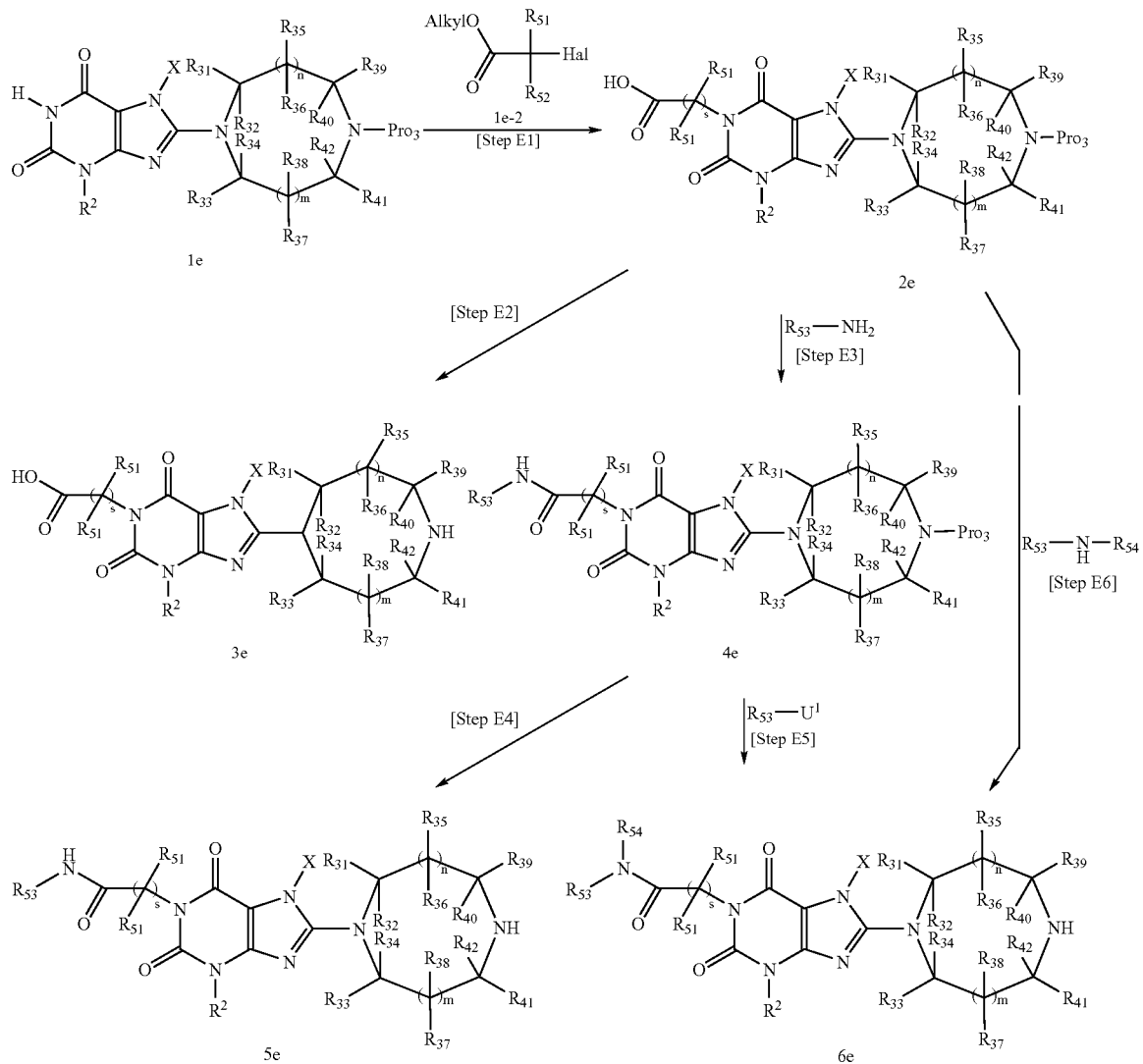

There is no particular limitation on the reaction conditions for the hydrolysis. For example, the hydrolysis may be performed by reacting an aqueous solution of lithium hydroxide, sodium hydroxide, and potassium hydroxide, in a solvent such as methanol, ethanol, propanol, dimethyl sulfoxide, N,N-dimethylformamide, N-methylpyrrolidone, dioxane, tetrahydrofuran, and at a temperature from 0° C. to 150° C.

[Step E2]

The step of removing Pro3 of compound (2e) to give compound (3e):

The reaction conditions for the removal of Pro3 are the same as those set forth in [Step A3] of production method A.

[Step E3]

The step of amidating compound (2e) to give compound (4e):

There is no particular limitation on the reaction conditions for the amidation. The amidation may be performed by reacting with the appropriate amine after just treating with an acylating agent such as ethyl chloroformate or isobutyl chloroformate, in a solvent such as acetonitrile, N,N-dimethylformamide, N-methylpyrrolidone, 1,4-dioxane, tetrahydrofuran, or dimethoxyethane, in the presence of organic bases such as triethylamine and N,N-diisopropylethyl amine, at a temperature from 0° C. to 150° C.

[Step E4]

The step of removing Pro3 of compound (4e) to give compound (5e):

The reaction conditions for the removal of Pro3 are the same as those set forth in [Step A3] of production method A.

[Step E5]

The step of alkylation of compound (5e), then removing Pro3 of the resulting intermediate to give (6e):

The reaction conditions for the alkylation are the same as those set forth in [Step C3] of production method C.

The reaction conditions for the removal of Pro3 are the same as those set forth in [Step A3] of production method A.

[Step E6]

The step of amidation of compound (2e), then removing Pro3 of the resulting intermediate to give (6e):

There is no particular limitation on the reaction conditions for the amidation. For example, the amidation may be performed by treating with a condensing agent such as 1,1'-carbonyldiimidazole or diethyl cyanophosphonate and in a solvent such as dimethyl sulfoxide, N,N-dimethylformamide, or tetrahydrofuran, then reacting with the appropriate amine. Organic bases such as triethylamine may be added to the reaction, if necessary. The reaction may be performed at a temperature from 0° C. to 150° C.

The reaction conditions for the removal of Pro3 are the same as those set forth in [Step A3] of production method A.

Production Method F

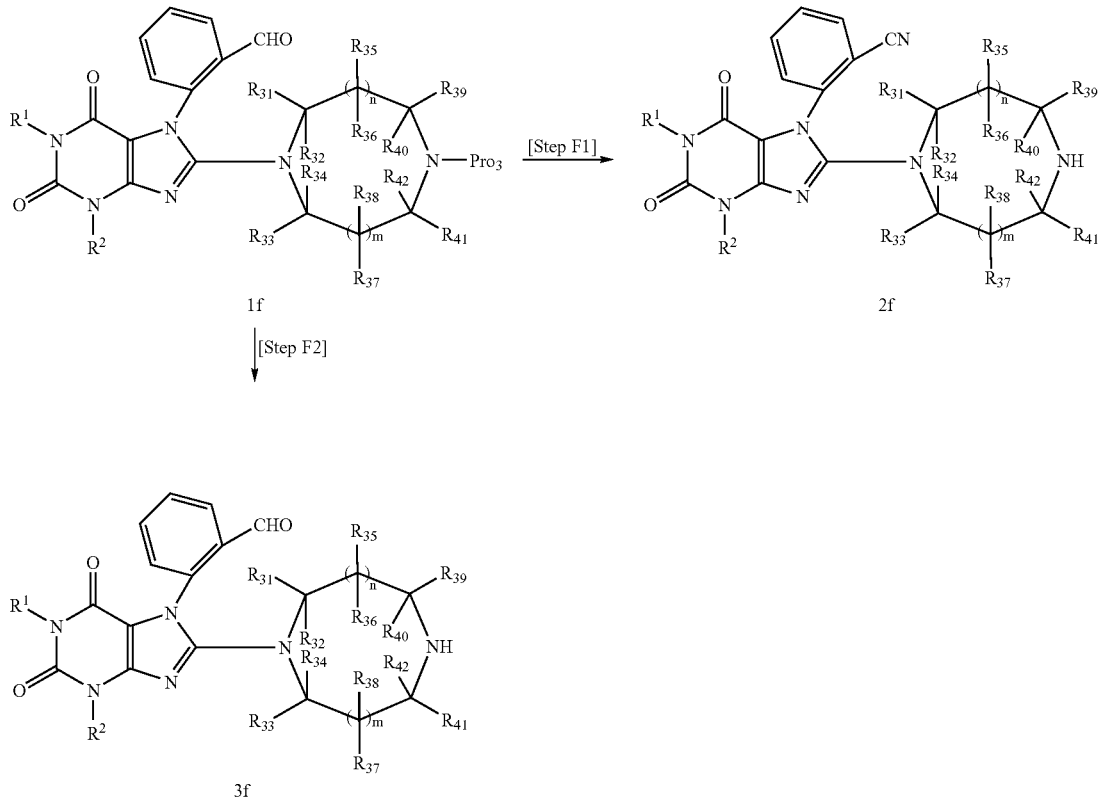

[Step F1]

The step of hydroxyimination of compound (1f) followed by sulfonylation and elimination of the generated hydroxyl group, then removing Pro3 of the resulting intermediate to give (2f):

There is no particular limitation on the reaction conditions for the hydroxyimination. For example, the reaction may be performed by reacting hydroxylamine hydrochloride in a solvent such as water, methanol, ethanol, propanol, dimethyl sulfoxide, N,N-dimethylformamide, N-methylpyrrolidone, dioxane, tetrahydrofuran, or toluene, and in the presence of bases such as potassium acetate or sodium acetate.

There is no particular limitation on the reaction conditions for the sulfonylation. For example, the reaction may be performed by reacting methanesulfonyl chloride, tosyl chloride, or 4-nitrobenzenesulfonyl chloride, in a solvent such as dichloromethane, chloroform, dioxane, tetrahydrofuran, toluene, and pyridine, in the presence of bases such as triethylamine, diisopropylethylamine, pyridine, and N,N-dimethylaminopyridine, and at a temperature from 0° C. to 150° C.

The reaction conditions for the removal of Pro3 are the same as those set forth in [Step A3] of production method A.

[Step F2]

The step of removing Pro3 of compound (1f) to give compound (3f):

The reaction conditions for the removal of Pro3 are the same as those set forth in [Step A3] of production method A.

Production Method G

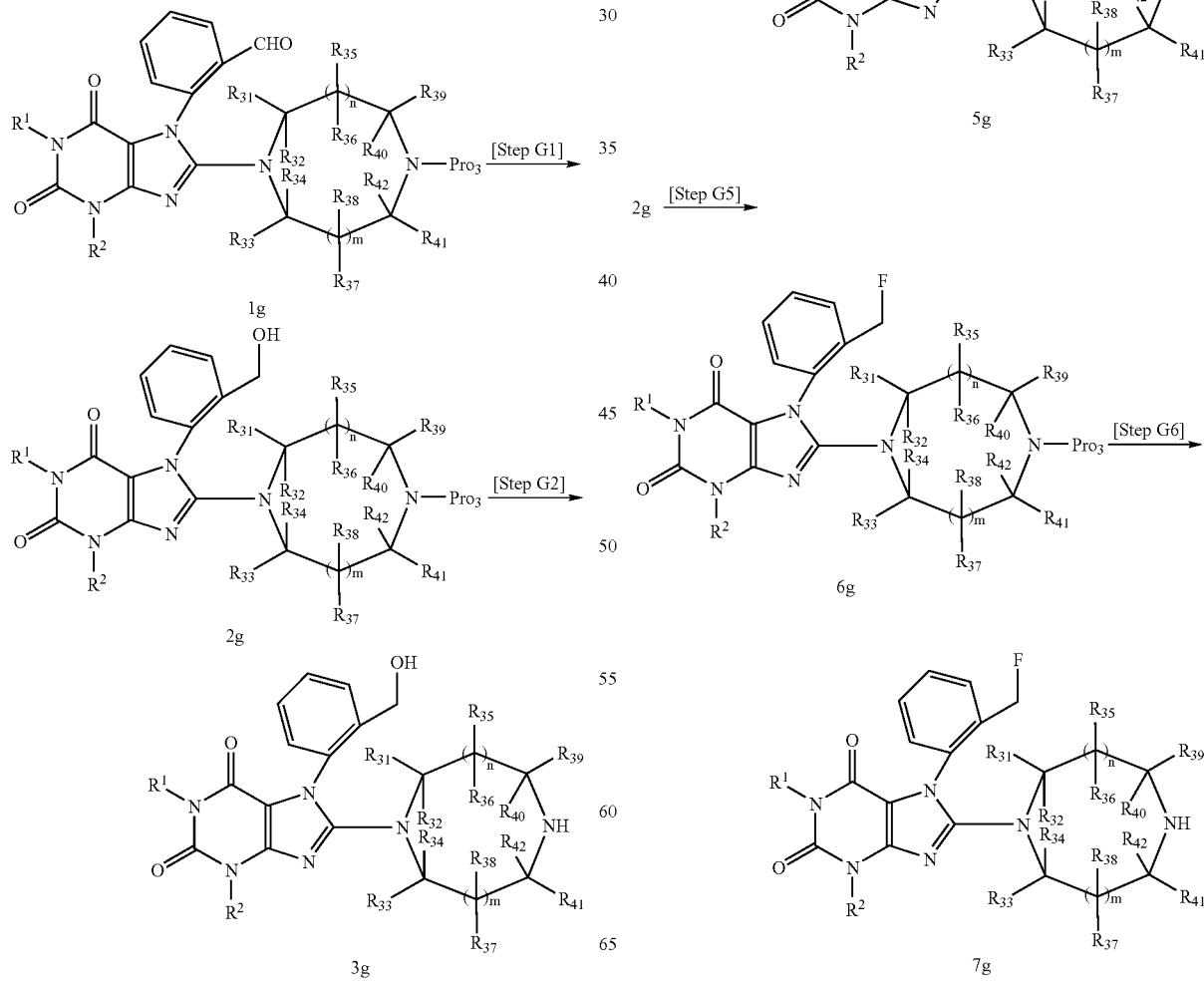

-continued

1g [Step G7]→

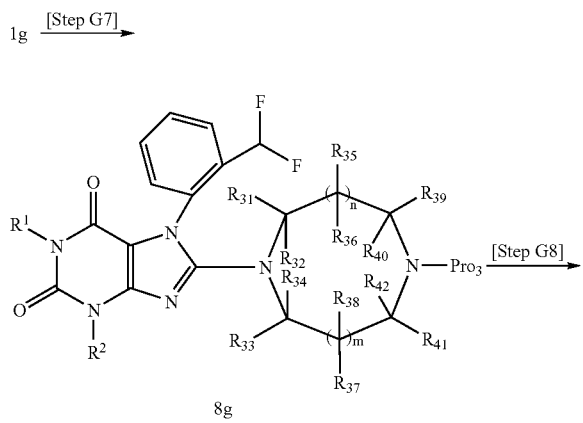

8g

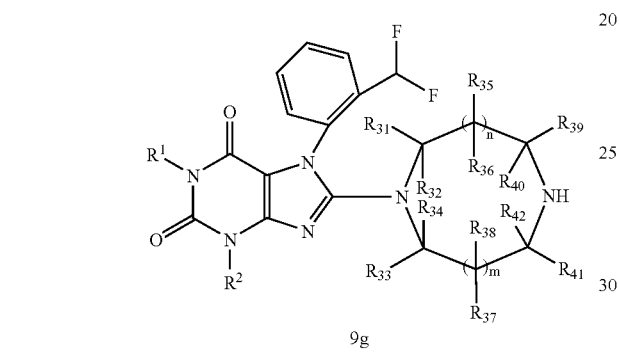

9g

2g [Step G9]→

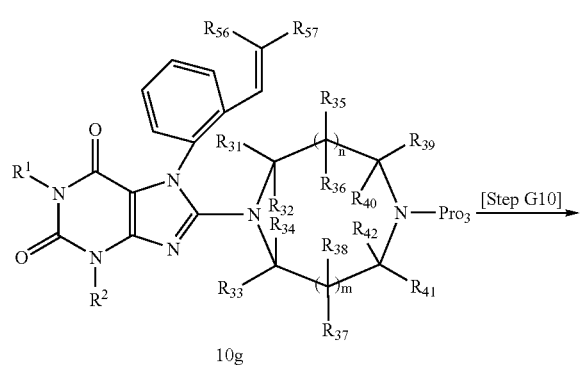

10g

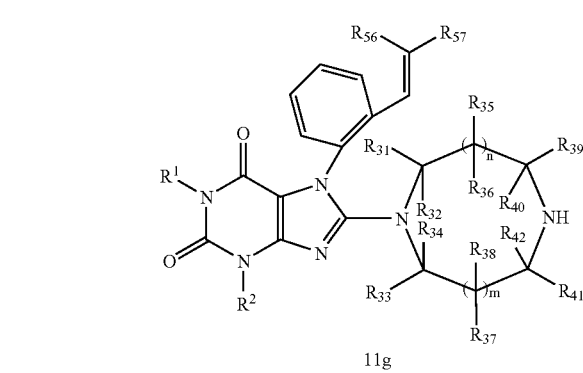

11g

10g [Step G11]→

-continued

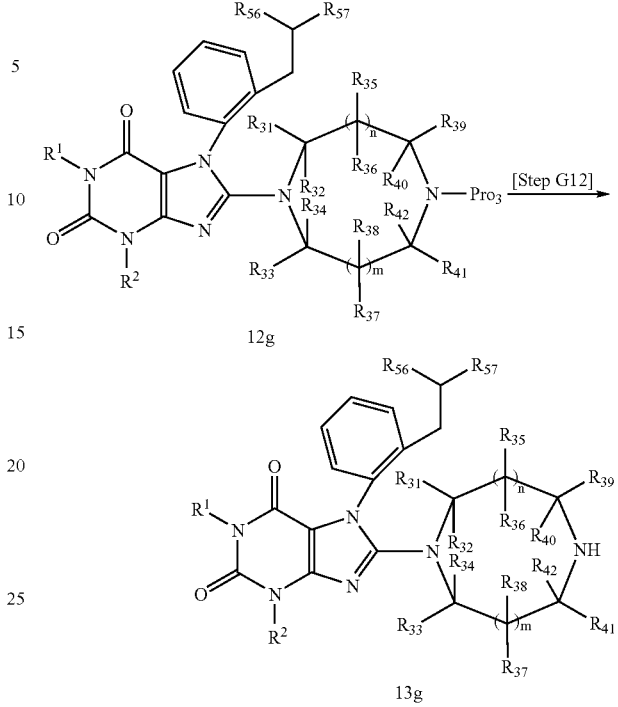

12g

13g

[Step G1]

The step of reducing compound (1g) to give compound (2g):

There is no particular limitation on the reaction conditions. The reaction may be performed by reacting a reducing agent such as lithium borohydride, sodium borohydride, or potassium borohydride; in a solvent such as methanol, ethanol, acetonitrile, N,N-dimethylformamide, N-methylpyrrolidone, 1,4-dioxane, tetrahydrofuran, dimethoxyethane, or a mixture thereof; and at a temperature from 0° C. to 150° C.

[Step G3]

The step of alkylating compound (2g) to give compound (4g):

There is no particular limitation on the reaction conditions for the alkylation. The reaction may be performed by reacting with an alkyl halide in a solvent such as acetonitrile, N,N-dimethylformamide, N-methylpyrrolidone, 1,4-dioxane, tetrahydrofuran, and dimethoxyethane, in the presence of bases such as lithium hydride, sodium hydride, potassium hydride, lithium hydroxide, sodium hydroxide, and potassium hydroxide.

[Step G5]

The step of fluorinating compound (2g) to give compound (6g):

There is no particular limitation on the reaction conditions. The reaction may be performed by reacting a fluorinating agent such as tris(diethylamino)sulfur trifluoride, in a solvent such as dichloromethane, 1,2-dichloroethane, acetonitrile, N,N-dimethylformamide, N-methylpyrrolidone, 1,4-dioxane, tetrahydrofuran, or dimethoxyethane, and at a temperature from −78° C. to 150° C.

[Step G7]

The step of fluorinating compound (1g) to give compound (8g):

There is no particular limitation on the reaction conditions. The reaction may be performed by reacting a fluorinating agent such as tris(diethylamino)sulfur trifluoride, in a solvent such as dichloromethane, 1,2-dichloroethane, acetonitrile, N,N-dimethylformamide, N-methylpyrrolidone, 1,4-dioxane, tetrahydrofuran, or dimethoxyethane, and at a temperature from −78° C. to 150° C.

[Step G9]

The step of olefination of compound (2g) to give the compound (10g):

There is no particular limitation on the reaction conditions. The reaction may be performed by reacting a reagent such as phosphonium salt or phosphonate ester, in a solvent such as dichloromethane, 1,2-dichloroethane, acetonitrile, N,N-dimethylformamide, N-methylpyrrolidone, 1,4-dioxane, tetrahydrofuran, or dimethoxyethane, in the presence of bases such as lithium hydride, sodium hydride, potassium hydride, potassium tert-butoxide, and butyl lithium, and at a temperature from −78° C. to 150° C.

[Step G11]

The step of reducing compound (10g) to give compound (12g):

There is no particular limitation on the reaction conditions for the reduction. For example, the reaction may be performed in a solvent such as methanol, ethanol, propanol, dimethyl sulfoxide, N,N-dimethylformamide, N-methylpyrrolidone, dioxane, tetrahydrofuran, or toluene, in the presence of a metal catalyst such as palladium-carbon, platinum oxide, and Raney nickel, under a hydrogen atmosphere at a temperature from 0° C. to 150° C.

[Step G2], [Step G4], [Step G6], [Step G8], [Step G10], and [Step G12]

The steps of removing Pro3 of compounds (2g), (4g), (6g), (8g), (10g), and (12g) to give compounds (3g), (5g), (7g), (9g), (11g), and (13g):

The reaction conditions for the removal of Pro3 are the same as those set forth in [Step A3] of production method A.

Production Method H

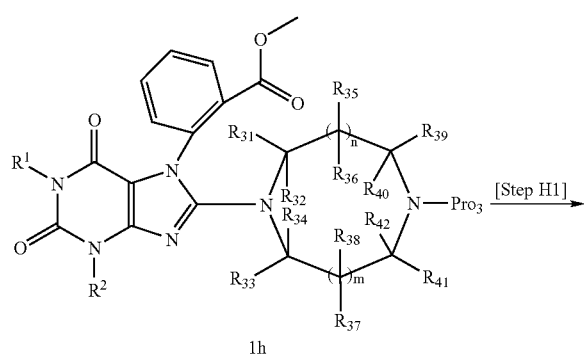

[Step H1]

The step of hydrolyzing compound (1 h) to give compound (2h):

There is no particular limitation on the reaction conditions for the hydrolysis. The hydrolysis may be performed by reacting an aqueous solution of lithium hydroxide, sodium hydroxide, potassium hydroxide, or such, in a solvent such as methanol, ethanol, acetonitrile, N,N-dimethylformamide, N-methylpyrrolidone, 1,4-dioxane, tetrahydrofuran, or dimethoxyethane, and at a temperature from 0° C. to 150° C.

[Step H3]

The step of amidating compound (2h) to give compound (4h):

The reaction conditions for the amidation are the same as those set forth in [Step E6] of production method E.

[Step H2] and [Step H4]

The steps of removing Pro3 of compounds (2h) and (4h) to give compounds (3h) and (5h):

The reaction conditions for the removal of Pro3 are the same as those set forth in [Step A3] of production method A.

Production Method I

An alternative method for producing compound (2d) in production method D

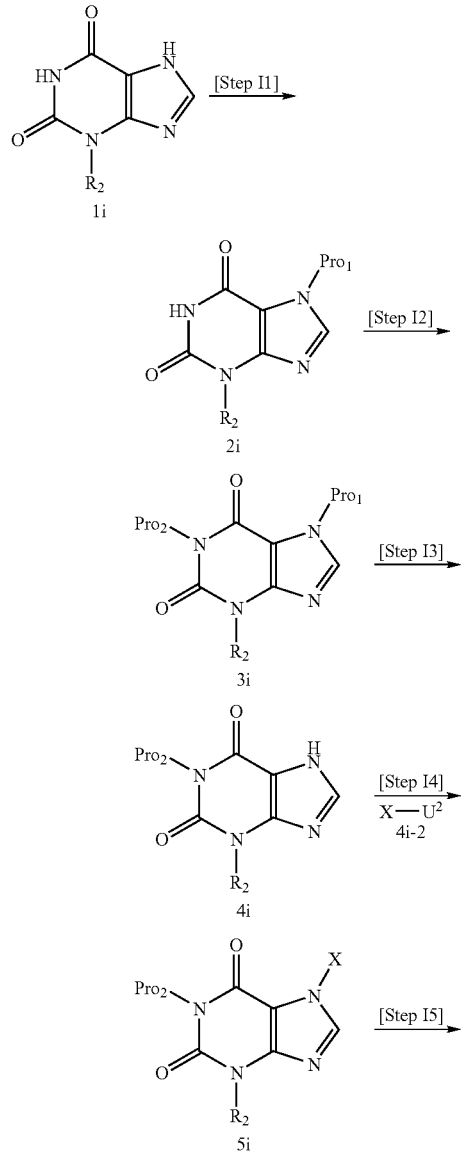

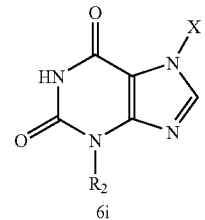

[Step I1]

The step of protecting the —NH group at position 7 of compound (1i) to give compound (2i):

There is no particular limitation on the —NH protecting group used or the reaction conditions used. For example, when the protecting group is benzyl, the reaction is performed by reacting an alkylating agent such as benzylbromide in a solvent such as acetonitrile, N,N-dimethylformamide, N-methylpyrrolidone, 1,4-dioxane, tetrahydrofuran or dimethoxyethane, in the presence of bases such as cesium carbonate, lithium carbonate, sodium carbonate or potassium carbonate, and at a temperature from 0° C. to 150° C.

[Step I2]

The step of protecting position 1 of compound (2i) to give compound (3i):

There is no particular limitation on the —NH protecting group used or the reaction conditions used. For example, when the protecting group is pivalyloxymethyl, the reaction is performed by reacting an alkylating agent such as chloromethyl pivalate in a solvent such as acetonitrile, N,N-dimethylformamide, N-methylpyrrolidone, 1,4-dioxane, tetrahydrofuran or dimethoxyethane, in the presence of bases such as cesium carbonate, lithium carbonate, sodium carbonate or potassium carbonate, and at a temperature from 0° C. to 150° C.

[Step I3]

The step of removing the protecting group at position 7 of compound (3i) to give compound (4i):

The reaction conditions vary with the protecting group used. For example, when the protecting group is benzyl, the reaction is performed in a solvent such as methanol, ethanol, propanol, dimethylsulfoxide, N,N-dimethylformamide, N-methylpyrrolidone, dioxane, tetrahydrofuran or toluene, in the presence of a metal catalyst such as palladium-carbon, platinum oxide and Raney Nickel, under a hydrogen atmosphere at a temperature from 0° C. to 150° C.

[Step I4]

The step of introducing a substituent into the —NH group at position 7 of compound (4i) to give compound (5i) by substituting compound (4i) with compound (4i-2):

The reaction conditions for the substitution are the same as those set forth in [Step A2] of production method A.

[Step I5]

The step of removing the protecting group at position 1 of compound (5i) to give compound (6i):

The reaction conditions vary with the protecting group used. For example, when the protecting group is pivalyloxymethyl, the reaction is performed by the action of bases such as sodium methoxide, sodium hydride, diazabicycloundec-7-ene in methanol or a mixed solution of methanol and tetrahydrofuran at a temperature from 0° C. to 150° C.

Production Method J

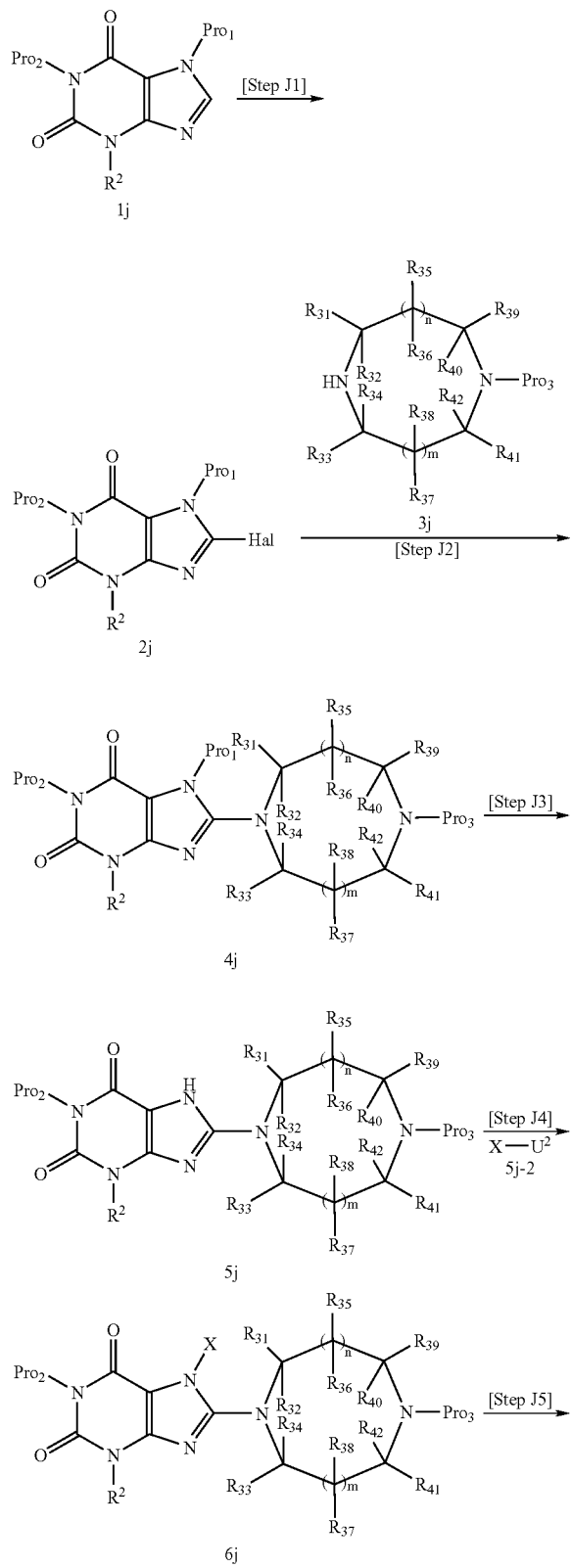

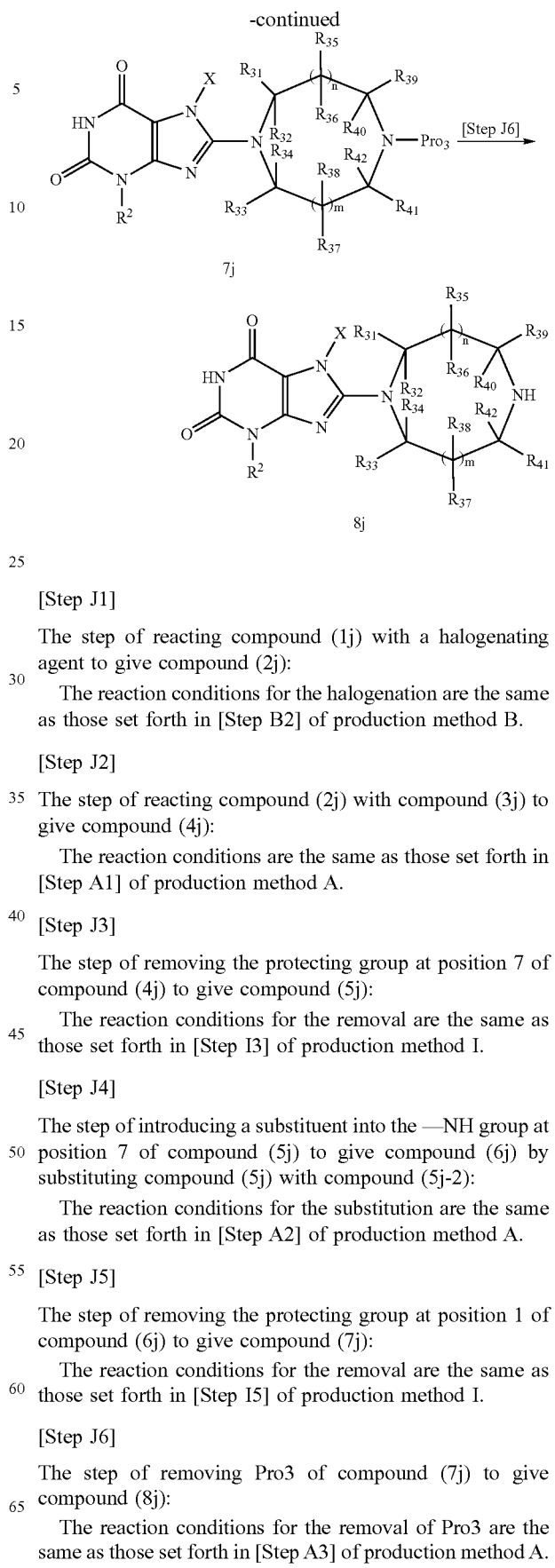

[Step J1]

The step of reacting compound (1j) with a halogenating agent to give compound (2j):

The reaction conditions for the halogenation are the same as those set forth in [Step B2] of production method B.

[Step J2]

The step of reacting compound (2j) with compound (3j) to give compound (4j):

The reaction conditions are the same as those set forth in [Step A1] of production method A.

[Step J3]

The step of removing the protecting group at position 7 of compound (4j) to give compound (5j):

The reaction conditions for the removal are the same as those set forth in [Step I3] of production method I.

[Step J4]

The step of introducing a substituent into the —NH group at position 7 of compound (5j) to give compound (6j) by substituting compound (5j) with compound (5j-2):

The reaction conditions for the substitution are the same as those set forth in [Step A2] of production method A.

[Step J5]

The step of removing the protecting group at position 1 of compound (6j) to give compound (7j):

The reaction conditions for the removal are the same as those set forth in [Step I5] of production method I.

[Step J6]

The step of removing Pro3 of compound (7j) to give compound (8j):

The reaction conditions for the removal of Pro3 are the same as those set forth in [Step A3] of production method A.

Production Method K
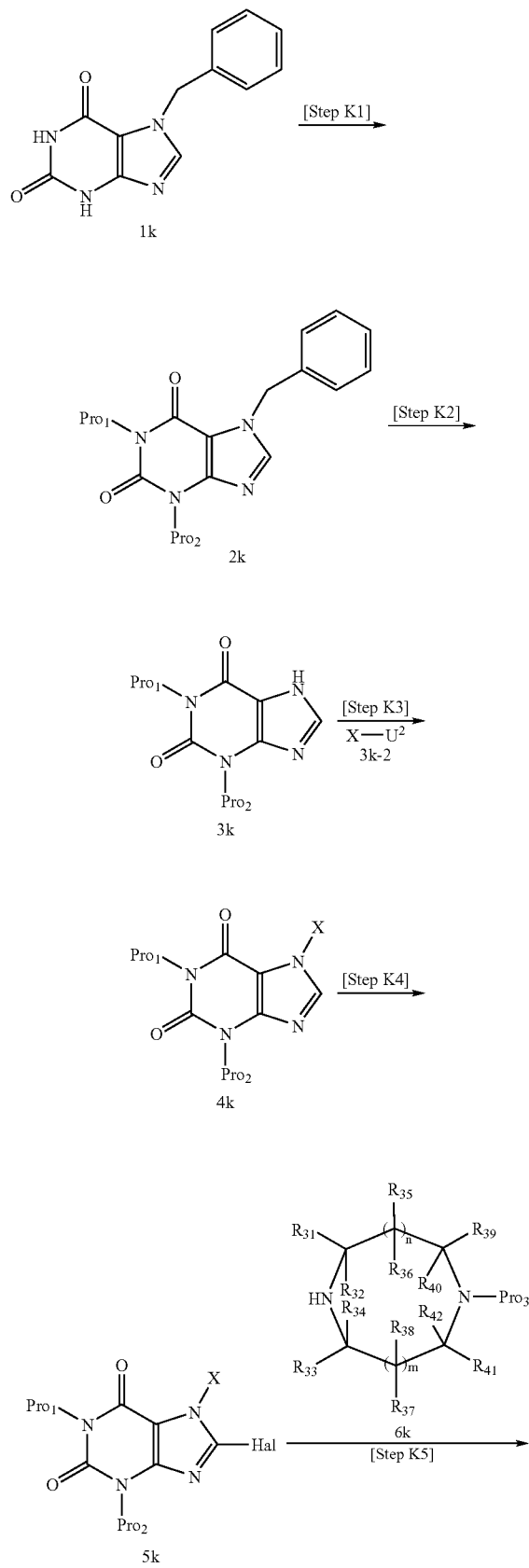
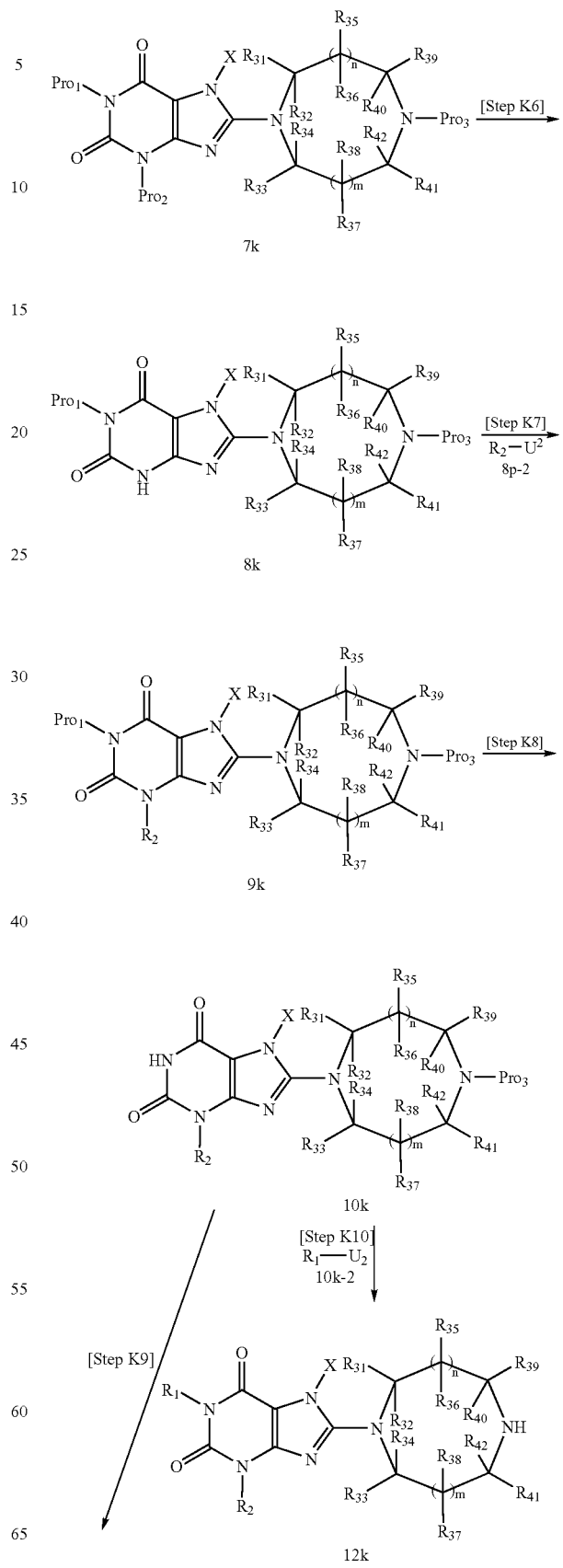

-continued

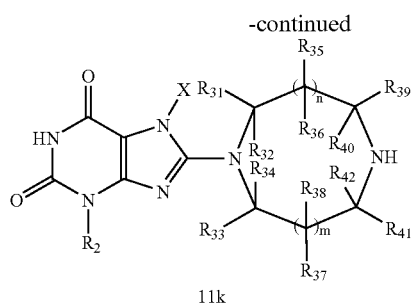

11k

[Step K1]

The step of protecting positions 1 and 3 of compound (1k) to give compound (2k):

The reaction conditions are the same as those set forth in [Step I2] of production method I.

[Step K2]

The step of removing the protecting group at position 7 of compound (2k) to give compound (3k):

The reaction conditions for the removal are the same as those set forth in [Step I3] of production method I.

[Step K3]

The step of introducing a substituent into the —NH group at position 7 of compound (3k) to give compound (4k) by substituting compound (3k) with compound (3k-2):

The reaction conditions for the substitution are the same as those set forth in [Step A2] of production method A.

[Step K4]

The step of reacting compound (4k) with a halogenating agent to give compound (5k):

The reaction conditions for the halogenation are the same as those set forth in [Step B2] of production method B.

[Step K5]

The step of reacting compound (5k) with compound (6k) to give compound (7k):

The reaction conditions are the same as those set forth in [Step A1] of production method A.

[Step K6]

The step of removing the protecting group at position 3 of compound (7k) to give compound (8k):

The reaction conditions for the removal are the same as those set forth in [Step I5] of production method I.

[Step K7]

The step of introducing a substituent into position 3 of compound (8k) to give compound (9k) by substituting compound (8k) with compound (8k-2):

The reaction conditions for the substitution are the same as those set forth in [Step A2] of production method A.

[Step K8]

The step of removing the protecting group at position 1 of compound (9k) to give compound (10k):

The reaction conditions for the removal are the same as those set forth in [Step I5] of production method I.

[Step K9]

The step of removing Pro3 of compound (10k) to give compound (11k):

The reaction conditions for the removal of Pro3 are the same as those set forth in [Step A3] of production method A.

[Step K10]

The step of introducing a substituent into position 1 of compound (10k) by substituting compound (10k) with compound (10k-2) followed by removal of Pro3 to give compound (12k):

The reaction conditions for the substitution are the same as those set forth in [Step A2] of production method A.

The reaction conditions for the removal of Pro3 are the same as those set forth in [Step A3] of production method A.

Production Method L

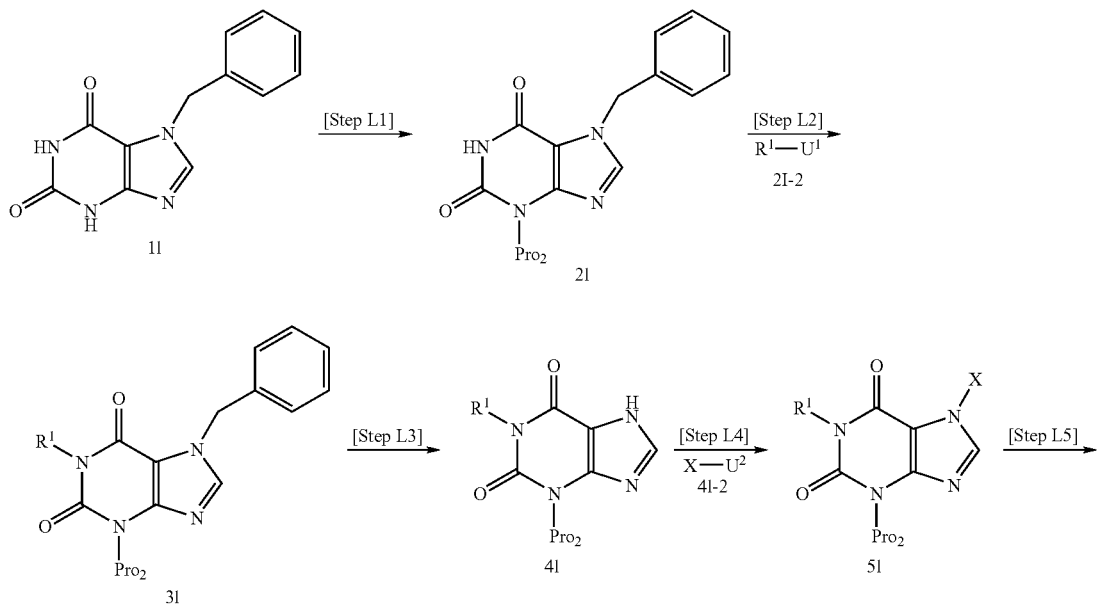

-continued

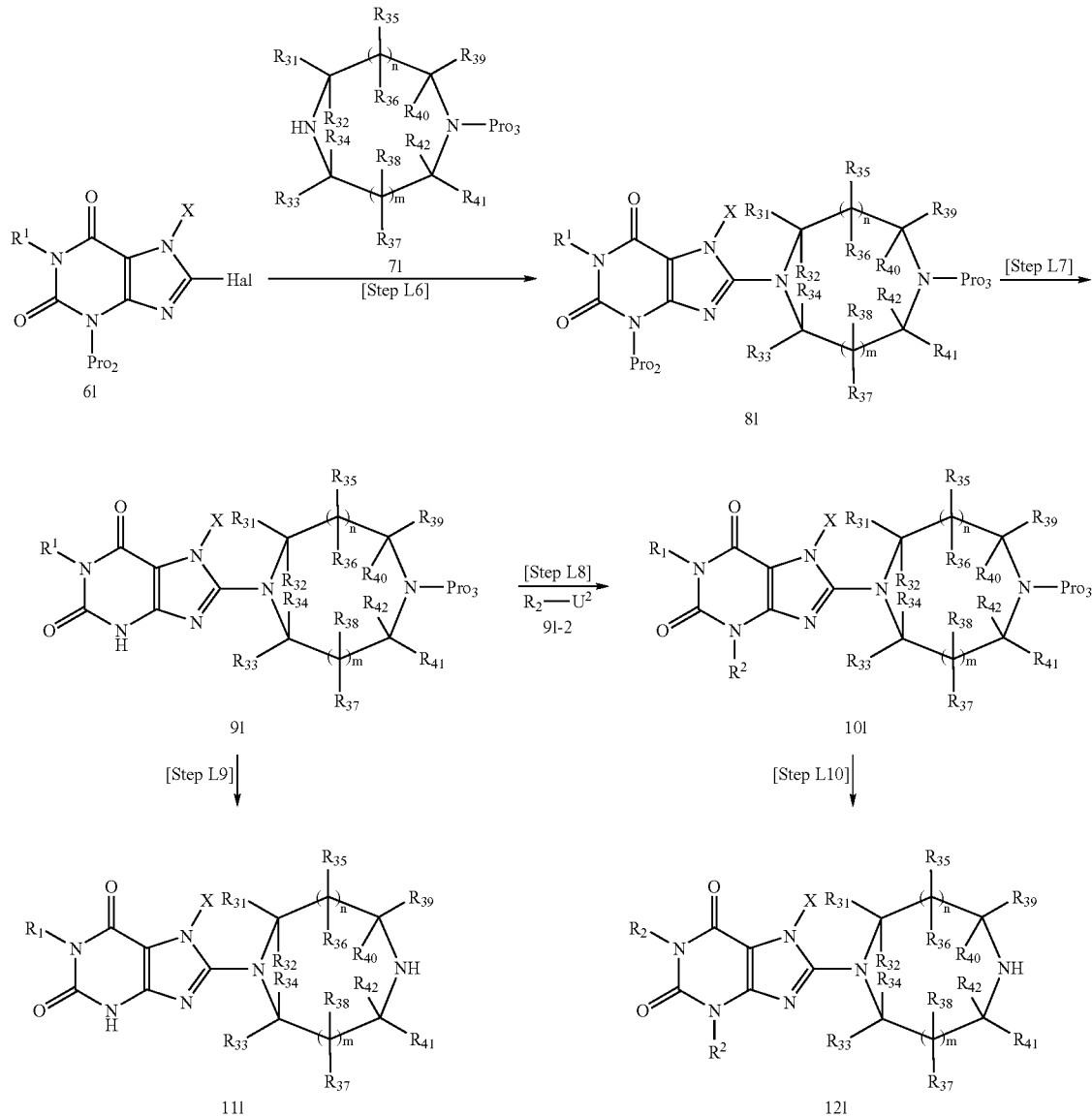

[Step L1]

The step of introducing a protecting group into the —NH group at position 3 of compound (11) [CAS No. 56160-64-6] to give compound (21) by reacting compound (11) with an amino-protecting agent:

Any reagents that are typically used for introducing a protecting group into an amino group may be used as amino-protecting agents. Specifically, for example, chloromethyl pivalate may be used. The reaction conditions may be adjusted to match the amino-protecting agent used. The reaction may be performed under conditions used for introducing protecting groups that are generally employed for the reagent.

The reaction may be performed using a reaction solvent such as acetonitrile, N,N-dimethylformamide, N-methylpyrrolidone, 1,4-dioxane, tetrahydrofuran or dimethoxyethane. The reaction may be performed in the presence or absence of bases such as cesium carbonate, lithium carbonate, sodium carbonate, potassium carbonate or sodium hydride. The reaction temperature may be from 0° C. to 150° C.

[Step L2]

The step of introducing a substituent into the nitrogen at position 1 of compound (21) to give compound (31) by substituting compound (21) with compound (21-2):

The reaction conditions for the substitution are the same as those set forth in [Step C3] of production method C.

[Step L3]

The step of removing the benzyl group in the 7 position of compound (31) to give compound (41):

The reaction conditions generally used for the elimination of a benzyl group may be used. Specifically, for example, the reaction may be performed in a solvent such as methanol, ethanol, propanol, dimethyl sulfoxide, N,N-dimethylformamide, N-methylpyrrolidone, dioxane, tetrahydrofuran, acetic acid or toluene, in the presence of a metal catalyst such as palladium-carbon, platinum oxide and Raney Nickel, under a hydrogen atmosphere at a temperature from 0° C. to 150° C.

[Step L4]

The step of introducing a substituent into the —NH group at position 7 of compound (4l) to give compound (5l) by substituting compound (4l) with compound (4l-2):

The reaction conditions for the substitution are the same as those set forth in [Step A2] of production method A.

[Step L5]

The step of reacting compound (5l) with a halogenating agent to give compound (6l):

The reaction conditions for the halogenation are the same as those set forth in [Step B2] of production method B.

[Step L6]

The step of reacting compound (6l) with compound (7l) to give compound (8l):

The reaction conditions are the same as those set forth in [Step A1] of production method A.

[Step L7]

The step of removing the protecting group at position 3 of compound (8l) to give compound (9l):

The reaction conditions may be adjusted to match the protecting group to be removed. The reaction may be performed under conditions that are generally used for removing the protecting group.

For example, when the protecting group is pivalyloxymethyl, the reaction may be performed by the action of bases such as sodium methoxide, sodium hydride, diazabicycloundec-7-ene in methanol or a mixed solution of methanol and tetrahydrofuran at a temperature from 0° C. to 150° C.

When the protecting group is (trimethylsilyl) ethoxymethyl, the reaction may be performed by the action of a reagent such as tetrabutylammonium fluoride or cesium fluoride, in a solvent such as acetonitrile, N,N-dimethylformamide, N-methylpyrrolidone, 1,4-dioxane, tetrahydrofuran or dimethoxyethane, and at a temperature from 0° C. to 150° C.

[Step L8]

The step of introducing a substituent into position 3 of compound (9l) to give compound (10l) by substituting compound (9l) with compound (9l-2):

The reaction conditions for the substitution are the same as those set forth in [Step A2] of production method A.

[Step L9] and [Step L10]

The step of removing the Pro3 of compounds (9l) and (10l) to give compounds (11l) and (12l):

The reaction conditions for removing Pro3 are the same as those set forth in [Step A3] of production method A.

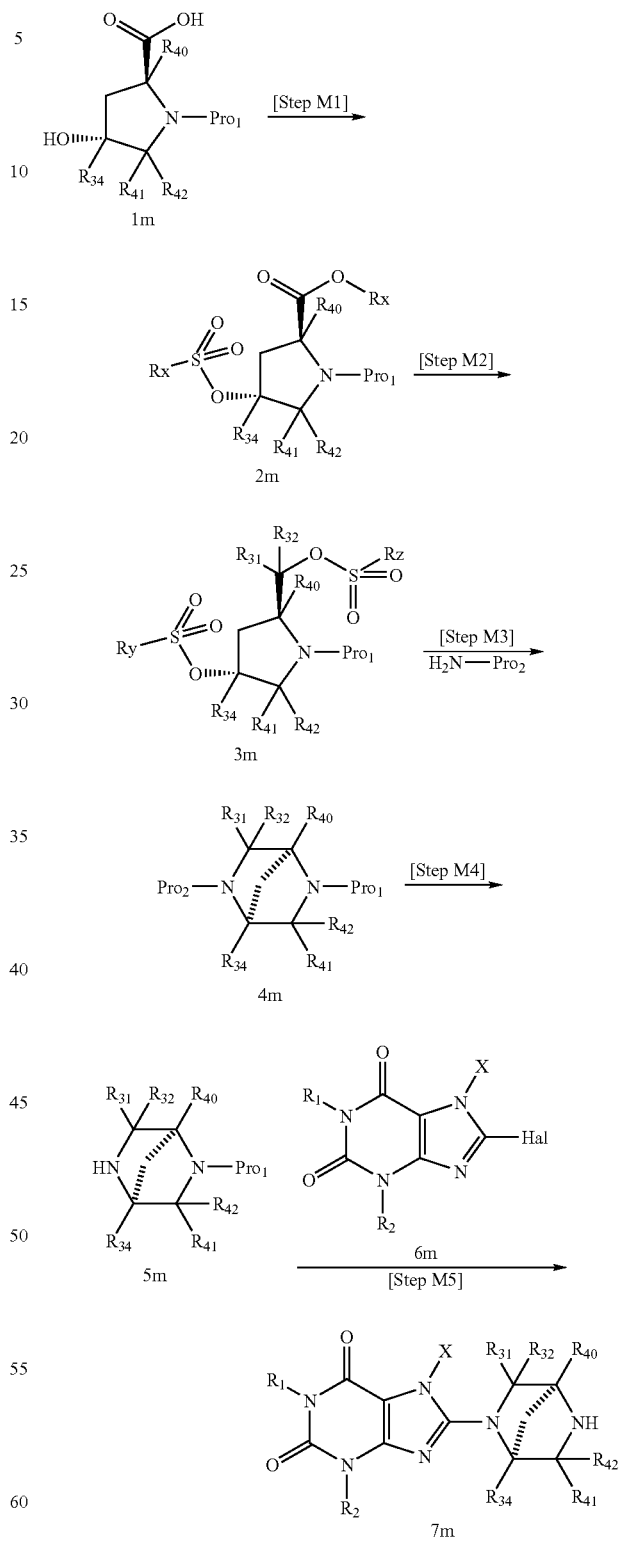

[Step M1]

The step of esterifying and then sulfonylating compound (1m) to give compound (2m):

There is no particular limitation on the conditions for the esterification. For example, the reaction may be performed by reacting an alkyl halide such as iodomethane, iodoethane, iodopropane or benzylbromide; in a solvent such as methanol, ethanol, propanol, dimethyl sulfoxide, N,N-dimethylformamide, N-methylpyrrolidone, dioxane, tetrahydrofuran or toluene; in the presence of a base such as lithium hydroxide, sodium hydroxide, potassium hydroxide, lithium carbonate, sodium carbonate, potassium carbonate, cesium carbonate, lithium hydride, sodium hydride, potassium hydride, butyl lithium, methyl lithium, lithium bis(trimethylsilyl)amide, sodium bis(trimethylsilyl)amide, or potassium bis(trimethylsilyl)amide; and at a temperature from 0° C. to 150° C.

The reaction conditions for the sulfonylation are the same as those set forth in [Step F1] of production method F.

[Step M2]

The step of reducing and then sulfonylating compound (2m) to give compound (3m):

The reaction conditions for the reduction are the same as those set forth in [Step G1] of production method G.

The reaction conditions for the sulfonylation are the same as those set forth in [Step F1] of production method F.

[Step M3]

The step of reacting compound (3m) with an amine to give compound (4m):

There is no particular limitation on the conditions for the reaction. For example, the reaction may be performed by mixing both substrates in a solvent such as N,N-dimethylformamide, N-methylpyrrolidone, methanol, ethanol, 1,4-dioxane, toluene or xylene, or alternatively, without a solvent in the presence of a base such as potassium carbonate, sodium carbonate, lithium carbonate, sodium hydride, lithium hydride or potassium hydride, at a temperature from 0° C. to 150° C.

[Step M4]

The step of removing Pro2 of compound (4m) to give compound (5m):

The conditions for the removal of Pro2 vary with the protection group used. For example, when tert-butoxycarbonyl is used, the removal may be performed using anhydrous hydrogen chloride in a methanol solution, anhydrous hydrogen chloride in an ethanol solution or anhydrous hydrogen chloride in a dioxane solution, trifluoroacetic acid, formic acid, etc. For example, when benzyl is used, the reaction is performed in a solvent such as methanol, ethanol, propanol, dimethylsulfoxide, N,N-dimethylformamide, N-methylpyrrolidone, dioxane, tetrahydrofuran or toluene, in the presence of a metal catalyst such as palladium-carbon, platinum oxide and Raney Nickel, under a hydrogen atmosphere at a temperature from 0° C. to 150° C.

[Step M5]

The step of reacting compound (5m) with compound (6m) and removing Pro1 to give compound (7m):

The reaction conditions for the coupling of compound (5m) with compound (6m) are the same as those set forth in [Step A1] of production method A.

The reaction conditions for the removal of Pro1 are the same as those set forth in [Step A3] of production method A.

The dosages of the pharmaceuticals of the present invention will vary and depend upon severity of symptoms, age, sex, body weight, dosage form, and the type of disease. Typically, 1–1000 mg per day is administered to adults in a single dose or several doses. There is no particular limitation on the dosage form of the pharmaceuticals of the present invention. They may be administered orally or parenterally via any conventional method. For example, they may be formulated into injections (for intravenous, intramuscular, subcutaneous or intraperitoneal injections), oral dosage forms (tablets, granules, powders, or capsules), preparations for percutaneous absorption, eye-drops, nasal drops and suppositories.

Conventional excipients, binding agents, lubricants, coloring agents, flavoring agents, stabilizers, emulsifiers, absorption enhancers and surfactants may be used for the above-mentioned formulations. These agents are combined with ingredients generally used as materials for producing pharmaceuticals and formulated via a conventional method.

To prepare injections, pH adjusters, buffers, suspending agents, solubilizing agents, antioxidants, preservatives, isotonic agents, and such may be added, if necessary, to a compound of the present invention, or a salt, or hydrate, or solvate thereof. Preparation may be conducted using any conventional method. The injections may be formulated into lyophilized products to be dissolved prior to use. The injections may be administered as intravenous, subcutaneous, intramuscular injections, etc.

Buffers and pH adjusters include, but are not limited to, organic or inorganic acids and/or salts thereof, sodium hydroxide, and meglumine. Suspending agents include, but are not limited to, methylcellulose, polysorbate 80, hydroxyethylcellulose, gum arabic, sodium carboxymethylcellulose, and polyoxyethylene sorbitan monolaurate. Solubilizing agents include, but are not limited to, polyoxyethylene hardened castor oil, polysorbate 80, nicotinic acid amide, and polyoxyethylene sorbitan monolaurate. Antioxidants include, but are not limited to, ascorbic acid, α-tocopherol, ethoxyquin, dibutyl hydroxy toluene, and butyl hydroxy anisole. Preservatives include, but are not limited to, paraoxy methylbenzoate, paraoxy ethylbenzoate, and sorbic acid.

Excipients, binding agents, disintegrants, lubricants, coloring agents, flavoring agents, antioxidants, and solubilizing agents etc. may be added, if necessary, to a compound of the present invention, or a salt hydrate or solvate thereof, in order to prepare an oral, solid dosage form. etc. The preparations may be formulated into tablets, coated tablets, granules, powders, and capsules by any conventional method.

Excipients include, but are not limited to, starch, corn starch, dextrin, glucose, lactose, saccharose, sugar alcohol, hardened oil, mannitol, crystalline cellulose, anhydrous silicic acid, calcium silicate, and dicalcium phosphate. Binding agents include, but are not limited to, polyvinylpyrrolidone, ethylcellulose, methylcellulose, gum arabic, hydroxypropylcellulose, hydroxypropyl methylcellulose, sodium carboxymethylcellulose, propylene glycol and sodium polyacrylate. Lubricants include, but are not limited to, magnesium stearate, talc and calcium stearate. Antioxidants include, but are not limited to, ascorbic acid, α-tocopherol, ethoxyquin, dibutyl hydroxy toluene and butyl hydroxy anisole. Furthermore, coloring or flavoring agents may be added. Tablets, granules and powders may be coated, as necessary.

A xanthine derivative exhibiting an excellent DPPIV inhibition effect was provided by the present invention.

Accordingly, a fused imidazole derivative of the present invention is useful as therapeutic/preventive agents, for example, such as a therapeutic agent for diabetes, a therapeutic agent for obesity, a therapeutic agent for hyperlipidemia, a therapeutic agent for AIDS, a therapeutic agent for osteoporosis, a therapeutic agent for gastrointestinal disorders, a therapeutic agent for angiogenesis, a therapeutic agent for sterility, antiphlogistics, an antiallergic agent, an immunomodulator, a hormone regulator, an antirheumatic, and a therapeutic agent for cancers.

In order to confirm the pharmaceutical effect by oral administration, oral effectiveness was confirmed by tests using glucose tolerance improvement action as an index to discover its usefulness as a medicine.

Any patents, patent applications, and publications cited herein are incorporated by reference.

The compounds of the present invention may be produced according to, for example, methods described in following Examples. However, the following Examples are provided only for illustrative purposes, and in any case, the compounds of the present invention are not limited thereto.

EXAMPLE 1

7-Allyl-3-methyl-8-(piperazin-1-yl)-3,7-dihydropurine-2,6-dione a) 8-Chloro-3-methyl-3,7-dihydropurine-2,6-dione

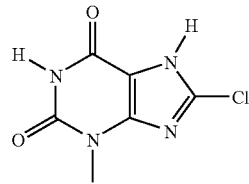

Nitric acid (9 ml) was slowly added dropwise to a suspension of 3-methylxanthine (10 g) in acetic acid (180 ml) at 100° C., and the resulting white suspension was stirred at 100° C. for 30 minutes followed by 140° C. for 20 minutes. After cooling the reaction solution to room temperature, the solvent was removed by distillation at reduced pressure at 60° C. to give a yellow solid. The resulting yellow solid was washed with water, and recrystallization from 0.5 M hydrochloric acid gave a pale yellow solid. A suspension of the solid in concentrated hydrochloric acid (500 ml) was stirred at 110° C. for 15 minutes, then the reaction solution was cooled to room temperature, and the solvent was removed by distillation at reduced pressure to give a yellow-white solid. Recrystallization of the resulting solid from water gave 6.75 g of the title compound.
$^1$H-NMR (d6-DMSO) δ: 3.32 (s, 3H) 11.23 (s, 1H) 14.20 (br s, 1H)

b) 7-Allyl-8-chloro-3-methyl-3,7-dihydropurine-2,6-dione

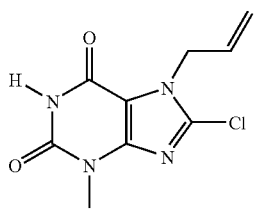

8-Chloro-3-methyl-3,7-dihydropurine-2,6-dione (868 mg) and potassium carbonate (628 mg) were suspended in N,N-dimethylformamide (10 ml), and allyl bromide was added dropwise thereto while cooling on ice. After stirring the reaction mixture at room temperature for 17 hours, the resulting white suspension was diluted with ethyl acetate (30 ml) and water (4 ml), and was filtered to give a white solid. The solid was washed with water and ethyl acetate to give 797 mg of the title compound.
$^1$H-NMR (d6-DMSO) δ: 3.32 (s, 3H) 4.88 (dd, J=3.6, 1.6 Hz, 2H) 4.98 (d, J=17 Hz, 1H) 5.22 (d, J=10.2 Hz, 1H) 5.92–6.03 (m, 1H) 11.31 (s, 1H)

c) 4-(7-Allyl-3-methyl-2,6-dioxo-2,3,6,7-tetrahydro-1H-purin-8-yl)piperazine-1-carboxylic acid tert-butyl ester

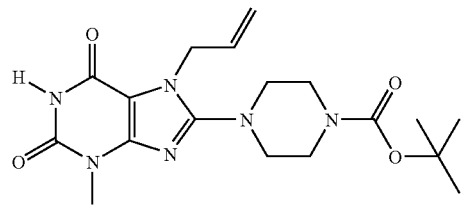

7-Allyl-8-chloro-3-methyl-3,7-dihydropurine-2,6-dione (420 mg) and 1-piperazine carboxylic acid tert-butyl ester (975 mg) were stirred at 150° C. for 50 minutes. After cooling to room temperature, the resulting reaction mixture was purified by silica gel column chromatography to obtain 584 mg of the title compound from a fraction eluted with ethyl acetate.
$^1$H-NMR (CDCl$_3$) δ: 1.48 (s, 9H) 3.23 (t, J=5.0 Hz, 4H) 3.49 (s, 3H) 3.56 (t, J=5.0 Hz, 4H) 4.71–4.73 (m, 2H) 5.12 (d, J=17.2 Hz, 1H) 5.28 (d, J=10.4 Hz, 1H) 6.02–6.12 (m, 1H) 7.88 (br s, 1H)

d) 7-Allyl-3-methyl-8-(piperazin-1-yl)-3,7-dihydropurine-2,6-dione

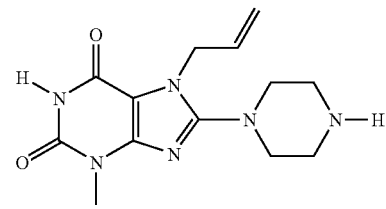

Trifluoroacetic acid (294 μl) was added dropwise to a solution of 4-(7-allyl-3-methyl-2,6-dioxo-2,3,6,7-tetrahydro-1H-purin-8-yl)piperazine-1-carboxylic acid tert-butyl ester (150 mg) in methylene chloride (2 ml), and the reaction mixture was stirred at room temperature for 1 hour and 30 minutes. The solvent was removed by distillation at reduced pressure from the reaction mixture. The residue was subjected to azeotropic distillation with toluene, and then was purified by silica gel column chromatography to give 85 mg of the title compound from a fraction eluted with methanol-ethyl acetate (1:10).

¹H-NMR (CDCl₃) δ: 2.98–3.01 (m, 4H) 3.24–3.26 (m, 4H) 3.49 (s, 3H) 4.69–4.71 (m, 2H) 5.12 (d, J=17.2 Hz, 1H) 5.26 (d, J=10.4 Hz, 1H) 6.01–6.09 (m, 1H)

EXAMPLE 2

3-Methyl-7-(2-pentynyl)-8-(piperazin-1-yl)-3,7-dihydropurine-2,6-dione trifluoroacetate

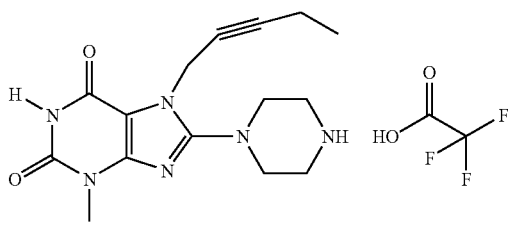

The title compound was obtained using 8-chloro-3-methyl-3,7-dihydropurine-2,6-dione and 1-bromo-2-pentyne, and steps similar to Example 1.
MS m/e (ESI) 317(MH⁺—CF₃COOH)

EXAMPLE 3

8-([1,4]Diazepan-1-yl)-3-methyl-7-(3-methylbut-2-enyl)-3,7-dihydropurine-2,6-dione trifluoroacetate a) 8-Chloro-3-methyl-7-(3-methylbut-2-enyl)-3,7-dihydropurine-2,6-dione

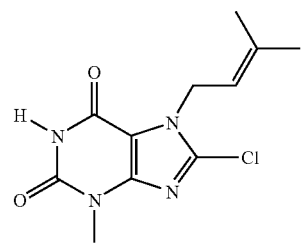

The title compound was obtained using 3-methylxanthine and 4-bromo-2-methyl-2-butene, and steps similar to Example 1.
¹H-NMR (d6-DMSO) δ: 1.70 (s, 3H) 1.79 (s, 3H) 3.30 (s, 3H) 4.87 (d, J=6.8 Hz, 2H) 5.22–5.30 (m, 1H) 11.30 (br s, 1H)

b) 8-([1,4]Diazepan-1-yl)-3-methyl-7-(3-methylbut-2-enyl)-3,7-dihydropurine-2,6-dione trifluoroacetate

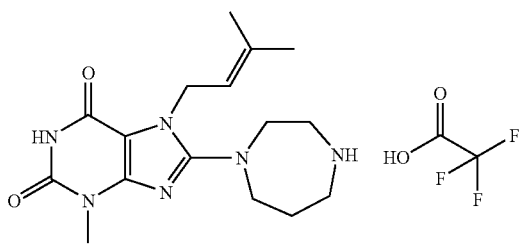

8-Chloro-3-methyl-7-(3-methylbut-2-enyl)-3,7-dihydropurine-2,6-dione (40 mg) and 1-homopiperazine carboxylic acid tert-butyl ester (87 μl) were stirred at 140° C. for 1 hour, then trifluoroacetic acid (0.5 ml) was added thereto, and the reaction mixture was stirred at room temperature for 30 minutes. After removing the solvent by distillation at reduced pressure from the reaction mixture, the residue was purified by HPLC with a reversed phase column using water-acetonitrile-trifluoroacetic acid system as eluent to give 46.8 mg of the title compound.
MS m/e (ESI) 333(MH⁺—CF₃COOH)

EXAMPLE 4

7-(2-Butynyl)-8-([1,4]diazepan-1-yl)-3-methyl-3,7-purine-2,6-dione trifluoroacetate

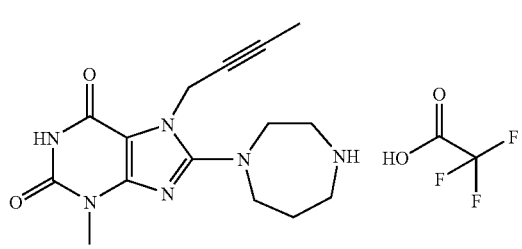

The title compound was obtained using 8-chloro-3-methyl-3,7-dihydropurine-2,6-dione and 1-bromo-2-butyne, and steps similar to Examples 1-b and 3-b.
MS m/e (ESI) 317(MH⁺—CF₃COOH)

EXAMPLE 5

[8-([1,4]diazepan-1-yl)-3-methyl-7-(3-methylbut-2-enyl)-2,6-dioxo-2,3,6,7-tetrahydropurin-1-yl]acetic acid ethyl ester trifluoroacetate

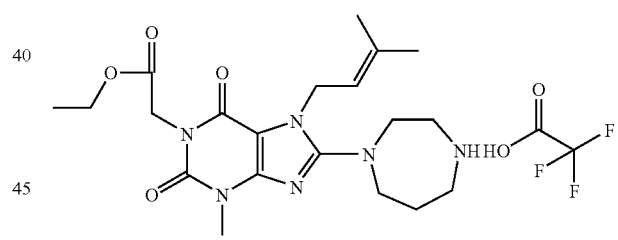

8-Chloro-3-methyl-7-(3-methylbut-2-enyl)-3,7-dihydropurine-2,6-dione (100 mg) and potassium carbonate (103 mg) were suspended in N,N-dimethylformamide (2 ml), ethyl iodoacetate (66 μl) was added thereto, and the mixture was stirred at 120° C. for 2 hours and 30 minutes. The reaction mixture was diluted with ethyl acetate and water, extracted with ethyl acetate, and after washing with water the solvent was removed by distillaion at reduced pressure from the organic layer to give a brown solid. The resulting brown solid (30 mg) and 1-homopiperazine carboxylic acid tert-butyl ester (49 μl) were stirred at 140° C. for 1 hour, then trifluoroacetic acid (0.5 ml) was added thereto, and the reaction mixture was stirred at room temperature for 30 minutes. After removing the solvent by distillation at reduced pressure from the reaction mixture, the residue was purified by HPLC with a reversed phase column using water-acetonitrile-trifluoroacetic acid system as eluent to give 21.2 mg of the title compound.
MS m/e (ESI) 419(MH⁺—CF₃COOH)

EXAMPLE 6

[7-(2-Butynyl)-8-([1,4]diazepan-1-yl)-3-methyl-2,6-dioxo-2,3,6,7-tetrahydropurin-1-yl]acetic acid ethyl ester trifluoroacetate

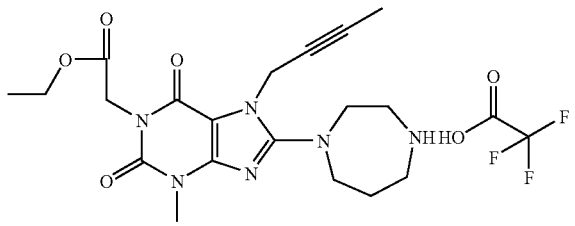

The title compound was obtained using 8-chloro-3-methyl-3,7-dihydropurine-2,6-dione and 1-bromo-2-butyne, and steps similar to Example 1-b followed by steps similar to Example 5.

MS m/e (ESI) 403(MH+—CF3COOH)

EXAMPLE 7

7-Allyl-1,3-dimethyl-8-(piperazin-1-yl)-3,7-dihydropurine-2,6-dione a) 7-Allyl-8-chloro-1,3-dimethyl-3,7-dihydropurine-2,6-dione

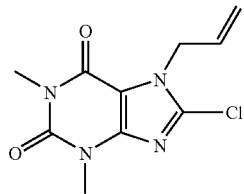

A mixture of 8-chloro-1,3-dimethyl-3,7-dihydropurine-2,6-dione (10.7 g), allyl bromide (5.2 ml), anhydrous potassium carbonate (10.3 g), and N,N-dimethylformamide (75 ml) was stirred at room temperature overnight. The reaction mixture was extracted with ethyl acetate and water, and the organic layer was washed with water and saturated brine, dried over anhydrous magnesium sulfate, and filtered through a small amount of silica gel. The silica gel was washed with ethyl acetate, and the eluate was concentrated under reduced pressure. Recrystallization of the residue from ethyl acetate (50 ml) and hexane (100 ml) gave 10.57 g of the title compound.

$^1$H-NMR (CDCl$_3$) δ: 3.40 (s, 3H) 3.56(s, 3H) 4.97 (d, J=6 Hz, 2H) 5.18 (d, J=17 Hz, 1H) 5.29 (d, J=10 Hz, 1H) 5.96 (ddt, J=10, 17, 6 Hz, 1H)

b) 4-(7-Allyl-1,3-dimethyl-2,6-dioxo-2,3,6,7-tetrahydro-1H-purin-8-yl)piperazine-1-carboxylic acid tert-butyl ester

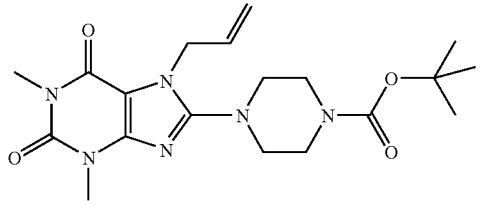

A mixture of 7-allyl-8-chloro-1,3-dimethyl-3,7-dihydropurine-2,6-dione (1.0 g), piperazine-1-carboxylic acid tert-butyl ester (1.1 g), 1,8-diazabicyclo[5,4,0]undec-7-ene (DBU) (0.59 ml), and 1-methylpyrrolidin-2-one (2 ml) were stirred under nitrogen atmosphere in an oil bath at 140° C. for 2 hours. The reaction mixture was extracted with ethyl acetate and water. The organic layer was washed with water followed by saturated brine, dried over anhydrous magnesium sulfate, and concentrated under reduced pressure. The residue was purified by silica gel column chromatography with 10–20% (20% 2-propanol/ethyl acetate)/hexane to give 1.5 g of the title compound.

$^1$H-NMR (CDCl$_3$) δ: 1.48 (s, 9H) 3.22 (t, J=5 Hz, 4H) 3.38 (s, 3H) 3.53 (s, 3H) 3.56 (t, J=5 Hz, 4H) 4.75 (d, J=5 Hz, 2H) 5.11 (d, J=17 Hz, 1H) 5.27 (d, J=10 Hz, 1H) 6.08 (ddt, J=10, 17, 5 Hz, 1H)

c) 7-Allyl-1,3-dimethyl-8-(piperazin-1-yl)-3,7-dihydropurine-2,6-dione

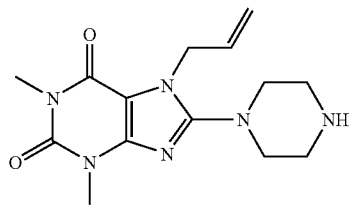

A mixture of 4-(7-allyl-1,3-dimethyl-2,6-dioxo-2,3,6,7-tetrahydro-1H-purin-8-yl)piperazine-1-carboxylic acid tert-butyl ester (1.5 g), trifluoroacetic acid (3 ml), and dichloromethane (10 ml) was stirred at room temperature for 3 hours. The reaction solution was concentrated under reduced pressure. Water (10 ml) and 5 M potassium carbonate aqueous solution (5 ml) were added to the residue, extracted with dichloromethane, then the organic layer was dried over anhydrous magnesium sulfate and concentrated under reduced pressure. The residue was recrystallized from ethyl acetate-hexane to give 750 mg of the title compound.

$^1$H-NMR (CDCl$_3$) δ: 3.00 (t, J=5 Hz, 4H) 3.24 (t, J=5 Hz, 4H) 3.38 (s, 3H) 3.55 (s, 3H) 4.74 (d, J=5 Hz, 2H) 5.11 (d, J=17 Hz, 1H) 5.26 (d, J=10 Hz, 1H) 6.08 (ddt, J=10, 17, 5 Hz, 1H)

EXAMPLE 8

1,3-Dimethyl-8-(piperazin-1-yl)-7-(2-propynyl)-3,7-dihydropurine-2,6-dione

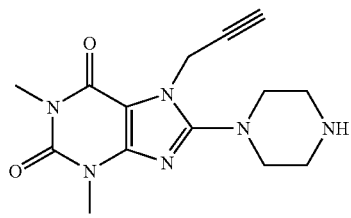

The title compound was synthesized using 3-bromopropyne instead of allyl bromide, and steps similar to Example 7.

$^1$H-NMR (CDCl$_3$) δ: 2.41 (t, J=2 Hz, 1H) 3.04 (t, J=5 Hz, 4H) 3.36 (t, J=5 Hz, 4H) 3.40 (s, 3H) 3.54 (s, 3H) 4.92 (d, J=2 Hz, 2H)

EXAMPLE 9

7-Allyl-8-(3,5-dimethylpiperazin-1-yl)-1,3-dimethyl-3,7-dihydropurine-2,6-dione

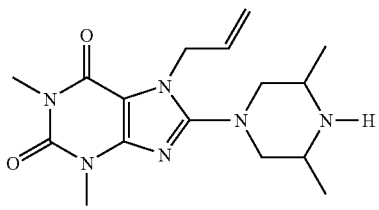

A suspension of 7-allyl-8-chloro-1,3-dimethyl-3,7-dihydropurine-2,6-dione (200 mg), cis-2,6-dimethylpiperazine (107 mg), and 1,8-diazabicyclo[5.4.0]undec-7-ene (128 μl) in 1-methyl-2-pyrrolidone (2 ml) was stirred at 150° C. for 50 minutes. The reaction mixture was diluted with ethyl acetate and water, and extracted with ethyl acetate. The aqueous layer was extracted with chloroform, and the combined organic layer was washed with water and dried over magnesium sulfate. The solvent was removed by distillation at reduced pressure to give brown oil. The oil was purified by silica gel column chromatography, and 111 mg of the title compound was obtained from a fraction eluted with methanol-ethyl acetate (1:10).

$^1$H-NMR (CDCl$_3$) δ: 1.09 (d, J=6.4 Hz, 6H) 2.56–2.61 (m, 2H) 3.02–3.09 (m, 2H) 3.38 (s, 3H) 3.43 (dd, J=12, 1.6 Hz, 2H) 3.54 (s, 3H) 4.71 (dd, J=3.4, 1.8 Hz, 2H) 5.12 (dd, J=17.2, 1.2 Hz, 1H) 5.27 (dd, J=10.4, 0.8 Hz, 1H) 6.04–6.14 (m, 1H)

EXAMPLE 10

7-(2-Butynyl)-1,3-dimethyl-8-(piperazin-1-yl)-3,7-dihydropurine-2,6-dione a) 4-[7-(2-Butynyl)-1,3-dimethyl-2,6-dioxo-2,3,6,7-tetrahydro-1H-purin-8-yl]piperazine-1-carboxylic acid tert-butyl ester

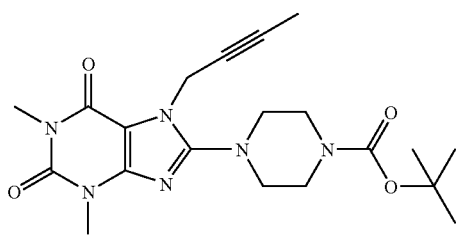

8-Chlorotheophylline (4.9 g) and potassium carbonate (5 g) were dissolved in N,N-dimethylformamide (100 ml), and 1-bromo-2-butyne (2.4 ml) was added thereto. After stirring at room temperature overnight, the reaction mixture was diluted with ethyl acetate, and washed with water. Insoluble white solid was collected through filtration, and washed with ethyl acetate to give 3.8 g of 7-(2-butynyl)-8-chloro-1,3-dimethyl-3,7-dihydropurine-2,6-dione. Then, the resulting 7-(2-butynyl)-8-chloro-1,3-dimethyl-3,7-dihydropurine-2,6-dione (1.8 g) and 1-piperazine carboxylic acid tert-butyl ester (3.7 g) were stirred at 150° C. for 1 hour. After cooling to room temperature, the reaction mixture was extracted with ethyl acetate, the organic layer was washed with water and saturated brine, and dried over an hydrous magnesium sulfate. The solvent was removed by distillation at reduced pressure. The residue was purified by silica gel column chromatography to obtain 1.6 g of the title compound from a fraction eluted with hexane-ethyl acetate (1:4).

$^1$H-NMR (CDCl$_3$) δ: 1.49 (s, 9H) 1.82 (t, J=2.4 Hz, 3H) 3.33–3.36 (m, 4H) 3.40 (s, 3H) 3.52 (s, 3H) 3.58–3.61 (m, 4H) 4.88 (q, J=2.4 Hz, 2H)

b) 7-(2-Butynyl)-1,3-dimethyl-8-(piperazin-1-yl)-3,7-dihydropurine-2,6-dione

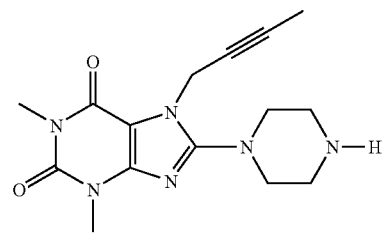

4-[7-(2-Butynyl)-1,3-dimethyl-2,6-dioxo-2,3,6,7-tetrahydro-1H-purin-8-yl]piperazine-1-carboxylic acid tert-butyl ester (2.5 g) was dissolved in trifluoroacetic acid (15 ml), and the solution was stirred at room temperature for 30 minutes. After removing the solvent by distillation at reduced pressure, the residue was purified by column chromatography using NH-silica gel (silica gel, which surface was treated with amino group: NH-DM2035 manufactured by Fuji Silysia Chemical Ltd.) to obtain 1.6 g of the title compound from a fraction eluted with ethyl acetate.

$^1$H-NMR (CDCl$_3$) δ: 1.82 (t, J=2.4 Hz, 3H) 3.13–3.16 (m, 4H) 3.40 (s, 3H) 3.46–3.48 (m, 4H) 3.52 (s, 3H) 4.87 (q, J=2.4 Hz, 2H)

EXAMPLE 11

7-Allyl-8-(2-hydroxymethylpiperazin-1-yl)-1,3-dimethyl-3,7-dihydropurine-2,6-dione trifluoroacetate a) 2-Hydroxymethylpiperazine-1,4-dicarboxylic acid di-tert-butyl ester

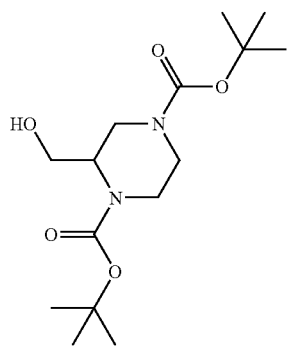

Triethylamine (6.06 g) and isobutyl chloroformate (7.51 g) were added to a solution of piperazine-1,2,4-tricarboxylic acid 1,4-di-tert-butyl ester (16.52 g) in tetrahydrofuran (200 ml) at −10° C., and the mixture was stirred for 3 hours. The reaction solution was filtered, and treated with 20 ml aqueous solution of sodium borohydride (7.72 g) at −10° C. After the mixture was stirred for 1 hour, ethyl acetate (500 ml) and water (200 ml) were added thereto, and excessive sodium borohydride was quenched with 1 N hydrochloric acid. The organic layer was washed with water (200 ml), followed by saturated aqueous solution of sodium chloride, and dried over anhydrous magnesium sulfate. Then, the solvent was removed by distillation at reduced pressure. The residue was purified by silica gel column chromatography to obtain 10.87 g of the title compound from a fraction eluted with hexane-ethyl acetate (1:1).

$^1$H-NMR (CDCl$_3$) δ: 1.46 (s, 9H) 1.47 (s, 9H) 2.70–3.12 (m, 3H) 3.44–3.70 (m, 2H) 3.77–3.90 (m, 1H) 3.91–4.05 (m, 1H) 4.15–4.23 (m, 1H)

b) 3-Hydroxymethylpiperazine-1-carboxylic acid tert-butyl ester

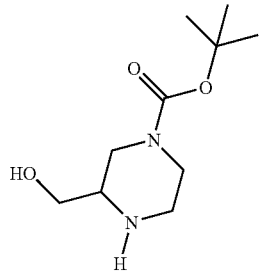

Sodium hydroxide (5.42 g) was added to a solution of 2-hydroxymethylpiperazine-1,4-dicarboxylic acid di-tert-butyl ester (10.87 g) in ethanol (300 ml), and the reaction mixture was heated to reflux for 16 hours. The solvent was removed by distillation at reduced pressure, and the residue was dissolved in ethyl acetate (400 ml) and water (50 ml). After the organic layer was dried over anhydrous magnesium sulfate, the solvent was removed by distillation at reduced pressure to give 8.46 g of the title compound.

$^1$H-NMR (CDCl$_3$) δ: 1.47 (s, 9H) 2.48–3.06 (m, 5H) 3.52 (dd, J=11.3, 8.1 Hz, 1H) 3.68 (dd, J=11.3, 3.2 Hz, 1H) 3.82–4.07 (m, 2H)

c) 4-(7-Allyl-1,3-dimethyl-2,6-dioxo-2,3,6,7-tetrahydro-1H-purin-8-yl)-3-hydroxymethylpiperazine-1-carboxylic acid tert-butyl ester

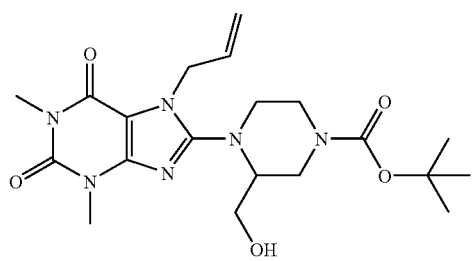

The title compound (0.224 g) was obtained using 3-hydroxymethylpiperazine-1-carboxylic acid tert-butyl ester (2.16 g) and steps similar to Example 1c).

$^1$H-NMR (CDCl$_3$) δ: 1.48 (s, 9H) 2.72–2.89 (m, 1H) 2.84–3.06 (m, 1H) 3.25–3.41 (m, 2H) 3.38 (s, 3H) 3.52 (s, 3H) 3.66–3.74 (m, 1H) 3.83–3.96 (m, 2H) 4.05–4.17 (m, 2H) 4.73 (dd, J=16.2, 5.2 Hz, 1H) 4.84 (dd, J=16.2, 3.2 Hz, 1H) 5.12 (d, J=17.2 Hz, 1H) 5.28 (d, J=11.0 Hz, 1H) 6.06 (dddd, J=17.2, 11.0, 5.2, 3.2 Hz, 1H)

d) 7-Allyl-8-(2-hydroxymethylpiperazin-1-yl)-1,3-dimethyl-3,7-dihydropurine-2,6-dione trifluoroacetate

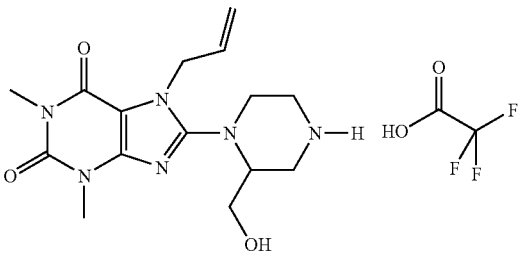

The title compound was obtained using 4-(7-Allyl-1,3-dimethyl-2,6-dioxo-2,3,6,7-tetrahydro-1H-purin-8-yl)-3-hydroxymethylpiperazine-1-carboxylic acid tert-butyl ester and steps similar to Example 1d).

MS m/e (ESI) 335(MH$^+$—CF$_3$COOH)

EXAMPLE 12

7-(2-Cyclopropylidene-ethyl)-1,3-dimethyl-8-(piperazin-1-yl)-3,7-dihydropurine-2,6-dione trifluoroacetate a) 8-Chloro-7-(2-cyclopropylidyne-ethyl)-1,3-dimethyl-3,7-dihydropurine-2,6-dione

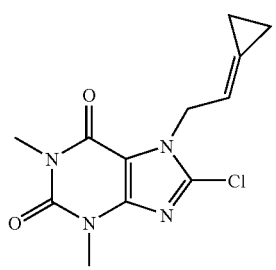

A solution of toluene-4-sulfonic acid 1-vinyl-cyclopropyl ester (0.262 g) in tetrahydrofuran (2.5 ml) was added to a solution of bis(dibenzylideneacetone)palladium (0.0288 g) and bis(diphenylphosphino)ethane (0.0239 g) in tetrahydrofuran (5 ml). Then, 8-chloro-1,3-dimethyl-3,7-dihydropurine-2,6-dione sodium salt (0.467 g) was added, and the reaction mixture was stirred for 24 hours. Ethyl acetate (100 ml) and water (50 ml) were added to the reaction mixture, and was filtered through Celite. The organic layer was dried over anhydrous magnesium sulfate, and the solvent was removed by distillation at reduced pressure. The residue was purified by silica gel column chromatography to obtain 0.079 g of the title compound from a fraction eluted with hexane-ethyl acetate (3:7).

$^1$H-NMR (CDCl$_3$) δ: 0.93–0.99 (m, 2H) 1.06–1.14 (m, 2H) 3.41 (s, 3H) 3.58 (s, 3H) 5.09 (m, 2H) 5.98 (m, 1H)

b) 4-[7-(2-Cyclopropylidene-ethyl)-1,3-dimethyl-2,6-dioxo-2,3,6,7-tetrahydro-1H-purin-8-yl]piperazine-1-carboxylic acid tert-butyl ester

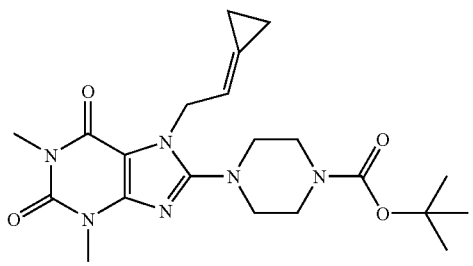

The title compound (0.060 g) was obtained using 8-chloro-7-(2-cyclopropylidene-ethyl)-1,3-dimethyl-3,7-dihydropurine-2,6-dione (0.077 g) and steps similar to Example 1c). This was used in the next reaction without further treatment.

c) 7-(2-Cyclopropylidene-ethyl)-1,3-dimethyl-8-(piperazin-1-yl)-3,7-dihydropurine-2,6-dione trifluoroacetate

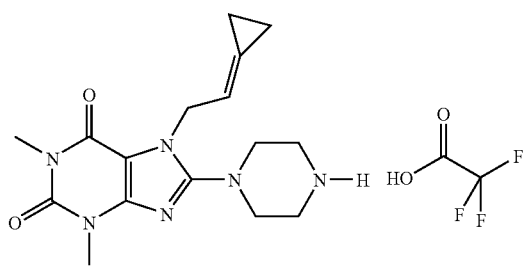

The title compound was obtained using 4-[7-(2-cyclopropylidene-ethyl)-1,3-dimethyl-2,6-dioxo-2,3,6,7-tetrahydro-1H-purin-8-yl]piperazine-1-carboxylic acid tert-butyl ester and steps similar to Example 1d).
MS m/e (ESI) 331(MH+—CF₃COOH)

EXAMPLE 13

1,3-Dimethyl-8-(piperazin-1-yl)-7-(prop-1,2-dienyl)-3,7-dihydropurine-2,6-dione trifluoroacetate a) 4-[1,3-Dimethyl-2,6-dioxo-7-(prop-1,2-dienyl)-2,3,6,7-tetrahydro-1H-purin-8-yl]piperazine-1-carboxylic acid tert-butyl ester

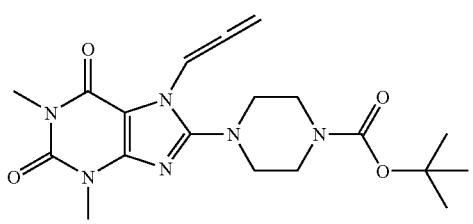

Tert-butanol (0.1 ml) and potassium tert-butoxide (0.015 g) were added to a solution of 4-[1,3-dimethyl-2,6-dioxo-7-(2-propynyl)-2,3,6,7-tetrahydro-1H-purin-8-yl]piperazine-1-carboxylic acid tert-butyl ester (0.402 g) in dimethyl sulfoxide (5 ml), and the reaction mixture was stirred at room temperature for 16 hours. Saturated aqueous solution of ammonium chloride (5 ml) was added, and the reaction solution was poured into ethyl acetate (50 ml) and water (30 ml). The organic layer was washed with 10% aqueous solution of acetic acid (50 ml), saturated aqueous solution of sodium bicarbonate (50 ml), and saturated aqueous solution of sodium chloride (50 ml) in order, and dried over anhydrous magnesium sulfate. The solvent was removed by distillation at reduced pressure. The residue was purified by silica gel column chromatography to obtain 0.176 g of the title compound from a fraction eluted with hexane-ethyl acetate (3:7).
¹H-NMR (CDCl₃) δ: 1.49 (s, 9H) 3.32–3.35 (m, 4H) 3.39 (s, 3H) 3.54 (s, 3H) 3.35–3.39 (m, 4H) 5.49 (d, J=6.1 Hz, 2H) 7.45 (t, J=6.1 Hz, 1H)

b) 1,3-Dimethyl-8-(piperazin-1-yl)-7-(prop-1,2-dienyl)-3,7-dihydropurine-2,6-dione trifluoroacetate

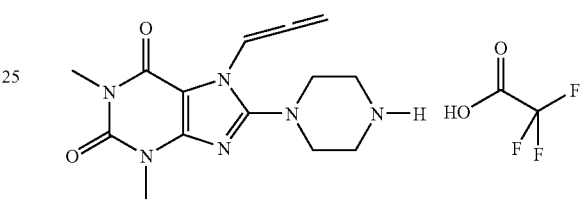

The title compound was obtained using 4-[1,3-dimethyl-2,6-dioxo-7-(prop-1,2-dienyl)-2,3,6,7-tetrahydro-1H-purin-8-yl]piperazine-1-carboxylic acid tert-butyl ester and steps similar to Example 1d).
¹H-NMR (CD₃OD) δ: 3.32 (s, 3H) 3.37–3.40 (m, 4H) 3.50 (s, 3H) 3.62–3.65 (m, 4H) 5.63 (d, J=6.8 Hz, 2H) 7.46 (t, J=6.8 Hz, 1H)

EXAMPLE 14

7-(2-Butynyl)-3-methyl-8-(piperazin-1-yl)-3,7-dihydropurine-2,6-dione a) 4-[7-(2-Butynyl)-3-methyl-2,6-dioxo-2,3,6,7-tetrahydro-1H-purin-8-yl]piperazine-1-carboxylic acid tert-butyl ester

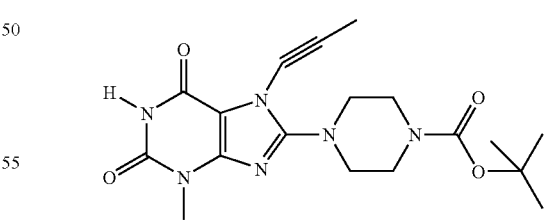

3-Methylxanthine (1.1 g) was dissolved in N,N-dimethylformamide (15 ml), and potassium carbonate (1.0 g) and 1-bromo-2-butyne (0.64 ml) were added thereto. After stirring at room temperature overnight, the reaction mixture was diluted with ethyl acetate, and washed with water. Insoluble white solid was collected by filtration, and washed with ethyl acetate to give 1.3 g of 7-(2-butynyl)-3-methyl-3,7-dihydropurine-2,6-dione. Then, the resulting 7-(2-butynyl)-3-methyl-3,7-dihydropurine-2,6-dione (1.3 g) was dissolved in N,N-dimethylformamide (15 ml), and N-chlorosuccinimide (0.89 g) was added while cooling on ice. After stirring at room temperature for 3 hours, the reaction mixture was diluted with ethyl acetate, and washed with water. Insoluble white solid was collected by filtration, and washed with ethyl acetate to give 1.1 g of 7-(2-butynyl)-8-chloro-3-methyl-3,7-dihydropurine-2,6-dione. The resulting 7-(2-butynyl)-8-chloro-3-methyl-3,7-dihydropurine-2,6-dione (1.4 g) and 1-piperazine carboxylic acid tert-butyl ester (2.8 g) were stirred at 150° C. for 1 hour. After cooling to room temperature, the reaction mixture was extracted with ethyl acetate, then the organic layer was washed with water and saturate brine, and was dried over anhydrous magnesium sulfate. The solvent was removed by distillation at reduced pressure. The residue was purified by silica gel column chromatography to obtain 1.1 g of the title compound from a fraction eluted with hexane-ethyl acetate (1:4).

$^1$H-NMR (CDCl$_3$) δ: 1.49 (s, 9H) 1.82 (t, J=2.4 Hz, 3H) 3.35–3.37 (m, 4H) 3.47 (s, 3H) 3.58–3.61 (m, 4H) 4.85 (q, J=2.4 Hz, 2H) 7.73 (s, 1H)

b) 7-(2-Butynyl)-3-methyl-8-(piperazin-1-yl)-3,7-dihydropurine-2,6-dione

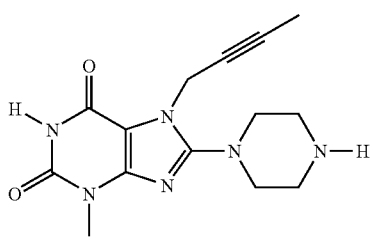

The title compound was obtained using 4-[7-(2-butynyl)-3-methyl-2,6-dioxo-2,3,6,7-tetrahydro-1H-purin-8-yl]piperazine-1-carboxylic acid tert-butyl ester and steps similar to Example 10-b).

$^1$H-NMR(CDCl$_3$) δ: 1.82 (t, J=2.4 Hz, 3H) 3.02–3.05 (m, 4H) 3.37–3.39 (m, 4H) 3.48 (s, 3H) 4.85 (q, J=2.4 Hz, 2H)

EXAMPLE 15

[7-(2-Butynyl)-3-methyl-2,6-dioxo-8-(piperazin-1-yl)-2,3,6,7-tetrahydropurin-1-yl]acetic acid methyl ester trifluoroacetate

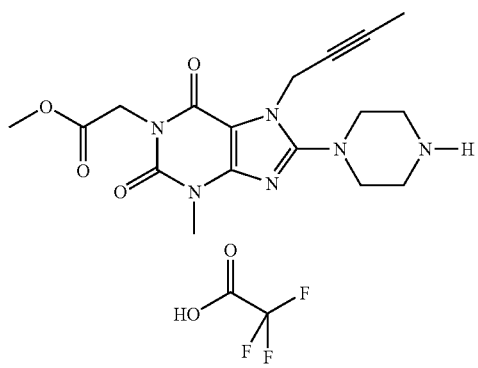

4-[7-(2-Butynyl)-3-methyl-2,6-dioxo-2,3,6,7-tetrahydro-1H-purin-8-yl]piperazine-1-carboxylic acid tert-butyl ester (15 mg) and potassium carbonate (7 mg) were dissolved in N,N-dimethylformamide (1 ml), and methyl bromoacetate (10 μl) was added thereto. The reaction mixture was stirred at room temperature overnight, then diluted with ethyl acetate, and washed with water. After removing the solvent by distillation, the residue was dissolved in trifluoroacetic acid (0.5 ml), and the reaction mixture was stirred for 30 minutes at room temperature. Then, the solvent was removed by distillation, and a half of the residue was purified by HPLC with a reversed phase column using water-acetonitrile-trifluoroacetic acid system as eluent to give 6.9 mg of the title compound.

MS m/e (ESI) 375(MH$^+$—CF$_3$COOH)

EXAMPLE 16

[7-(2-Butynyl)-3-methyl-2,6-dioxo-8-(piperazin-1-yl)-2,3,6,7-tetrahydropurin-1-yl]acetic acid ethyl ester trifluoroacetate

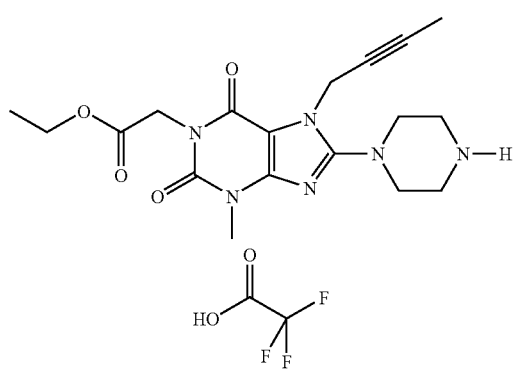

The title compound was obtained using ethyl bromoacetate and steps similar to Example 15.

MS m/e (ESI) 389(MH$^+$—CF$_3$COOH)

EXAMPLE 17

7-(2-Butynyl)-1-(2-methoxyethyl)-3-methyl-8-(piperazin-1-yl)-3,7-dihydropurine-2,6-dione trifluoroacetate

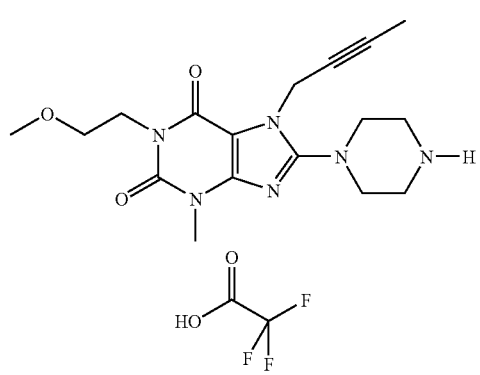

The title compound was obtained using 2-bromoethyl methyl ether and steps similar to Example 15.

MS m/e (ESI) 361(MH$^+$—CF$_3$COOH)

EXAMPLE 18

7-(2-Butynyl)-1-(2-ethoxyethyl)-3-methyl-8-(piperazin-1-yl)-3,7-dihydropurine-2,6-dione trifluoroacetate

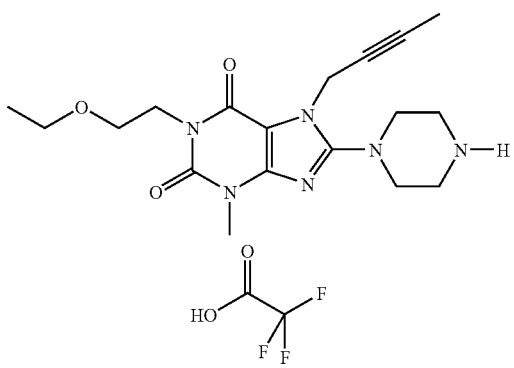

The title compound was obtained using 2-bromoethyl ethyl ether and steps similar to Example 15.

MS m/e (ESI) 375(MH$^+$—CF$_3$COOH)

EXAMPLE 19

7-(2-Butynyl)-3-methyl-8-(piperazin-1-yl)-1-(2-propynyl)-3,7-dihydropurine-2,6-dione trifluoroacetate

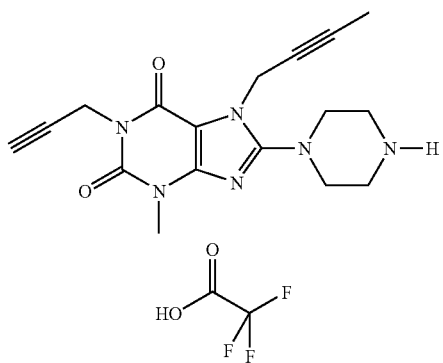

The title compound was obtained using propargyl bromide and steps similar to Example 15.

MS m/e (ESI) 341(MH$^+$—CF$_3$COOH)

EXAMPLE 20

1,7-Bis(2-butynyl)-3-methyl-8-(piperazin-1-yl)-3,7-dihydropurine-2,6-dione trifluoroacetate

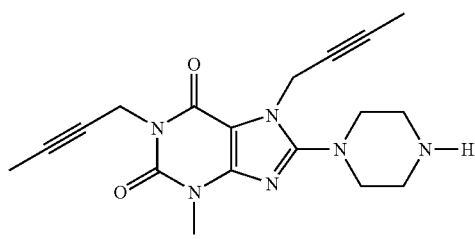

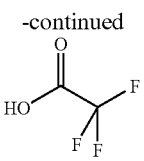

The title compound was obtained using 1-bromo-2-butyne and steps similar to Example 15.

MS m/e (ESI) 355(MH$^+$—CF$_3$COOH)

EXAMPLE 21

[7-(2-Butynyl)-3-methyl-2,6-dioxo-8-(piperazin-1-yl)-2,3,6,7-tetrahydropurin-1-yl]acetonitrile trifluoroacetate

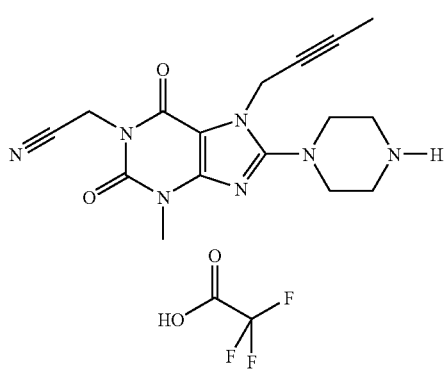

The title compound was obtained using bromoacetonitrile and steps similar to Example 15.

MS m/e (ESI) 342(MH$^+$—CF$_3$COOH)

EXAMPLE 22

7-(2-Butynyl)-1-ethyl-3-methyl-8-(piperazin-1-yl)-3,7-dihydropurine-2,6-dione trifluoroacetate

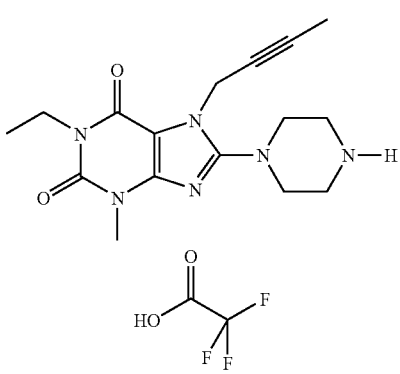

The title compound was obtained using ethyl iodide and steps similar to Example 15.

MS m/e (ESI) 331(MH$^+$—CF$_3$COOH)

EXAMPLE 23

7-(2-Butynyl)-1-isopropyl-3-methyl-8-(piperazin-1-yl)-3,7-dihydropurine-2,6-dione trifluoroacetate

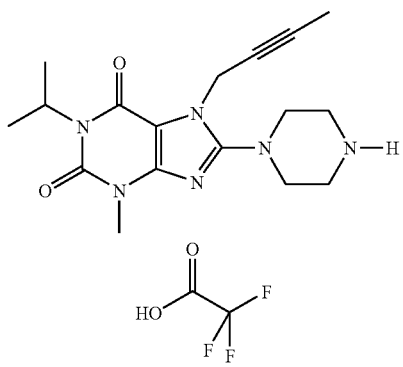

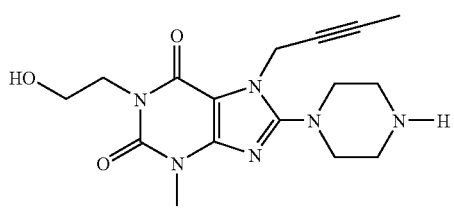

The title compound was obtained using isopropyl iodide and steps similar to Example 15.

MS m/e (ESI) 345(MH⁺—CF₃COOH)

EXAMPLE 24

4-[7-(2-Butynyl)-3-methyl-2,6-dioxo-8-(piperazin-1-yl)-2,3,6,7-tetrahydropurin-1-yl]butyric acid ethyl ester trifluoroacetate

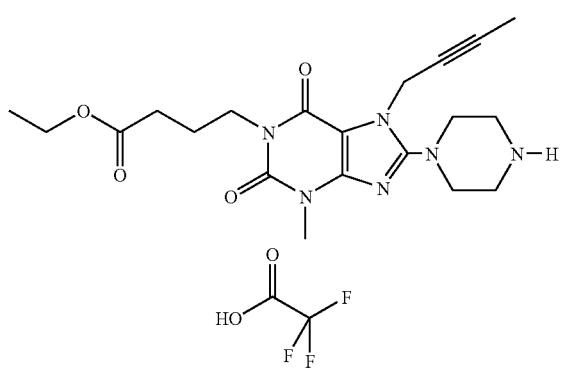

The title compound was obtained using ethyl 4-bromobutanoate and steps similar to Example 15.

MS m/e (ESI) 417(MH⁺—CF₃COOH)

EXAMPLE 25

7-(2-Butynyl)-1-(2-hydroxyethyl)-3-methyl-8-(piperazin-1-yl)-3,7-dihydropurine-2,6-dione trifluoroacetate

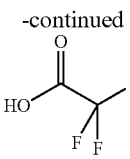

The title compound was obtained using 2-(2-bromoethoxy)tetrahydro-2H-pyran and steps similar to Example 15.

MS m/e (ESI) 347 (MH⁺—CF₃COOH)

EXAMPLE 26

1-Benzyl-7-(2-butynyl)-3-methyl-8-(piperazin-1-yl)-3,7-dihydropurine-2,6-dione trifluoroacetate

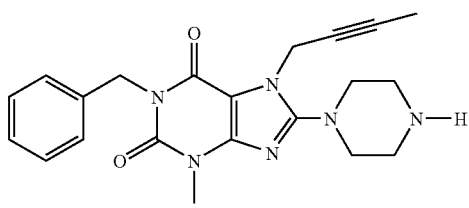

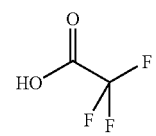

The title compound was obtained using benzyl bromide and steps similar to Example 15.

MS m/e (ESI) 393(MH⁺—CF₃COOH)

EXAMPLE 27

7-(2-Butynyl)-1-(4-chlorobenzyl)-3-methyl-8-(piperazin-1-yl)-3,7-dihydropurine-2,6-dione trifluoroacetate

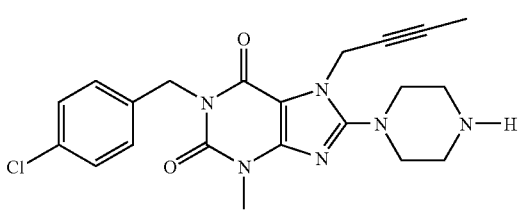

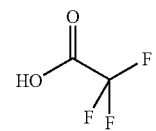

The title compound was obtained using 4-chlorobenzyl bromide and steps similar to Example 15.

MS m/e (ESI) 427(MH⁺—CF₃COOH)

EXAMPLE 28

7-(2-Butynyl)-1-(3-chlorobenzyl)-3-methyl-8-(piperazin-1-yl)-3,7-dihydropurine-2,6-dione trifluoroacetate

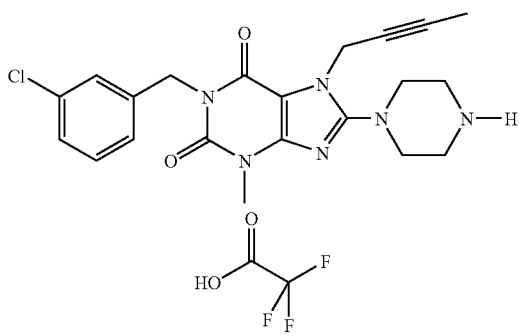

The title compound was obtained using 3-chlorobenzyl bromide and steps similar to Example 15.
MS m/e (ESI) 427(MH+—CF₃COOH)

EXAMPLE 29

7-(2-Butynyl)-1-(2-chlorobenzyl)-3-methyl-8-(piperazin-1-yl)-3,7-dihydropurine-2,6-dione trifluoroacetate

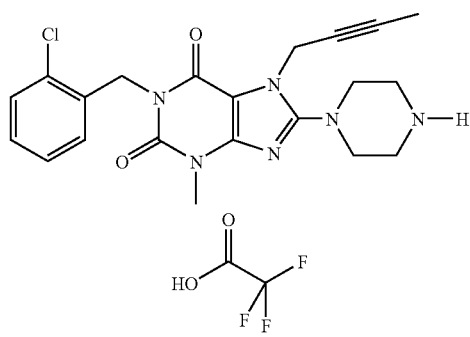

The title compound was obtained using 2-chlorobenzyl bromide and steps similar to Example 15.
MS m/e (ESI) 427(MH+—CF₃COOH)

EXAMPLE 30

7-(2-Butynyl)-3-methyl-1-(2-oxo-2-phenylethyl)-8-(piperazin-1-yl)-3,7-dihydropurine-2,6-dione trifluoroacetate

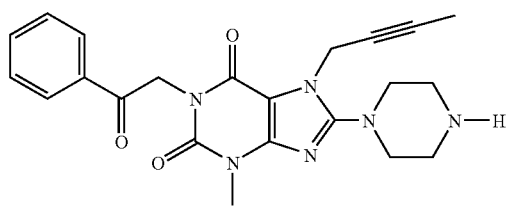

-continued

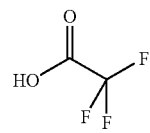

The title compound was obtained using 2-bromoacetophenone and steps similar to Example 15.
MS m/e (ESI) 421(MH+—CF₃COOH)

EXAMPLE 31

7-(2-Butynyl)-1-[2-(4-chlorophenyl)-2-oxoethyl]-3-methyl-8-(piperazin-1-yl)-3,7-dihydropurine-2,6-dione trifluoroacetate

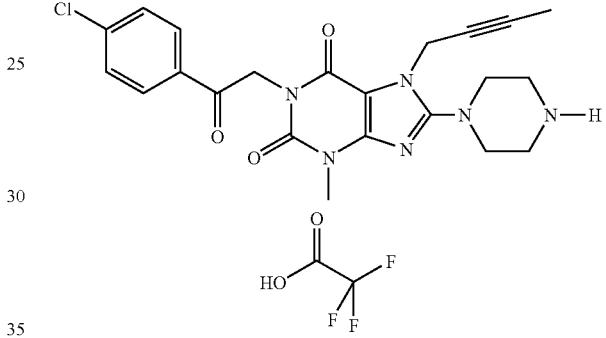

The title compound was obtained using 2-bromo-4'-chloroacetophenone and steps similar to Example 15.
MS m/e (ESI) 455(MH+—CF₃COOH)

EXAMPLE 32

7-(2-Butynyl)-3-methyl-1-(2-oxopropyl)-8-(piperazin-1-yl)-3,7-dihydropurine-2,6-dione trifluoroacetate

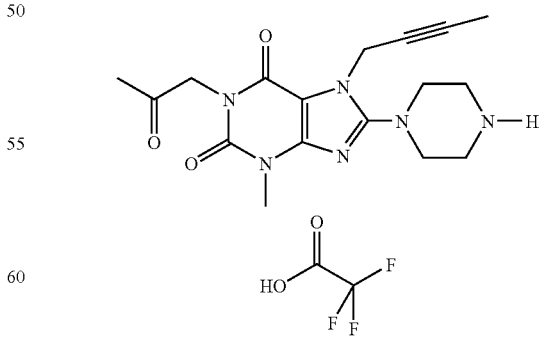

The title compound was obtained using bromoacetone and steps similar to Example 15.
MS m/e (ESI) 359(MH+—CF₃COOH)

EXAMPLE 33

1-(2-Benzyloxyethyl)-7-(2-butynyl)-3-methyl-8-(piperazin-1-yl)-3,7-dihydropurine-2,6-dione trifluoroacetate

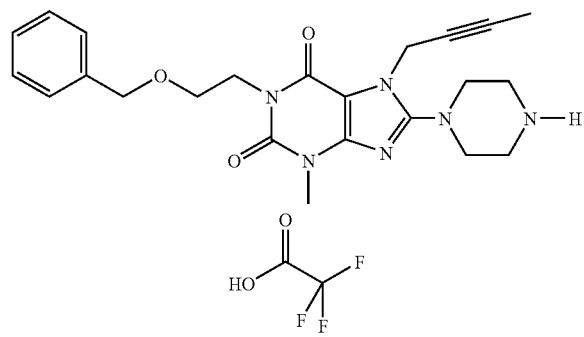

The title compound was obtained using benzyl 2-bromoethyl ether and steps similar to Example 15.
MS m/e (ESI) 437(MH$^+$—CF$_3$COOH)

EXAMPLE 34

7-(2-Butynyl)-3-methyl-1-(2-phenoxyethyl)-8-(piperazin-1-yl)-3,7-dihydropurine-2,6-dione trifluoroacetate

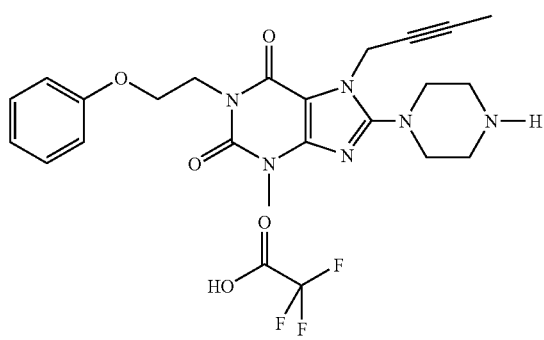

The title compound was obtained using 2-phenoxyethyl bromide and steps similar to Example 15.
MS m/e (ESI) 423(MH$^+$—CF$_3$COOH)

EXAMPLE 35

7-(2-Butynyl)-3-methyl-1-(1-phenylethyl)-8-(piperazin-1-yl)-3,7-dihydropurine-2,6-dione trifluoroacetate

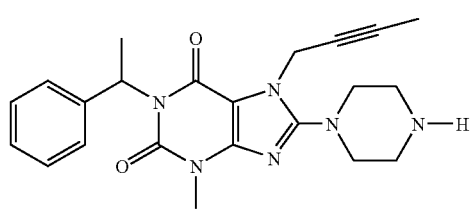

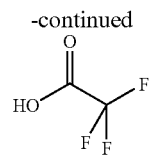

The title compound was obtained using (1-bromoethyl)benzene and steps similar to Example 15.
MS m/e (ESI) 407(MH$^+$—CF$_3$COOH)

EXAMPLE 36

7-(2-Butynyl)-3-methyl-1-(2-oxobutyl)-8-(piperazin-1-yl)-3,7-dihydropurine-2,6-dione trifluoroacetate

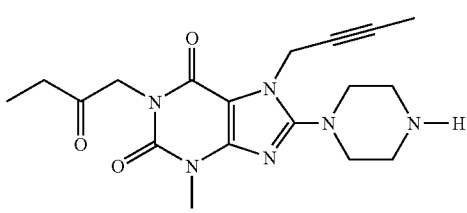

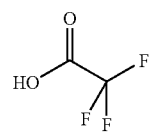

The title compound was obtained using 1-bromo-2-butanone and steps similar to Example 15.
MS m/e (ESI) 373(MH$^+$—CF$_3$COOH)

EXAMPLE 37

4-[7-(2-Butynyl)-3-methyl-2,6-dioxo-8-(piperazin-1-yl)-2,3,6,7-tetrahydropurin-1-ylmethyl]benzonitrile trifluoroacetate

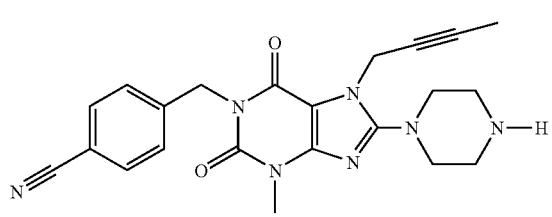

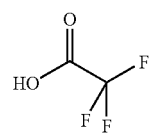

The title compound was obtained using 4-cyanobenzyl bromide and steps similar to Example 15.
MS m/e (ESI) 418(MH$^+$—CF$_3$COOH)

EXAMPLE 38

3-[7-(2-Butynyl)-3-methyl-2,6-dioxo-8-(piperazin-1-yl)-2,3,6,7-tetrahydropurin-1-ylmethyl]benzonitrile trifluoroacetate

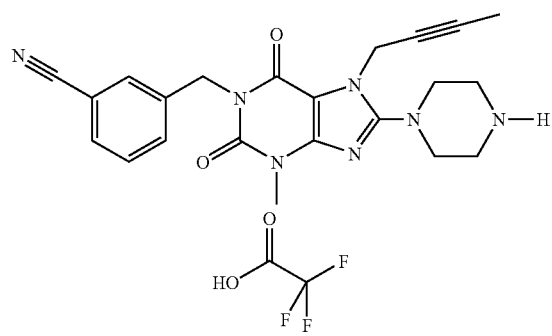

The title compound was obtained using 3-cyanobenzyl bromide and steps similar to Example 15.
MS m/e (ESI) 418(MH$^+$—CF$_3$COOH)

EXAMPLE 39

2-[7-(2-Butynyl)-3-methyl-2,6-dioxo-8-(piperazin-1-yl)-2,3,6,7-tetrahydropurin-1-ylmethyl]-benzonitrile trifluoroacetate

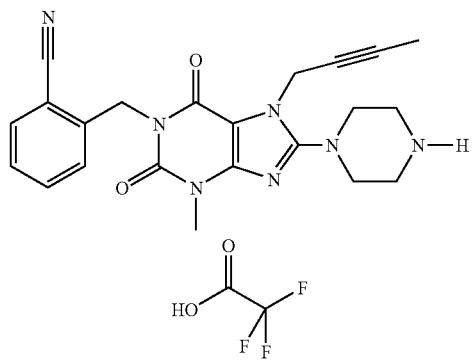

The title compound was obtained using 2-cyanobenzyl bromide and steps similar to Example 15.
MS m/e (ESI) 418(MH$^+$—CF$_3$COOH)

EXAMPLE 40

4-[7-(2-Butynyl)-3-methyl-2,6-dioxo-8-(piperazin-1-yl)-2,3,6,7-tetrahydropurin-1-ylmethyl]benzoic acid methyl ester trifluoroacetate

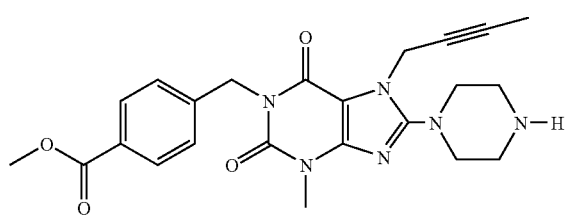

-continued

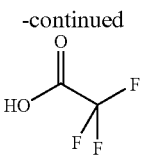

The title compound was obtained using 4-(bromomethyl)benzoic acid methyl ester and steps similar to Example 15.
MS m/e (ESI) 451(MH$^+$—CF$_3$COOH)

EXAMPLE 41

3-[7-(2-Butynyl)-3-methyl-2,6-dioxo-8-(piperazin-1-yl)-2,3,6,7-tetrahydropurin-1-ylmethyl]benzoic acid methyl ester trifluoroacetate

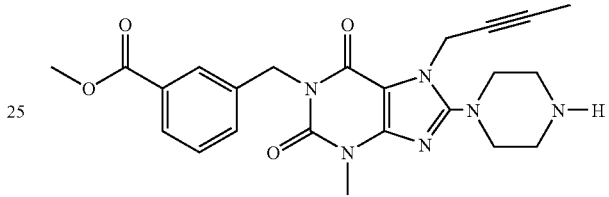

The title compound was obtained using 3-(bromomethyl)benzoic acid methyl ester and steps similar to Example 15.
MS m/e (ESI) 451(MH$^+$—CF$_3$COOH)

EXAMPLE 42

7-(2-Butynyl)-3-methyl-1-(2-phenylethyl)-8-(piperazin-1-yl)-3,7-dihydropurine-2,6-dione trifluoroacetate

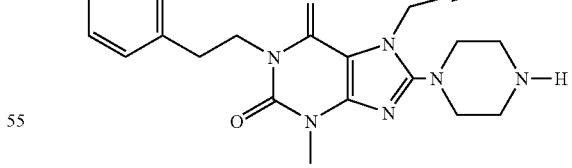

The title compound was obtained using (2-bromoethyl)benzene and steps similar to Example 15.
MS m/e (ESI) 407(MH$^+$—CF$_3$COOH)

EXAMPLE 43

7-(2-Butynyl)-3-methyl-8-(piperazin-1-yl)-1-(pyridin-3-ylmethyl)-3,7-dihydropurine-2,6-dione trifluoroacetate

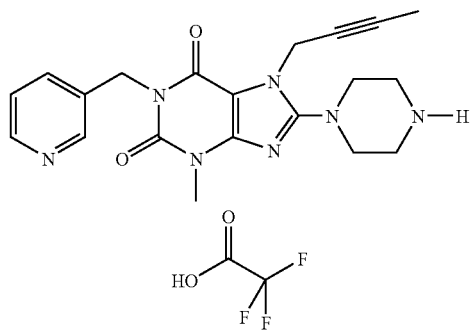

The title compound was obtained using 3-(bromomethyl)pyridine hydrobromide and steps similar to Example 15.
MS m/e (ESI) 394(MH$^+$—CF$_3$COOH)

EXAMPLE 44

7-(2-Butynyl)-3-methyl-8-(piperazin-1-yl)-1-(pyridin-4-ylmethyl)-3,7-dihydropurine-2,6-dione trifluoroacetate

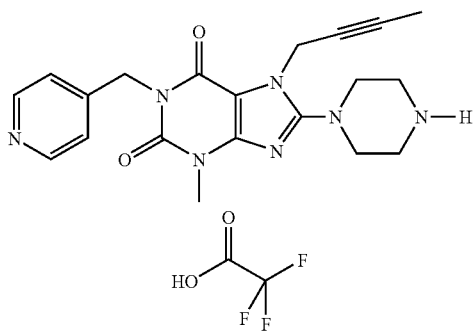

The title compound was obtained using 4-(bromomethyl)pyridine hydrobromide and steps similar to Example 15.
MS m/e (ESI) 394(MH$^+$—CF$_3$COOH)

EXAMPLE 45

2-[7-(2-Butynyl)-3-methyl-2,6-dioxo-8-(piperazin-1-yl)-2,3,6,7-tetrahydropurin-1-yl]ethyl acetate trifluoroacetate a) 4-[7-(2-Butynyl)-1-(2-hydroxyethyl)-3-methyl-2,6-dioxo-2,3,6,7-tetrahydro-1H-purin-8-yl]piperazine-1-carboxylic acid tert-butyl ester

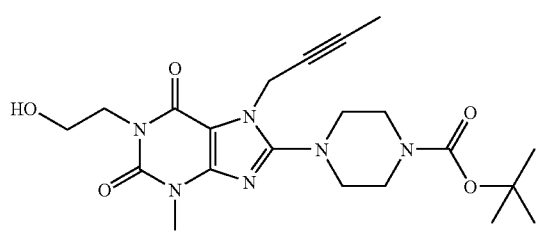

4-[3-Methyl-7-(2-butynyl)-2,6-dioxo-2,3,6,7-tetrahydro-1H-purin-8-yl]piperazine-1-carboxylic acid tert-butyl ester (0.30 g) and potassium carbonate (0.21 g) were dissolved in N,N-dimethylformamide (10 ml), and 2-(2-bromoethoxy)tetrahydro-2H-pyran (0.23 ml) was added thereto. After stirring at room temperature overnight, the reaction mixture was diluted with ethyl acetate, washed with water, and dried over magnesium sulfate. After removing the solvent by distillation, ethanol (10 ml) and pyridinium p-toluenesulfonate (60 mg) were added to the resulting residue, and the reaction mixture was stirred at 60° C. for 3 hours. The reaction solution was distilled. The residue was purified by silica gel column chromatography to obtain 0.14 g of the title compound from a fraction eluted with hexane-ethyl acetate (1:5).

$^1$H-NMR (CDCl$_3$) δ: 1.49 (s, 9H) 1.82 (t, J=2.4 Hz, 3H) 3.34–3.37 (m, 4H) 3.51 (s, 3H) 3.58–3.60 (m, 4H) 3.87 (t, J=7.2 Hz, 2H) 4.28 (t, J=7.2 Hz, 2H) 4.85 (q, J=2.4 Hz, 2H)

b) 2-[7-(2-Butynyl)-3-methyl-2,6-dioxo-8-(piperazin-1-yl)-2,3,6,7-tetrahydropurin-1-yl]-ethyl acetate trifluoroacetate

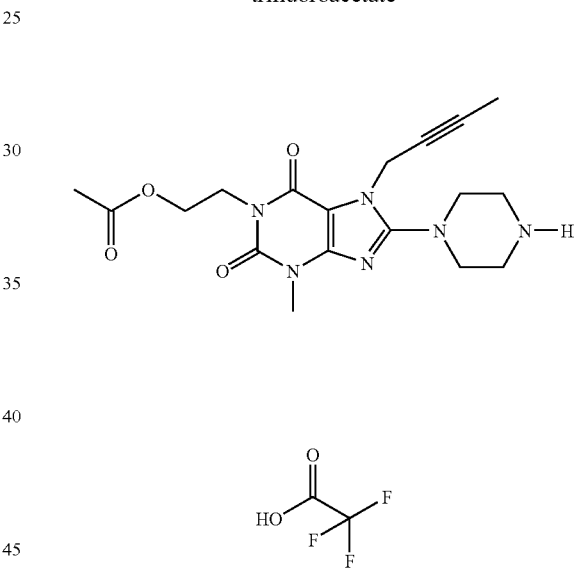

4-[7-(2-Butynyl)-1-(2-hydroxyethyl)-3-methyl-2,6-dioxo-2,3,6,7-tetrahydro-1H-purin-8-yl]piperazine-1-carboxylic acid tert-butyl ester (20 mg) was dissolved in dichloromethane (1 ml), and triethylamine (14 μl), dimethylaminopyridine (5 mg), and acetyl chloride (4 μl) were added thereto while cooling on ice. The reaction mixture was stirred at room temperature for 2 hours, then diluted with ethyl acetate, washed with water, and dried over anhydrous magnesium sulfate. The organic layer was concentrated by distillation. The residue was dissolved in trifluoroacetic acid (0.5 ml), and the reaction mixture was stirred at room temperature for 30 minutes. After removing the solvent by distillation, a half of the residue was purified by HPLC with a reversed phase column using water-acetonitrile-trifluoroacetic acid system as eluent to give 4.9 mg of the title compound.

MS m/e (ESI) 389(MH$^+$—CF$_3$COOH)

EXAMPLE 46

2-[7-(2-Butynyl)-3-methyl-2,6-dioxo-8-(piperazin-1-yl)-2,3,6,7-tetrahydropurin-1-yl]-ethyl benzoate trifluoroacetate

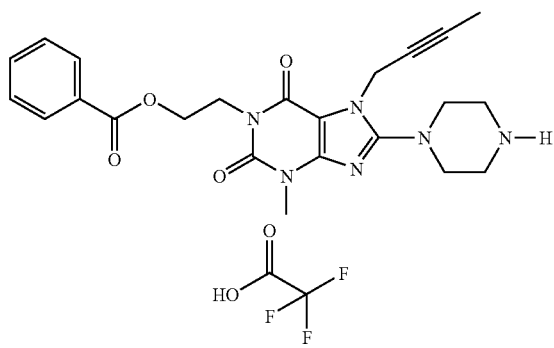

The title compound was obtained using benzoyl chloride and steps similar to Example 45-b).
MS m/e (ESI) 451(MH$^+$—CF$_3$COOH)

EXAMPLE 47

3-Methyl-7-(3-methylbut-2-enyl)-8-(piperazin-1-yl)-3,7-dihydropurine-2,6-dione a) 4-[3-Methyl-7-(3-methylbut-2-enyl)-2,6-dioxo-2,3,6,7-tetrahydro-1H-purin-8-yl]piperazine-1-carboxylic acid tert-butyl ester

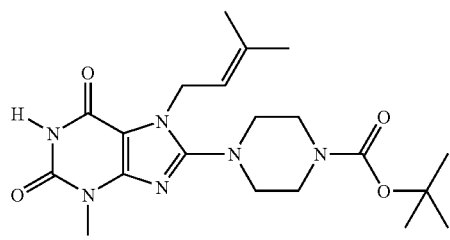

The title compound was obtained using 3-methylxanthine and 1-bromo-3-methyl-2-butene, and steps similar to Example 14-a).
$^1$H-NMR (CDCl$_3$) δ: 1.48 (s, 9H) 1.74 (s, 3H) 1.75 (s, 3H) 3.17–3.20 (m, 4H) 3.47 (s, 3H) 3.56–3.58 (m, 4H) 4.70 (d, J=6.0 Hz, 2H) 5.38 (t, J=6.0 Hz, 1H) 7.71 (s, 1H)

b) 3-Methyl-7-(3-methylbut-2-enyl)-8-(piperazin-1-yl)-3,7-dihydropurine-2,6-dione

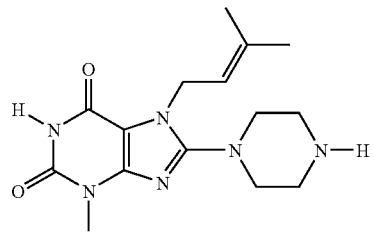

The title compound was obtained using 4-[3-methyl-7-(3-methylbut-2-enyl)-2,6-dioxo-2,3,6,7-tetrahydro-1H-purin-8-yl]piperazine-1-carboxylic acid tert-butyl ester and steps similar to Example 10b).
$^1$H-NMR (CDCl$_3$) δ: 1.67 (s, 3H) 1.68 (s, 3H) 2.94–2.96 (m, 4H) 3.14–3.16 (m, 4H) 3.42 (s, 3H) 4.61 (d, J=6.0 Hz, 2H) 5.33 (t, J=6.0 Hz, 1H)

EXAMPLE 48

1-Ethyl-3-methyl-7-(3-methylbut-2-enyl)-8-(piperazin-1-yl)-3,7-dihydropurine-2,6-dione trifluoroacetate

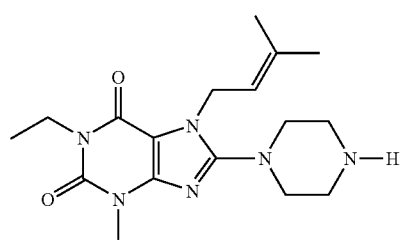

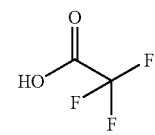

The title compound was obtained using ethyl iodide and steps similar to Example 15.
MS m/e (ESI) 347(MH$^+$—CF$_3$COOH)

EXAMPLE 49

1-Allyl-3-methyl-7-(3-methylbut-2-enyl)-8-(piperazin-1-yl)-3,7-dihydropurine-2,6-dione trifluoroacetate

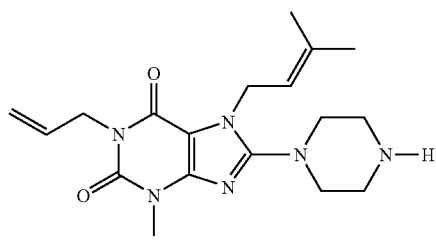

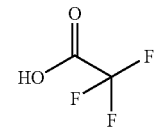

The title compound was obtained using allyl bromide and steps similar to Example 15.
MS m/e (ESI) 359(MH$^+$—CF$_3$COOH)

EXAMPLE 50

1-Benzyl-3-methyl-7-(3-methylbut-2-enyl)-8-(piperazin-1-yl)-3,7-dihydropurine-2,6-dione trifluoroacetate

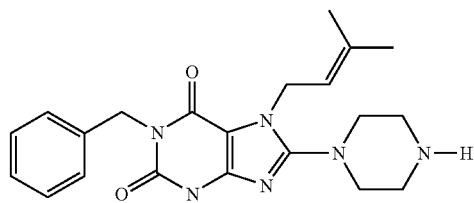

The title compound was obtained using benzyl bromide and steps similar to Example 15.
MS m/e (ESI) 409(MH⁺—CF₃COOH)

EXAMPLE 51

1,3-Dimethyl-7-(3-methylbut-2-enyl)-8-(piperazin-1-yl)-3,7-dihydropurine-2,6-dione trifluoroacetate

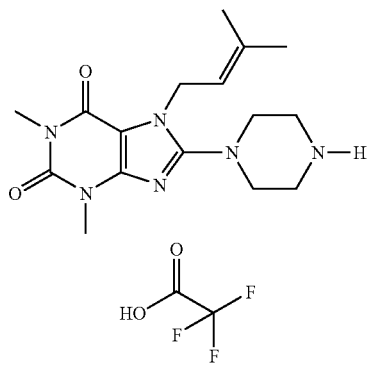

The title compound was obtained using methyl iodide and steps similar to Example 15.
MS m/e (ESI) 333(MH⁺—CF₃COOH)

EXAMPLE 52

3-Methyl-7-(3-methylbut-2-enyl)-8-(piperazin-1-yl)-1-propyl-3,7-dihydropurine-2,6-dione trifluoroacetate

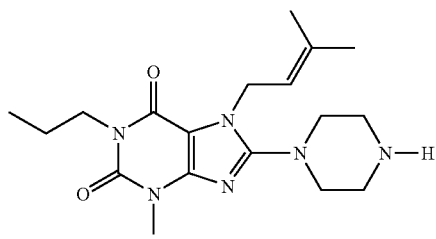

-continued

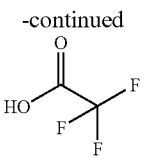

The title compound was obtained using propyl iodide and steps similar to Example 15.
MS m/e (ESI) 361(MH⁺—CF₃COOH)

EXAMPLE 53

3-Methyl-1,7-bis-(3-methylbut-2-enyl)-8-(piperazin-1-yl)-3,7-dihydropurine-2,6-dione trifluoroacetate

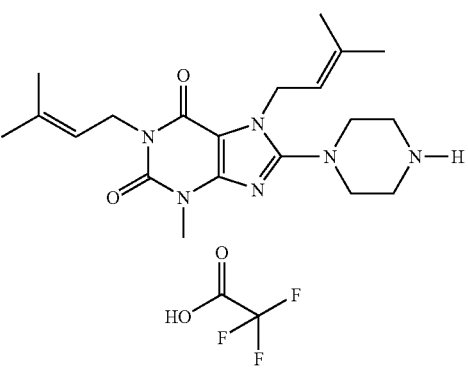

The title compound was obtained using 1-bromo-3-methyl-2-butene and steps similar to Example 15.
MS m/e (ESI) 382(MH⁺—CF₃COOH)

EXAMPLE 54

3-Methyl-7-(3-methylbut-2-enyl)-8-(piperazin-1-yl)-1-(2-propynyl)-3,7-dihydropurine-2,6-dione trifluoroacetate

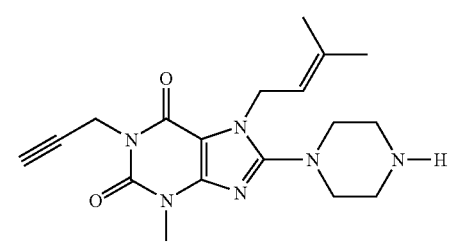

The title compound was obtained using propargyl bromide and steps similar to Example 15.
MS m/e (ESI) 357(MH⁺—CF₃COOH)

EXAMPLE 55

[3-Methyl-7-(3-methylbut-2-enyl)-2,6-dioxo-8-(piperazin-1-yl)-2,3,6,7-tetrahydropurin-1-yl]acetic acid ethyl ester trifluoroacetate

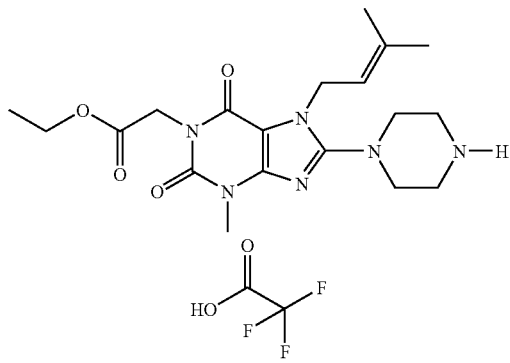

The title compound was obtained using ethyl bromoacetate and steps similar to Example 15.
MS m/e (ESI) 404(MH$^+$—CF$_3$COOH)

EXAMPLE 56

1-(2-Hydroxyethyl)-3-methyl-7-(3-methylbut-2-enyl)-8-(piperazin-1-yl)-3,7-dihydropurine-2,6-dione trifluoroacetate

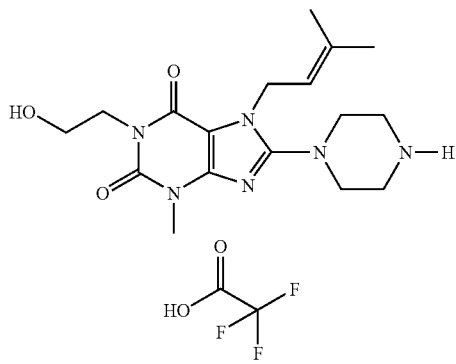

The title compound was obtained using 2-(2-bromoethoxy)tetrahydro-2H-pyran and steps similar to Example 15.
MS m/e (ESI) 363(MH$^+$—CF$_3$COOH)

EXAMPLE 57

3-Methyl-7-(3-methylbut-2-enyl)-1-(2-oxopropyl)-8-(piperazin-1-yl)-3,7-dihydropurine-2,6-dione trifluoroacetate

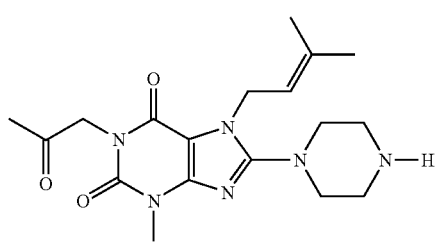

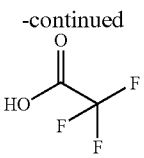

The title compound was obtained using bromoacetone and steps similar to Example 15.
MS m/e (ESI) 375(MH$^+$—CF$_3$COOH)

EXAMPLE 58

2-[3-Methyl-7-(3-methylbut-2-enyl)-2,6-dioxo-8-(piperazin-1-yl)-2,3,6,7-tetrahydropurin-1-yl]acetamide trifluoroacetate

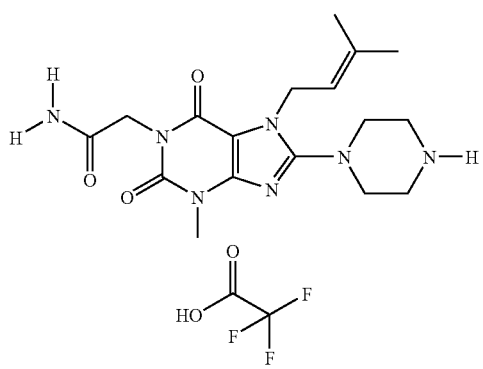

The title compound was obtained using 2-bromoacetamide and steps similar to Example 15.
MS m/e (ESI) 376(MH$^+$—CF$_3$COOH)

EXAMPLE 59

1-(2-Methoxyethyl)-3-methyl-7-(3-methylbut-2-enyl)-8-(piperazin-1-yl)-3,7-dihydropurine-2,6-dione trifluoroacetate

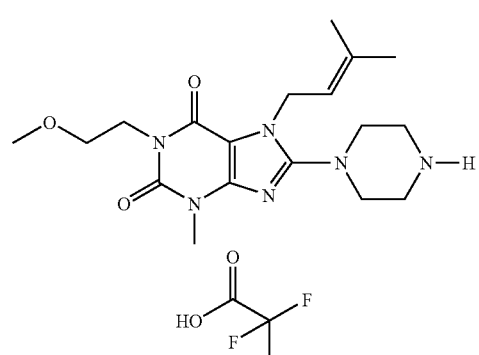

The title compound was obtained using 2-bromoethyl methyl ether and steps similar to Example 15.
MS m/e (ESI) 377(MH$^+$—CF$_3$COOH)

EXAMPLE 60

[3-Methyl-7-(3-methylbut-2-enyl)-2,6-dioxo-8-(piperazin-1-yl)-2,3,6,7-tetrahydropurin-1-yl]acetonitrile trifluoroacetate

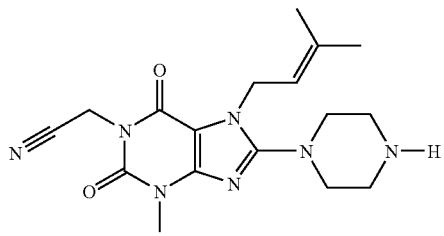

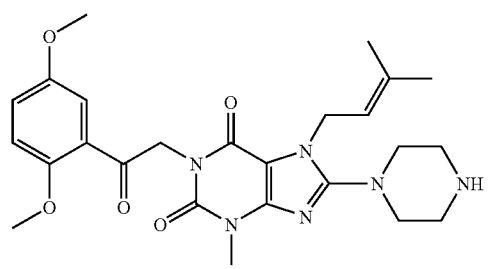

The title compound was obtained using bromoacetonitrile and steps similar to Example 15.
MS m/e (ESI) 358(MH⁺—CF₃COOH)

EXAMPLE 61

1-[2-(4-Diethylaminophenyl)-2-oxoethyl]-3-methyl-7-(3-methylbut-2-enyl)-8-(piperazin-1-yl)-3,7-dihydropurine-2,6-dione trifluoroacetate

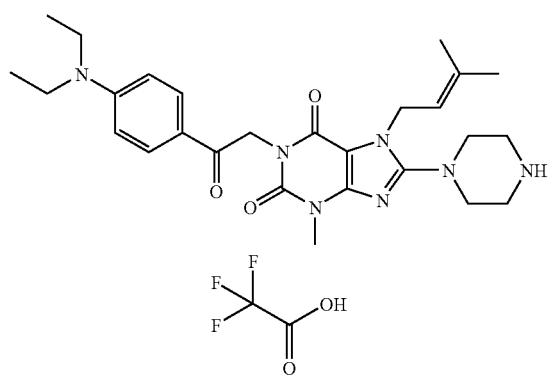

The title compound was obtained using 2-bromo-4'-(diethylamino)acetophenone and steps similar to Example 15.
MS m/e (ESI) 508(MH⁺—CF₃COOH)

EXAMPLE 62

1-[2-(2,5-Dimethoxyphenyl)-2-oxoethyl]-3-methyl-7-(3-methylbut-2-enyl)-8-(piperazin-1-yl)-3,7-dihydropurine-2,6-dione trifluoroacetate

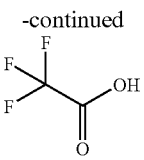

The title compound was obtained using 2-bromo-2',5'-dimethoxyacetophenone and steps similar to Example 15.
MS m/e (ESI) 497(MH⁺—CF₃COOH)

EXAMPLE 63

3-Methyl-7-(3-methylbut-2-enyl)-1-[2-oxo-2-[4-(pyrrolidin-1-yl)phenyl]ethyl]-8-(piperazin-1-yl)-3,7-dihydropurine-2,6-dione trifluoroacetate

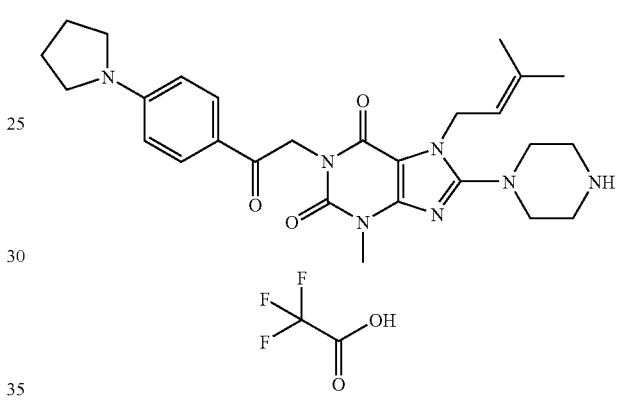

The title compound was obtained using 2-bromo-4'-(pyrrolidin-1-yl)acetophenone and steps similar to Example 15.
MS m/e (ESI) 506(MH⁺—CF₃COOH)

EXAMPLE 64

3-Methyl-7-(3-methylbut-2-enyl)-1-[2-(2-nitrophenyl)-2-oxoethyl]-8-(piperazin-1-yl)-3,7-dihydropurine-2,6-dione trifluoroacetate

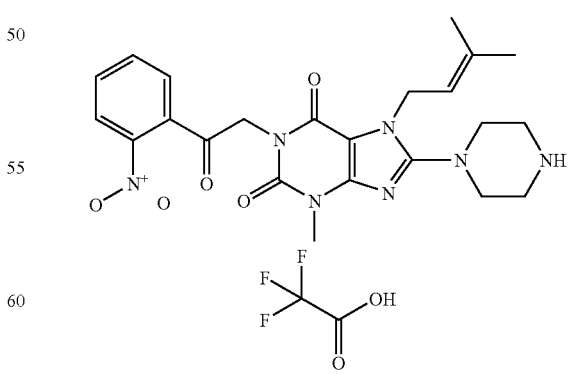

The title compound was obtained using 2-bromo-2'-nitroacetophenone and steps similar to Example 15.
MS m/e (ESI) 482(MH⁺—CF₃COOH)

EXAMPLE 65

3-Methyl-7-(3-methylbut-2-enyl)-1-(2-oxo-2-phenylethyl)-8-(piperazin-1-yl)-3,7-dihydropurine-2,6-dione trifluoroacetate

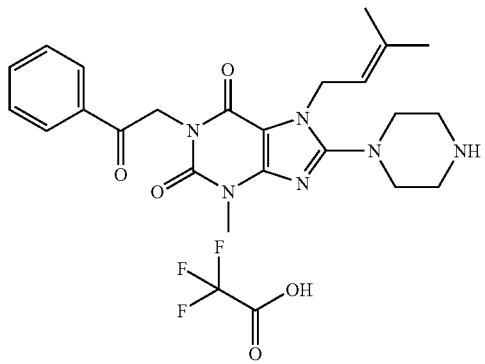

The title compound was obtained using 2-bromoacetophenone and steps similar to Example 15.
MS m/e (ESI) 437(MH$^+$—CF$_3$COOH)

EXAMPLE 66

3-Methyl-7-(3-methylbut-2-enyl)-1-(2-oxo-2-para-tolylethyl)-8-(piperazin-1-yl)-3,7-dihydropurine-2,6-dione trifluoroacetate

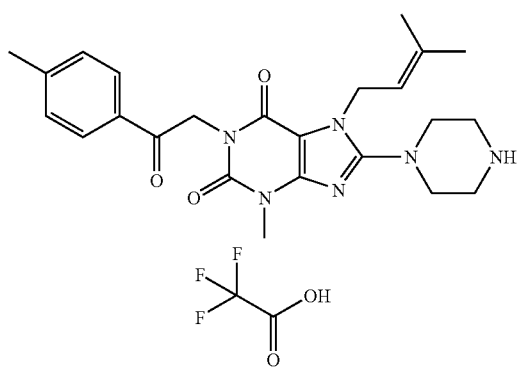

The title compound was obtained using 2-bromo-4'-methylacetophenone and steps similar to Example 15.
MS m/e (ESI) 451(MH$^+$—CF$_3$COOH)

EXAMPLE 67

1-[2-(4-Chlorophenyl)-2-oxoethyl]-3-methyl-7-(3-methylbut-2-enyl)-8-(piperazin-1-yl)-3,7-dihydropurine-2,6-dione trifluoroacetate

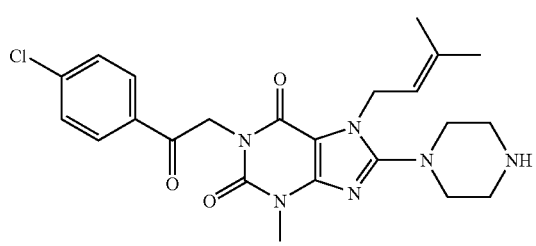

-continued

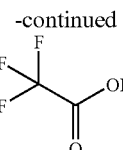

The title compound was obtained using 2-bromo-4'-chloroacetophenone and steps similar to Example 15.
MS m/e (ESI) 471(MH$^+$—CF$_3$COOH)

EXAMPLE 68

3-Methyl-7-(3-methylbut-2-enyl)-1-[2-(4-nitrophenyl)-2-oxoethyl]-8-(piperazin-1-yl)-3,7-dihydropurine-2,6-dione trifluoroacetate

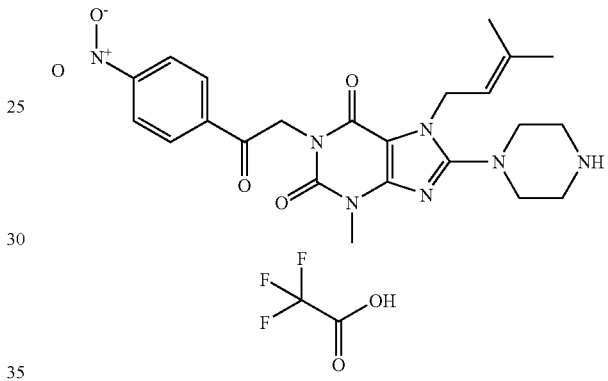

The title compound was obtained using 2-bromo-4'-nitroacetophenone and steps similar to Example 15.
MS m/e (ESI) 482(MH$^+$—CF$_3$COOH)

EXAMPLE 69

1-[2-(2,4-Dimethoxyphenyl)-2-oxoethyl]-3-methyl-7-(3-methylbut-2-enyl)-8-(piperazin-1-yl)-3,7-dihydropurine-2,6-dione trifluoroacetate

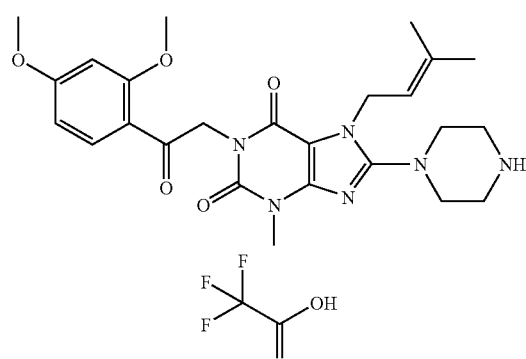

The title compound was obtained using 2-bromo-2',4'-dimethoxyacetophenone and steps similar to Example 15.
MS m/e (ESI) 497(MH$^+$—CF$_3$COOH)

EXAMPLE 70

4-[2-[3-Methyl-7-(3-methylbut-2-enyl)-2,6-dioxo-8-(piperazin-1-yl)-2,3,6,7-tetrahydropurin-1-yl]acetyl]benzonitrile trifluoroacetate

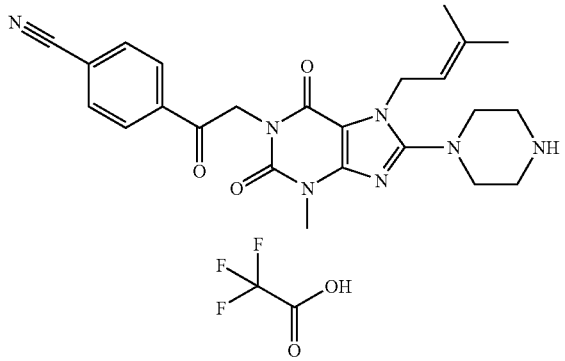

The title compound was obtained using 4-cyanophenacyl bromide and steps similar to Example 15.

MS m/e (ESI) 462(MH+—CF₃COOH)

EXAMPLE 71

1-[2-(2-Methoxyphenyl)-2-oxoethyl]-3-methyl-7-(3-methylbut-2-enyl)-8-(piperazin-1-yl)-3,7-dihydropurine-2,6-dione trifluoroacetate

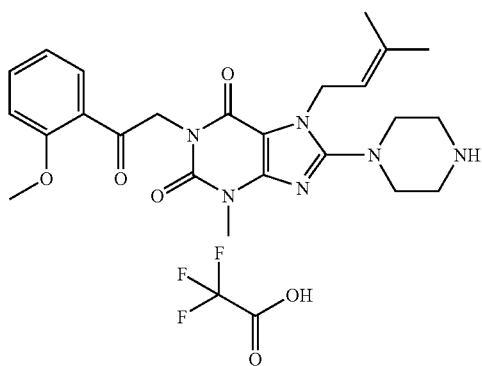

The title compound was obtained using 2-bromo-2'-methoxyacetophenone and steps similar to Example 15.

MS m/e (ESI) 467(MH+—CF₃COOH)

EXAMPLE 72

1-[2-(3-Methoxyphenyl)-2-oxoethyl]-3-methyl-7-(3-methylbut-2-enyl)-8-(piperazin-1-yl)-3,7-dihydropurine-2,6-dione trifluoroacetate

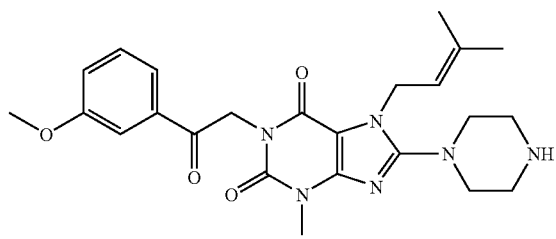

-continued

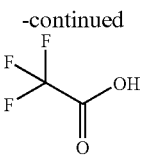

The title compound was obtained using 2-bromo-3'-methoxyacetophenone and steps similar to Example 15.

MS m/e (ESI) 467(MH+—CF₃COOH)

EXAMPLE 73

3-Methyl-7-(3-methylbut-2-enyl)-1-[2-oxo-2-(thiophen-3-yl)ethyl]-8-(piperazin-1-yl)-3,7-dihydropurine-2,6-dione trifluoroacetate

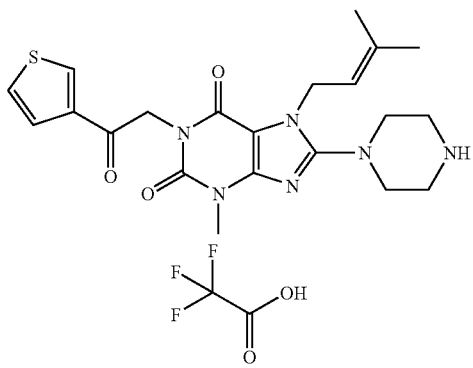

The title compound was obtained using 2-bromo-1-(3-thienyl)-1-ethanone and steps similar to Example 15.

MS m/e (ESI) 443(MH+—CF₃COOH)

EXAMPLE 74

3-Methyl-7-(3-methylbut-2-enyl)-1-[2-oxo-2-(pyridin-3-yl)ethyl]-8-(piperazin-1-yl)-3,7-dihydropurine-2,6-dione trifluoroacetate

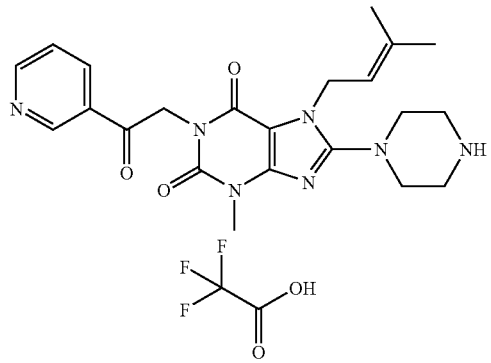

The title compound was obtained using 3-(bromoacetyl)pyridine and steps similar to Example 15.

MS m/e (ESI) 438(MH+—CF₃COOH)

EXAMPLE 75

1-Benzenesulfonylmethyl-3-methyl-7-(3-methylbut-2-enyl)-8-(piperazin-1-yl)-3,7-dihydropurine-2,6-dione trifluoroacetate

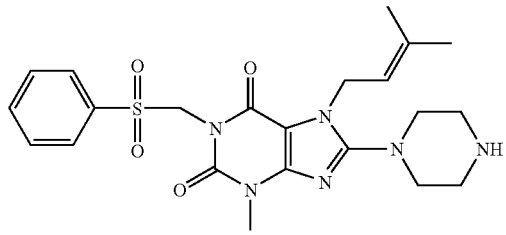

The title compound was obtained using chloromethylphenyl sulfone and steps similar to Example 15.
MS m/e (ESI) 473(MH⁺—CF₃COOH)

EXAMPLE 76

3-Methyl-7-(3-methylbut-2-enyl)-1-(2-phenylethyl)-8-(piperazin-1-yl)-3,7-dihydropurine-2,6-dione trifluoroacetate

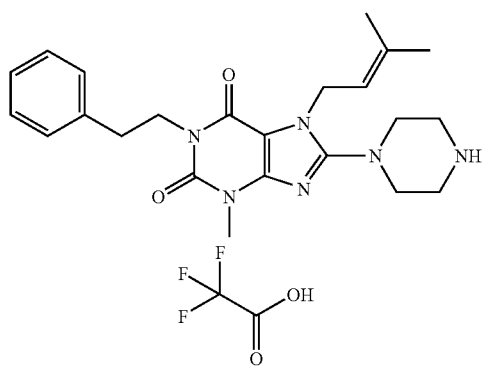

The title compound was obtained using (2-bromoethyl)benzene and steps similar to Example 15.
MS m/e (ESI) 423(MH⁺—CF₃COOH)

EXAMPLE 77

3-Methyl-7-(3-methylbut-2-enyl)-1-[2-(4-nitrophenyl)ethyl]-8-(piperazin-1-yl)-3,7-dihydropurine-2,6-dione trifluoroacetate

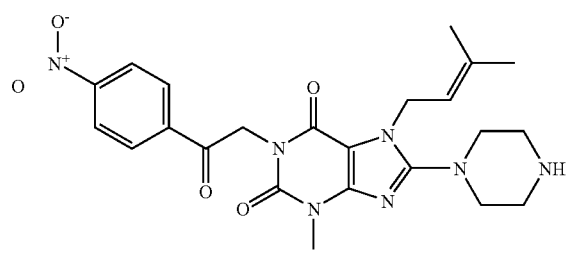

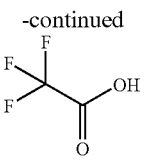

The title compound was obtained using 4-nitrophenethyl bromide and steps similar to Example 15.
MS m/e (ESI) 468(MH⁺—CF₃COOH)

EXAMPLE 78

1-[2-(4-Methoxyphenyl)ethyl]-3-methyl-7-(3-methylbut-2-enyl)-8-(piperazin-1-yl)-3,7-dihydropurine-2,6-dione trifluoroacetate

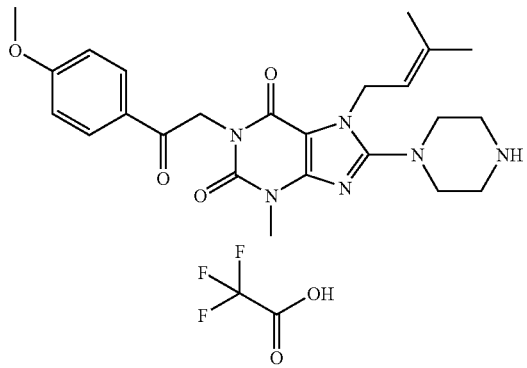

The title compound was obtained using 1-(2-chloroethyl)-4-methoxybenzene and steps similar to Example 15.
MS m/e (ESI) 453(MH⁺—CF₃COOH)

EXAMPLE 79

3-Methyl-7-(3-methylbut-2-enyl)-1-(1-methyl-2-phenylethyl)-8-(piperazin-1-yl)-3,7-dihydropurine-2,6-dione trifluoroacetate

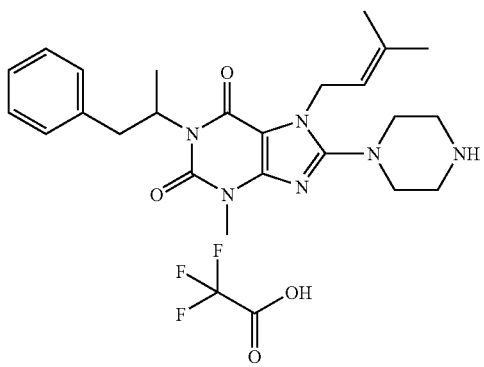

The title compound was obtained using 2-bromo-1-phenylpropane and steps similar to Example 15.
MS m/e (ESI) 437(MH⁺—CF₃COOH)

EXAMPLE 80

3-Methyl-7-(3-methylbut-2-enyl)-8-(piperazin-1-yl)-1-[2-(pyrrol-1-yl)ethyl]-3,7-dihydropurine-2,6-dione trifluoroacetate

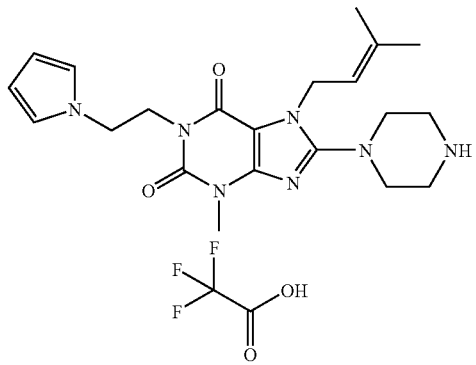

The title compound was obtained using 1-(2-bromoethyl) pyrrole and steps similar to Example 15.

MS m/e (ESI) 412(MH$^+$—CF$_3$COOH)

EXAMPLE 81

3-Methyl-7-(3-methylbut-2-enyl)-1-(1-oxoindan-2-yl)-8-(piperazin-1-yl)-3,7-dihydropurine-2,6-dione trifluoroacetate

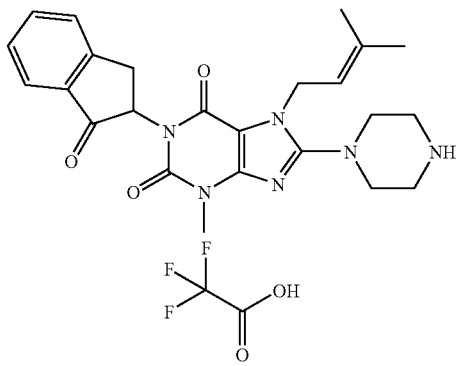

The title compound was obtained using 2-bromo-1-indanone and steps similar to Example 15.

MS m/e (ESI) 449(MH$^+$—CF$_3$COOH)

EXAMPLE 82

3-Methyl-7-(3-methylbut-2-enyl)-1-(3-phenylpropyl)-8-(piperazin-1-yl)-3,7-dihydropurine-2,6-dione trifluoroacetate

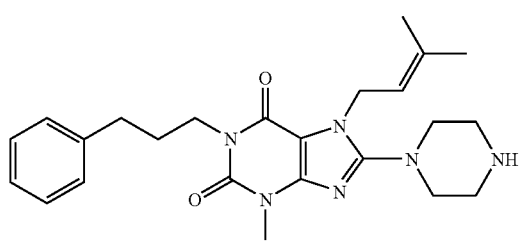

-continued

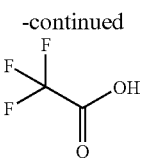

The title compound was obtained using 1-bromo-3-phenylpropane and steps similar to Example 15.

MS m/e (ESI) 437(MH$^+$—CF$_3$COOH)

EXAMPLE 83

4-[2-[3-Methyl-7-(3-methylbut-2-enyl)-2,6-dioxo-8-(piperazin-1-yl)-2,3,6,7-tetrahydropurin-1-yl]ethyl] benzoic acid trifluoroacetate

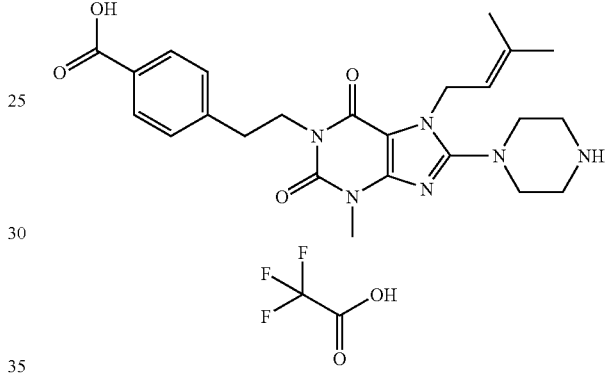

The title compound was obtained using 4-(2-bromoethyl) benzoic acid and steps similar to Example 15.

MS m/e (ESI) 467(MH$^+$—CF$_3$COOH)

EXAMPLE 84

3-Methyl-7-(3-methylbut-2-enyl)-1-(2-phenoxyethyl)-8-(piperazin-1-yl)-3,7-dihydropurine-2,6-dione trifluoroacetate

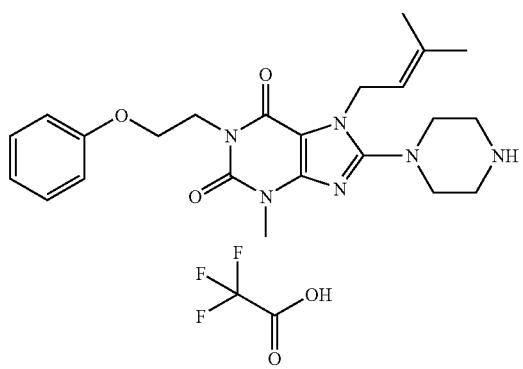

The title compound was obtained using 2-phenoxyethyl bromide and steps similar to Example 15.

MS m/e (ESI) 439(MH$^+$—CF$_3$COOH)

EXAMPLE 85

3-Methyl-7-(3-methylbut-2-enyl)-1-(3-phenoxypropyl)-8-(piperazin-1-yl)-3,7-dihydropurine-2,6-dione trifluoroacetate

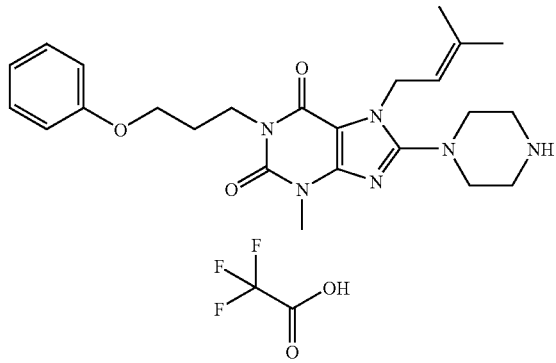

The title compound was obtained using 3-phenoxypropyl bromide and steps similar to Example 15.
MS m/e (ESI) 453(MH$^+$—CF$_3$COOH)

EXAMPLE 86

2-[3-Methyl-7-(3-methylbut-2-enyl)-2,6-dioxo-8-(piperazin-1-yl)-2,3,6,7-tetrahydropurin-1-ylmethyl]benzonitrile trifluoroacetate

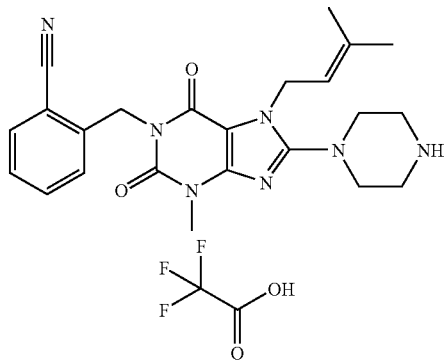

The title compound was obtained using α-bromo-o-tolunitrile and steps similar to Example 15.
MS m/e (ESI) 434(MH$^+$—CF$_3$COOH)

EXAMPLE 87

1-(2,6-Dichloropyridin-4-ylmethyl)-3-methyl-7-(3-methylbut-2-enyl)-1-8-(piperazin-1-yl)-3,7-dihydropurine-2,6-dione trifluoroacetate

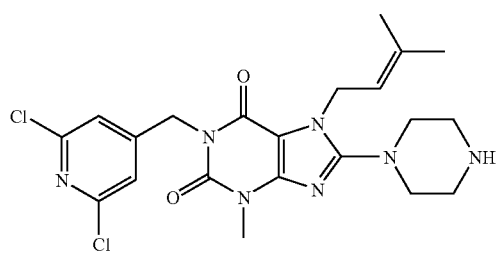

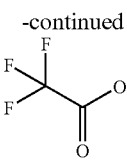

The title compound was obtained using 4-(bromomethyl)-2,6-dichloropyridine and steps similar to Example 15.
MS m/e (ESI) 479(MH$^+$—CF$_3$COOH)

EXAMPLE 88

3-Methyl-7-(3-methylbut-2-enyl)-1-(2-nitrobenzyl)-8-(piperazin-1-yl)-3,7-dihydropurine-2,6-dione trifluoroacetate

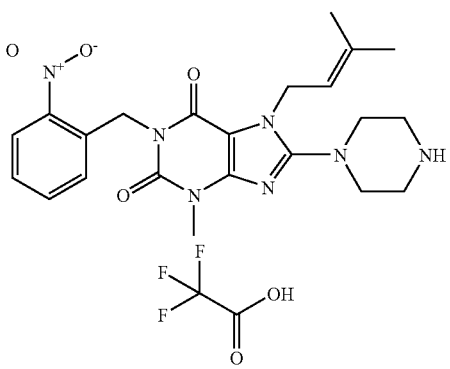

The title compound was obtained using 2-nitrobenzyl bromide and steps similar to Example 15.
MS m/e (ESI) 454(MH$^+$—CF$_3$COOH)

EXAMPLE 89

1-(2-Fluorobenzyl)-3-methyl-7-(3-methylbut-2-enyl)-8-(piperazin-1-yl)-3,7-dihydropurine-2,6-dione trifluoroacetate

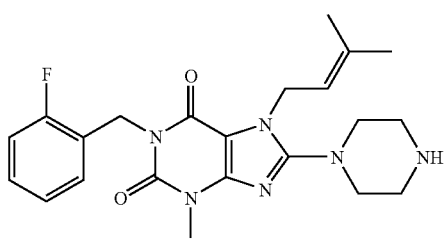

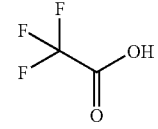

The title compound was obtained using 2-fluorobenzyl bromide and steps similar to Example 15.
MS m/e (ESI) 427(MH$^+$—CF$_3$COOH)

EXAMPLE 90

1-(2-Chloroethyl)-3-methyl-7-(3-methylbut-2-enyl)-8-(piperazin-1-yl)-3,7-dihydropurine-2,6-dione trifluoroacetate

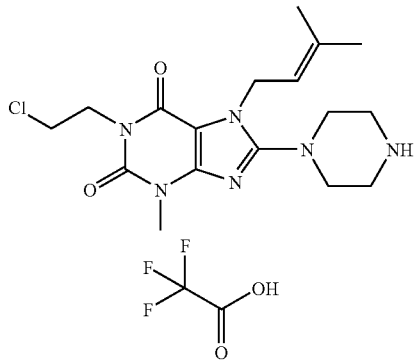

The title compound was obtained using 1-bromo-2-chloroethane and steps similar to Example 15.

MS m/e (ESI) 381(MH$^+$—CF$_3$COOH)

EXAMPLE 91

1-(3-Benzyloxypropyl)-3-methyl-7-(3-methylbut-2-enyl)-8-(piperazin-1-yl)-3,7-dihydropurine-2,6-dione trifluoroacetate

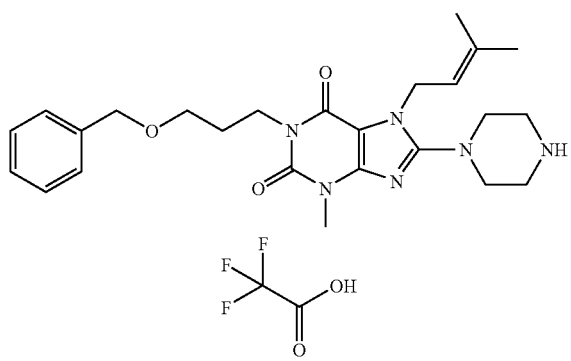

The title compound was obtained using benzyl 3-bromopropylether and steps similar to Example 15.

MS m/e (ESI) 467(MH$^+$—CF$_3$COOH)

EXAMPLE 92

1-(3,3-Dimethyl-2-oxobutyl)-3-methyl-7-(3-methylbut-2-enyl)-8-(piperazin-1-yl)-3,7-dihydropurine-2,6-dione trifluoroacetate

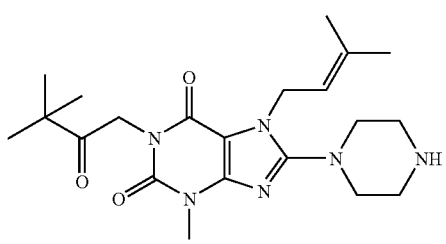

-continued

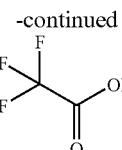

The title compound was obtained using 1-bromo-3,3-dimethyl-2-butanone and steps similar to Example 15.

MS m/e (ESI) 417(MH$^+$—CF$_3$COOH)

EXAMPLE 93

3-[3-Methyl-7-(3-methylbut-2-enyl)-2,6-dioxo-8-(piperazin-1-yl)-2,3,6,7-tetrahydropurin-1-yl]propionic acid ethyl ester trifluoroacetate

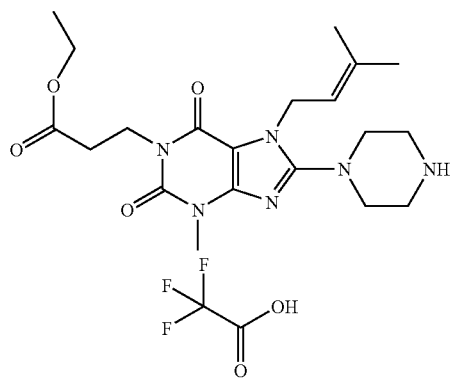

The title compound was obtained using ethyl 3-bromopropionate and steps similar to Example 15.

MS m/e (ESI) 467(MH$^+$—CF$_3$COOH)

EXAMPLE 94

[3-Methyl-7-(3-methylbut-2-enyl)-2,6-dioxo-8-(piperazin-1-yl)-2,3,6,7-tetrahydropurin-1-yl]acetic acid benzyl ester trifluoroacetate

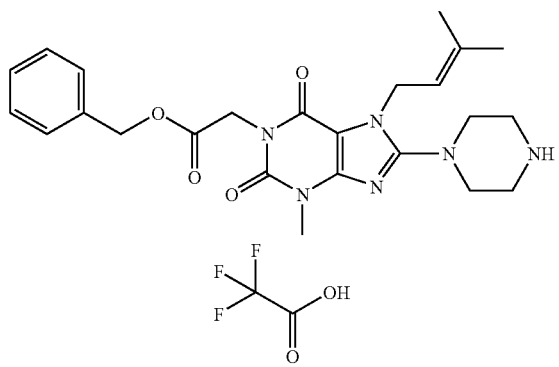

The title compound was obtained using benzyl bromoacetate and steps similar to Example 15.

MS m/e (ESI) 467(MH$^+$—CF$_3$COOH)

EXAMPLE 95

1-(2-Hydroxy-2-phenylethyl)-3-methyl-7-(3-methyl-but-2-enyl)-8-(piperazin-1-yl)-3,7-dihydropurine-2,6-dione trifluoroacetate a) 2-Bromo-1-phenylethanol

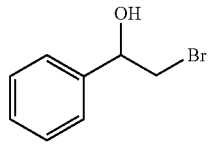

2-Bromoacetophenone (1 g) was dissolved in tetrahydrofuran (8 ml), and a solution of borane-dimethylamine (326 mg) in tetrahydrofuran (6 ml) was added thereto at room temperature. After the reaction mixture was stirred at room temperature for 60 hours, methanol (1 ml) and 1 M hydrochloric acid aqueous solution (5 ml) were added thereto, and the mixture was extracted with diethyl ether. The organic layer was washed with saturated brine, and dried over anhydrous magnesium sulfate. After removing the solvent by distillation from the organic layer, the residue was purified by silica gel column chromatography to obtain the title compound from a fraction eluted with hexane-ethyl acetate (5:1).

$^1$H-NMR(CDCl$_3$) δ: 2.63 (d, J=3.2 Hz, 1H) 3.52–3.57 (m, 1H) 3.63–3.66 (m, 1H) 4.91–4.94 (m, 1H) 7.32–7.39 (m, 5H)

b) 1-(2-Hydroxy-2-phenylethyl)-3-methyl-7-(3-methylbut-2-enyl)-8-(piperazin-1-yl)-3,7-dihydropurine-2,6-dione trifluoroacetate

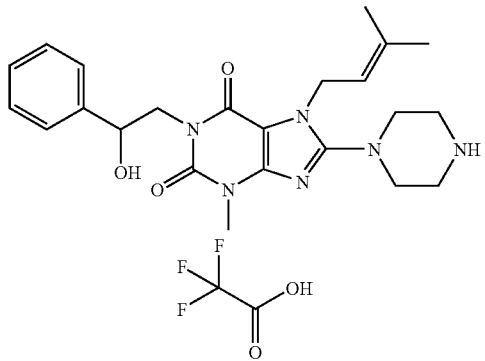

The title compound was obtained using 2-bromo-1-phenylethanol and steps similar to Example 15.
MS m/e (ESI) 439(MH$^+$—CF$_3$COOH)

EXAMPLE 96

4-[3-Methyl-7-(3-methylbut-2-enyl)-2,6-dioxo-8-(piperazin-1-yl)-2,3,6,7-tetrahydropurin-1-yl]butyric acid ethyl ester trifluoroacetate

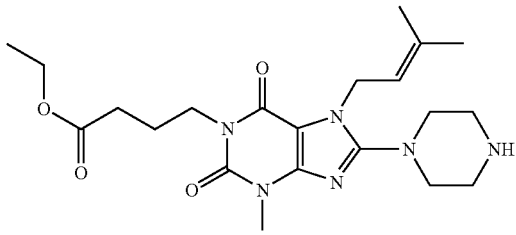

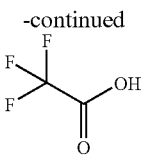

The title compound was obtained using ethyl 4-bromobutyrate and steps similar to Example 15.
MS m/e (ESI) 433(MH$^+$—CF$_3$COOH)

EXAMPLE 97

3-Methyl-7-(3-methylbut-2-enyl)-1-(2-oxotetrahydrofuran-3-yl)-8-(piperazin-1-yl)-3,7-dihydropurine-2,6-dione trifluoroacetate

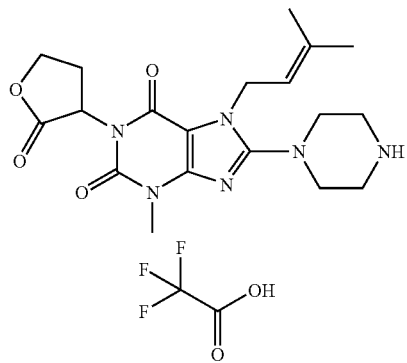

The title compound was obtained using α-bromo-γ-butyrolactone and steps similar to Example 15.
MS m/e (ESI) 403(MH$^+$—CF$_3$COOH)

EXAMPLE 98

2-[3-Methyl-7-(3-methylbut-2-enyl)-2,6-dioxo-8-(piperazin-1-yl)-2,3,6,7-tetrahydropurin-1-yl]ethyl benzoate trifluoroacetate

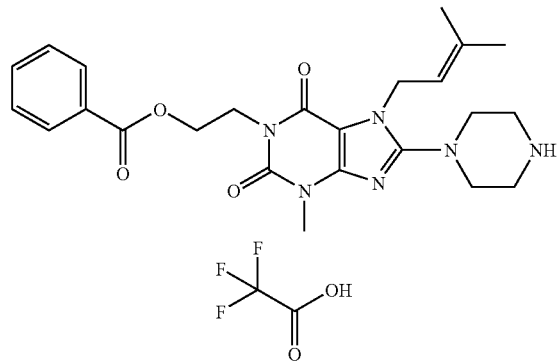

The title compound was obtained using 2-bromoethyl benzoate and steps similar to Example 15.
MS m/e (ESI) 467(MH$^+$—CF$_3$COOH)

EXAMPLE 99

2-[3-Methyl-7-(3-methylbut-2-enyl)-2,6-dioxo-8-(piperazin-1-yl)-2,3,6,7-tetrahydropurin-1-yl]propionic acid methyl ester trifluoroacetate

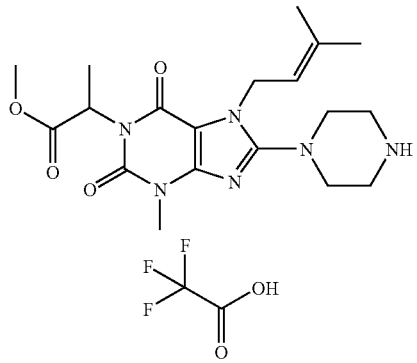

The title compound was obtained using methyl 2-bromopropionate and steps similar to Example 15.
MS m/e (ESI) 405(MH+—CF₃COOH)

EXAMPLE 100

7-(3-Methylbut-2-enyl)-8-(piperazin-1-yl)-3-propyl-3,7-dihydropurine-2,6-dione trifluoroacetate

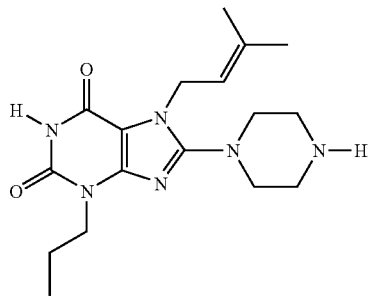

4-[7-(3-methylbut-2-enyl)-3-propyl-2,6-dioxo-2,3,6,7-tetrahydro-1H-purin-8-yl]piperadine-1-carboxylic acid tert-butyl ester was obtained using 3-propylxanthine and 1-bromo-3-methyl-2-butene, and steps similar to Example 14a). Then, the title compound was obtained using steps similar to Example 10b).
MS m/e (ESI) 347(MH+—CF₃COOH)

EXAMPLE 101

1,3-Dimethyl-7-(2-methylallyl)-8-(piperazin-1-yl)-3,7-dihydropurine-2,6-dione trifluoroacetate

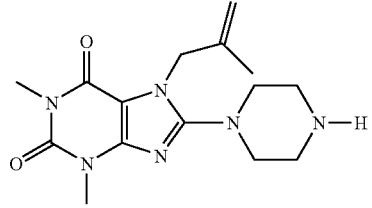

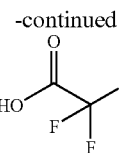

The title compound was obtained using 8-chlorotheophylline and 3-bromo-2-methylpropene, and steps similar to Example 10a) followed by steps similar to Example 15.
MS m/e (ESI) 319(MH+—CF₃COOH)

EXAMPLE 102

7-Allyl-1-ethyl-3-methyl-8-(piperazin-1-yl)-3,7-dihydropurine-2,6-dione trifluoroacetate

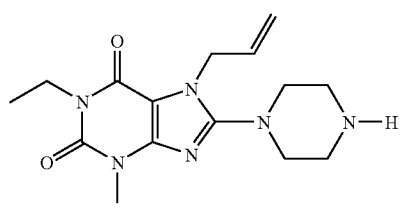

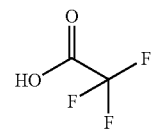

The title compound was obtained using ethyl iodide and steps similar to Example 15.
MS m/e (ESI) 319(MH+—CF₃COOH)

EXAMPLE 103

1,7-Diallyl-3-methyl-8-(piperazin-1-yl)-3,7-dihydropurine-2,6-dione trifluoroacetate

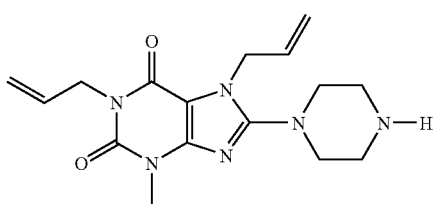

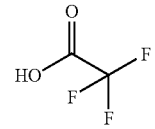

The title compound was obtained using allyl bromide and steps similar to Example 15.
MS m/e (ESI) 331(MH+—CF₃COOH)

EXAMPLE 104

7-Allyl-3-methyl-8-(piperazin-1-yl)-1-(2-propynyl)-3,7-dihydropurine-2,6-dione trifluoroacetate

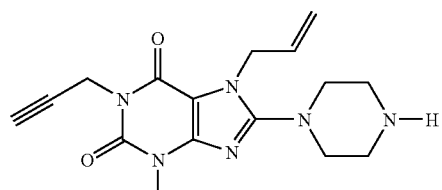

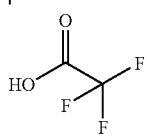

The title compound was obtained using propargyl bromide and steps similar to Example 15.
MS m/e (ESI) 329(MH⁺—CF₃COOH)

EXAMPLE 105

7-Allyl-1-benzyl-3-methyl-8-(piperazin-1-yl)-3,7-dihydropurine-2,6-dione trifluoroacetate

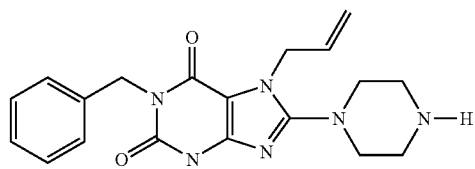

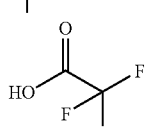

The title compound was obtained using benzyl bromide and steps similar to Example 15.
MS m/e (ESI) 381(MH⁺—CF₃COOH)

EXAMPLE 106

[7-Allyl-3-methyl-2,6-dioxo-8-(piperazin-1-yl)-2,3,6,7-tetrahydropurin-1-yl]acetic acid ethyl ester trifluoroacetate

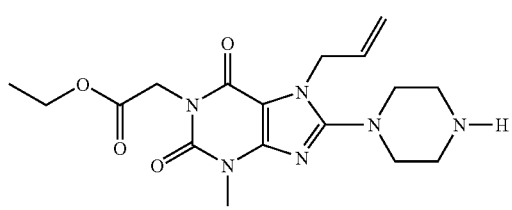

-continued

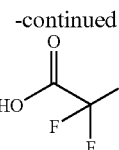

The title compound was obtained using ethyl bromoacetate and steps similar to Example 15.
MS m/e (ESI) 377(MH⁺—CF₃COOH)

EXAMPLE 107

2-[7-Allyl-3-methyl-2,6-dioxo-8-(piperazin-1-yl)-2,3,6,7-tetrahydropurin-1-yl]acetamide trifluoroacetate

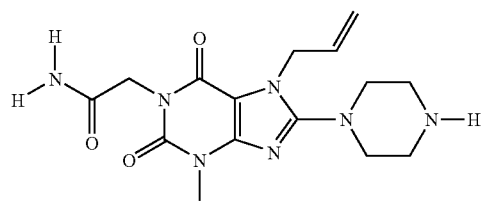

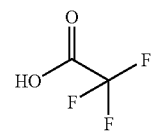

The title compound was obtained using 2-bromoacetamide and steps similar to Example 15.
MS m/e (ESI) 348(MH⁺—CF₃COOH)

EXAMPLE 108

7-Allyl-(2-methoxyethyl)-3-methyl-piperazin-1-yl)-3,7-dihydropurine-2,6-dione trifluoroacetate

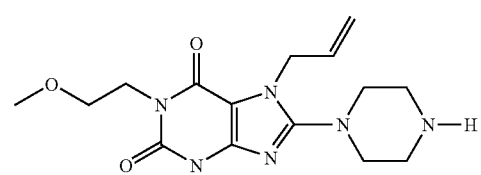

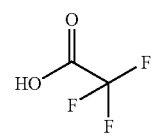

The title compound was obtained using 2-bromoethyl methyl ether and steps similar to Example 15.
MS m/e (ESI) 349(MH⁺—CF₃COOH)

EXAMPLE 109

7-Allyl-1-(2-hydroxyethyl)-3-methyl-8-(piperazin-1-yl)-3,7-dihydropurine-2,6-dione trifluoroacetate

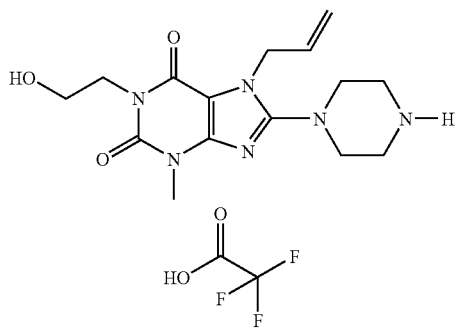

The title compound was obtained using 2-(2-bromoethoxy)tetrahydro-2H-pyran and steps similar to Example 15.
MS m/e (ESI) 335(MH$^+$—CF$_3$COOH)

EXAMPLE 110

[7-Allyl-3-methyl-2,6-dioxo-8-(piperazin-1-yl)-2,3,6,7-tetrahydropurin-1-yl]acetonitrile trifluoroacetate

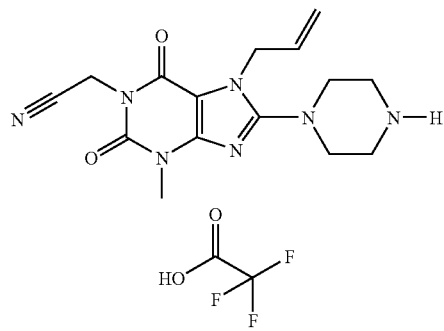

The title compound was obtained using bromoacetonitrile and steps similar to Example 15.
MS m/e (ESI) 330(MH$^+$—CF$_3$COOH)

EXAMPLE 111

7-Allyl-3-methyl-1-(2-oxo-2-phenylethyl)-8-(piperazin-1-yl)-3,7-dihydropurine-2,6-dione trifluoroacetate

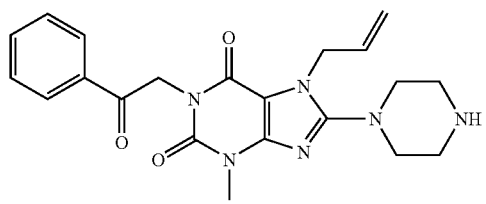

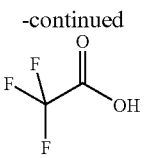

The title compound was obtained using phenacyl bromide and steps similar to Example 15.
MS m/e (ESI) 453[(M+2Na—H)$^+$—CF$_3$COOH]

EXAMPLE 112

[3-Methyl-7-(3-methylbut-2-enyl)-2,6-dioxo-8-(piperazin-1-yl)-2,3,6,7-tetrahydropurin-1-yl]acetic acid trifluoroacetate

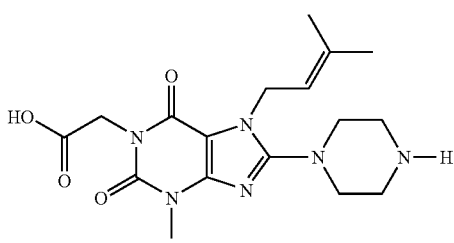

4-[3-Methyl-7-(3-methylbut-2-enyl)-2,6-dioxo-2,3,6,7-tetrahydro-1H-purin-8-yl]piperazine-1-carboxylic acid tert-butyl ester (70 mg) and potassium carbonate (28 mg) were dissolved in N,N-dimethylformamide (1.5 ml), and ethyl bromoacetate (22 µl) was added thereto. After stirring at room temperature overnight, the reaction mixture was diluted with ethyl acetate, and washed with water. The organic layer was concentrated by distillation, and ethanol (1.5 ml) and 2 N sodium hydroxide aqueous solution (0.5 ml) were added to the resulting residue. The reaction mixture was stirred at room temperature for 3 hours, diluted with water, and neutralized with 2 N hydrochloric acid. After the mixture was extracted with ethyl acetate, the organic layer was concentrated by distillation to give 75 mg of 4-[1-carboxymethyl-3-methyl-7-(3-methylbut-2-enyl)-2,6-dioxo-2,3,6,7-tetrahydro-1H-purin-8-yl]piperazine-1-carboxylic acid tert-butyl ester. Then, the resulting 4-[1-carboxymethyl-3-methyl-7-(3-methylbut-2-enyl)-2,6-dioxo-2,3,6,7-tetrahydro-1H-purin-8-yl]piperazine-1-carboxylic acid tert-butyl ester (10 mg) was dissolved in trifluoroacetic acid (0.5 ml), and the reaction mixture was stirred at room temperature for 30 minutes. After the solvent was removed by distillation, a half of the residue was purified by HPLC with a reversed phase column using water-acetonitrile-trifluoroacetic acid system as eluent to give 5.9 mg of the title compound.
MS m/e (ESI) 377(MH$^+$—CF$_3$COOH)

EXAMPLE 113

4-[3-Methyl-7-(3-methylbut-2-enyl)-2,6-dioxo-8-(piperazin-1-yl)-2,3,6,7-tetrahydropurin-1-yl]butanoic acid trifluoroacetate

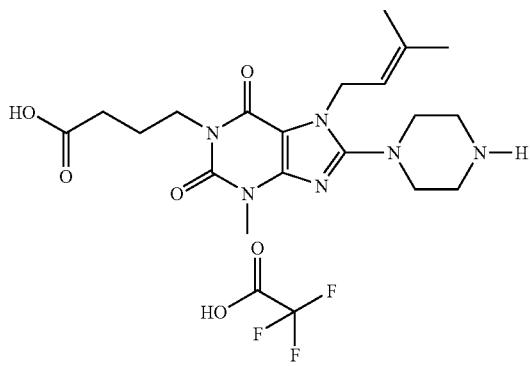

The title compound was obtained using ethyl 4-bromobutanoate and steps similar to Example 112.
MS m/e (ESI) 405(MH$^+$—CF$_3$COOH)

EXAMPLE 114

4-[3-Methyl-7-(3-methylbut-2-enyl)-2,6-dioxo-8-(piperazin-1-yl)-2,3,6,7-tetrahydropurin-1-yl]-2-butenoic acid trifluoroacetate

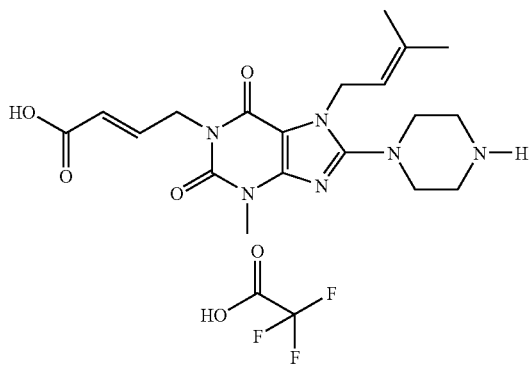

The title compound was obtained using ethyl 4-bromocrotonate and steps similar to Example 112.
MS m/e (ESI) 403(MH$^+$—CF$_3$COOH)

EXAMPLE 115

[7-(2-Butynyl)-1-(2-ethoxyethyl)-3-methyl-8-(piperazin-1-yl)-2,6-dioxo-2,3,6,7-tetrahydropurin-1-yl]acetic acid trifluoroacetate

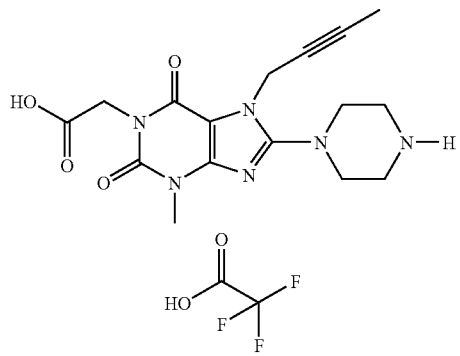

The title compound was obtained using ethyl bromoacetate and steps similar to Example 112.
MS m/e (ESI) 361(MH$^+$—CF$_3$COOH)

EXAMPLE 116

N-Benzyl-2-[7-(2-butynyl)-3-methyl-2,6-dioxo-8-(piperazin-1-yl)-2,3,6,7-tetrahydropurin-1-yl]-acetamide trifluoroacetate

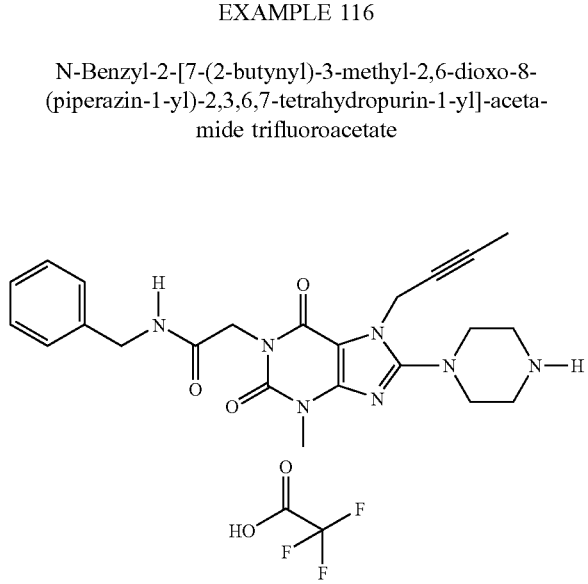

4-[1-Carboxymethyl-3-methyl-7-(2-butynyl)-2,6-dioxo-2,3,6,7-tetrahydro-1H-purin-8-yl]piperazine-1-carboxylic acid tert-butyl ester (25 mg) was dissolved in N,N-dimethylformamide (1 ml), and benzylamine (6 µl), diethyl cyanophosphonate (9 µl), and triethylamine (8 µl) were added thereto. The reaction mixture was stirred at room temperature for 5 hours, diluted with ethyl acetate, washed with water, and dried over anhydrous magnesium sulfate. After removing the solvent by distillation, the residue was dissolved in trifluoroacetic acid (0.5 ml), and the reaction mixture was stirred at room temperature for 30 minutes. Then, the solvent was removed by distillation, and a half of the residue was purified by HPLC with a reversed phase column using water-acetonitrile-trifluoroacetic acid system as eluent to give 0.77 mg of the title compound.
MS m/e (ESI) 450(MH$^+$—CF$_3$COOH)

EXAMPLE 117

2-[7-(2-Butynyl)-3-methyl-2,6-dioxo-8-(piperazin-1-yl)-2,3,6,7-tetrahydropurin-1-yl]-N-phenylacetamide trifluoroacetate

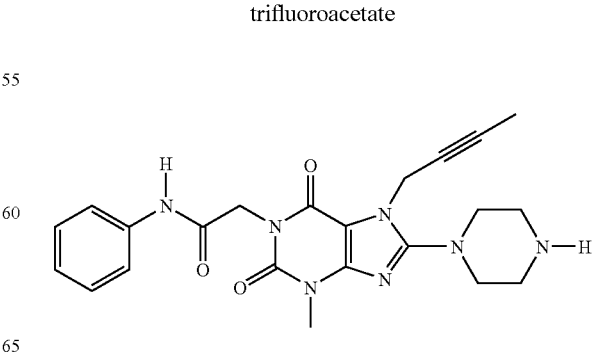

-continued

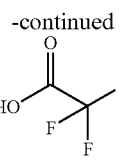

4-[1-Carboxymethyl-3-methyl-7-(2-butynyl)-2,6-dioxo-2,3,6,7-tetrahydro-1H-purin-8-yl]piperazine-1-carboxylic acid tert-butyl ester (25 mg) was dissolved in tetrahydrofuran (1 ml), and aniline (5 µl), 1,1-carbonyldiimidazole (9 mg), and triethylamine (8 µl) were added thereto. The reaction mixture was stirred at 60° C. for 5 hours, diluted with ethyl acetate, washed with water, and dried over anhydrous magnesium sulfate. After removing the solvent by distillation, the residue was dissolved in trifluoroacetic acid (0.5 ml), and the reaction mixture was stirred at room temperature for 30 minutes. Then, the solvent was removed by distillation, and a half of the residue was purified by HPLC with a reversed phase column using water-acetonitrile-trifluoroacetic acid system as eluent to give 2.74 mg of the title compound.

MS m/e (ESI) 436(MH$^+$—CF$_3$COOH)

EXAMPLE 118

N-Methyl-2-[3-methyl-7-(3-methylbut-2-enyl)-2,6-dioxo-8-(piperazin-1-yl)-2,3,6,7-tetrahydropurin-1-yl]acetamide trifluoroacetate

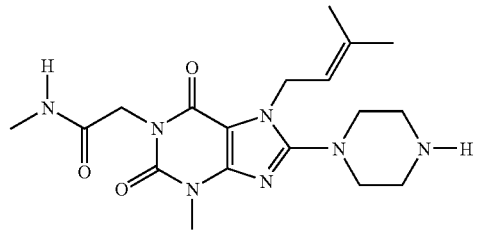

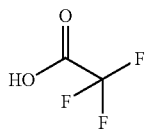

4-[1-Carboxymethyl-3-methyl-7-(3-methylbut-2-enyl)-2,6-dioxo-2,3,6,7-tetrahydro-1H-purin-8-yl]piperazine-1-carboxylic acid tert-butyl ester (38 mg) was dissolved in tetrahydrofuran (1 ml). Cooling on ice, ethyl chlorocarbonate (8.4 µl) and triethylamine (12 µl) were added thereto, and the reaction mixture was stirred for 10 minutes. Then, 40% methylamine aqueous solution was added thereto, and the reaction mixture was stirred at room temperature for 1 hour. After removing the solvent by distillation, a half of the residue was dissolved in trifluoroacetic acid (0.5 ml), and the reaction mixture was stirred at room temperature for 30 minutes. Then, the solvent was removed by distillation, and a half of the residue was purified by HPLC with a reversed phase column using water-acetonitrile-trifluoroacetic acid system as eluent to give 2.9 mg of the title compound.

MS m/e (ESI) 390(MH$^+$—CF$_3$COOH)

EXAMPLE 119

N-Ethyl-2-[3-methyl-7-(3-methylbut-2-enyl)-2,6-dioxo-8-(piperazin-1-yl)-2,3,6,7-tetrahydropurin-1-yl]acetamide trifluoroacetate

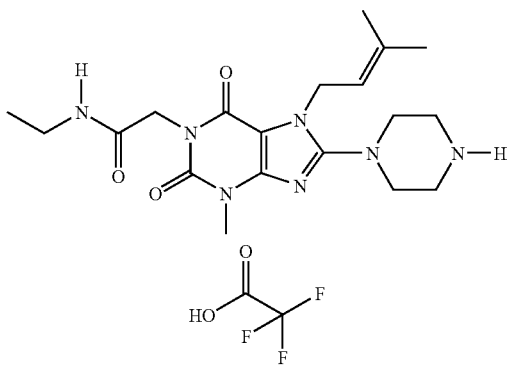

The title compound was obtained using 2 M solution of ethylamine in tetrahydrofuran and steps similar to Example 118.

MS m/e (ESI) 404(MH$^+$—CF$_3$COOH)

EXAMPLE 120

N,N-Dimethyl-2-[3-methyl-7-(3-methylbut-2-enyl)-2,6-dioxo-8-(piperazin-1-yl)-2,3,6,7-tetrahydropurin-1-yl]acetamide trifluoroacetate

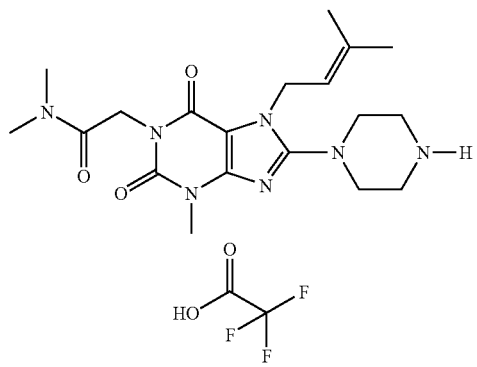

4-[1-Carboxymethyl-3-methyl-7-(3-methylbut-2-enyl)-2,6-dioxo-2,3,6,7-tetrahydro-1H-purin-8-yl]piperazine-1-carboxylic acid tert-butyl ester (38 mg) was dissolved in tetrahydrofuran (1 ml). Cooling on ice, ethyl chlorocarbonate (8.4 µl) and triethylamine (12 µl) were added thereto, and the reaction mixture was stirred for 10 minutes. Then, 40% methylamine aqueous solution was added thereto, and the reaction mixture was stirred at room temperature for 1 hour. After removing the solvent by distillation, a half of the residue was dissolved in tetrahydrofuran(1 ml), and sodium hydride (20 mg) and methyl iodide (20 µl) were added thereto. The reaction mixture was stirred at room temperature overnight, then diluted with ethyl acetate, and washed with water. The organic layer was concentrated by distillation, the resulting residue was dissolved in trifluoroacetic acid (0.5 ml), and the reaction mixture was stirred at room temperature for 30 minutes. After removing the solvent by distillation, a half of the residue was purified by HPLC with a reversed phase column using water-acetonitrile-trifluoroacetic acid system as eluent to give 1.7 mg of the title compound.

MS m/e (ESI) 404(MH$^+$—CF$_3$COOH)

EXAMPLE 121

[7-Allyl-3-methyl-2,6-dioxo-8-(piperazin-1-yl)-2,3,6,7-tetrahydropurin-1-yl]acetic acid trifluoroacetate

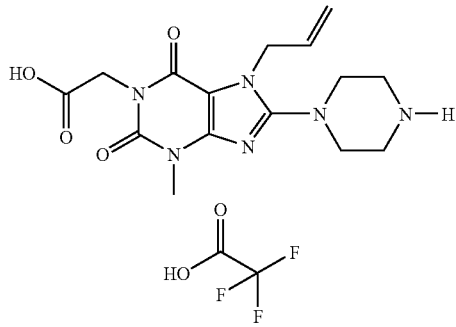

The title compound was obtained using ethyl bromoacetate and steps similar to Example 112.
MS m/e (ESI) 349(MH$^+$—CF$_3$COOH)

EXAMPLE 122

N-Methyl-2-[7-allyl-3-methyl-2,6-dioxo-8-(piperazin-1-yl)-2,3,6,7-tetrahydropurin-1-yl]acetamide trifluoroacetate

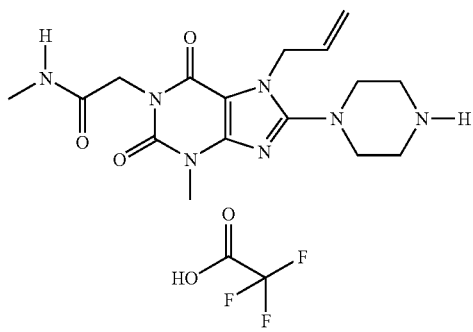

4-[7-allyl-1-carboxymethyl-3-methyl-2,6-dioxo-2,3,6,7-tetrahydro-1H-purin-8-yl]piperazine-1-carboxylic acid tert-butyl ester was obtained using ethyl bromoacetate and steps similar to Example 112. Then, the title compound was obtained using steps similar to Example 118.
MS m/e (ESI) 362(MH$^+$—CF$_3$COOH)

EXAMPLE 123

7-(2-Methoxyphenyl)-1,3-dimethyl-8-(piperazin-1-yl)-3,7-dihydropurine-2,6-dione trifluoroacetate a) 4-(1,3-Dimethyl-2,6-dioxo-2,3,6,7-tetrahydro-1H-purin-8-yl)piperazine-1-carboxylic acid tert-butyl ester

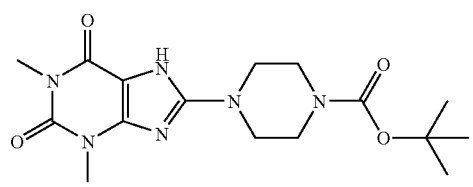

8-Chlorotheophylline (3.5 g) and piperazine-1-carboxylic acid tert-butyl ester (11.69 g) were mixed, and stirred at 110° C. overnight. Then, the reaction mixture was diluted with ethyl acetate and water, insoluble white solid was collected by filtration, and washed with ethyl acetate to give 3.65 g of the title compound.

$^1$H-NMR(CDCl$_3$) δ: 1.48 (s, 9H) 3.38 (s, 3H) 3.54–3.57 (m, 7H) 3.66–3.69 (m, 4H) 11.58 (s, 1H)

b) 7-(2-Methoxyphenyl)-1,3-dimethyl-8-(piperazin-1-yl)-3,7-dihydropurine-2,6-dione trifluoroacetate

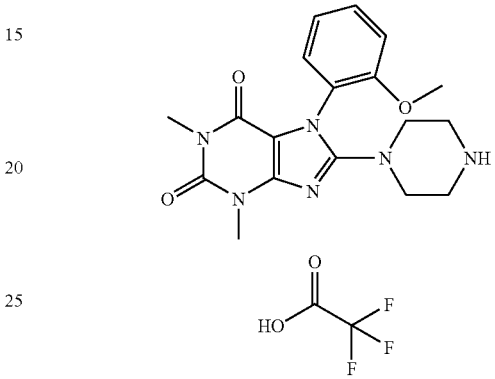

4-(1,3-Dimethyl-2,6-dioxo-2,3,6,7-tetrahydro-1H-purin-8-yl)piperazine-1-carboxylic acid tert-butyl ester (11 mg), 2-methoxyphenyl boronic acid (15 mg), and copper (II) acetate (10 mg) were suspended in anhydrous tetrahydrofuran (0.5 ml); and pyridine (0.1 ml) was added thereto. The reaction mixture was stirred at room temperature for 5 days, and filtered through a short column packed with NH-silica gel. The filtrate was concentrated. The residue was dissolved in trifluoroacetic acid (0.5 ml), and the reaction mixture was stirred at room temperature for 30 minutes. After removing the solvent by distillation, the residue was purified by reversed phase high performance liquid chromatography to give 3.53 mg of the title compound.

$^1$H-NMR(CDCl$_3$) δ: 3.05–3.20 (m, 4H) 3.29 (s, 3H) 3.50–3.51 (m, 7H) 3.81 (s, 3H) 7.04–7.07 (m, 2H) 7.26–7.30 (m, 1H) 7.47 (dt, J=2.0, 8.0 Hz, 1H)

MS m/e (ESI) 371(MH$^+$—CF$_3$COOH)

EXAMPLE 124

7-Phenyl-1,3-dimethyl-8-(piperazin-1-yl)-3,7-dihydropurine-2,6-dione trifluoroacetate

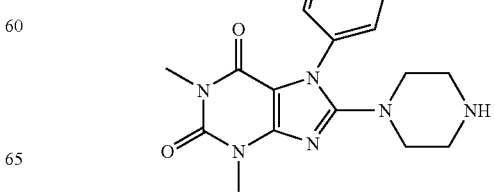

-continued

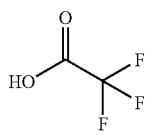

The title compound was obtained using phenyl boronic acid and steps similar to Example 123b).

MS m/e (ESI) 341(MH⁺—CF₃COOH)

EXAMPLE 125

7-(2-Ethoxyphenyl)-1,3-dimethyl-8-(piperazin-1-yl)-3,7-dihydropurine-2,6-dione trifluoroacetate

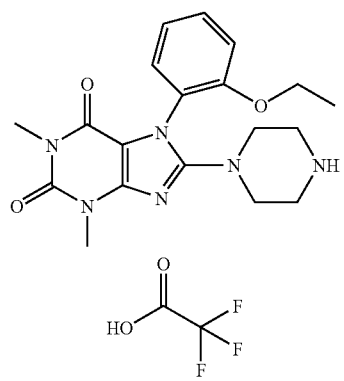

The title compound was obtained using 2-ethoxyphenyl boronic acid and steps similar to Example 123b).

MS m/e (ESI) 385(MH⁺—CF₃COOH)

EXAMPLE 126

7-(2-Methylphenyl)-1,3-dimethyl-8-(piperazin-1-yl)-3,7-dihydropurine-2,6-dione trifluoroacetate The title compound was obtained using 2-methylphenyl boronic acid and steps similar to Example 123b).

MS m/e (ESI) 355(MH⁺—CF₃COOH)

EXAMPLE 127

1,3-Dimethyl-7-(naphthalen-1-yl)-8-(piperazin-1-yl)-3,7-dihydropurine-2,6-dione trifluoroacetate The title compound was obtained using 1-naphthalene boronic acid and steps similar to Example 123b).

MS m/e (ESI) 391(MH⁺—CF₃COOH)

EXAMPLE 128

7-(2,5-Dimethylphenyl)-1,3-dimethyl-8-(piperazin-1-yl)-3,7-dihydropurine-2,6-dione trifluoroacetate

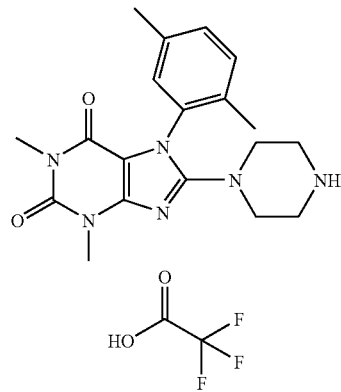

The title compound was obtained using 2,5-dimethylphenyl boronic acid and steps similar to Example 123b).

MS m/e (ESI) 369(MH⁺—CF₃COOH)

EXAMPLE 129

7-(2-Fluorophenyl)-1,3-dimethyl-8-(piperazin-1-yl)-3,7-dihydropurine-2,6-dione trifluoroacetate

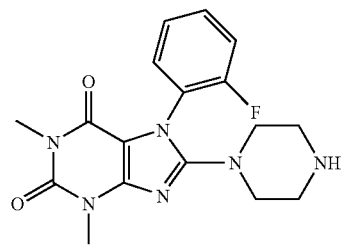

-continued

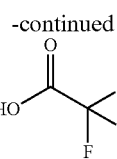

The title compound was obtained using 2-fluorophenyl boronic acid and steps similar to Example 123b).
MS m/e (ESI) 359(MH⁺—CF₃COOH)

EXAMPLE 130

7-(2-Methoxycarbonylphenyl)-1,3-dimethyl-8-(piperazin-1-yl)-3,7-dihydropurine-2,6-dione trifluoroacetate

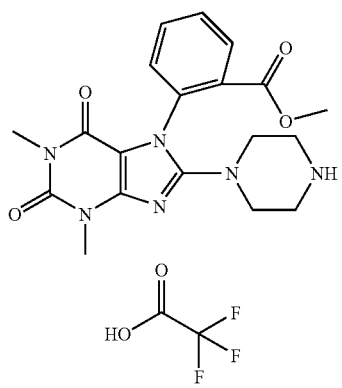

The title compound was obtained using 2-methoxycarbonylphenyl boronic acid and steps similar to Example 123b).
MS m/e (ESI) 399(MH⁺—CF₃COOH)

EXAMPLE 131

7-(2-Acetylphenyl)-1,3-dimethyl-8-(piperazin-1-yl)-3,7-dihydropurine-2,6-dione trifluoroacetate

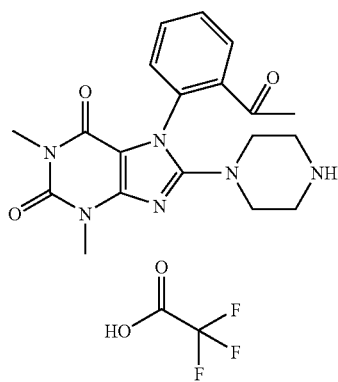

The title compound was obtained using 2-acetylphenyl boronic acid and steps similar to Example 123b).
MS m/e (ESI) 383(MH⁺—CF₃COOH)

EXAMPLE 132

7-(3-Chlorophenyl)-1,3-dimethyl-8-(piperazin-1-yl)-3,7-dihydropurine-2,6-dione trifluoroacetate

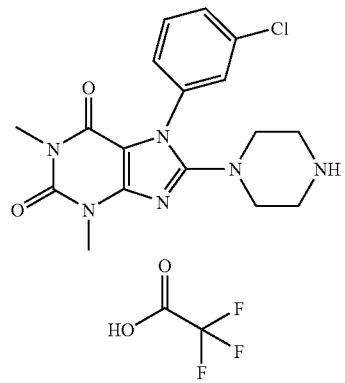

The title compound was obtained using 3-chlorophenyl boronic acid and steps similar to Example 123b).
MS m/e (ESI) 375(MH⁺—CF₃COOH)

EXAMPLE 133

7-(3-Thiophene)-1,3-dimethyl-8-(piperazin-1-yl)-3,7-dihydropurine-2,6-dione trifluoroacetate

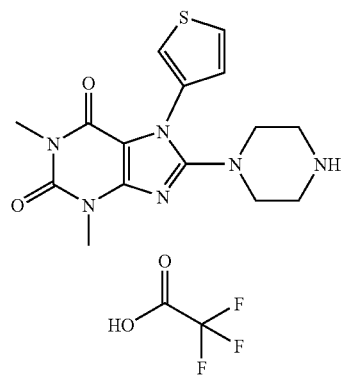

The title compound was obtained using 3-thiophene boronic acid and steps similar to Example 123b).
MS m/e (ESI) 347(MH⁺—CF₃COOH)

EXAMPLE 134

7-(Benzo[b]thiophen-3-yl)-1,3-dimethyl-8-(piperazin-1-yl)-3,7-dihydropurine-2,6-dione trifluoroacetate

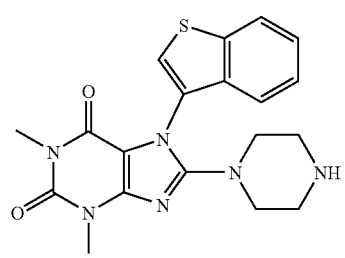

-continued

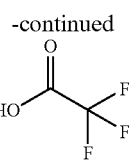

The title compound was obtained using 3-benzothiophene boronic acid and steps similar to Example 123b).
MS m/e (ESI) 397(MH⁺—CF₃COOH)

EXAMPLE 135

1,3-Dimethyl-8-(piperazin-1-yl)-7-(quinolin-8-yl)-3,7-dihydropurine-2,6-dione trifluoroacetate

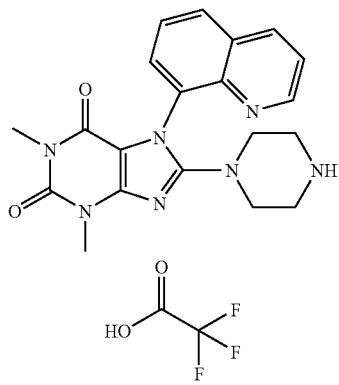

The title compound was obtained using 8-quinoline boronic acid and steps similar to Example 123b).
MS m/e (ESI) 392(MH⁺—CF₃COOH)

EXAMPLE 136

7-(2-Benzyloxyphenyl)-1,3-dimethyl-8-(piperazin-1-yl)-3,7-dihydropurine-2,6-dione trifluoroacetate

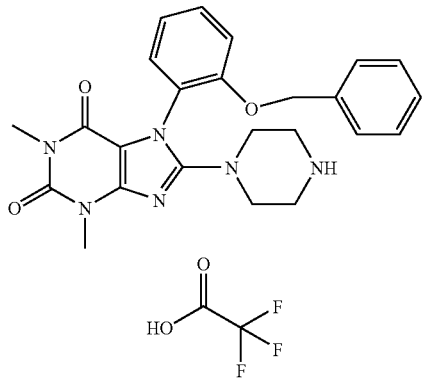

4-[7-(2-benzyloxyphenyl)-1,3-dimethyl-2,6-dioxo-2,3,6,7-tetrahydro-1H-purin-8-yl]piperazine-1-carboxylic acid tert-butyl ester was obtained using (2-benzyloxy)phenyl boronic acid and steps similar to Example 123. This was dissolved in trifluoroacetic acid, and the solution was concentrated. The residue was purified by reversed phase high performance liquid chromatography to give the title compound.
MS m/e (ESI) 447(MH⁺—CF₃COOH)

EXAMPLE 137

7-(2-Hydroxyphenyl)-1,3-dimethyl-8-(piperazin-1-yl)-3,7-dihydropurine-2,6-dione trifluoroacetate

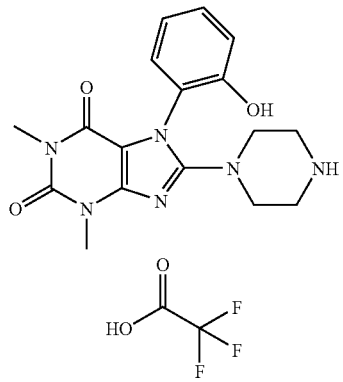

4-[7-(2-Benzyloxyphenyl)-1,3-dimethyl-2,6-dioxo-2,3,6,7-tetrahydro-1H-purin-8-yl]piperazine-1-carboxylic acid tert-butyl ester of Example 136 was debenzylated with 10% palladium on carbon-hydrogen/tetrahydrofuran-methanol, and the title compound was obtained using steps similar to Example 136.
MS m/e (ESI) 357(MH⁺—CF₃COOH)

EXAMPLE 138

7-(2-Carboxyphenyl)-1,3-dimethyl-8-(piperazin-1-yl)-3,7-dihydropurine-2,6-dione trifluoroacetate

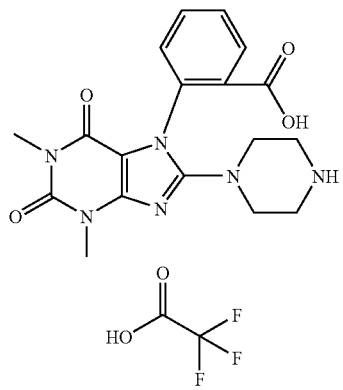

4-[7-(2-methoxycarbonylphenyl)-1,3-dimethyl-2,6-dioxo-2,3,6,7-tetrahydro-1H-purin-8-yl]piperazine-1-carboxylic acid tert-butyl ester was obtained using 2-methoxycarbonylphenyl boronic acid and steps similar to Example 130. This product (1.63 g) was dissolved in ethanol (20 ml) and tetrahydrofuran (10 ml), and 5 N sodium hydroxide aqueous solution (2 ml) was added thereto. The reaction mixture was stirred at room temperature overnight, neutralized with 1 N hydrochloric acid, and extracted with ethyl acetate. The organic layer was dried over anhydrous magnesium sulfate, filtered, and the filtrate was concentrated under reduced pressure to give 1.43 g of 4-[7-(2-carboxyphenyl)-1,3-dimethyl-2,6-dioxo-2,3,6,7-tetrahydro-1H-purin-8-yl]piperazine-1-carboxylic acid tert-butylester. This product (15 mg) was dissolved in trifluoroacetic acid, and the solution was concentrated. The residue was purified by reversed phase high performance liquid chromatography to give 9.09 mg of the title compound.

MS m/e (ESI) 385(MH$^+$—CF$_3$COOH)

EXAMPLE 139

2-(1,3-Dimethyl-2,6-dioxo-8-(piperazin-1-yl)-1,2,3,6-tetrahydropurin-7-yl)benzamide trifluoroacetate

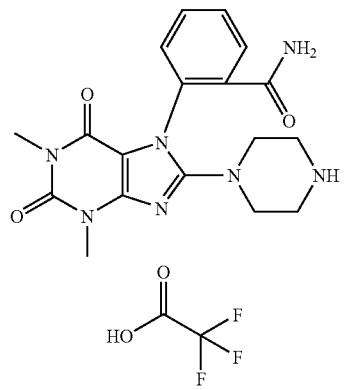

4-[7-(2-Carboxyphenyl)-1,3-dimethyl-2,6-dioxo-2,3,6,7-tetrahydro-1H-purin-8-yl]piperazine-1-carboxylic acid tert-butyl ester (15 mg) was dissolved in tetrahydrofuran (1 ml), and triethylamine (7 μl) and ethyl chlorocarbonate (4 μl) were added thereto. Thirty percent aqueous ammonia was added, and the reaction mixture was stirred at room temperature overnight. The reaction solution was diluted with ethyl acetate, and washed with water. The organic layer was dried over anhydrous magnesium sulfate, filtered, and the filtrate was concentrated under reduced pressure. The residue was dissolved in trifluoroacetic acid, and the solution was concentrated. The residue was purified by reversed phase high performance liquid chromatography to give 7.09 mg of the title compound.

MS m/e (ESI) 384(MH$^+$—CF$_3$COOH)

EXAMPLE 140

[7-(2-Methoxyphenyl)-3-methyl-2,6-dioxo-8-(piperazin-1-yl)-2,3,6,7-tetrahydropurin-1-yl]-acetic acid ethyl ester trifluoroacetate a) 7-Benzyl-8-chloro-3-methyl-3,7-dihydropurine-2,6-dione

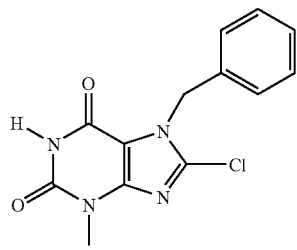

8-Chloro-3-methyl-3,7-dihydropurine-2,6-dione (200 mg) and potassium carbonate (152 mg) were suspended in N,N-dimethylformamide (10 ml), and benzyl bromide was added dropwise thereto while cooling on ice. The reaction mixture was left standing till reaching room temperature, and was stirred at room temperature for 13 hours. The resulting white suspension was diluted with ethyl acetate and water, and filtered to give 133 mg of the title compound.

$^1$H-NMR(d6-DMSO) δ: 3.32 (s, 3H) 5.49 (s, 2H) 7.25–7.39 (m, 5H) 11.37 (br s, 1H)

b) 4-(7-Benzyl-3-methyl-2,6-dioxo-2,3,6,7-tetrahydro-1H-purin-8-yl)piperazine-1-carboxylic acid tert-butyl ester

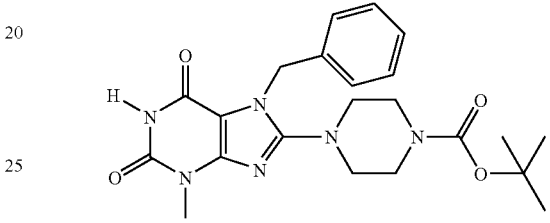

7-Benzyl-8-chloro-3-methyl-3,7-dihydropurine-2,6-dione (130 mg) and 1-piperazine carboxylic acid tert-butyl ester (250 mg) were stirred at 150° C. for 1 hour. The reaction mixture was diluted with ethyl acetate, and the resulting suspension was filtered to give white solid. This solid was purified by silica gel column chromatography to obtain 190 mg of the title compound from a fraction eluted with ethyl acetate.

$^1$H-NMR(d6-DMSO) δ: 1.40 (s, 9H) 3.09 (s, 3H) 3.25–3.42 (m, 8H) 5.35 (s, 2H) 7.18–7.38 (m, 5H) 10.97 (br s, 1H)

c) 4-[7-(Benzyl)-1-(ethoxycarbonylmethyl)-3-methyl-2,6-dioxo-2,3,6,7-tetrahydro-1H-purin-8-yl]piperazine-1-carboxylic acid tert-butyl ester

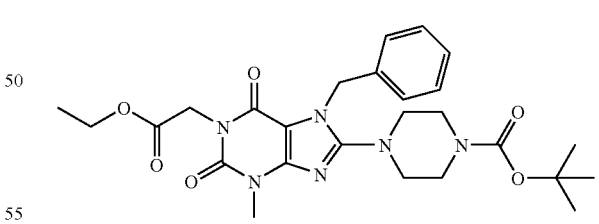

4-[7-(Benzyl)-3-methyl-2,6-dioxo-2,3,6,7-tetrahydro-1H-purin-8-yl]piperazine-1-carboxylic acid tert-butyl ester (182 mg) was dissolved in N,N-dimethylformamide (2 ml), and potassium carbonate (90 mg) and ethyl bromoacetate (0.06 ml) were added thereto. The reaction solution was stirred at room temperature overnight, diluted with ethyl acetate, and washed with water. The organic layer was dried over anhydrous magnesium sulfate, filtered, and the filtrate was concentrated under reduced pressure to give the title compound.

d) 4-[1-(Ethoxycarbonylmethyl)-3-methyl-2,6-dioxo-2,3,6,7-tetrahydro-1H-purin-8-yl]piperazine-1-carboxylic acid tert-butyl ester

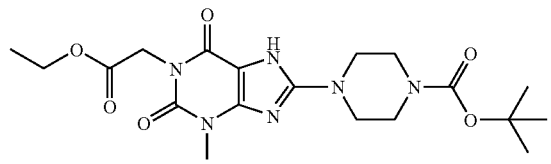

4-[7-Benzyl-1-(ethoxycarbonylmethyl)-3-methyl-2,6-dioxo-2,3,6,7-tetrahydro-1H-purin-8-yl]piperazine-1-carboxylic acid tert-butyl ester was dissolved in acetic acid, and palladium hydroxide (ca. 10 mg) was added thereto. The reaction mixture was stirred at room temperature under hydrogen atmosphere overnight, filtered, and the filtrate was concentrated. The residue was dissolved in ethyl acetate, and washed with saturated aqueous solution of sodium bicarbonate. The organic layer was dried over anhydrous magnesium sulfate, filtered, and the filtrate was concentrated under reduced pressure to give 111 mg of the title compound.

e) 4-[7-(2-Methoxyphenyl)-1-(ethoxycarbonylmethyl)-3-methyl-2,6-dioxo-2,3,6,7-tetrahydro-1H-purin-8-yl]piperazine-1-carboxylic acid tert-butyl ester

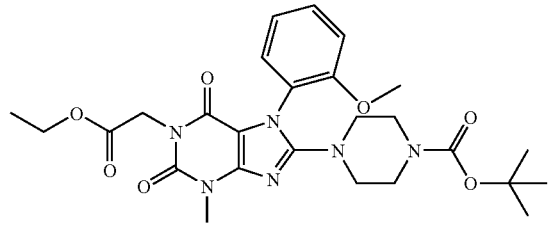

4-[1-(Ethoxycarbonylmethyl)-3-methyl-2,6-dioxo-2,3,6,7-tetrahydro-1H-purin-8-yl]piperazine-1-carboxylic acid tert-butyl ester, 2-methoxyphenyl boronic acid (60 mg), and copper (II) acetate (200 mg) were dissolved in anhydrous tetrahydrofuran (5 ml), and pyridine (0.2 ml) was added thereto. The reaction mixture was stirred at room temperature for 3 days, filtered through a short column packed with NH-silica gel, and the filtrate was concentrated. The residue was purified by silica gel column chromatography to obtain 18 mg of the title compound from a fraction eluted with hexane-ethyl acetate (1:1).

f) [7-(2-Methoxyphenyl)-3-methyl-2,6-dioxo-8-(piperazin-1-yl)-2,3,6,7-tetrahydropurin-1-yl]acetic acid ethyl ester trifluoroacetate

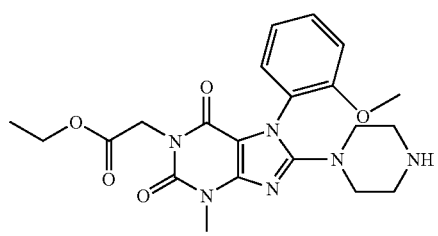

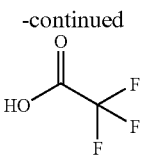

4-[7-(2-Methoxyphenyl)-1-(ethoxycarbonylmethyl)-3-methyl-2,6-dioxo-2,3,6,7-tetrahydro-1H-purin-8-yl]piperazine-1-carboxylic acid tert-butyl ester (10 mg) was dissolved in trifluoroacetic acid (0.5 ml), and the reaction mixture was stirred at room temperature for 30 minutes. After the solvent was removed, the residue was purified by reversed phase high performance liquid chromatography to give 4.92 mg of the title compound.

MS m/e (ESI) 443(MH$^+$—CF$_3$COOH)

EXAMPLE 141

[7-(2-Methoxyphenyl)-3-methyl-2,6-dioxo-8-(piperazin-1-yl)-2,3,6,7-tetrahydropurin-1-yl]acetic acid trifluoroacetate a) 4-[7-(2-Methoxyphenyl)-1-(carboxymethyl)-3-methyl-2,6-dioxo-2,3,6,7-tetrahydro-1H-purin-8-yl]piperazine-1-carboxylic acid tert-butyl ester

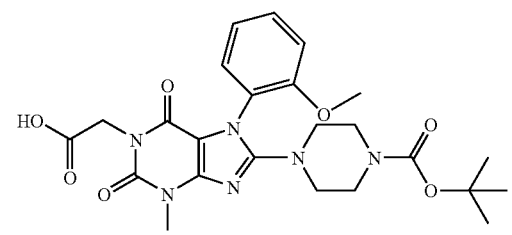

4-[7-(2-Methoxyphenyl)-1-(ethoxycarbonylmethyl)-3-methyl-2,6-dioxo-2,3,6,7-tetrahydro-1H-purin-8-yl]piperazine-1-carboxylic acid tert-butyl ester (9 mg) was dissolved in ethanol (1 ml), and 5 N sodium hydroxide aqueous solution (0.1 ml) was added thereto. The reaction mixture was left standing at room temperature for 5 hours, and neutralized with 1 N hydrochloric acid. The reaction mixture was extracted with ethyl acetate, the organic layer was dried over anhydrous magnesium sulfate, and was filtered. The filtrate was concentrated under reduced pressure to give 3 mg of the title compound.

b) [7-(2-Methoxyphenyl)-3-methyl-2,6-dioxo-8-(piperazin-1-yl)-2,3,6,7-tetrahydropurin-1-yl]-acetic acid trifluoroacetate

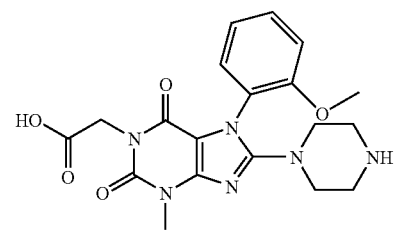

-continued

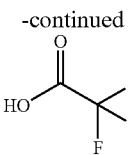

4-[7-(2-Methoxyphenyl)-1-(carboxymethyl)-3-methyl-2,6-dioxo-2,3,6,7-tetrahydro-1H-purin-8-yl]piperazine-1-carboxylic acid tert-butyl ester (3 mg) was dissolved in trifluoroacetic acid (0.5 ml), and the reaction mixture was stirred at room temperature for 30 minutes. After the solvent was removed, the residue was purified by reversed phase high performance liquid chromatography to give 4.14 mg of the title compound.

MS m/e (ESI) 415(MH$^+$—CF$_3$COOH)

EXAMPLE 142

7-(2-Cyanophenyl)-1,3-dimethyl-8-(piperazin-1-yl)-3,7-dihydropurine-2,6-dione trifluoroacetate a) 4-[7-(2-Formylphenyl)-1,3-dimethyl-2,6-dioxo-2,3,6,7-tetrahydro-1H-purin-8-yl]piperazine-1-carboxylic acid tert-butyl ester

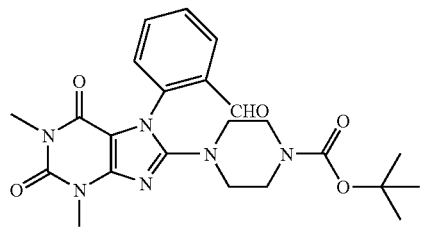

4-(1,3-Dimethyl-2,6-dioxo-2,3,6,7-tetrahydro-1H-purin-8-yl)piperazine-1-carboxylic acid tert-butyl ester (226 mg), 2-formylphenyl boronic acid (200 mg), and copper (II) acetate (200 mg) were suspended in anhydrous tetrahydrofuran (5 ml), and pyridine (0.2 ml) was added thereto. The reaction mixture was stirred at room temperature for 5 days, filtered through a short column filled with silica gel, and the filtrate was concentrated. The residue was purified by silica gel column chromatography to obtain 51 mg of the title compound from a fraction eluted with hexane-ethyl acetate (1:1).

$^1$H-NMR(CDCl$_3$) δ: 1.42 (s, 9H) 3.10–3.14 (m, 4H) 3.25–3.34 (m, 7H) 3.60 (s, 3H) 7.53 (dd, J=1.2, 8.0 Hz, 1H) 7.63–7.67 (m, 1H) 7.73–7.78 (m, 1H) 8.02–8.04 (m, 1H) 9.86 (s, 1H)

b) 7-(2-Cyanophenyl)-1,3-dimethyl-8-(piperazin-1-yl)-3,7-dihydropurine-2,6-dione trifluoroacetate

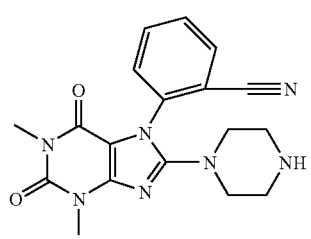

-continued

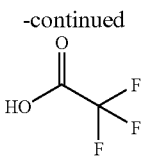

4-[7-(2-Formylphenyl)-1,3-dimethyl-2,6-dioxo-2,3,6,7-tetrahydro-1H-purin-8-yl]piperazine-1-carboxylic acid tert-butyl ester (13 mg) and hydroxylamine hydrochloride (10 mg) were dissolved in ethanol (1 ml) and water (0.2 ml), and potassium acetate (ca. 10 mg) was added thereto. The reaction solution was stirred for 0.5 hour at room temperature, diluted with ethyl acetate, and washed with sodium bicarbonate aqueous solution. The organic layer was dried over anhydrous magnesium sulfate, filtered, and the filtrate was concentrated under reduced pressure to give 4-[7-[2-(hydroxyiminomethyl)phenyl]-1,3-dimethyl-2,6-dioxo-2,3,6,7-tetrahydro-1H-purin-8-yl]piperazine-1-carboxylic acid tert-butyl ester. This was dissolved in dichloromethane (0.5 ml) and triethylamine (ca. 0.05 ml) and methanesulfonyl chloride (0.05 ml) were added thereto. The reaction mixture was stirred at room temperature for 0.5 hour, and the solvent was removed. The residue was dissolved in trifluoroacetic acid, and the solution was concentrated. The residue was purified by reversed phase high performance liquid chromatography to give 4.14 mg of the title compound.

MS m/e (ESI) 366(MH$^+$—CF$_3$COOH)

EXAMPLE 143

7-(2-Hydroxymethylphenyl)-1,3-dimethyl-8-(piperazin-1-yl)-3,7-dihydropurine-2,6-dione trifluoroacetate

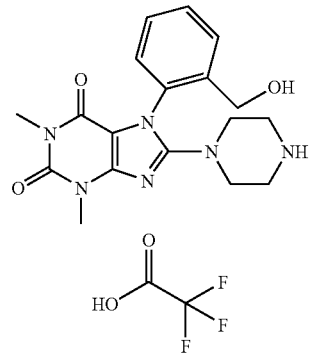

EXAMPLE 144

7-(2-Trifluoroacetoxymethylphenyl)-1,3-dimethyl-8-(piperazin-1-yl)-3,7-dihydropurine-2,6-dione trifluoroacetate

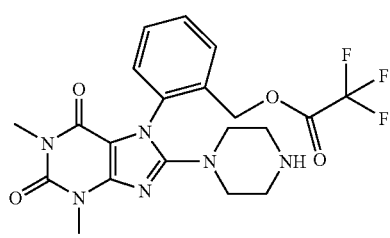

-continued

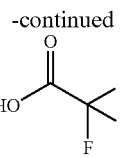

4-[7-(2-Formylphenyl)-1,3-dimethyl-2,6-dioxo-2,3,6,7-tetrahydro-1H-purin-8-yl]piperazine-1-carboxylic acid tert-butyl ester (27 mg) was dissolved in anhydrous tetrahydrofuran (0.5 ml) and ethanol (0.5 ml), and sodium borohydride (20 mg) was added thereto. The reaction solution was stirred at room temperature for 1 hour, diluted with ethyl acetate, and washed with 1 N hydrochloric acid. The organic layer was dried over anhydrous magnesium sulfate, filtered, and the filtrate was concentrated under reduced pressure to give 28 mg of 4-[7-(2-hydroxymethylphenyl)-1,3-dimethyl-2,6-dioxo-2,3,6,7-tetrahydro-1H-purin-8-yl]piperazine-1-carboxylic acid tert-butyl ester. This product (8 mg) was dissolved in trifluoroacetic acid, and the solution was concentrated. The residue was purified by reversed phase high performance liquid chromatography to give 1.60 mg of 7-(2-hydroxymethylphenyl)-1,3-dimethyl-8-(piperazin-1-yl)-3,7-dihydropurine-2,6-dione trifluoroacetate [MS m/e (ESI) 371(MH$^+$—CF$_3$COOH)] and 0.46 mg of 7-(2-trifluoroacetoxymethylphenyl)-1,3-dimethyl-8-(piperazin-1-yl)-3,7-dihydropurine-2,6-dione trifluoroacetate [MS m/e (ESI) 467(MH$^+$—CF$_3$COOH)].

EXAMPLE 145

7-(2-Fluoromethylphenyl)-1,3-dimethyl-8-(piperazin-1-yl)-3,7-dihydropurine-2,6-dione trifluoroacetate

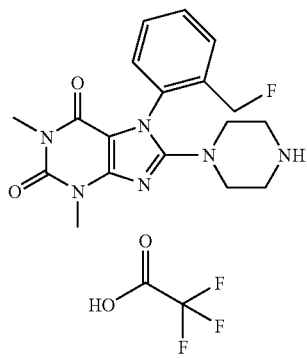

4-[7-(2-Hydroxymethylphenyl)-1,3-dimethyl-2,6-dioxo-2,3,6,7-tetrahydro-1H-purin-8-yl]piperazine-1-carboxylic acid tert-butyl ester (10 mg) was dissolved in dichloromethane (1 ml), and tris(diethylamino)sulfur trifluoride (0.01 ml) was added thereto. The reaction solution was stirred at room temperature overnight, diluted with ethyl acetate, and washed with water. The organic layer was dried over anhydrous magnesium sulfate, filtered, and the filtrate was concentrated under reduced pressure. The residue was dissolved in trifluoroacetic acid, and the solution was concentrated. The residue was purified by reversed phase high performance liquid chromatography to give 1.28 mg of the title compound.

MS m/e (ESI) 373(MH$^+$—CF$_3$COOH)

EXAMPLE 146

7-(2-Methoxymethylphenyl)-1,3-dimethyl-8-(piperazin-1-yl)-3,7-dihydropurine-2,6-dione trifluoroacetate

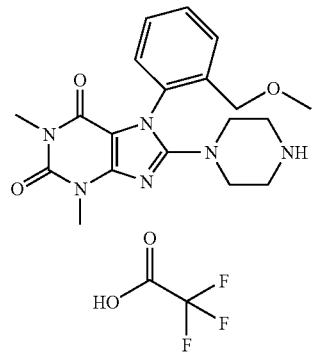

4-[7-(2-Hydroxymethylphenyl)-1,3-dimethyl-2,6-dioxo-2,3,6,7-tetrahydro-1H-purin-8-yl]piperazine-1-carboxylic acid tert-butyl ester (10 mg) was dissolved in tetrahydrofuran (1 ml), and methyl iodide (0.1 ml) and sodium hydride (10 mg) were added thereto. The reaction solution was stirred at room temperature for 3 days, diluted with ethyl acetate, and washed with water. The organic layer was dried over anhydrous magnesium sulfate, filtered, and the filtrate was concentrated under reduced pressure. The residue was dissolved in trifluoroacetic acid, and the solution was concentrated. The residue was purified by reversed phase high performance liquid chromatography to give 3.11 mg of the title compound:

MS m/e (ESI) 385(MH$^+$—CF$_3$COOH)

EXAMPLE 147

7-(2-Vinylphenyl)-1,3-dimethyl-8-(piperazin-1-yl)-3,7-dihydropurine-2,6-dione trifluoroacetate

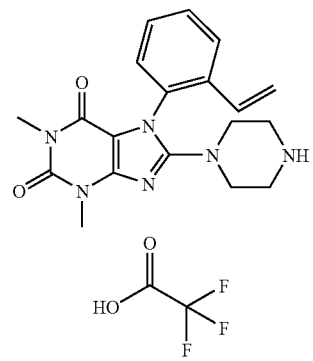

Potassium tert-butoxide (9 mg) was dissolved in tetrahydrofuran (1 ml), and methyl triphenyl phosphonium bromide (31 mg) was added thereto. The reaction mixture was stirred at room temperature for 30 minutes, and a solution of 4-[7-(2-formylphenyl)-1,3-dimethyl-2,6-dioxo-2,3,6,7-tetrahydro-1H-purin-8-yl]piperazine-1-carboxylic acid tert-butyl ester (20 mg) in tetrahydrofuran (1 ml) was added thereto. The reaction solution was stirred at room temperature for 1 hour, diluted with ethyl acetate, and washed with water. The organic layer was dried over anhydrous magnesium sulfate, filtered, and the filtrate was concentrated under reduced pressure to give 40 mg of 4-[7-(2-vinylphenyl)-1,3-dimethyl-2,6-dioxo-2,3,6,7-tetrahydro-1H-purin-8-yl]piperazine-1-carboxylic acid tert-butyl ester. This product (12 mg) was dissolved in trifluoroacetic acid, and the solution was concentrated. The residue was purified by reversed phase high performance liquid chromatography to give 4.38 mg of the title compound.
MS m/e (ESI) 367(MH$^+$—CF$_3$COOH)

EXAMPLE 148

7-(2-Ethylphenyl)-1,3-dimethyl-8-(piperazin-1-yl)-3,7-dihydropurine-2,6-dione trifluoroacetate

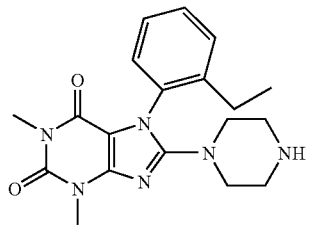

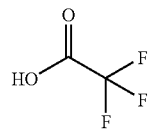

4-[7-(2-Vinylphenyl)-1,3-dimethyl-2,6-dioxo-2,3,6,7-tetrahydro-1H-purin-8-yl]piperazine-1-carboxylic acid tert-butyl ester (28 mg) was dissolved in tetrahydrofuran (0.5 ml) and ethanol (1 ml), and 10% palladium on carbon (10 mg) was added thereto. The reaction mixture was stirred under hydrogen atmosphere at room temperature for 6 hours, filtered through Celite, and the filtrate was concentrated. The residue was dissolved in trifluoroacetic acid, and the solution was concentrated. The residue was purified by reversed phase high performance liquid chromatography to give 9.54 mg of the title compound.
MS m/e (ESI) 369(MH$^+$—CF$_3$COOH)

EXAMPLE 149

7-[2-(1-Propenyl)phenyl]-1,3-dimethyl-8-(piperazin-1-yl)-3,7-dihydropurine-2,6-dione trifluoroacetate

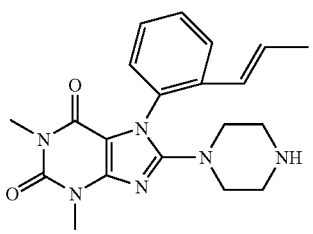

-continued

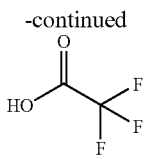

The title compound was obtained using ethyl triphenyl phosphonium bromide and steps similar to Example 147.
MS m/e (ESI) 381(MH$^+$—CF$_3$COOH)

EXAMPLE 150

3-[2-(1,3-Dimethyl-2,6-dioxo-8-(piperazin-1-yl)-1,2,3,6-tetrahydropurin-7-yl)-phenyl]acrylic acid ethyl ester trifluoroacetate

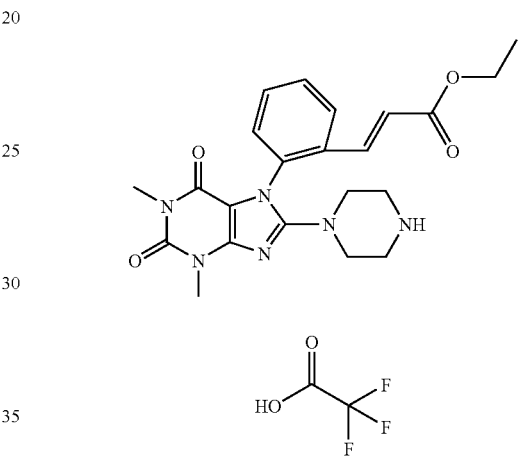

The title compound was obtained using triethyl phosphonoacetate and steps similar to Example 147.
MS m/e (ESI) 439(MH$^+$—CF$_3$COOH)

EXAMPLE 151

7-(2-Formylphenyl)-1,3-dimethyl-8-(piperazin-1-yl)-3,7-dihydropurine-2,6-dione trifluoroacetate

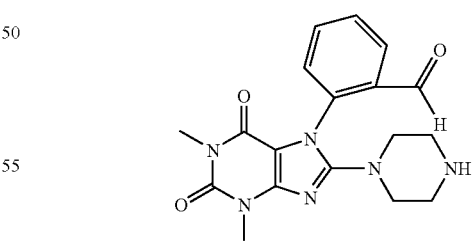

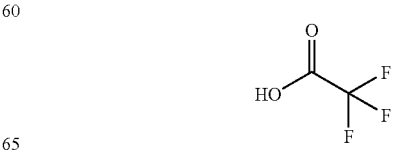

EXAMPLE 152

7-(2-Difluoromethylphenyl)-1,3-dimethyl-8-(piperazin-1-yl)-3,7-dihydropurine-2,6-dione trifluoroacetate

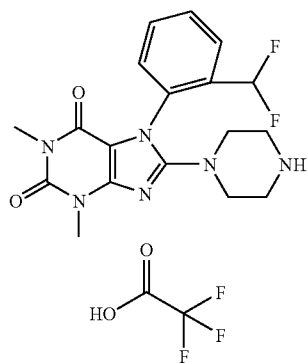

4-[7-(2-Formylphenyl)-1,3-dimethyl-2,6-dioxo-2,3,6,7-tetrahydro-1H-purin-8-yl]piperazine-1-carboxylic acid tert-butyl ester (10 mg) was dissolved in dichloromethane (1 ml), and tris(diethylamino)sulfur trifluoride (0.1 ml) was added thereto. The reaction solution was stirred at room temperature overnight, diluted with ethyl acetate, and washed with water. The organic layer was dried over anhydrous magnesium sulfate, filtered, and the filtrate was concentrated under reduced pressure. The residue was dissolved in trifluoroacetic acid, and the solution was concentrated. The residue was purified by reversed phase high performance liquid chromatography to give 4.56 mg of 7-(2-formylphenyl)-1,3-dimethyl-8-(piperazin-1-yl)-3,7-dihydropurine-2,6-dione trifluoroacetate [MS m/e (ESI) 369(MH$^+$—CF$_3$COOH)] and 0.32 mg of 7-(2-difluoromethylphenyl)-1,3-dimethyl-8-(piperazin-1-yl)-3,7-dihydropurine-2,6-dione trifluoroacetate [MS m/e (ESI) 391(MH$^+$—CF$_3$COOH)].

EXAMPLE 153

7-(2-Chlorophenyl)-1,3-dimethyl-8-(piperazin-1-yl)-3,7-dihydropurine-2,6-dione a) 7-(2-Chlorophenyl)-1,3-dimethyl-3,7-dihydropurine-2,6-dione

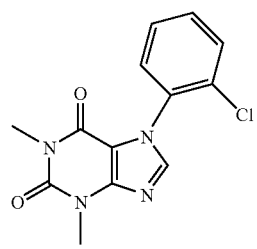

Theophylline (510 mg), 2-chlorophenyl boronic acid (1 g), and copper (II) acetate (220 mg) were suspended in N,N-dimethylformamide (10 ml), and pyridine (1 ml) was added thereto. The reaction mixture was stirred at room temperature overnight, diluted with ethyl acetate, and washed with 30% aqueous ammonia. The organic layer was dried over anhydrous magnesium sulfate, filtered, and the filtrate was concentrated under reduced pressure. The residue was triturated with ether to give 147 mg of the title compound.

$^1$H-NMR(CDCl$_3$) δ: 3.72 (s, 3H) 3.68 (s, 3H) 7.43–7.51 (m, 3H) 7.57–7.60 (m, 1H) 7.68 (s, 1H)

b) 8-Chloro-7-(2-chlorophenyl)-1,3-dimethyl-3,7-dihydropurine-2,6-dione

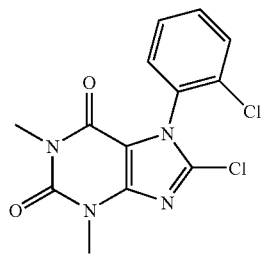

7-(2-Chlorophenyl)-1,3-dimethyl-3,7-dihydropurine-2,6-dione (138 mg) and N-chlorosuccinimide (78 mg) were suspended in N,N-dimethylformamide (1 ml). The reaction mixture was stirred at room temperature for 2 hours, diluted with ethyl acetate, and washed with water. The organic layer was dried over anhydrous magnesium sulfate, filtered, and the filtrate was concentrated under reduced pressure to give 151 mg of the title compound.

c) 4-[7-(2-Chlorophenyl)-1,3-dimethyl-2,6-dioxo-2,3,6,7-tetrahydro-1H-purin-8-yl]piperazine-1-carboxylic acid tert-butyl ester

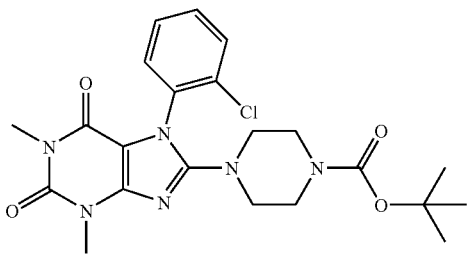

8-Chloro-7-(2-chlorophenyl)-1,3-dimethyl-3,7-dihydropurine-2,6-dione (142 mg) and piperazine-1-carboxylic acid tert-butyl ester (500 mg) were mixed, and the reaction mixture was stirred at 150° C. for 4 hours, diluted with ethyl acetate, and washed with water. The organic layer was dried over anhydrous magnesium sulfate, filtered, and the filtrate was concentrated under reduced pressure. The residue was purified by silica gel column chromatography to obtain 143 mg of the title compound from a fraction eluted with hexane-ethyl acetate (2:3).

$^1$H-NMR (CDCl$_3$) δ: 1.43 (s, 9H) 3.21–3.23 (m, 4H) 3.30 (s, 3H) 3.31–3.35 (m, 4H) 3.58 (s, 3H) 7.42–7.51 (m, 3H) 7.55–7.57 (m, 1H)

d) 7-(2-Chlorophenyl)-1,3-dimethyl-8-(piperazin-1-yl)-3,7-dihydropurine 2,6-dione

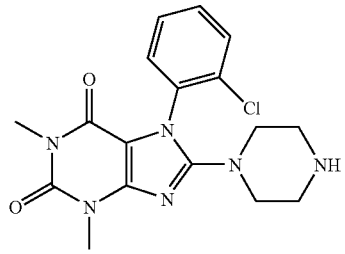

4-[7-(2-Chlorophenyl)-1,3-dimethyl-2,6-dioxo-2,3,6,7-tetrahydro-1H-purin-8-yl]piperazine-1-carboxylic acid tert-butyl ester (102 mg) was dissolved in trifluoroacetic acid (5 ml), and the solution was stirred at room temperature for 30 minutes. After the solvent was removed, the residue was purified by column chromatography using NH-silica gel to obtain 109 mg of the title compound from a fraction eluted with ethyl acetate-methanol (9:1).

$^1$H-NMR(CDCl$_3$) δ: 2.77 (dt, J=1.6, 4.8 Hz, 4H) 3.24 (t, J=5.2 Hz, 4H) 3.30 (s, 3H) 3.58 (s, 3H) 7.41–7.44 (m, 2H) 7.48–7.51 (m, 1H) 7.55–7.56 (m, 1H)

EXAMPLE 154

7-(2-Chlorophenyl)-8-(2,5-diaza-bicyclo[2.2.1]hept-2-yl)-1,3-dimethyl-3,7-dihydropurine-2,6-dione trifluoroacetate a) 2-(Hydroxymethyl)-4-(methanesulfonyloxy)pyrrolidine-1-carboxylic acid tert-butyl ester

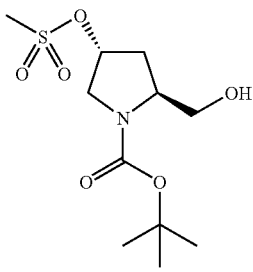

4-(Methanesulfonyloxy)pyrrolidine-1,2-dicarboxylic acid 1-tert-butyl ester 2-methyl ester (1.972 g) was dissolved in tetrahydrofuran (40 ml), and lithium borohydride (300 mg) was added thereto. The reaction mixture was stirred at room temperature overnight, additional lithium borohydride (1000 mg) was added, and the mixture was stirred at room temperature for 2 hours. 1 N Hydrochloric acid was added to the reaction solution, and then was extracted with ethyl acetate. The organic layer was dried over anhydrous magnesium sulfate, filtered, and the filtrate was concentrated under reduced pressure to give 1.715 g of the title compound.

b) 2-(Methanesulfonyloxymethyl)-4-(methanesulfonyloxy)pyrrolidine-1-carboxylic acid tert-butyl ester

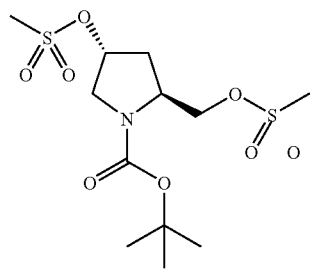

2-(Hydroxymethyl)-4-(methanesulfonyloxy)pyrrolidine-1-carboxylic acid tert-butyl ester (1.715 g) was dissolved in pyridine (20 ml), and methanesulfonylchloride (0.6 ml) was added thereto. The reaction mixture was stirred at room temperature overnight, diluted with ethyl acetate, and washed with 1 N hydrochloric acid. The organic layer was dried over anhydrous magnesium sulfate, filtered, and the filtrate was concentrated under reduced pressure to give 2 g of the title compound.

c) 5-Benzyl-2,5-(diaza-bicyclo[2.2.1]heptane)-2-carboxylic acid tert-butyl ester

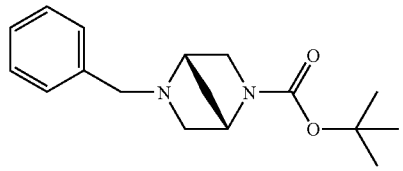

2-(Methanesulfonyloxymethyl)-4-(methanesulfonyloxy)pyrrolidine-1-carboxylic acid tert-butyl ester (1.88 g) was dissolved in benzylamine (10 ml), and the reaction solution was stirred at 60° C. overnight, then diluted with ethyl acetate, and washed with water. The organic layer was dried over anhydrous magnesium sulfate, filtered, and the filtrate was concentrated under reduced pressure. The residue was purified by silica gel column chromatography to obtain 1.221 g of the title compound from a fraction eluted with hexane-ethyl acetate (1:2).

$^1$H-NMR(CDCl$_3$) δ: 1.46 (s, 9H) 1.60–1.74 (m, 1H) 1.86 (brt, J=8.0 Hz, 1H) 2.54, 2.73 (each d, J=9.6 Hz, 1H) 2.85–2.93 (m, 1H) 3.11–3.19 (m, 1H) 3.45 (d, J=13.6 Hz, 1H) 3.50, 3.63 (each d, J=10.0 and 10.4 Hz, 1H) 3.73 (d, J=8.0 Hz, 2H) 4.24, 4.38 (each s, 1H) 7.22–7.35 (m, 5H)

d) 2,5-(Diaza-bicyclo[2.2.1]heptane)-2-carboxylic acid tert-butyl ester

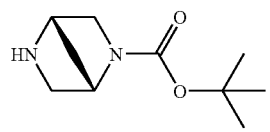

5-Benzyl-2,5-(diaza-bicyclo[2.2.1]heptane)-2-carboxylic acid tert-butyl ester (1.221 g) was dissolved in ethanol (50 ml), and 10% palladium on carbon (1 g) was added thereto. The reaction mixture was stirred under hydrogen atmosphere at room temperature for 3 days, filtered, and the filtrate was concentrated under reduced pressure to give 820 mg of the title compound.

e) 7-(2-Chlorophenyl)-8-(2,5-diaza-bicyclo[2.2.1] hept-2-yl)-1,3-dimethyl-3,7-dihydropurine-2,6-dione trifluoroacetate

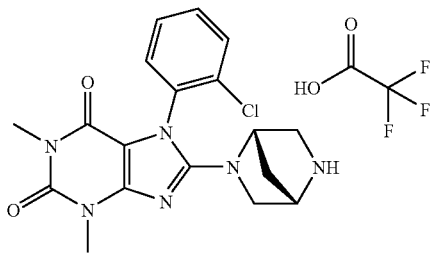

2,5-(Diaza-bicyclo[2.2.1]heptane)-2-carboxylic acid tert-butyl ester (50 mg) and 8-chloro-7-(2-chlorophenyl)-1,3-dimethyl-3,7-dihydropurine-2,6-dione (10 mg) were mixed, and the mixture was stirred at 150° C. for 3 hours. The residue was dissolved in trifluoroacetic acid, and the solution was concentrated. The residue was purified by reversed phase high performance liquid chromatography to give 5.10 mg of the title compound.

MS m/e (ESI) 387(MH$^+$—CF$_3$COOH)

EXAMPLE 155

7-(2-Methoxyphenyl)-1,3-dimethyl-8-(piperazin-1-yl)-3,7-dihydropurine-2,6-dione trifluoroacetate a) 7-(2-Methoxyphenyl)-1,3-dimethyl-3,7-dihydropurine-2,6-dione

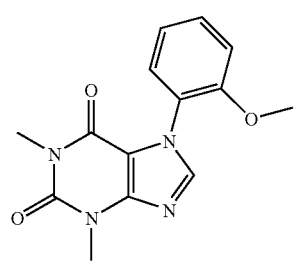

The title compound was obtained using 2-methoxyphenyl boronic acid and steps similar to Example 153a).

$^1$H-NMR(CDCl$_3$) δ: 3.37 (s, 3H) 3.66 (s, 3H) 3.81 (s, 3H) 7.05–7.09 (m, 2H) 7.35 (dd, J=2.0, 8.8 Hz, 1H) 7.46 (dt, J=2.0, 8.0 Hz, 1H) 7.68 (s, 1H)

b) 8-Chloro-7-(2-methoxyphenyl)-1,3-dimethyl-3,7-dihydropurine-2,6-dione

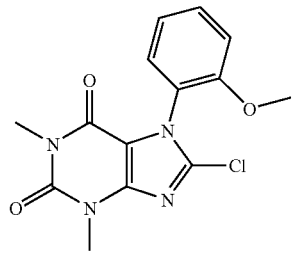

The title compound was obtained using 7-(2-methoxyphenyl)-1,3-dimethyl-3,7-dihydropurine-2,6-dione and steps similar to Example 153b).

c) 8-Chloro-7-(2-methoxyphenyl)-1,3-dimethyl-3,7-dihydropurine-2,6-dione trifluoroacetate

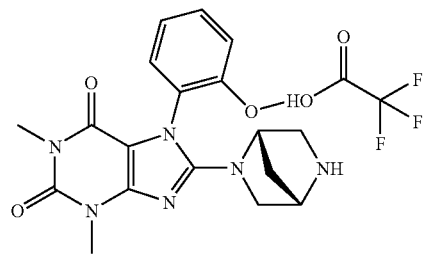

The title compound was obtained using 8-chloro-7-(2-methoxyphenyl)-1,3-dimethyl-3,7-dihydropurine-2,6-dione and steps similar to Example 154e).

MS m/e (ESI) 383(MH$^+$—CF$_3$COOH)

EXAMPLE 156

7-(2-Chlorophenyl)-3-methyl-8-(piperazin-1-yl)-3,7-dihydropurine-2,6-dione trifluoroacetate a) 7-Benzyl-3-methyl-3,7-dihydropurine-2,6-dione

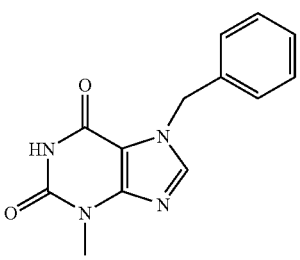

3-Methylxanthine (2.882 g) was suspended in N,N-dimethylformamide (40 ml), and potassium carbonate (3 g) and benzyl bromide (2.5 ml) was added thereto. The reaction mixture was stirred at room temperature overnight, diluted with ethyl acetate, and washed with 1 N hydrochloric acid.

The deposited crystals were collected by filtration and washed with ethyl acetate to give 3.18 g of the title compound.

¹H-NMR (d⁶-DMSO) δ: 3.32 (s, 3H) 5.42 (s, 2H) 7.27–7.35 (m, 5H) 8.21 (s, 1H) 11.13 (s, 1H)

b) 2,2-Dimethylpropionic acid 7-benzyl-3-methyl-2,6-dioxo-2,3,6,7-tetrahydropurin-1-ylmethyl ester

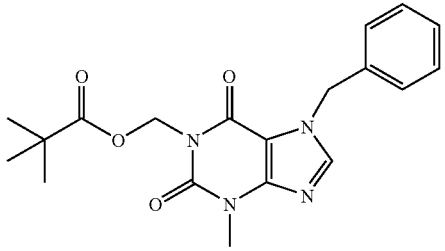

7-Benzyl-3-methyl-3,7-dihydropurine-2,6-dione (3.18 g) was suspended in N,N-dimethylformamide (40 ml), and potassium carbonate (2.6 g) and chloromethyl pivalate (2.15 ml) were added thereto. The reaction solution was stirred at 40° C. overnight, then diluted with ethyl acetate, and washed with 1 N hydrochloric acid. The organic layer was dried over anhydrous magnesium sulfate, filtered, and the filtrate was concentrated under reduced pressure. The residue was purified by silica gel column chromatography to obtain 4.26 g of the title compound from a fraction eluted with hexane-ethyl acetate (1:3).

¹H-NMR(CDCl₃) δ: 1.19 (s, 9H) 3.58 (s, 3H) 5.48 (s, 2H) 6.04 (s, 2H) 7.32–7.39 (m, 5H) 7.58 (s, 1H)

c) 2,2-Dimethylpropionic acid 3-methyl-2,6-dioxo-2,3,6,7-tetrahydropurin-1-ylmethyl ester

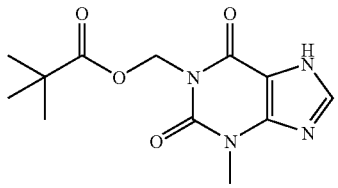

2,2-Dimethylpropionic acid 7-benzyl-3-methyl-2,6-dioxo-2,3,6,7-tetrahydropurin-1-ylmethyl ester (4.26 g) was dissolved in acetic acid (100 ml), and 10% palladium on carbon (1.5 g) was added thereto. The reaction mixture was stirred under hydrogen atmosphere at room temperature overnight, filtered through Celite, and the filtrate was concentrated to give 2.98 g of the title compound.

¹H-NMR(CDCl₃) δ: 1.19 (s, 9H) 3.66 (s, 3H) 6.12 (s, 2H) 7.86 (s, 1H)

d) 2,2-Dimethyl-propionic acid 7-(2-chlorophenyl)-3-methyl-2,6-dioxo-2,3,6,7-tetrahydropurin-1-ylmethyl ester

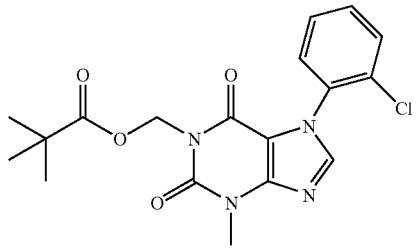

The title compound was obtained using 2,2-dimethylpropionic acid 3-methyl-2,6-dioxo-2,3,6,7-tetrahydropurin-1-ylmethyl ester and steps similar to Example 153a).

e) 8-Chloro-7-(2-chlorophenyl)-3-methyl-3,7-dihydropurine-2,6-dione

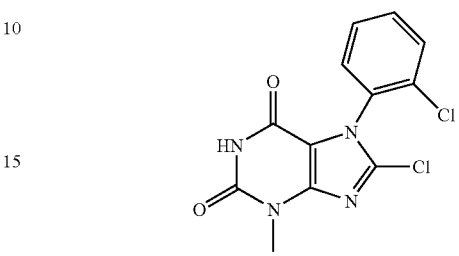

2,2-Dimethyl-propionic acid 7-(2-chlorophenyl)-3-methyl-2,6-dioxo-2,3,6,7-tetrahydropurin-1-ylmethyl ester (144 mg) was dissolved in methanol (2 ml) and tetrahydrofuran (1 ml), and sodium hydride (20 mg) was added thereto. The reaction solution was stirred at room temperature overnight, diluted with ethyl acetate, and washed with 1 N hydrochloric acid. The organic layer was dried over anhydrous magnesium sulfate, filtered, and the filtrate was concentrated under reduced pressure. The residue was triturated with ethyl acetate-diethyl ether to give 72 mg of 7-(2-chlorophenyl)-3-methyl-3,7-dihydropurine-2,6-dione. This was dissolved in N,N-dimethylformamide (1 ml), and N-chlorosuccinimide (35 mg) was added thereto. The reaction solution was stirred at room temperature overnight, diluted with ethyl acetate, and washed with 1 N hydrochloric acid. The organic layer was dried over anhydrous magnesium sulfate, filtered, and the filtrate was concentrated under reduced pressure to give 58 mg of the title compound.

¹H-NMR(CDCl₃) δ: 3.59 (s, 3H) 7.42 (dd, J=1.6, 7.6 Hz, 1H) 7.47 (dt, J=1.6, 9.2 Hz, 1H) 7.54 (dt, J=1.6, 7.2 Hz, 1H) 7.61 (dt, J=1.6, 7.6 Hz, 1H) 7.93 (br, 1H)

f) 4-[7-(2-Chlorophenyl)-3-methyl-2,6-dioxo-2,3,6,7-tetrahydro-1H-purin-8-yl]piperazine-1-carboxylic acid tert-butyl ester

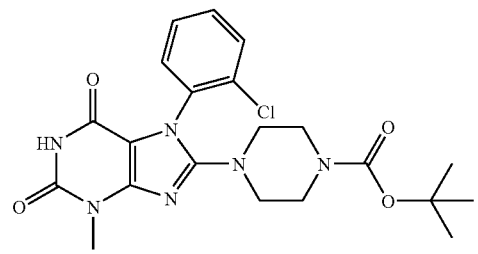

8-Chloro-7-(2-chlorophenyl)-3-methyl-3,7-dihydropurine-2,6-dione (58 mg) and 1-(tert-butoxycarbonyl)piperazine (150 mg) were mixed. The reaction solution was stirred at 150° C. for 4 hours, then diluted with ethyl acetate, and washed with water. The organic layer was dried over anhydrous magnesium sulfate, filtered, and the filtrate was concentrated under reduced pressure. The residue was purified by silica gel chromatography to obtain 44 mg of the title compound from a fraction eluted with ethyl acetate.

$^1$H-NMR(CDCl$_3$) δ: 1.41 (s, 9H) 3.17–3.24 (m, 4H) 3.25–3.41 (m, 4H) 3.53 (s, 3H) 7.41–7.51 (m, 3H) 7.55 (dd, J=2.0, 7.6 Hz, 1H) 7.66 (br, 1H)

g) 7-(2-Chlorophenyl)-3-methyl-8-(piperazin-1-yl)-3,7-dihydropurine-2,6-dione trifluoroacetate

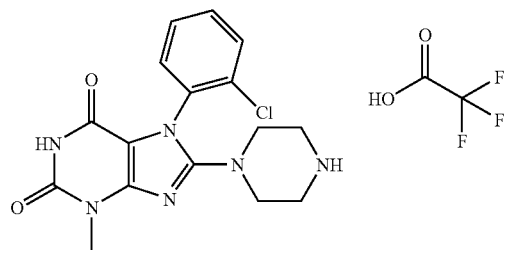

4-[7-(2-Chlorophenyl)-3-methyl-2,6-dioxo-2,3,6,7-tetrahydro-1H-purin-8-yl]piperazine-1-carboxylic acid tert-butyl ester (8 mg) was dissolved in trifluoroacetic acid, and the solution was concentrated. The residue was purified by reversed phase high performance liquid chromatography to give 3.86 mg of the title compound.

MS m/e (ESI) 361(MH$^+$—CF$_3$COOH)

$^1$H-NMR(CDCl$_3$) δ: 2.76–2.79 (m, 4H) 3.23–3.26 (m, 4H) 3.53 (s, 3H) 7.40–7.43 (m, 2H) 7.48–7.53 (m, 2H)

EXAMPLE 157

[7-(2-Chlorophenyl)-3-methyl-2,6-dioxo-8-(piperazin-1-yl)-2,3,6,7-tetrahydropurin-1-yl]-acetic acid methyl ester trifluoroacetate

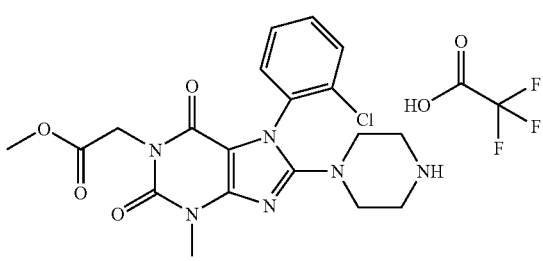

4-[7-(2-Chlorophenyl)-3-methyl-2,6-dioxo-2,3,6,7-tetrahydro-1H-purin-8-yl]piperazine-1-carboxylic acid tert-butyl ester (18 mg) was dissolved in N,N-dimethylformamide (1 ml), and methyl bromoacetate (0.1 ml) and potassium carbonate (10 mg) were added thereto. The reaction solution was stirred at room temperature for 3 days, then diluted with ethyl acetate, and washed with water. The organic layer was dried over anhydrous magnesium sulfate, filtered, and the filtrate was concentrated under reduced pressure. The residue was dissolved in trifluoroacetic acid, and the solution was concentrated. The residue was purified by reversed phase high performance liquid chromatography to give 8.79 mg of the title compound.

MS m/e (ESI) 433(MH$^+$—CF$_3$COOH)

EXAMPLE 158

[7-(2-Chlorophenyl)-3-methyl-2,6-dioxo-8-(piperazin-1-yl)-2,3,6,7-tetrahydropurin-1-yl]-acetonitrile trifluoroacetate

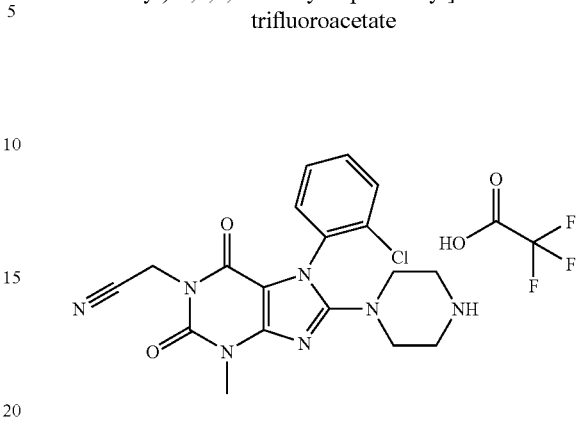

EXAMPLE 159

[7-(2-Chlorophenyl)-3-methyl-2,6-dioxo-8-(piperazin-1-yl)-2,3,6,7-tetrahydropurin-1-yl]-acetamide trifluoroacetate

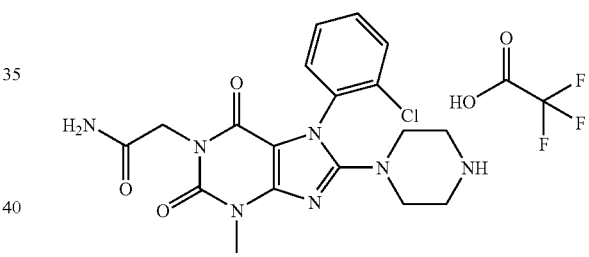

4-[7-(2-Chlorophenyl)-3-methyl-2,6-dioxo-2,3,6,7-tetrahydro-1H-purin-8-yl]piperazine-1-carboxylic acid tert-butyl ester (18 mg) was dissolved in N,N-dimethylformamide (1 ml), and bromoacetonitrile (0.1 ml) and potassium carbonate (10 mg) were added thereto. The reaction solution was stirred at room temperature for 3 days, then diluted with ethyl acetate, and washed with water. The organic layer was dried over anhydrous magnesium sulfate, filtered, and the filtrate was concentrated under reduced pressure. The residue was dissolved in acetonitrile (1 ml), and trimethylsilyl iodide (0.05 ml) was added thereto. The reaction solution was stirred at room temperature for 1 hour, then methanol was added thereto, and the solution was concentrated. The residue was purified by reversed phase high performance liquid chromatography to give 7.43 mg of [7-(2-chlorophenyl)-3-methyl-2,6-dioxo-8-(piperazin-1-yl)-2,3,6,7-tetrahydropurin-1-yl]-acetonitrile trifluoroacetate [MS m/e (ESI) 400(MH$^+$—CF$_3$COOH)] and 3.71 mg of [7-(2-chlorophenyl)-3-methyl-2,6-dioxo-8-(piperazin-1-yl)-2,3,6,7-tetrahydropurin-1-yl]-acetamide trifluoroacetate [MS m/e (ESI) 418(MH$^+$—CF$_3$COOH)].

EXAMPLE 160

7-(2-Chlorophenyl)-3-methyl-1-(2-phenethyl)-8-(piperazin-1-yl)-3,7-dihydropurine-2,6-dione trifluoroacetate

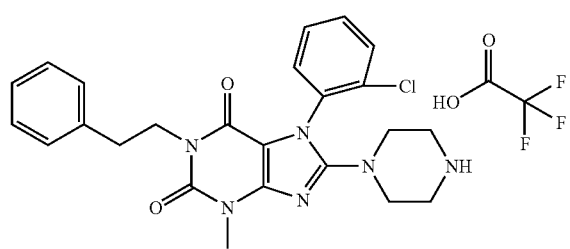

The title compound was obtained using 2-phenethyl bromide and steps similar to Example 157.
MS m/e (ESI) 465(MH$^+$—CF$_3$COOH)

EXAMPLE 161

7-(2-Chlorophenyl)-3-methyl-1-(2-phenoxyethyl)-8-(piperazin-1-yl)-3,7-dihydropurine-2,6-dione trifluoroacetate

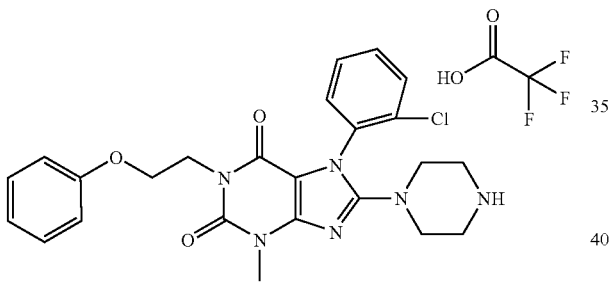

The title compound was obtained using 2-phenoxyethyl bromide and steps similar to Example 157.
MS m/e (ESI) 481(MH$^+$—CF$_3$COOH)

EXAMPLE 162

7-(2-Chlorophenyl)-3-methyl-1-(2-oxo-2-phenylethyl)-8-(piperazin-1-yl)-3,7-dihydropurine-2,6-dione trifluoroacetate

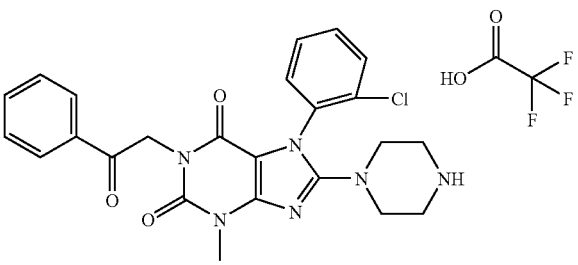

The title compound was obtained using phenacyl bromide and steps similar to Example 157.
MS m/e (ESI) 479(MH$^+$—CF$_3$COOH)

EXAMPLE 163

7-(2-Chlorophenyl)-3-methyl-1-(2-cyanobenzyl)-8-(piperazin-1-yl)-3,7-dihydropurine-2,6-dione trifluoroacetate

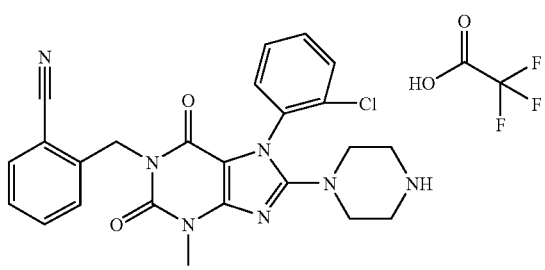

The title compound was obtained using 2-cyanobenzyl bromide and steps similar to Example 157.
MS m/e (ESI) 476(MH$^+$—CF$_3$COOH)

EXAMPLE 164

7-(2-Methoxyphenyl)-3-methyl-8-(piperazin-1-yl)-3,7-dihydropurine-2,6-dione trifluoroacetate

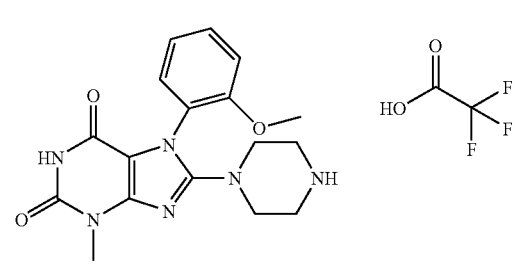

The title compound was obtained using 2-methoxyphenyl boronic acid and steps similar to Example 156.
MS m/e (ESI) 476(MH$^+$—CF$_3$COOH)

EXAMPLE 165

[7-(2-Methoxyphenyl)-3-methyl-2,6-dioxo-8-(piperazin-1-yl)-2,3,6,7-tetrahydropurin-1-yl]acetic acid methyl ester trifluoroacetate

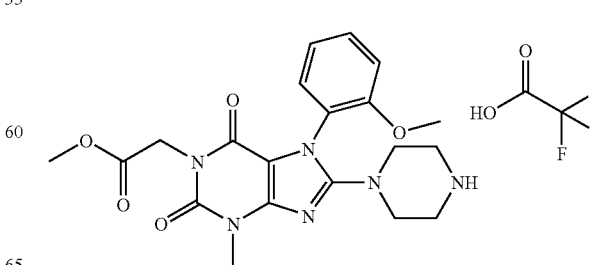

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and steps similar to Example 157.

MS m/e (ESI) 429(MH$^+$—CF$_3$COOH)

EXAMPLE 166

[7-(2-Methoxyphenyl)-3-methyl-2,6-dioxo-8-(piperazin-1-yl)-2,3,6,7-tetrahydropurin-1-yl]acetonitrile trifluoroacetate

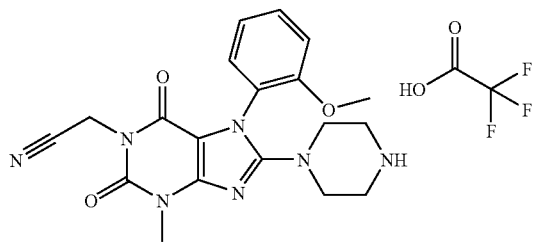

EXAMPLE 167

2-[7-(2-Methoxyphenyl)-3-methyl-2,6-dioxo-8-(piperazin-1-yl)-2,3,6,7-tetrahydropurin-1-yl]acetamide trifluoroacetate

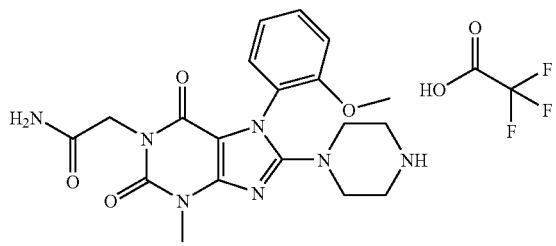

[7-(2-methoxyphenyl)-3-methyl-2,6-dioxo-8-(piperazin-1-yl)-2,3,6,7-tetrahydropurin-1-yl]acetonitrile trifluoroacetate [MS m/e (ESI) 396(MH$^+$—CF$_3$COOH)] and 2-[7-(2-methoxyphenyl)-3-methyl-2,6-dioxo-8-(piperazin-1-yl)-2,3,6,7-tetrahydropurin-1-yl]acetamide trifluoroacetate [MS m/e (ESI) 414(MH$^+$—CF$_3$COOH)] were obtained using 4-[7-(2-methoxyphenyl)-3-methyl-2,6-dioxo-2,3,6,7-tetrahydro-1H-purin-8-yl]piperazine-1-carboxylic acid tert-butyl ester, and steps similar to Examples 158 and 159.

EXAMPLE 168

7-(2-Methoxyphenyl)-3-methyl-1-(2-oxo-2-phenylethyl)-8-(piperazin-1-yl)-3,7-dihydropurine-2,6-dione trifluoroacetate

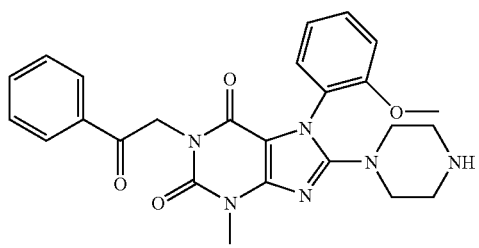

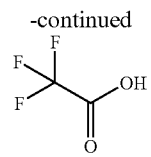

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and 2-bromoacetophenone, and steps similar to Example 157.

MS m/e (ESI) 475(MH$^+$—CF$_3$COOH)

EXAMPLE 169

7-(2-Methoxyphenyl)-3-methyl-1-(2-phenylethyl)-8-(piperazin-1-yl)-3,7-dihydropurine-2,6-dione trifluoroacetate

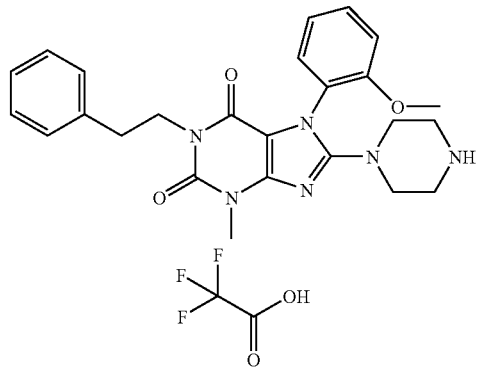

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and (2-bromoethyl)benzene, and steps similar to Example 157.

MS m/e (ESI) 461(MH$^+$—CF$_3$COOH)

EXAMPLE 170

2-[7-(2-Methoxyphenyl)-3-methyl-2,6-dioxo-8-(piperazin-1-yl)-2,3,6,7-tetrahydropurin-1-ylmethyl]benzonitrile trifluoroacetate

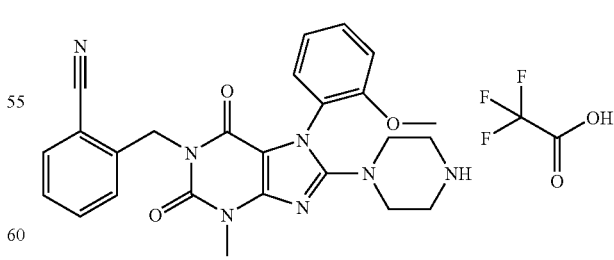

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and α-bromo-o-tolunitrile, and steps similar to Example 157.

MS m/e (ESI) 472(MH$^+$—CF$_3$COOH)

EXAMPLE 171

7-(2-Methoxyphenyl)-3-methyl-1-(2-phenoxyethyl)-8-(piperazin-1-yl)-3,7-dihydropurine-2,6-dione trifluoroacetate

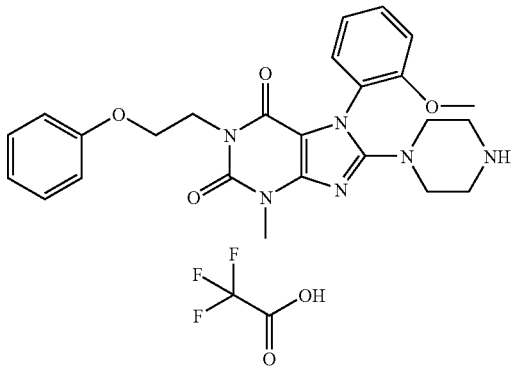

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and 2-phenoxyethyl bromide, and steps similar to Example 157.
MS m/e (ESI) 477(MH$^+$—CF$_3$COOH)

EXAMPLE 172

7-(2-Methoxyphenyl)-3-methyl-8-(piperazin-1-yl)-1-(2-propynyl)-3,7-dihydropurine-2,6-dione trifluoroacetate

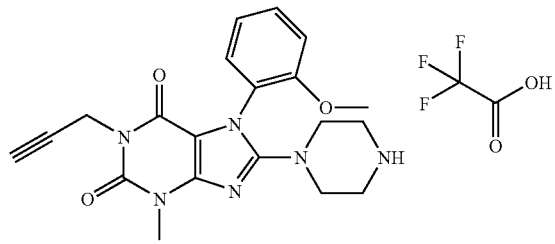

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and propargyl bromide, and steps similar to Example 157.
MS m/e (ESI) 395(MH$^+$—CF$_3$COOH)

EXAMPLE 173

7-(2-Methoxyphenyl)-3-methyl-1-(1-phenylethyl)-8-(piperazin-1-yl)-3,7-dihydropurine-2,6-dione trifluoroacetate

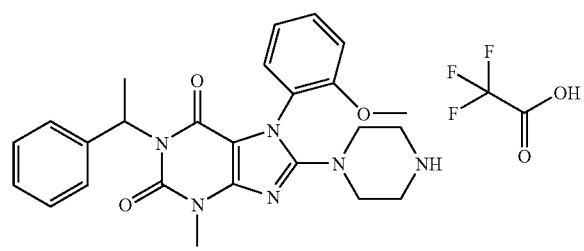

The title compound was obtained using 4-[7-(2-methoxyphenyl)-3-methyl-2,6-dioxo-2,3,6,7-tetrahydro-1H-purin-8-yl]piperazine-1-carboxylic acid tert-butyl ester and (1-bromoethyl)benzene, and steps similar to Example 157.
MS m/e (ESI) 461(MH$^+$—CF$_3$COOH)

EXAMPLE 174

7-(2-Vinylphenyl)-3-methyl-8-(piperazin-1-yl)-3,7-dihydropurine-2,6-dione a) 4-[7-Benzyl-1-(2,2-dimethylpropionyloxymethyl)-3-methyl-2,6-dioxo-2,3,6,7-tetrahydro-1H-purin-8-yl]piperazine-1-carboxylic acid tert-butyl ester

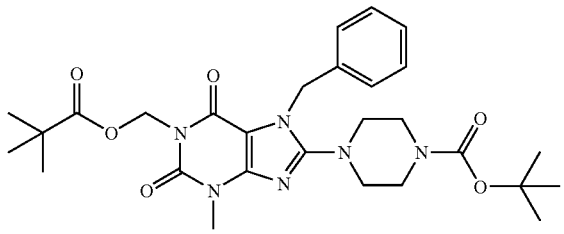

The title compound was obtained using 2,2-dimethylpropionic acid 7-benzyl-3-methyl-2,6-dioxo-2,3,6,7-tetrahydropurin-1-ylmethyl ester, and steps similar to Examples 156e) and f).

b) 4-[1-(2,2-Dimethylpropionyloxymethyl)-3-methyl-2,6-dioxo-2,3,6,7-tetrahydro-1H-purin-8-yl]piperazine-1-carboxylic acid tert-butyl ester

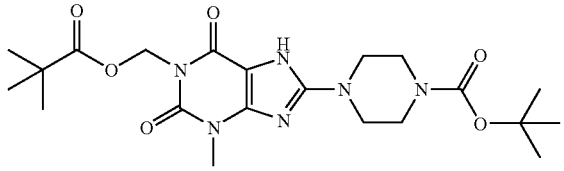

4-[7-Benzyl-1-(2,2-dimethylpropionyloxymethyl)-3-methyl-2,6-dioxo-2,3,6,7-tetrahydro-1H-purin-8-yl]piperazine-1-carboxylic acid tert-butyl ester (2.227 g) was dissolved in acetic acid (100 ml), and 10% palladium on carbon (1 g) was added thereto. The reaction mixture was stirred under hydrogen atmosphere at room temperature overnight, filtered, and the filtrate was concentrated to give 1.89 g of the title compound.
$^1$H-NMR(CDCl$_3$) δ: 1.09 (s, 9H) 1.41 (s, 9H) 3.36 (s, 3H) 3.37–3.42 (m, 4H) 3.45–3.50 (m, 4H) 5.82 (s, 2H)

c) 4-[1-(2,2-Dimethylpropionyloxymethyl)-7-(2-vinylphenyl)-3-methyl-2,6-dioxo-2,3,6,7-tetrahydro-1H-purin-8-yl]piperazine-1-carboxylic acid tert-butyl ester

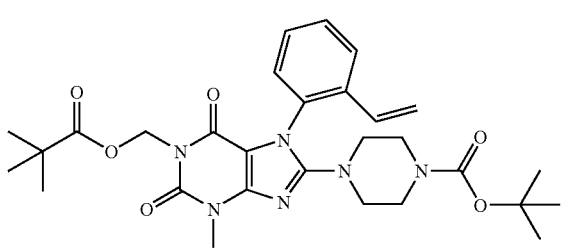

The title compound was obtained using 4-[1-(2,2-dimethylpropionyloxymethyl)-3-methyl-2,6-dioxo-2,3,6,7-tetrahydro-1H-purin-8-yl]piperazine-1-carboxylic acid tert-butyl ester, and steps similar to Examples 142 and 147.

$^1$H-NMR(CDCl$_3$) δ: 1.15 (s, 9H) 1.58 (s, 9H) 3.18 (br, 4H) 3.30 (br, 4H) 3.58 (s, 3H) 5.32 (d, J=11.2 Hz, 1H) 5.75 (d, J=17.2 Hz, 1H) 6.39 (dd, J=10.8, 17.2 Hz, 1H) 7.34 (dd, J=1.2, 7.6 Hz, 1H) 7.40 (dt, J=1.6, 7.2 Hz, 1H) 7.46 (dt, J=1.6, 7.6 Hz, 1H) 7.69 (dd, J=1.6, 8.0 Hz, 1H)

d) 7-(2-Vinylphenyl)-3-methyl-8-(piperazin-1-yl)-3,7-dihydropurine-2,6-dione

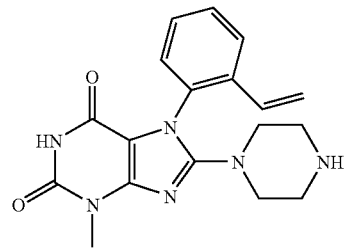

4-[1-(2,2-Dimethylpropionyloxymethyl)-7-(2-vinylphenyl)-3-methyl-2,6-dioxo-2,3,6,7-tetrahydro-1H-purin-8-yl]piperazine-1-carboxylic acid tert-butyl ester (187 mg) was dissolved in methanol (3 ml), and sodium hydride (14 mg) was added thereto. The reaction solution was stirred at room temperature overnight, then neutralized with 1 N hydrochloric acid, and extracted with ethyl acetate. The organic layer was dried over anhydrous magnesium sulfate, filtered, and the solvent was removed by distillation. The residue was purified by silica gel chromatography to obtain 108 mg of 4-[3-methyl-2,6-dioxo-7-(2-vinylphenyl)-2,3,6,7-tetrahydro-1H-purin-8-yl]piperazine-1-carboxylic acid tert-butyl ester from a fraction eluted with hexane-ethyl acetate (3:2). This was dissolved in trifluoroacetic acid (2 ml), and the solution was concentrated. The residue was purified by NH-silica gel to obtain 84 mg of the title compound from a fraction eluted with ethyl acetate-methanol (15:1).

$^1$H-NMR(CDCl$_3$) δ: 2.73 (t, J=5.2 Hz, 4H) 3.19 (t, J=5.2 Hz, 4H) 3.54 (s, 3H) 5.32 (dd, J=1.2, 10.8 Hz, 1H) 5.74 (d, J=0.8, 17.2 Hz, 1H) 6.41 (dd, J=10.8, 17.2 Hz, 1H) 7.33 (dd, J=1.2, 6.0 Hz, 1H) 7.38 (dt, J=1.6, 7.6 Hz, 1H) 7.45 (dt, J=1.6, 7.6 Hz, 1H) 7.68 (dd, J=1.6, 8.0 Hz, 1H)

EXAMPLE 175

7-(2-Chlorophenyl)-3-ethyl-8-(piperazin-1-yl)-3,7-dihydro-purine-2,6-dione trifluoroacetate a) 2-Amino-7-benzyl-1,7-dihydropurin-6-one hydrochloride

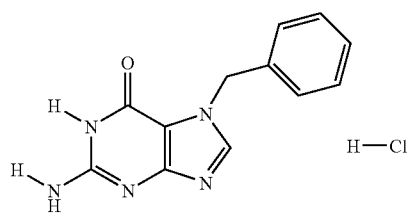

Benzyl bromide (100 ml) was added dropwise to a suspension of guanosine (100 g) in dimethyl sulfoxide (500 ml) at room temperature, and the resulting reaction mixture was stirred at room temperature for 4 hours. Then, concentrated hydrochloric acid (250 ml) was added thereto. The reaction mixture was stirred at room temperature for 30 minutes, poured into methanol (3 L), and stirred overnight. Deposited crystals were collected by filtration, washed with methanol, and then dried by ventilation at 60° C. for 24 hours to give 82.5 g of the title compound.

$^1$H-NMR(d6-DMSO) δ: 5.23 (s, 2H) 7.32–7.42 (m, 5H) 8.92 (s, 1H)

b) 7-Benzyl-3,7-dihydropurine-2,6-dione

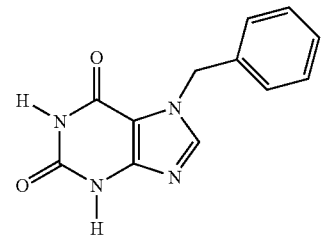

A white suspension of 2-amino-7-benzyl-1,7-dihydropurin-6-one hydrochloride (12.88 g) in acetic acid (320 ml) and water (32 ml) was stirred at 110° C. for 10 minutes, and then at 50° C. for 10 minutes. Aqueous solution (32 ml) of sodium nitrite (12.88 g) was slowly added dropwise at 50° C. thereto. The reaction mixture was stirred at 50° C. for 15 hours, and the resulting pale brown suspension was collected by filtration to give 4.27 g of the title compound.

$^1$H-NMR(d6-DMSO) δ: 5.39 (s, 2H) 7.27–7.35 (m, 5H) 8.11(s, 1H) 10.86 (s, 1H) 11.57 (s, 1H)

c) 2,2-Dimethyl-propionic acid [7-benzyl-3-(2,2-dimethyl-propionyloxymethyl)-2,6-dioxo-2,3,6,7-tetrahydropurin-1-yl]methyl ester

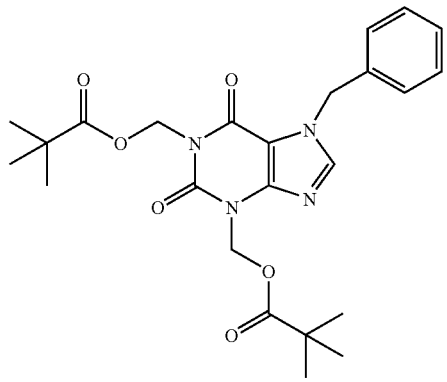

7-Benzylxanthine (9.54 g) was dissolved in N,N-dimethylformamide (250 ml), and potassium carbonate (17 g) and chloromethyl pivalate (14.2 ml) were added thereto. The reaction solution was stirred at 50° C. overnight, then diluted with ethyl acetate, and washed with water and 1 N hydrochloric acid. The organic layer was dried over anhydrous magnesium sulfate, filtered, and the solvent was removed by distillation. The residue was purified by silica gel chromatography to obtain 12.8 g of the title compound from a fraction eluted with hexane-ethyl acetate (3:2).

d) 2,2-Dimethylpropionic acid [3-(2,2-dimethylpropionyloxymethyl)-2,6-dioxo-2,3,6,7-tetrahydropurin-1-yl]methyl ester

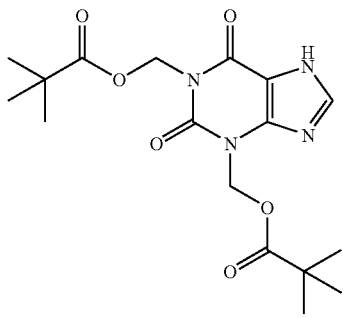

The title compound was obtained using 2,2-dimethylpropionic acid [7-benzyl-3-(2,2-dimethylpropionyloxymethyl)-2,6-dioxo-2,3,6,7-tetrahydro-purin-1-yl]methyl ester and steps similar to Example 174 b).

e) 2,2-Dimethylpropionic acid [7-(2-chlorophenyl)-3-(2,2-dimethylpropionyloxymethyl)-2,6-dioxo-2,3,6,7-tetrahydropurin-1-yl]methyl ester

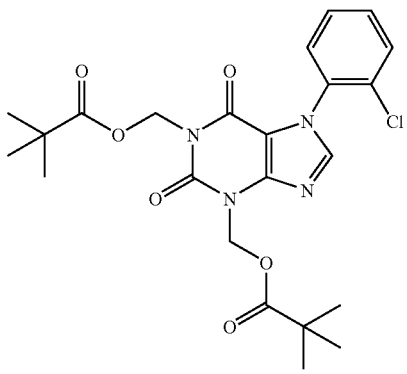

The title compound was obtained using 2,2-dimethylpropionic acid [3-(2,2-dimethylpropionyloxymethyl)-2,6-dioxo-2,3,6,7-tetrahydropurin-1-yl]methyl ester and steps similar to Example 156d).
$^1$H-NMR(CDCl$_3$) δ: 1.16 (s, 9H) 1.22 (s, 9H) 5.99 (s, 2H) 6.19 (s, 2H) 7.42–7.52 (m, 3H) 7.58–7.61 (m, 1H) 7.73 (s, 1H)

f) 4-[7-(2-Chlorophenyl)-1,3-bis-(2,2-dimethylpropionyloxymethyl)-2,6-dioxo-2,3,6,7-tetrahydro-1H-purin-8-yl]piperazine-1-carboxylic acid tert-butyl ester

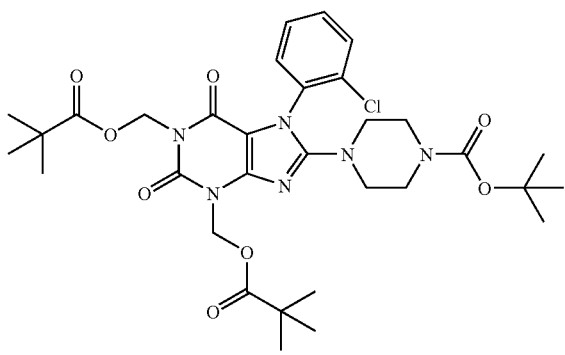

The title compound was obtained using 2,2-dimethylpropionic acid [7-(2-chlorophenyl)-3-(2,2-dimethylpropionyloxymethyl)-2,6-dioxo-2,3,6,7-tetrahydropurin-1-yl]methyl ester, and steps similar to Examples 156e) and f).
$^1$H-NMR(CDCl$_3$) δ: 1.16 (s, 9H) 1.23 (s, 9H) 1.44 (s, 9H) 3.20–3.35 (m, 4H) 3.32–3.37 (m, 4H) 5.92 (s, 2H) 6.09 (s, 2H) 7.41–7.49 (m, 2H) 7.52–7.57 (m, 2H)

g) 4-[7-(2-Chlorophenyl)-1-(2,2-dimethylpropionyloxymethyl)-2,6-dioxo-2,3,6,7-tetrahydro-1H-purin-8-yl]piperazine-1-carboxylic acid tert-butyl ester

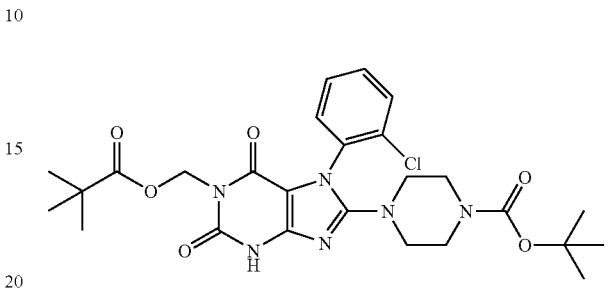

4-[7-(2-Chlorophenyl)-1,3-bis-(2,2-dimethylpropionyloxymethyl)-2,6-dioxo-2,3,6,7-tetrahydro-1H-purin-8-yl]piperazine-1-carboxylic acid tert-butyl ester (2.227 g) was dissolved in tetrahydrofuran (10 ml) and methanol (20 ml), and 1,8-diazabicyclo[5,4,0]undec-7-ene (0.518 ml) was added thereto. The reaction mixture was stirred at room temperature overnight, and 1 N hydrochloric acid was added. Deposited solid was collected by filtration and dried to give 1.025 g of the title compound.
$^1$H-NMR(CDCl$_3$) δ: 1.16 (s, 9H) 1.44 (s, 9H) 3.22–3.24 (m, 4H) 3.33–3.35 (m, 4H) 5.90 (s, 2H) 7.43–7.47 (m, 2H) 7.51–7.57 (m, 2H) 8.71 (brs, 1H)

h) 7-(2-Chlorophenyl)-3-ethyl-8-(piperazin-1-yl)-3,7-dihydropurine-2,6-dione trifluoroacetate

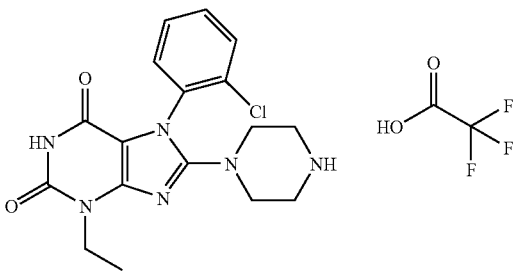

4-[7-(2-Chlorophenyl)-1-(2,2-dimethylpropionyloxymethyl)-2,6-dioxo-2,3,6,7-tetrahydro-1H-purin-8-yl]piperazine-1-carboxylic acid tert-butyl ester (8 mg) was dissolved in N,N-dimethylformamide (0.3 ml), and ethyl iodide (0.05 ml) and potassium carbonate (20 mg) were added thereto. The reaction mixture was stirred at 50° C. overnight. Ethyl acetate was added to the reaction solution, and the solution was washed with water. The organic layer was concentrated. The residue was dissolved in methanol, and sodium hydride (5 mg) was added thereto. The reaction solution was stirred at room temperature for 3 hours, neutralized with 1 N hydrochloric acid, and extracted with ethyl acetate. The solvent was concentrated, and the residue was dissolved in trifluoroacetic acid. The solution was concentrated, and the residue was purified by reversed phase high performance liquid chromatography to give 4.49 mg of the title compound.
MS m/e (ESI) 375(MH$^+$—CF$_3$COOH)

EXAMPLE 176

7-(2-Chlorophenyl)-3-propyl-8-(piperazin-1-yl)-3,7-dihydropurine-2,6-dione trifluoroacetate

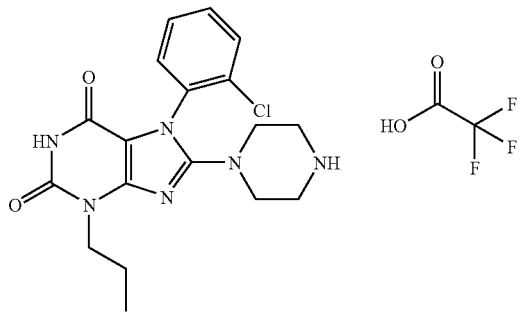

The title compound was obtained using iodopropane and steps similar to Example 175h).
MS m/e (ESI) 389(MH$^+$—CF$_3$COOH)

EXAMPLE 177

7-(2-Chlorophenyl)-3-isopropyl-8-(piperazin-1-yl)-3,7-dihydropurine-2,6-dione trifluoroacetate

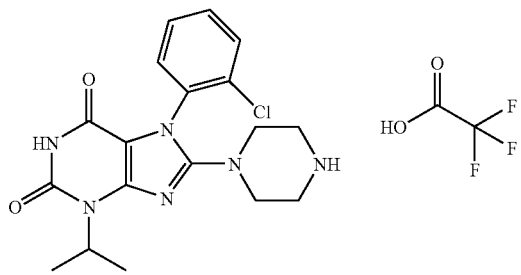

The title compound was obtained using 2-iodopropane and steps similar to Example 175h).
MS m/e (ESI) 389(MH$^+$—CF$_3$COOH)

EXAMPLE 178

7-(2-Chlorophenyl)-3-cyclopropylmethyl-8-(piperazin-1-yl)-3,7-dihydropurine-2,6-dione trifluoroacetate

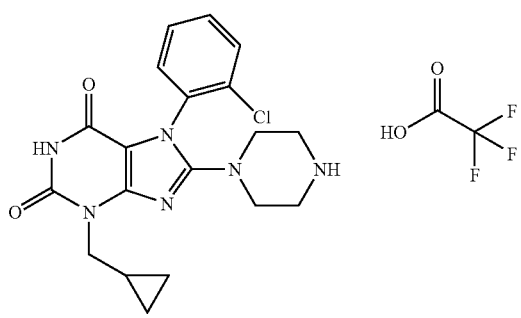

The title compound was obtained using bromomethyl cyclopropane and steps similar to Example 175h).
MS m/e (ESI) 401(MH$^+$—CF$_3$COOH)

EXAMPLE 179

7-(2-Chlorophenyl)-3-cyclobutylmethyl-8-(piperazin-1-yl)-3,7-dihydropurine-2,6-dione trifluoroacetate

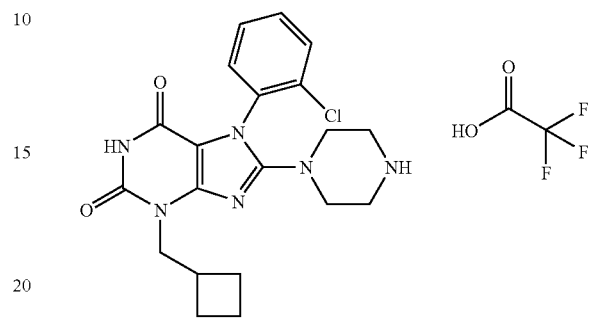

The title compound was obtained using bromomethyl cyclobutane and steps similar to Example 175h).
MS m/e (ESI) 415(MH$^+$—CF$_3$COOH)

EXAMPLE 180

7-(2-Chlorophenyl)-3-(2-tetrahydrofuranyl)methyl-8-(piperazin-1-yl)-3,7-dihydropurine-2,6-dione trifluoroacetate

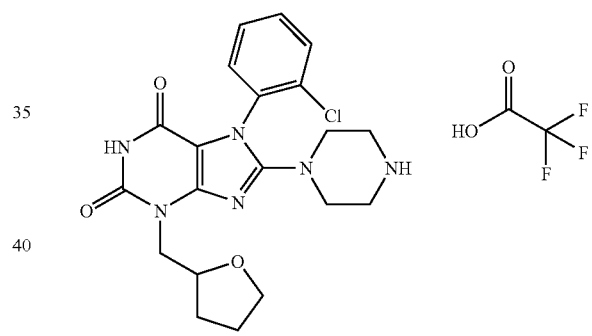

The title compound was obtained using 2-bromomethyl tetrahydrofuran and steps similar to Example 175h).
MS m/e (ESI) 431(MH$^+$—CF$_3$COOH)

EXAMPLE 181

7-(2-Chlorophenyl)-3-cyclobutyl-8-(piperazin-1-yl)-3,7-dihydropurine-2,6-dione trifluoroacetate

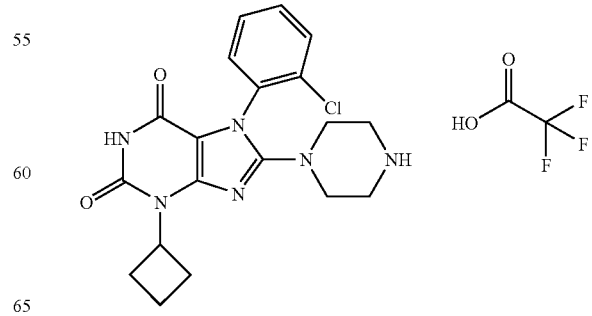

The title compound was obtained using cyclobutyl bromide and steps similar to Example 175h).
MS m/e (ESI) 401(MH$^+$—CF$_3$COOH)

EXAMPLE 182

7-(2-Chlorophenyl)-3-cyclopentyl-8-(piperazin-1-yl)-3,7-dihydropurine-2,6-dione trifluoroacetate

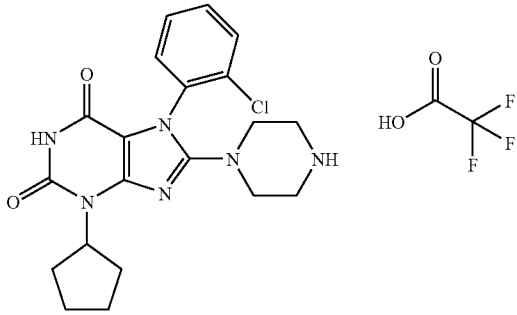

The title compound was obtained using cyclopentyl bromide and steps similar to Example 175h).
MS m/e (ESI) 415(MH$^+$—CF$_3$COOH)

EXAMPLE 183

7-(2-Chlorophenyl)-3-(2-hydroxyethyl)-8-(piperazin-1-yl)-3,7-dihydropurine-2,6-dione trifluoroacetate

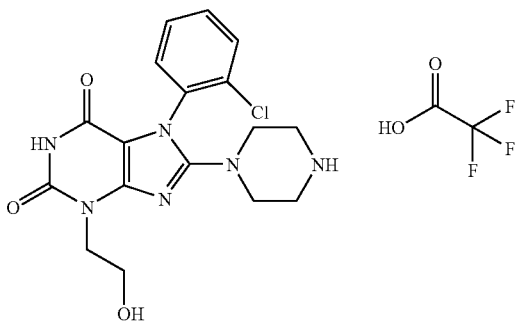

The title compound was obtained using 2-bromoethanol and steps similar to Example 175h).
MS m/e (ESI) 391(MH$^+$—CF$_3$COOH)

EXAMPLE 184

7-(2-Chlorophenyl)-3-(2-hydroxypropyl)-8-(piperazin-1-yl)-3,7-dihydropurine-2,6-dione trifluoroacetate

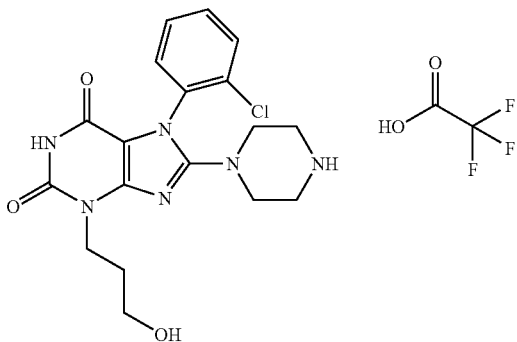

The title compound was obtained using 3-bromopropanol and steps similar to Example 175h).
MS m/e (ESI) 405(MH$^+$—CF$_3$COOH)

EXAMPLE 185

7-(2-Chlorophenyl)-3-(2-fluoroethyl)-8-(piperazin-1-yl)-3,7-dihydropurine-2,6-dione trifluoroacetate

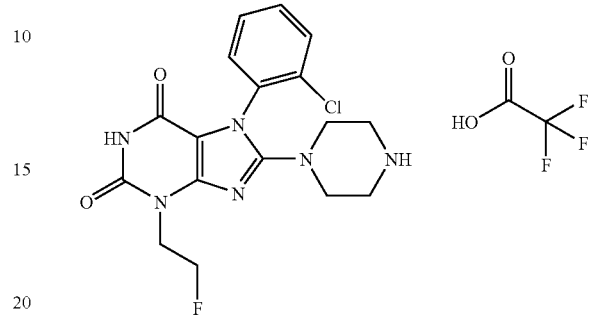

The title compound was obtained using 2-bromofluoroethane and steps similar to Example 175h).
MS m/e (ESI) 393(MH$^+$—CF$_3$COOH)

EXAMPLE 186

7-(2-Chlorophenyl)-3-(2-fluoropropyl)-8-(piperazin-1-yl)-3,7-dihydropurine-2,6-dione trifluoroacetate

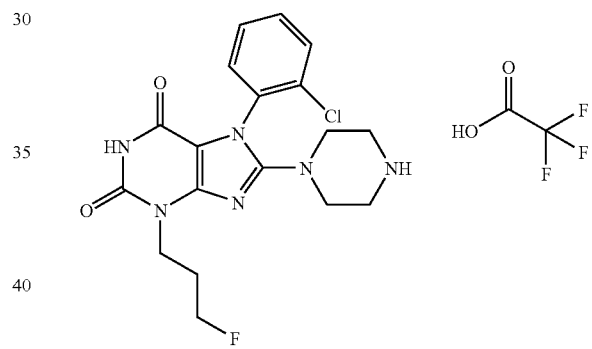

The title compound was obtained using 3-iodofluoropropane and steps similar to Example 175h).
MS m/e (ESI) 407(MH$^+$—CF$_3$COOH)

EXAMPLE 187

7-(2-Chlorophenyl)-3-(2-ethoxyethyl)-8-(piperazin-1-yl)-3,7-dihydropurine-2,6-dione trifluoroacetate

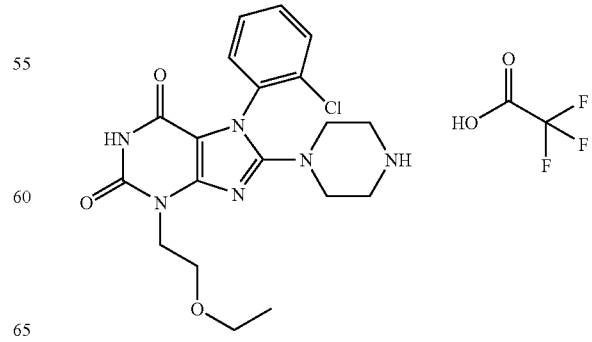

The title compound was obtained using 2-ethoxyethyl bromide and steps similar to Example 175h).

MS m/e (ESI) 419(MH$^+$—CF$_3$COOH)

EXAMPLE 188

7-(2-Chlorophenyl)-3-(2-phenoxyethyl)-8-(piperazin-1-yl)-3,7-dihydropurine-2,6-dione trifluoroacetate

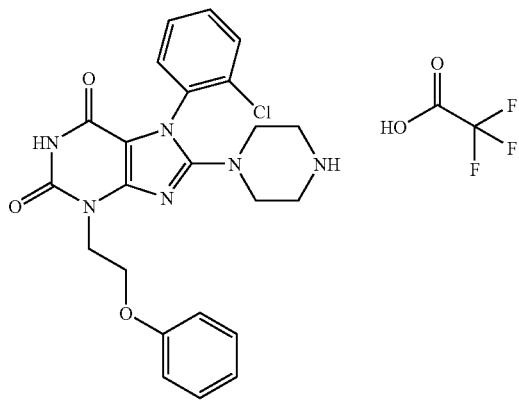

The title compound was obtained using 2-phenoxyethyl bromide and steps similar to Example 175h).

MS m/e (ESI) 4.67(MH$^+$—CF$_3$COOH)

EXAMPLE 189

7-(2-Chlorophenyl)-3-(2-butenyl)-8-(piperazin-1-yl)-3,7-dihydropurine-2,6-dione trifluoroacetate

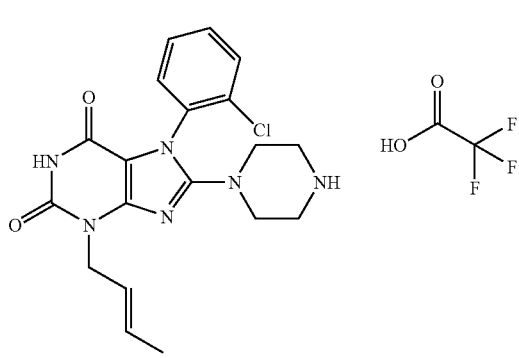

The title compound was obtained using crotyl bromide and steps similar to Example 175h).

MS m/e (ESI) 401(MH$^+$—CF$_3$COOH)

EXAMPLE 190

7-(2-Chlorophenyl)-3-benzyl-8-(piperazin-1-yl)-3,7-dihydropurine-2,6-dione trifluoroacetate

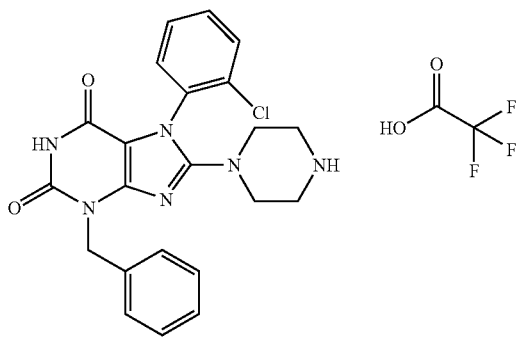

The title compound was obtained using benzyl bromide and steps similar to Example 175h).

MS m/e (ESI) 437(MH$^+$—CF$_3$COOH)

EXAMPLE 191

7-(2-Chlorophenyl)-3-(2-oxo-2-phenethyl)-8-(piperazin-1-yl)-3,7-dihydropurine-2,6-dione trifluoroacetate

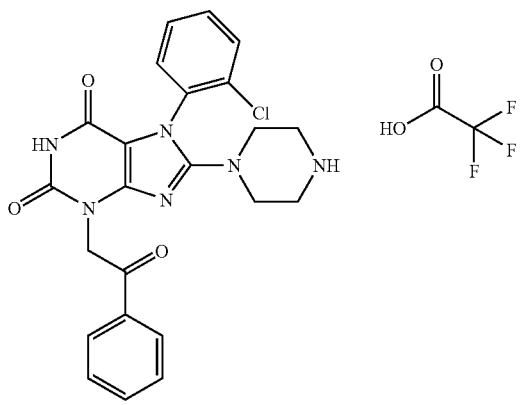

The title compound was obtained using phenacyl bromide and steps similar to Example 175h).

MS m/e (ESI) 465(MH$^+$—CF$_3$COOH)

EXAMPLE 192

7-(2-Chlorophenyl)-3-(2-oxotetrahydrofuran-3-yl)-8-(piperazin-1-yl)-3,7-dihydropurine-2,6-dione trifluoroacetate

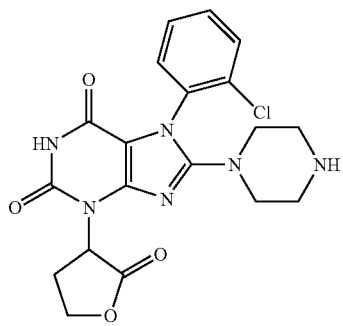
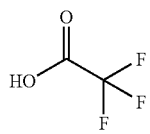

EXAMPLE 193

2-[7-(2-Chlorophenyl)-2,6-dioxo-8-(piperazin-1-yl)-1,2,6,7-tetrahydropurin-3-yl]-4-hydroxybutyric acid trifluoroacetate

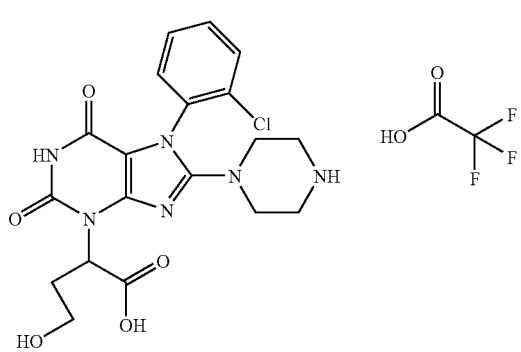
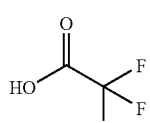

7-(2-Chlorophenyl)-3-(2-oxotetrahydrofuran-3-yl)-8-(piperazin-1-yl)-3,7-dihydropurine-2,6-dione trifluoroacetate [MS m/e (ESI) 431(MH$^+$—CF$_3$COOH)] and 2-[7-(2-chlorophenyl)-2,6-dioxo-8-(piperazin-1-yl)-1,2,6,7-tetrahydropurin-3-yl]-4-hydroxybutyric acid trifluoroacetate [MS m/e (ESI) 449(MH$^+$—CF$_3$COOH)] were obtained using α-bromo-γ-butyrolactone and steps similar to Example 175h).

EXAMPLE 194

2-[7-(2-Chlorophenyl)-2,6-dioxo-8-(piperazin-1-yl)-1,2,6,7-tetrahydropurin-3-yl]-acetamide trifluoroacetate

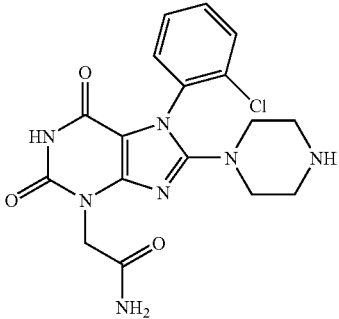
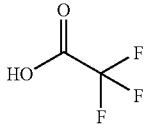

The title compound was obtained using 2-bromoacetamide and steps similar to Example 175h).

$^1$H-NMR (d$^6$-DMSO) δ: 2.97–3.04 (m, 4H) 3.22–3.34 (m, 4H) 4.43 (s, 2H) 7.18 (brs, 1H) 7.49–7.59 (m, 2H) 7.62 (s, 1H) 7.66–7.71 (m, 2H) 10.90 (s, 1H)

MS m/e (ESI) 404(MH$^+$—CF$_3$COOH)

EXAMPLE 195

2-[7-(2-Chlorophenyl)-2,6-dioxo-8-(piperazin-1-yl)-1,2,6,7-tetrahydropurin-3-yl]-acetonitrile trifluoroacetate

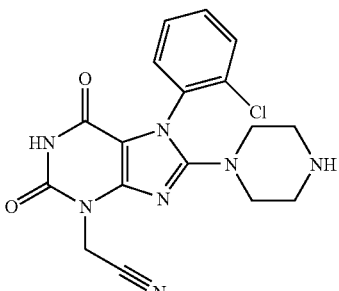
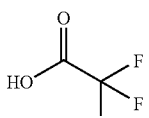

The title compound was obtained using 2-bromoacetonitrile and steps similar to Example 175h).

MS m/e (ESI) 386(MH$^+$—CF$_3$COOH)

EXAMPLE 196

7-(2-Chlorophenyl)-3-phenyl-8-(piperazin-1-yl)-3,7-dihydropurine-2,6-dione trifluoroacetate

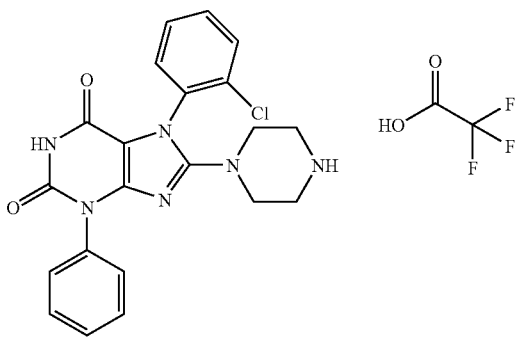

4-[7-(2-Chlorophenyl)-1-(2,2-dimethylpropionyloxymethyl)-2,6-dioxo-2,3,6,7-tetrahydro-1H-purin-8-yl]piperazine-1-carboxylic acid tert-butyl ester (10 mg) was dissolved in N,N-dimethylformamide (0.3 ml) and phenylboronic acid (15 mg), copper (II) acetate (10 mg) and pyridine (0.05 ml) were added to the solution, and the mixture was stirred at room temperature for 3 days. The reaction mixture was filtered through a short column filled with silica gel. Ethyl acetate was added to the filtrate and the mixture was washed with water. The organic layer was concentrated. The residue was dissolved in methanol, sodium hydride (5 mg) was added to the mixture, and the mixture was stirred at room temperature for 3 hours. The reaction mixture was neutralized with 1N hydrochloric acid, and extracted with ethyl acetate. The solvent was removed, then the residue was dissolved in trifluoroacetic acid, and concentrated. The residue was purified by reversed phase high performance liquid chromatography to give 1.39 mg of the title compound.

MS m/e (ESI) 423(MH$^+$—CF$_3$COOH)

EXAMPLE 197

7-(2-Chlorophenyl)-3-(4-fluorophenyl)-8-(piperazin-1-yl)-3,7-dihydropurine-2,6-dione trifluoroacetate

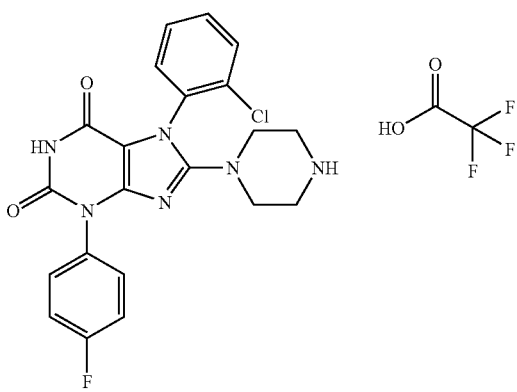

The title compound was obtained using 4-fluorophenylboronic acid and steps similar to Example 196.

MS m/e (ESI) 441(MH$^+$—CF$_3$COOH)

EXAMPLE 198

7-(2-Chlorophenyl)-3-(3-chlorophenyl)-8-(piperazin-1-yl)-3,7-dihydropurine-2,6-dione trifluoroacetate

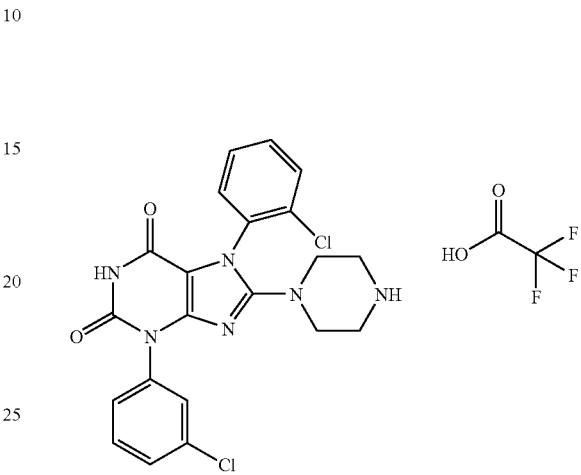

The title compound was obtained using 3-chlorophenylboronic acid and steps similar to Example 196.

MS m/e (ESI) 457(MH$^+$—CF$_3$COOH)

EXAMPLE 199

7-(2-Chlorophenyl)-3-(4-chlorophenyl)-8-(piperazin-1-yl)-3,7-dihydropurine-2,6-dione trifluoroacetate

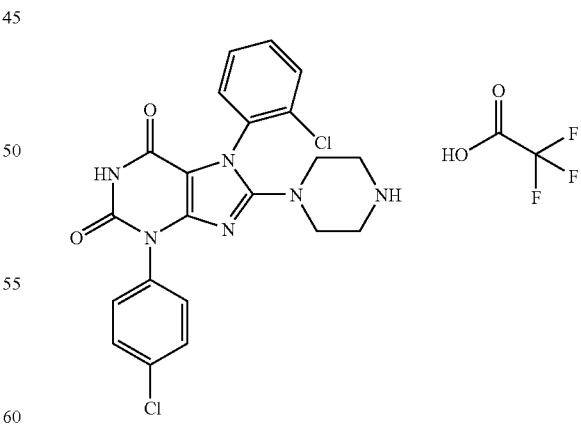

The title compound was obtained using 4-chlorophenylboronic acid and steps similar to Example 196.

MS m/e (ESI) 457(MH$^+$—CF$_3$COOH)

EXAMPLE 200

7-(2-Chlorophenyl)-3-(3-methoxyphenyl)-8-(piperazin-1-yl)-3,7-dihydropurine-2,6-dione trifluoroacetate

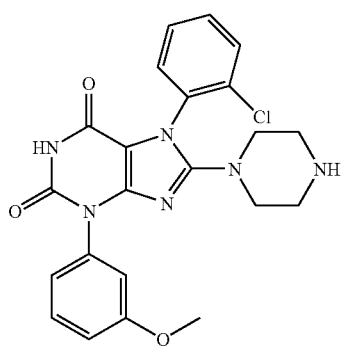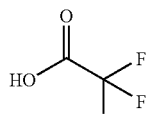

The title compound was obtained using 3-methoxyphenylboronic acid and steps similar to Example 196.
MS m/e (ESI) 453(MH+—CF3COOH)

EXAMPLE 201

7-(2-Chlorophenyl)-3-(4-methoxyphenyl)-8-(piperazin-1-yl)-3,7-dihydropurine-2,6-dione trifluoroacetate

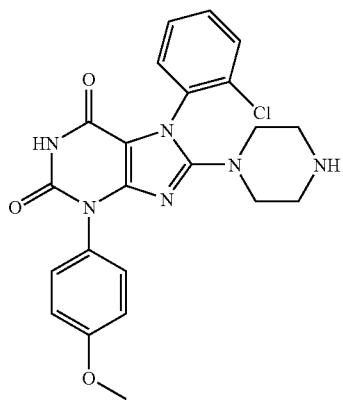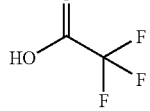

The title compound was obtained using 4-methoxyphenylboronic acid and steps similar to Example 196.
MS m/e (ESI) 453(MH+—CF3COOH)

EXAMPLE 202

7-(2-Chlorophenyl)-3-(3-cyanophenyl)-8-(piperazin-1-yl)-3,7-dihydropurine-2,6-dione trifluoroacetate

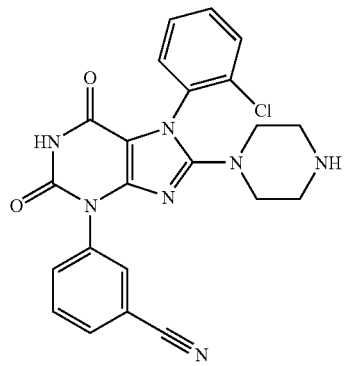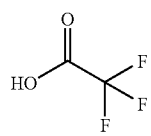

The title compound was obtained using 3-cyanophenylboronic acid and steps similar to Example 196.
MS m/e (ESI) 448(MH+—CF3COOH)

EXAMPLE 203

7-(2-Chlorophenyl)-3-(4-cyanophenyl)-8-(piperazin-1-yl)-3,7-dihydropurine-2,6-dione trifluoroacetate

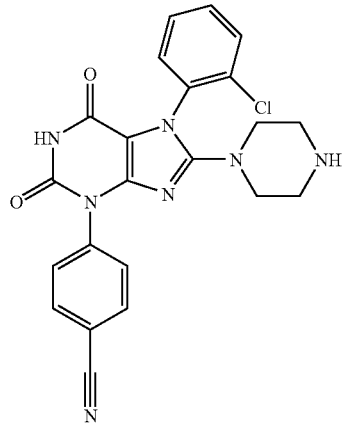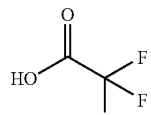

The title compound was obtained using 4-cyanophenylboronic acid and steps similar to Example 196.
MS m/e (ESI) 448(MH+—CF3COOH)

EXAMPLE 204

7-(2-Chlorophenyl)-3-(3-methoxycarbonylphenyl)-8-(piperazin-1-yl)-3,7-dihydropurine-2,6-dione trifluoroacetate

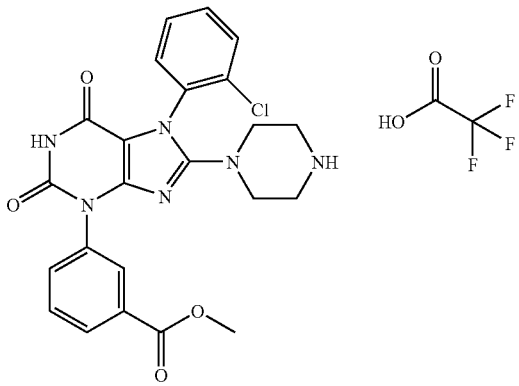

The title compound was obtained using 3-methoxycarbonylphenylboronic acid and steps similar to Example 196.
MS m/e (ESI) 481(MH$^+$—CF$_3$COOH)

EXAMPLE 205

7-(2-Chlorophenyl)-3-(4-methoxycarbonylphenyl)-8-(piperazin-1-yl)-3,7-dihydropurine-2,6-dione trifluoroacetate

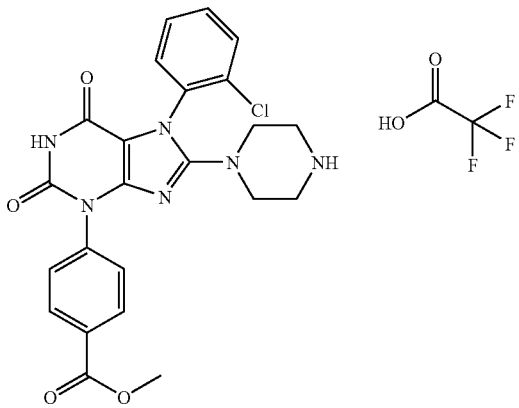

The title compound was obtained using 4-methoxycarbonylphenylboronic acid and steps similar to Example 196.
MS m/e (ESI) 481(MH$^+$—CF$_3$COOH)

EXAMPLE 206

7-(2-Chlorophenyl)-3-(benzo[1,3]dioxol-5-yl)-8-(piperazin-1-yl)-3,7-dihydropurine-2,6-dione trifluoroacetate

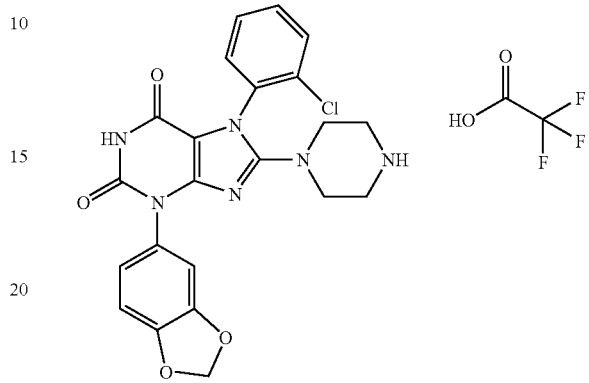

The title compound was obtained using benzo[1,3]dioxol-5-ylboronic acid and steps similar to Example 196.
MS m/e (ESI) 467(MH$^+$—CF$_3$COOH)

EXAMPLE 207

[7-(2-Chlorophenyl)-1-methyl-2,6-dioxo-8-(piperazin-1-yl)-1,2,6,7-tetrahydropurin-3-yl]acetic acid methyl ester trifluoroacetate a) 4-[7-(2-Chlorophenyl)-1-(2,2-dimethylpropionyloxymethyl)-3-methoxycarbonylmethyl-2,6-dioxo-2,3,6,7-tetrahydro-1H-purin-8-yl]piperazine-1-carboxylic acid tert-butyl ester

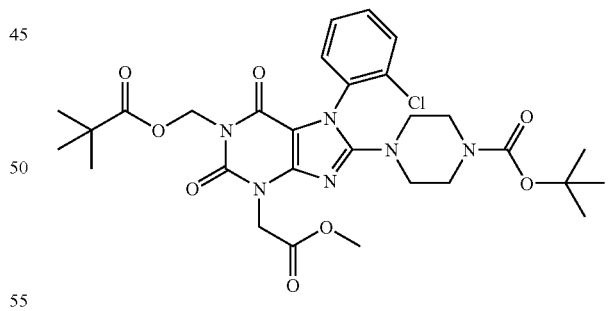

4-[7-(2-Chlorophenyl)-1-(2,2-dimethylpropionyloxymethyl)-2,6-dioxo-2,3,6,7-tetrahydro-1H-purin-8-yl]piperazine-1-carboxylic acid tert-butyl ester (107 mg) was dissolved in N,N-dimethylformamide (2 ml), and methyl bromoacetate (0.025 ml) and potassium carbonate (50 mg) were added to the solution. Then, the mixture was stirred at room temperature overnight. Ethyl acetate was added to the reaction mixture, and the mixture was washed with water. The organic layer was concentrated to give 139 mg of the title compound.

b) 4-[7-(2-Chlorophenyl)-3-methoxycarbonylmethyl-1-methyl-2,6-dioxo-2,3,6,7-tetrahydro-1H-purin-8-yl]piperazine-1-carboxylic acid tert-butyl ester

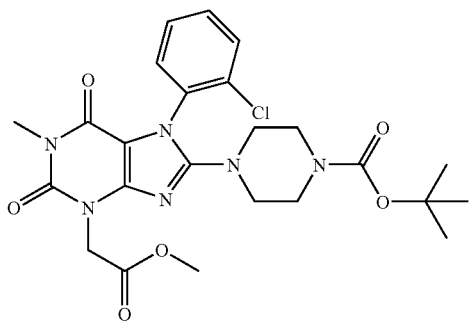

4-[7-(2-Chlorophenyl)-1-(2,2-dimethylpropionyloxymethyl)-3-methoxycarbonylmethyl-2,6-dioxo-2,3,6,7-tetrahydro-1H-purin-8-yl]piperazine-1-carboxylic acid tert-butyl ester (139 mg) was dissolved in tetrahydrofuran (1 ml) and methanol (1 ml), and sodium hydride (10 mg) was added to the solution. Then, the mixture was stirred at room temperature for 1 hour. The mixture was neutralized by adding 1N Hydrochloric acid, and was extracted with ethyl acetate. The organic layer was dried over anhydrous magnesium sulfate, and filtered. The solvent was removed by distillation to give 100 mg of 4-[7-(2-chlorophenyl)-3-methoxycarbonylmethyl-2,6-dioxo-2,3,6,7-tetrahydro-1H-purin-8-yl]piperazine-1-carboxylic acid tert-butyl ester. This compound was dissolved in N,N-dimethylformamide (2 ml) and potassium carbonate (20 mg) and methyl iodide (0.02 ml) were added to the solution. The mixture was stirred at room temperature for 3 days. The mixture was diluted with ethyl acetate, and washed with water and 1N hydrochloric acid. The organic layer was dried over anhydrous magnesium sulfate, and filtered. The solvent was removed by distillation to give 108 mg of the title compound.

c) [7-(2-Chlorophenyl)-1-methyl-2,6-dioxo-8-(piperazin-1-yl)-1,2,6,7-tetrahydropurin-3-yl]acetic acid methyl ester trifluoroacetate

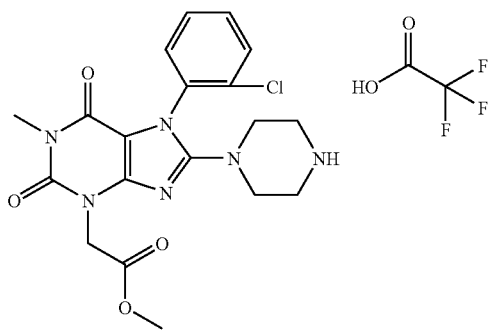

4-[7-(2-Chlorophenyl)-3-methoxycarbonylmethyl-1-methyl-2,6-dioxo-2,3,6,7-tetrahydro-1H-purin-8-yl]piperazine-1-carboxylic acid tert-butyl ester (26 mg) was dissolved in trifluoroacetic acid, and concentrated. The residue was purified by reversed phase high performance liquid chromatography to give 8.09 mg of the title compound.

$^1$H-NMR (d$^6$-DMSO) δ: 3.15–3.18 (m, 4H) 3.25 (s, 3H) 3.45–3.48 (m, 4H) 3.80 (s, 3H) 4.86 (s, 2H) 7.51–7.60 (m, 2H) 7.64–7.68 (m, 2H)

MS m/e (ESI) 433(MH$^+$—CF$_3$COOH)

EXAMPLE 208

[7-(2-Chlorophenyl)-1-methyl-2,6-dioxo-8-(piperazin-1-yl)-1,2,6,7-tetrahydropurin-3-yl]acetic acid trifluoroacetate a) 4-[7-(2-Chlorophenyl)-3-carbonylmethyl-1-methyl-2,6-dioxo-2,3,6,7-tetrahydro-1H-purin-8-yl]piperazine-1-carboxylic acid tert-butyl ester

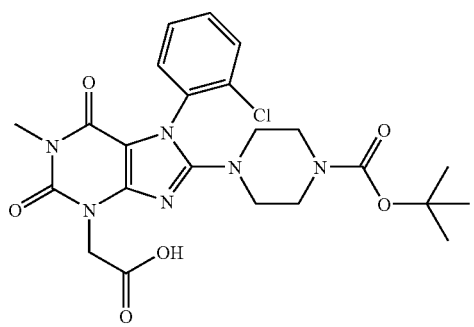

4-[7-(2-Chlorophenyl)-3-methoxycarbonylmethyl-1-methyl-2,6-dioxo-2,3,6,7-tetrahydro-1H-purin-8-yl]piperazine-1-carboxylic acid tert-butyl ester (87 mg) was dissolved in methanol (2 ml), and 5N aqueous sodium hydroxide solution (0.2 ml) was added to the solution. Then, the mixture was stirred at room temperature for 2 hours. The mixture was neutralized with 1N hydrochloric acid, and extracted with ethyl acetate. The organic layer was dried over anhydrous magnesium sulfate and filtered. The solvent was removed by distillation to give the title compound.

b) [7-(2-Chlorophenyl)-1-methyl-2,6-dioxo-8-(piperazin-1-yl)-1,2,6,7-tetrahydropurin-3-yl]acetic acid trifluoroacetate

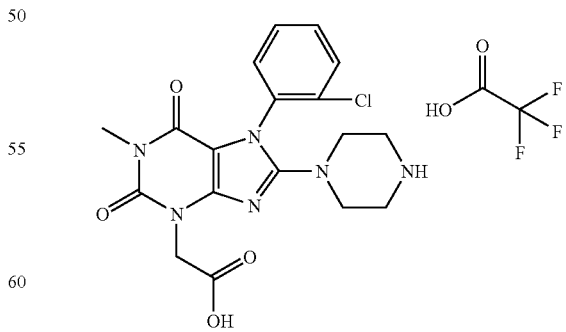

4-[7-(2-Chlorophenyl)-3-carboxymethyl-1-methyl-2,6-dioxo-2,3,6,7-tetrahydro-1H-purin-8-yl]piperazine-1-carboxylic acid tert-butyl ester (26 mg) was dissolved in trifluoroacetic acid, and was concentrated. The residue was purified by reversed phase high performance liquid chromatography to give 10.73 mg of the title compound.

$^1$H-NMR(d$^6$-DMSO) δ: 3.15–3.18 (m, 4H) 3.26 (s, 3H) 3.46–3.49 (m, 4H) 4.80 (s, 2H) 7.50–7.59 (m, 2H) 7.63–7.68 (m, 2H)

MS m/e (ESI) 419(MH$^+$—CF$_3$COOH)

EXAMPLE 209

2-[7-(2-Chlorophenyl)-1-methyl-2,6-dioxo-8-(piperazin-1-yl)-1,2,6,7-tetrahydropurin-3-yl]acetamide trifluoroacetate a) 4-[7-(2-Chlorophenyl)-3-acetamide-1-methyl-2,6-dioxo-2,3,6,7-tetrahydro-1H-purin-8-yl]piperazine-1-carboxylic acid tert-butyl ester

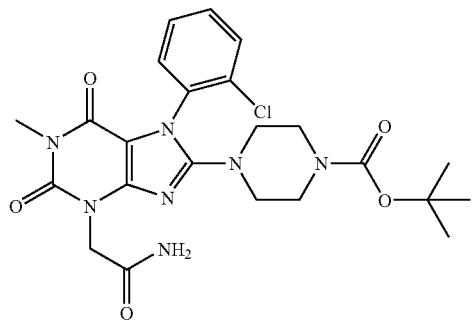

4-[7-(2-Chlorophenyl)-3-carboxymethyl-1-methyl-2,6-dioxo-2,3,6,7-tetrahydro-1H-purin-8-yl]piperazine-1-carboxylic acid tert-butyl ester (53 mg) was dissolved in tetrahydrofuran (1 ml), and triethylamine (0.03 ml) and ethyl chlorocarbonate (0.015 ml) were added to the solution. The mixture was stirred at room temperature for 15 minutes and 30% aqueous ammonia solution (0.1 ml) was added to the mixture. The reaction mixture was diluted with ethyl acetate, and washed with water and 1N hydrochloric acid. The organic layer was dried over anhydrous magnesium sulfate and filtered. The solvent was removed by distillation to give 53 mg of the title compound.

b) 2-[7-(2-Chlorophenyl)-1-methyl-2,6-dioxo-8-(piperazin-1-yl)-1,2,6,7-tetrahydropurin-3-yl]acetamide trifluoroacetate

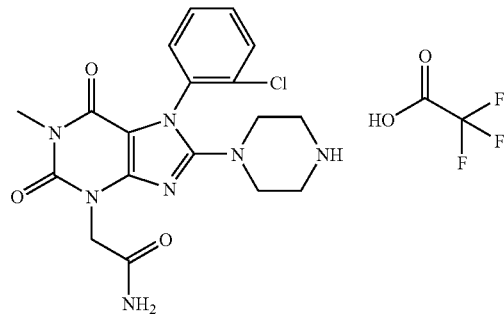

4-[7-(2-Chlorophenyl)-3-acetamido-1-methyl-2,6-dioxo-2,3,6,7-tetrahydro-1H-purin-8-yl]piperazine-1-carboxylic acid tert-butyl ester (53 mg) was dissolved in trifluoroacetic acid and concentrated. The residue was purified by reversed phase high performance liquid chromatography to give 23.31 mg of the title compound.

$^1$H-NMR(d$^6$-DMSO) δ: 3.15–3.18 (m, 4H) 3.26 (s, 3H) 3.45–3.48 (m, 4H) 4.76 (s, 2H) 7.50–7.59 (m, 2H) 7.62–7.68 (m, 2H)

MS m/e (ESI) 418(MH$^+$—CF$_3$COOH)

EXAMPLE 210

[7-(2-Chlorophenyl)-2,6-dioxo-8-(piperazin-1-yl)-1,2,6,7-tetrahydropurin-3-yl]acetic acid methyl ester trifluoroacetate

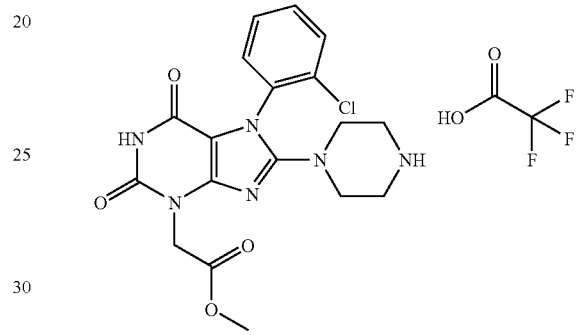

The title compound was obtained using 4-[7-(2-chlorophenyl)-3-methoxycarbonylmethyl-2,6-dioxo-2,3,6,7-tetrahydro-1H-purin-8-yl]piperazine-1-carboxylic acid tert-butyl ester and steps similar to Example 207c).

MS m/e (ESI) 419(MH$^+$—CF$_3$COOH)

EXAMPLE 211

[7-(2-Chlorophenyl)-2,6-dioxo-8-(piperazin-1-yl)-1,2,6,7-tetrahydropurin-3-yl]acetic acid trifluoroacetate

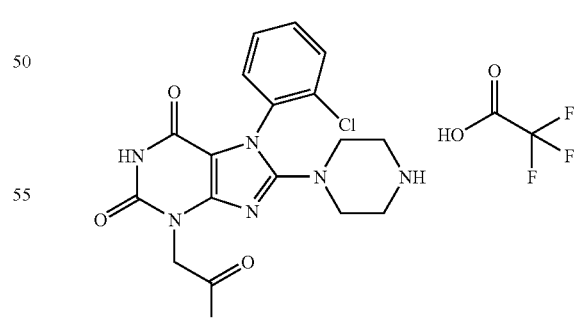

The title compound was obtained using 4-[7-(2-chlorophenyl)-3-methoxycarbonylmethyl-2,6-dioxo-2,3,6,7-tetrahydro-1H-purin-8-yl]piperazine-1-carboxylic acid tert-butyl ester, and steps similar to Example 208a) and b).

MS m/e (ESI) 405(MH$^+$—CF$_3$COOH)

EXAMPLE 212

[7-(2-Chlorophenyl)-2,6-dioxo-1-phenethyl-8-(piperazin-1-yl)-1,2,6,7-tetrahydropurin-3-yl]acetic acid methyl ester trifluoroacetate a) 4-[7-(2-Chlorophenyl)-3-methoxycarbonylmethyl-2,6-dioxo-1-phenethyl-2,3,6,7-tetrahydro-1H-purin-8-yl]piperazine-1-carboxylic acid tert-butyl ester

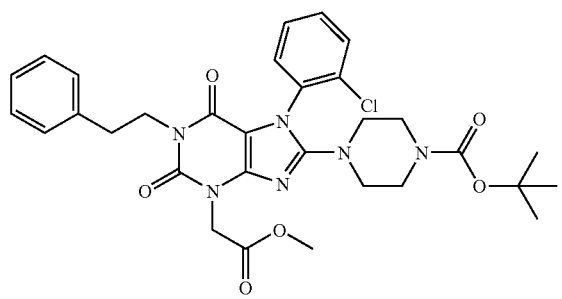

4-[7-(2-Chlorophenyl)-3-methoxycarbonylmethyl-2,6-dioxo-2,3,6,7-tetrahydro-1H-purin-8-yl]piperazine-1-carboxylic acid tert-butyl ester (49 mg) was dissolved in N,N-dimethylformamide (1 ml), and potassium carbonate (20 mg) and 2-phenethyl bromide (0.03 ml) were added to the solution. Then, the mixture was stirred at 50° C. overnight. The reaction mixture was diluted with ethyl acetate, and washed with water and 1N hydrochloric acid. The organic layer was dried over anhydrous magnesium sulfate and filtered. The solvent was removed by distillation to give 52 mg of the title compound.

b) [7-(2-Chlorophenyl)-2,6-dioxo-1-phenethyl-8-(piperazin-1-yl)-1,2,6,7-tetrahydropurin-3-yl]acetic acid methyl ester trifluoroacetate

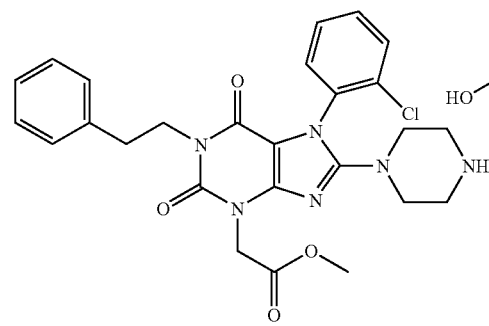

The title compound was obtained using 4-[7-(2-chlorophenyl)-3-methoxycarbonylmethyl-2,6-dioxo-1-phenethyl-2,3,6,7-tetrahydro-1H-purin-8-yl]piperazine-1-carboxylic acid tert-butyl ester and steps similar to Example 207 c).

MS m/e (ESI) 523(MH$^+$—CF$_3$COOH)

EXAMPLE 213

[7-(2-Chlorophenyl)-2,6-dioxo-1-phenethyl-8-(piperazin-1-yl)-1,2,6,7-tetrahydropurin-3-yl]acetic acid trifluoroacetate The title compound was obtained using 4-[7-(2-chlorophenyl)-3-methoxycarbonylmethyl-2,6-dioxo-1-phenethyl-2,3,6,7-tetrahydro-1H-purin-8-yl]piperazine-1-carboxylic acid tert-butyl ester, and steps similar to Example 208 a) and b).

MS m/e (ESI) 509(MH$^+$—CF$_3$COOH)

EXAMPLE 214

2-[7-(2-chlorophenyl)-2,6-dioxo-1-phenethyl-8-(piperazin-1-yl)-1,2,6,7-tetrahydropurin-3-yl]acetamide trifluoroacetate The title compound was obtained using 4-[7-(2-chlorophenyl)-3-carboxymethyl-2,6-dioxo-1-phenethyl-2,3,6,7-tetrahydro-1H-purin-8-yl]piperazine-1-carboxylic acid tert-butyl ester, and steps similar to Example 209 a) and b).

MS m/e (ESI) 508(MH$^+$—CF$_3$COOH)

EXAMPLE 215

[7-(2-Chlorophenyl)-1-methyl-8-(piperazin-1-yl)]-3,7-dihydropurine-*ne*-2,6-dione trifluoroacetate a) 2,2-Dimethylpropionic acid [7-benzyl-2,6-dioxo-1,2,6,7-tetrahydropurin-3-yl]methyl ester

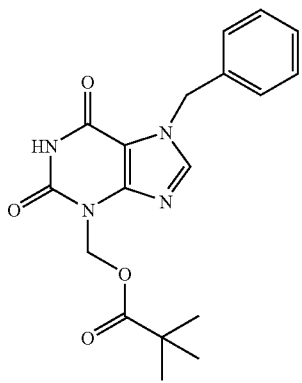

7-Benzylxanthine (8.66 g) was dissolved in N,N-dimethylformamide (300 ml); sodium hydride (1.57 g) and chloromethyl pivalate (7.7 ml) were added to the solution; and the mixture was stirred at room temperature overnight. The reaction mixture was diluted with ethyl acetate, and washed with water and 1N hydrochloric acid. The organic layer was dried over anhydrous magnesium sulfate and filtered. Then, the solvent was removed by distillation. The residue was purified by silica gel column chromatography to give 2.66 g of the title compound from the elution fraction of hexane-ethyl acetate 1:1.

$^1$H-NMR(CDCl$_3$) δ: 1.18 (s, 9H) 5.45 (s, 2H) 6.06 (s, 2H) 7.34–7.39 (m, 5H) 7.58 (s, 1H) 8.18 (s, 1H)

b) 2,2-Dimethylpropionic acid [7-benzyl-1-methyl-2,6-dioxo-1,2,6,7-tetrahydropurin-3-yl]methyl ester

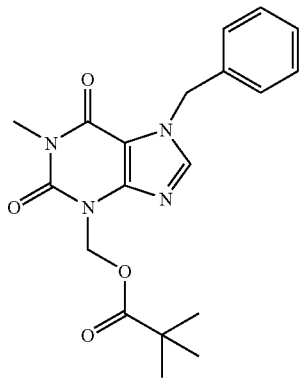

2,2-Dimethylpropionic Acid [7-benzyl-2,6-dioxo-1,2,6,7-tetrahydropurin-3-yl]methyl ester (2.66 g) was dissolved in N,N-dimethylformamide (30 ml), potassium carbonate (1.6 g) and iodomethane (1 ml) were added to the solution, and the mixture was stirred at room temperature overnight. The reaction mixture was diluted with ethyl acetate, and washed with water and 1N hydrochloric acid. The organic layer was dried over anhydrous magnesium sulfate and filtered. Then, the solvent was removed by distillation. The residue was triturated with toluene to give 2.16 g of the title compound.

$^1$H-NMR(CDCl$_3$) δ: 1.18 (s, 9H) 3.41 (s, 3H) 5.49 (s, 2H) 6.11 (s, 2H) 7.26–7.39 (m, 5H) 7.57 (s, 1H)

c) 2,2-Dimethylpropionic acid [1-methyl-2,6-dioxo-1,2,6,7-tetrahydropurin-3-yl]methyl ester

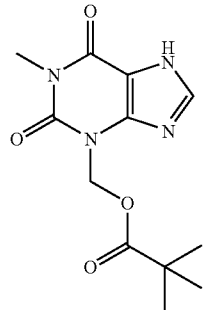

2.16 g of the title compound was obtained using 2,2-dimethylpropionic acid [7-benzyl-1-methyl-2,6-dioxo-1,2,6,7-tetrahydropurin-3-yl]methyl ester and steps similar to Example 175 d).

$^1$H-NMR(CDCl$_3$) δ: 1.19 (s, 9H) 3.48 (s, 3H) 6.17 (s, 2H) 7.83 (s, 1H)

d) 2,2-Dimethylpropionic acid [7-(2-chlorophenyl)-1-methyl-2,6-dioxo-1,2,6,7-tetrahydropurin-3-yl]methyl ester

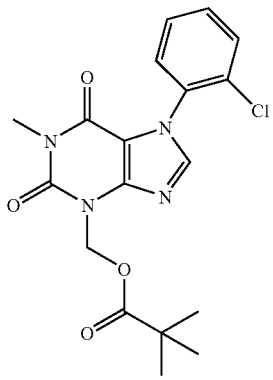

The title compound was obtained using 2,2-dimethylpropionic acid [1-methyl-2,6-dioxo-1,2,6,7-tetrahydropurin-3-yl]methyl ester and steps similar to Example 175 e).

e) 4-[7-(2-Chlorophenyl)-3-(2,2-dimethyl-propionyloxymethyl)-1-methyl-2,6-dioxo-2,3,6,7-tetrahydro-1H-purin-8-yl]piperazine-1-carboxylic acid tert-butyl ester

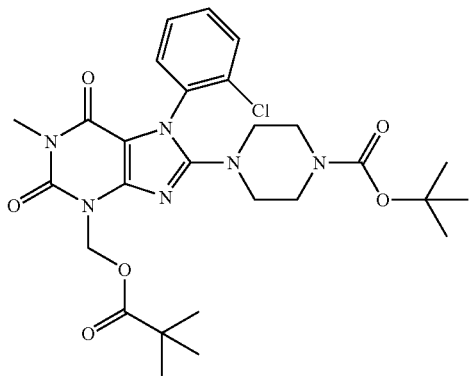

The title compound was obtained using 2,2-dimethylpropionic acid [7-(2-chlorophenyl)-1-methyl-2,6-dioxo-1,2,6,7-tetrahydropurin-3-yl]methyl ester and steps similar to Example 175 f).

f) 4-[7-(2-Chlorophenyl)-1-methyl-2,6-dioxo-2,3,6,7-tetrahydro-1H-purin-8-yl]piperazine-1-carboxylic acid tert-butyl ester

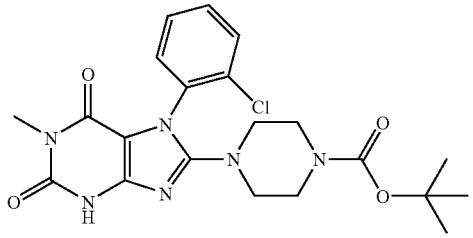

The title compound was obtained using 4-[7-(2-chlorophenyl)-3-(2,2-dimethyl-propionyloxymethyl)-1-methyl-2,6-dioxo-2,3,6,7-tetrahydro-1H-purin-8-yl]piperazine-1-carboxylic acid tert-butyl ester and steps similar to Example 156 e).

$^1$H-NMR(d$^6$-DMSO) δ: 1.35 (s, 9H) 3.04 (s, 3H) 3.06–3.12 (m, 4H) 3.17–3.22 (m, 4H) 7.48 (dt, J=1.6, 7.6 Hz, 1H) 7.53 (dt, J=2.0, 7.6 Hz, 1H) 7.63 (dd, J=2.0, 8.0 Hz, 1H) 7.65 (dd, J=1.6, 8.0 Hz, 1H)

g) 7-(2-Chlorophenyl)-1-methyl-8-(piperazin-1-yl)-3,7-dihydropurine-2,6-dione trifluoroacetate

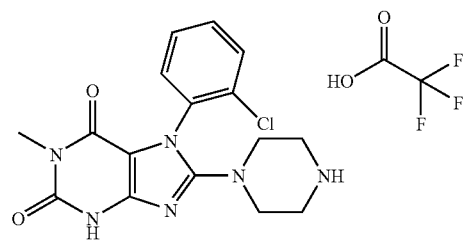

The title compound was obtained using 4-[7-(2-chlorophenyl)-1-methyl-2,6-dioxo-2,3,6,7-tetrahydro-1H-purin-8-yl]piperazine-1-carboxylic acid tert-butyl ester and steps similar to Example 209 b).

$^1$H-NMR(d$^6$-DMSO) δ: 2.95–3.03 (m, 4H) 3.14 (s, 3H) 3.23–3.34 (m, 4H) 7.49–7.62 (m, 2H) 7.66–7.71 (m, 2H) 10.90 (s, 1H)

MS m/e (ESI) 361(MH$^+$—CF$_3$COOH)

EXAMPLE 216

7-(2-Butynyl)-3-ethyl-1-methyl-8-(piperazin-1-yl)-3,7-dihydropurine-2,6-dione trifluoroacetate a) 2,2-Dimethylpropionic acid [7-(2-butynyl)-1-methyl-2,6-dioxo-1,2,6,7-tetrahydropurin-3-yl]methyl ester

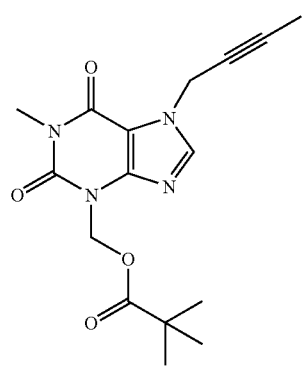

2,2-Dimethylpropionic acid [1-methyl-2,6-dioxo-1,2,6,7-tetrahydropurin-3-yl]methyl ester (1.871 g) was dissolved in N,N-dimethylformamide (30 ml), potassium carbonate (1.5 g) and 2-butynyl bromide (0.7 ml) were added to the solution, and the mixture was stirred at room temperature overnight. The reaction mixture was diluted with ethyl acetate, and washed with water and 1N hydrochloric acid. The organic layer was dried over anhydrous magnesium sulfate and filtered. Then, the solvent was removed by distillation. The residue was purified by silica gel column chromatography to give 2.12 g of the title compound from the elution fraction of hexane-ethyl acetate (3:2).

b) 7-(2-Butynyl)-1-methyl-3,7-dihydropurine-2,6-dione

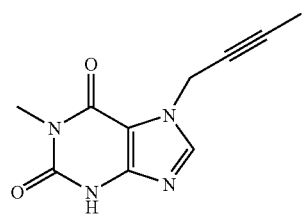

The title compound was obtained using 2,2-dimethylpropionic acid [7-(2-butynyl)-1-methyl-2,6-dioxo-1,2,6,7-tetrahydropurin-3-yl]methyl ester and steps similar to Example 215 f).

$^1$H-NMR(CDCl$_3$) δ: 1.91 (t, J=2.4 Hz, 3H) 3.39 (s, 3H) 5.10 (s, 2H) 7.93 (s, 1H) 10.62 (s, 1H)

c) 4-[7-(2-Butynyl)-1-methyl-2,6-dioxo-2,3,6,7-tetrahydro-1H-purin-8-yl]piperazine-1-carboxylic acid tert-butyl ester

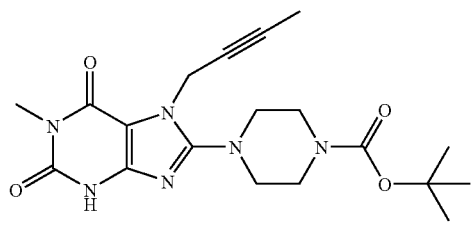

The title compound was obtained using 7-(2-butynyl)-1-methyl-3,7-dihydropurine-2,6-dione and steps similar to Example 215 e).

$^1$H-NMR(CDCl$_3$) δ: 1.48 (s, 9H) 1.83 (t, J=2.4 Hz, 3H) 3.37 (s, 3H) 3.37–3.39 (m, 4H) 3.58–3.60 (m, 4H) 4.87 (s, 2H) 9.68 (s, 1H)

d) 7-(2-Butynyl)-3-ethyl-1-methyl-8-(piperazin-1-yl)-3,7-dihydropurine-2,6-dione trifluoroacetate

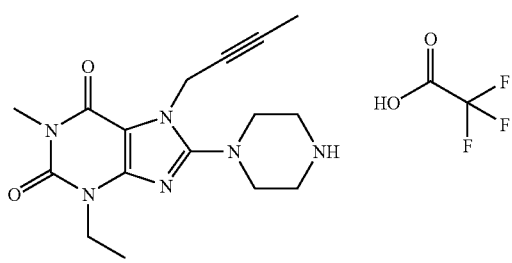

The title compound was obtained using 4-[7-(2-butynyl)-1-methyl-2,6-dioxo-2,3,6,7-tetrahydro-1H-purin-8-yl]piperazine-1-carboxylic acid tert-butyl ester and steps similar to Example 175 h).

MS m/e (ESI) 331(MH$^+$—CF$_3$COOH)

EXAMPLE 217

7-(2-Butynyl)-1-methyl-8-(piperazin-1-yl)-3,7-dihydropurine-2,6-dione trifluoroacetate

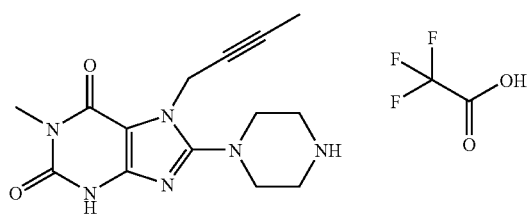

The title compound was obtained using 4-[7-(2-butynyl)-1-methyl-2,6-dioxo-2,3,6,7-tetrahydro-1H-purin-8-yl]piperazine-1-carboxylic acid tert-butyl ester and steps similar to Example 175 h).

MS m/e (ESI) 303(MH$^+$—CF$_3$COOH)

EXAMPLE 218

7-(2-Butynyl)-3-benzyl-1-methyl-8-(piperazin-1-yl)-3,7-dihydropurine-2,6-dione trifluoroacetate

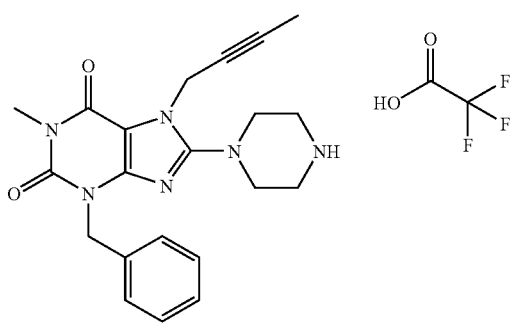

The title compound was obtained using benzyl bromide and steps similar to Example 216 d).

$^1$H-NMR(CDCl$_3$) δ: 1.83 (t, J=2.4 Hz, 3H) 3.03–3.06 (m, 4H) 3.38 (s, 3H) 3.38–3.41 (m, 4H) 4.84 (q, J=2.4 Hz, 2H) 5.21 (s, 2H) 7.26–7.30 (m, 3H) 7.52–7.54 (m, 2H)

MS m/e (ESI) 393(MH$^+$—CF$_3$COOH)

EXAMPLE 219

[7-(2-Butynyl)-1-methyl-2,6-dioxo-8-(piperazin-1-yl)-1,2,6,7-tetrahydropurin-3-yl]acetic acid methyl ester trifluoroacetate

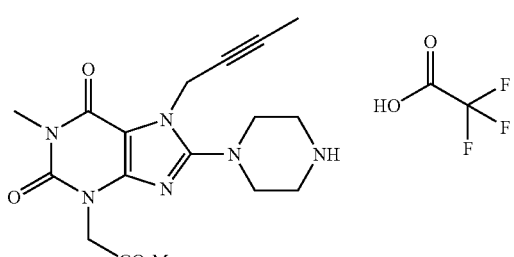

The title compound was obtained using methyl bromoacetate and steps similar to Example 216 d).

$^1$H-NMR(CDCl$_3$) δ: 1.84 (t, J=2.4 Hz, 3H) 3.00–3.03 (m, 4H) 3.34–3.36 (m, 4H) 3.40 (s, 3H) 3.79 (s, 3H) 4.78 (s, 2H) 4.84 (q, J=2.4 Hz, 2H)

MS m/e (ESI) 375(MH$^+$—CF$_3$COOH)

EXAMPLE 220

[7-(2-Butynyl)-1-methyl-2,6-dioxo-8-(piperazin-1-yl)-1,2,6,7-tetrahydropurin-3-yl] acetic acid trifluoroacetate

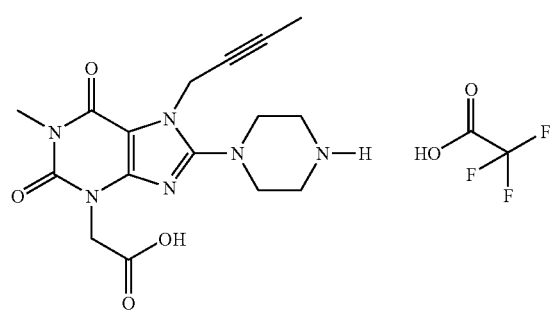

4-[7-(2-Butynyl)-1-methyl-3-methoxycarbonylmethyl-2,6-dioxo-2,3,6,7-tetrahydro-1H-purin-8-yl]piperazine-1-carboxylic acid tert-butyl ester (13 mg) was added to ethanol (1.0 ml) and 2N aqueous sodium hydroxide solution (0.2 ml), and the mixture was stirred at room temperature for 3 hours. The reaction mixture was diluted with water, and neutralized with 2N hydrochloric acid. After the mixture was extracted with ethyl acetate, the organic layer was dried over anhydrous magnesium sulfate. The solvent was removed by distillation, and the residue was dissolved in trifluoroacetic acid (0.5 ml). Then, the mixture was stirred at room temperature for 30 minutes. After removing the solvent by distillation, a half of the residue was purified by HPLC with a reversed phase column using water-acetonitrile-trifluoroacetic acid system as eluting solvent to give 4.0 mg of the title compound.

MS m/e (ESI) 361(MH$^+$—CF$_3$COOH)

EXAMPLE 221

7-(2-Butynyl)-3-(4-chlorobenzyl)-1-methyl-8-(piperazin-1-yl)-3,7-dihydropurine-2,6-dione trifluoroacetate

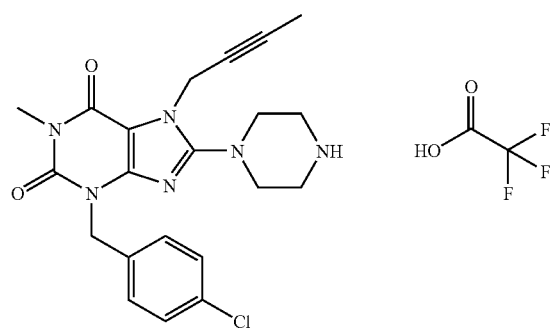

The title compound was obtained using 4-chlorobenzyl bromide and steps similar to Example 216 d).

MS m/e (ESI) 427(MH$^+$—CF$_3$COOH)

EXAMPLE 222

7-(2-Butynyl)-3-cyclobutyl-1-methyl-8-(piperazin-1-yl)-3,7-dihydropurine-2,6-dione trifluoroacetate

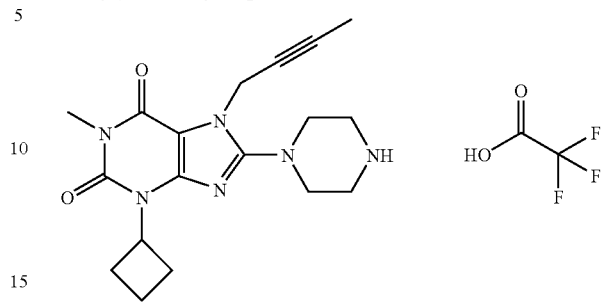

4-[7-(2-Butynyl)-1-methyl-2,6-dioxo-2,3,6,7-tetrahydro-1H-purin-8-yl]piperazine-1-carboxylic acid tert-butyl ester (8 mg) was dissolved in N,N-dimethylformamide (0.4 ml), potassium carbonate (10 mg) and cyclobutyl bromide (0.01 ml) were added to the solution, and the mixture was stirred at 50° C. overnight. The reaction mixture was diluted with ethyl acetate, and the organic layer was concentrated. The residue was dissolved in trifluoroacetic acid and concentrated. The residue was purified using reversed phase high performance liquid chromatography to give 3.72 mg of the title compound.

MS m/e (ESI) 357(MH$^+$—CF$_3$COOH)

EXAMPLE 223

7-(2-Butynyl)-3-(2-butynyl)-1-methyl-8-(piperazin-1-yl)-3,7-dihydropurine-2,6-dione trifluoroacetate

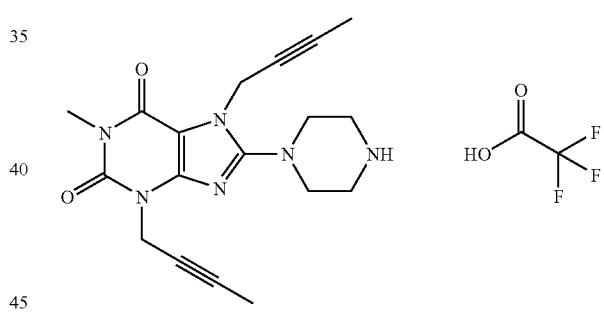

The title compound was obtained using 1-bromo-2-butyne and steps similar to Example 222.

MS m/e (ESI) 355(MH$^+$—CF$_3$COOH)

EXAMPLE 224

7-(2-Butynyl)-3-cyanomethyl-1-methyl-8-(piperazin-1-yl)-3,7-dihydropurine-2,6-dione trifluoroacetate

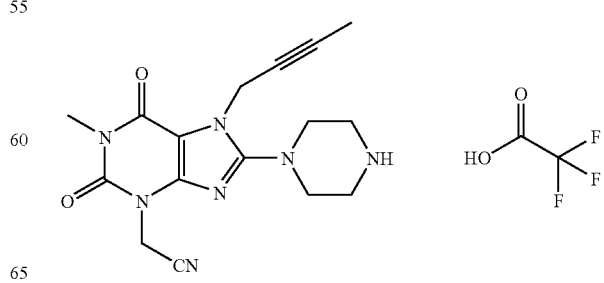

The title compound was obtained using bromoacetonitrile and steps similar to Example 222.
MS m/e (ESI) 342(MH⁺—CF₃COOH)

EXAMPLE 225

7-(2-Butynyl)-3-(2-hydroxyethyl)-1-methyl-8-(piperazin-1-yl)-3,7-dihydropurine-2,6-dione trifluoroacetate

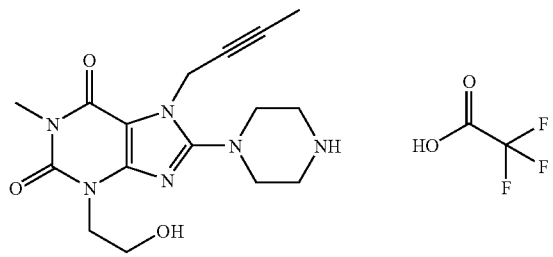

The title compound was obtained using 2-iodoethanol and steps similar to Example 222.
MS m/e (ESI) 347(MH⁺—CF₃COOH)

EXAMPLE 226

7-(2-Butynyl)-3-(2-tetrahydrofuranyl)methyl-1-methyl-8-(piperazin-1-yl)-3,7-dihydropurine-2,6-dione trifluoroacetate

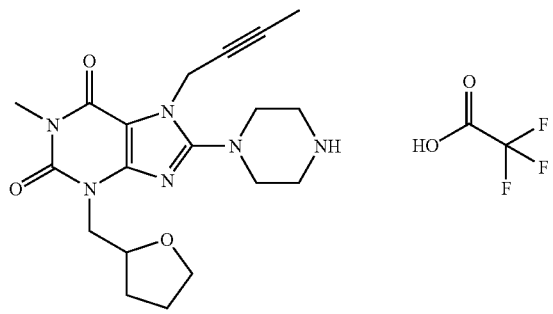

The title compound was obtained using 2-bromomethyltetrahydrofuran and steps similar to Example 222.
¹H-NMR(CDCl₃) δ: 1.70–1.77 (m, 1H) 1.84 (t, J=2.4 Hz, 3H) 1.88–1.93 (m, 1H) 1.97–2.06 (m, 2H) 3.01–3.04 (m, 4H) 3.34–3.36 (m, 4H) 3.39 (s, 3H) 3.77 (dd, J=8.4, 14.0 Hz, 1H) 3.92–3.97 (m, 2H) 4.19 (dd, J=8.4, 13.6 Hz, 1H) 4.45–4.50 (m, 1H) 4.83 (q, J=2.4 Hz, 2H)
MS m/e (ESI) 387(MH⁺—CF₃COOH)

EXAMPLE 227

7-(2-Butynyl)-3-(2-methylpropyl)-1-methyl-8-(piperazin-1-yl)-3,7-dihydropurine-2,6-dione trifluoroacetate

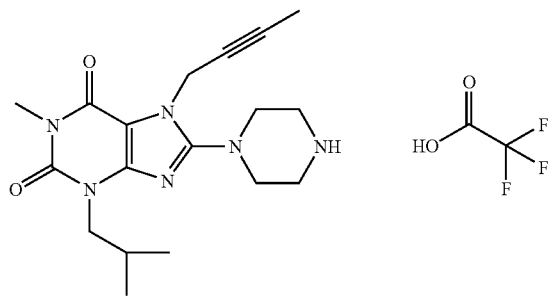

The title compound was obtained using isobutyl bromide and steps similar to Example 222.
MS m/e (ESI) 359(MH⁺—CF₃COOH)

EXAMPLE 228

7-(2-Butynyl)-3-cyclobutylmethyl-1-methyl-8-(piperazin-1-yl)-3,7-dihydropurine-2,6-dione trifluoroacetate

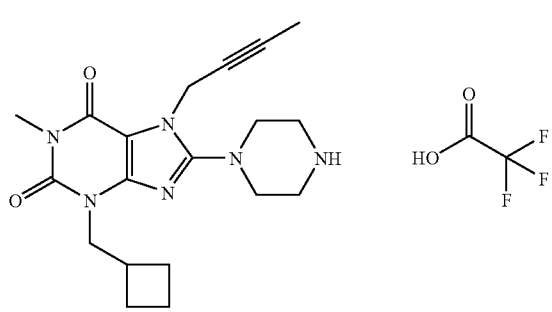

The title compound was obtained using cyclobutylmethyl bromide and steps similar to Example 222.
¹H-NMR(CDCl₃) δ: 1.83 (t, J=2.4 Hz, 3H) 1.85–1.91 (m, 1H) 1.98–2.05 (m, 2H) 2.81–2.87 (m, 1H) 3.02–3.05 (m, 4H) 3.36–3.37 (m, 4H) 3.38 (s, 3H) 4.09 (d, J=7.2 Hz, 1H) 4.85 (q, J=2.4 Hz, 2H)
MS m/e (ESI) 371(MH⁺—CF₃COOH)

EXAMPLE 229

7-(2-Butynyl)-3-(3-trifluoromethylpropyl)-1-methyl-8-(piperazin-1-yl)-3,7-dihydropurine-2,6-dione trifluoroacetate

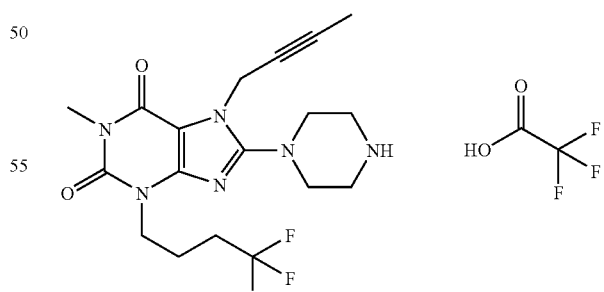

The title compound was obtained using 3-trifluoromethylpropyl bromide and steps similar to Example 222.
MS m/e (ESI) 413(MH⁺—CF₃COOH)

EXAMPLE 230

7-(2-Butynyl)-3-(3-fluoropropyl)-1-methyl-8-(piperazin-1-yl)-3,7-dihydropurine-2,6-dione trifluoroacetate

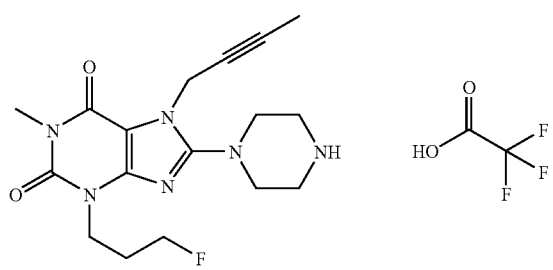

The title compound was obtained using 3-fluoro-1-bromopropane and steps similar to Example 222.
MS m/e (ESI) 363(MH$^+$—CF$_3$COOH)

EXAMPLE 231

7-(2-Butynyl)-3-(2,2-difluoroethyl)-1-methyl-8-(piperazin-1-yl)-3,7-dihydropurine-2,6-dione trifluoroacetate

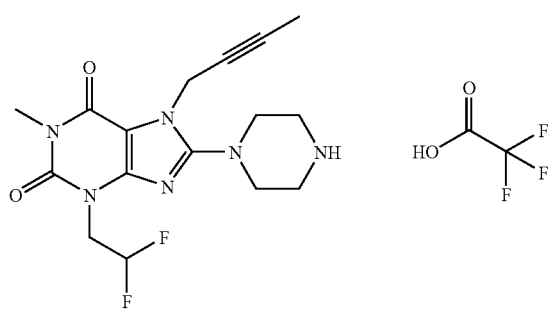

The title compound was obtained using 2,2-difluoroethyl bromide and steps similar to Example 222.
MS m/e (ESI) 367(MH$^+$—CF$_3$COOH)

EXAMPLE 232

7-(2-Butynyl)-3-(2-fluoroethyl)-1-methyl-8-(piperazin-1-yl)-3,7-dihydropurine-2,6-dione trifluoroacetate

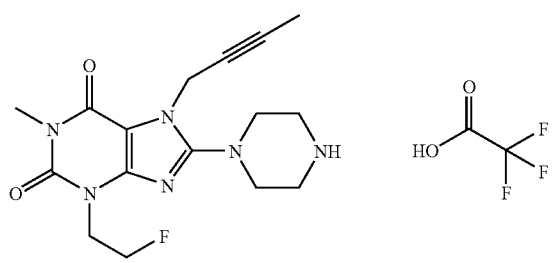

The title compound was obtained using 1-iodo-2-fluoroethane and steps similar to Example 222.
MS m/e (ESI) 349(MH$^+$—CF$_3$COOH)

EXAMPLE 233

7-(2-Butynyl)-3-cyclopropylmethyl-1-methyl-8-(piperazin-1-yl)-3,7-dihydropurine-2,6-dione trifluoroacetate

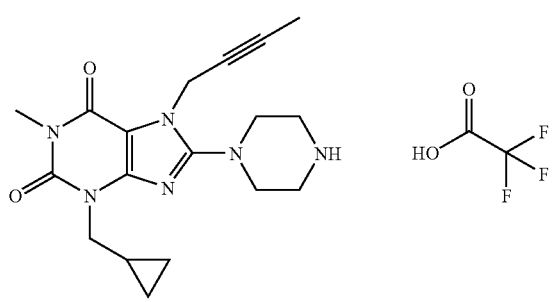

The title compound was obtained using bromomethylcyclopropane Example 222.
MS m/e (ESI) 357(MH$^+$—CF$_3$COOH)

EXAMPLE 234

7-(2-Butynyl)-3-(2,2,2-trifluoroethyl)-1-methyl-8-(piperazin-1-yl)-3,7-dihydropurine-2,6-dione trifluoroacetate

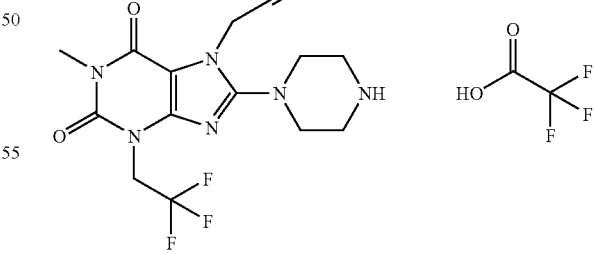

The title compound was obtained using 1-iodo-2,2,2-trifluoroethane and steps similar to Example 222.
MS m/e (ESI) 385(MH$^+$—CF$_3$COOH)

EXAMPLE 235

7-(2-Butynyl)-3-[(2-oxo-2-(4-chlorophenyl)ethyl)]-1-methyl-8-piperazin-1-yl)-3,7-dihydropurine-2,6-dione trifluoroacetate

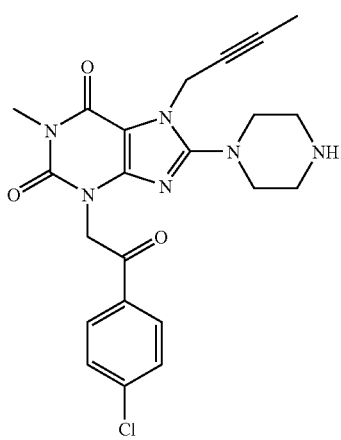 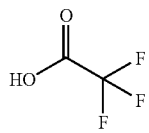

The title compound was obtained using 4-chlorophenacyl bromide and steps similar to Example 222.
MS m/e (ESI) 455(MH⁺—CF₃COOH)

EXAMPLE 236

2-[7-(2-Butynyl)-1-methyl-2,6-dioxo-8-(piperazin-1-yl)-1,2,6,7-tetrahydropurin-3-yl]acetamide trifluoroacetate

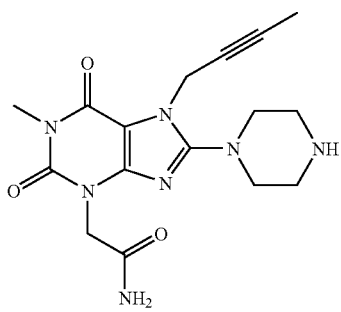 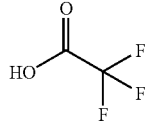

The title compound was obtained using 2-bromoacetamide and steps similar to Example 222.
¹H-NMR(CDCl₃) δ: 1.68 (t, J=2.4 Hz, 3H) 3.15–3.19 (m, 4H) 3.23 (s, 3H) 3.46–3.51 (m, 4H) 4.55 (s, 2H) 4.71 (q, J=2.4 Hz, 2H) 6.00 (br, 1H) 6.91 (br, 1H)
MS m/e (ESI) 360(MH⁺—CF₃COOH)

EXAMPLE 237

7-(2-Butynyl)-3-(3-hydroxypropyl)-1-methyl-8-(piperazin-1-yl)-3,7-dihydropurine-2,6-dione trifluoroacetate

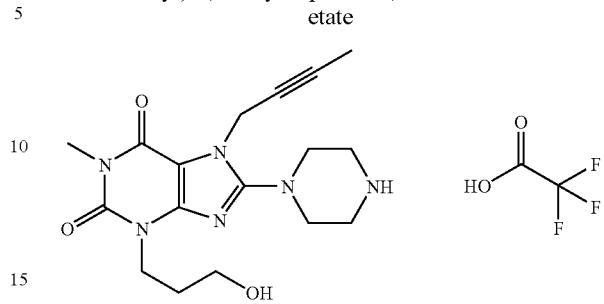 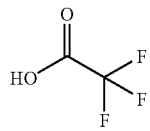

The title compound was obtained using 3-iodopropanol and steps similar to Example 222.
MS m/e (ESI) 361(MH⁺—CF₃COOH)

EXAMPLE 238

7-(2-Butynyl)-3-(2-benzyloxyethyl)-1-methyl-8-(piperazin-1-yl)-3,7-dihydropurine-2,6-dione trifluoroacetate

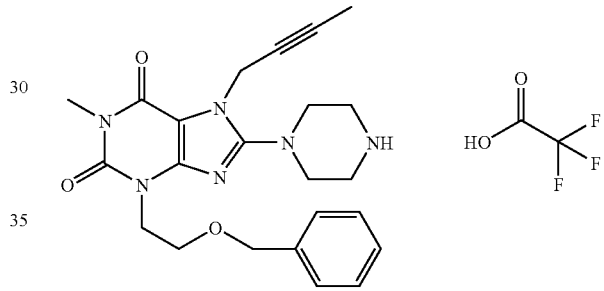 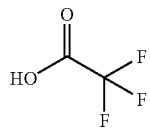

The title compound was obtained using 2-benzyloxyethyl bromide and steps similar to Example 222.
MS m/e (ESI) 437(MH⁺—CF₃COOH)

EXAMPLE 239

2-[7-(2-Butynyl)-1-methyl-2,6-dioxo-8-(piperazin-1-yl)-1,2,6,7-tetrahydropurin-3-yl]propioamide trifluoroacetate

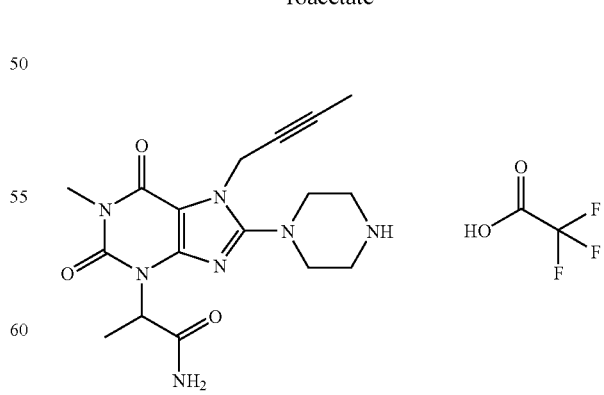 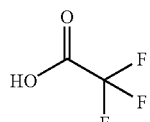

The title compound was obtained using 2-bromopropionamide and steps similar to Example 222.
MS m/e (ESI) 374(MH⁺—CF₃COOH)

EXAMPLE 240

[7-(2-Butynyl)-1-methyl-2,6-dioxo-8-(piperazin-1-yl)-1,2,6,7-tetrahydropurin-3-yl]phenyl acetic acid methyl ester trifluoroacetate

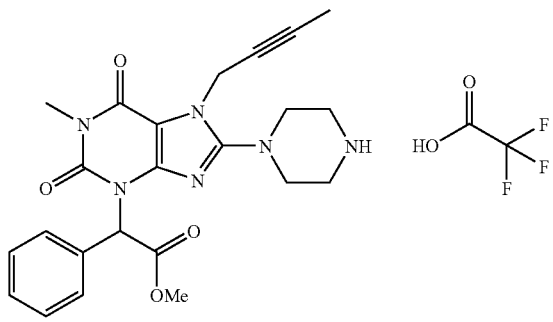

The title compound was obtained using 2-bromophenylacetic acid methyl ester and steps similar to Example 222.
$^1$H-NMR(CDCl$_3$) δ: 1.83 (t, J=2.4 Hz, 3H) 3.02–3.05 (m, 4H) 3.36–3.38 (m, 4H) 3.37 (s, 3H) 3.80 (s, 3H) 4.82 (q, J=2.4 Hz, 2H) 6.50 (s, 1H) 7.30–7.32 (m, 3H) 7.65–7.67 (m, 2H)
MS m/e (ESI) 451(MH$^+$—CF$_3$COOH)

EXAMPLE 241

7-(2-Butynyl)-3-(2-diethylaminoethyl)-1-methyl-8-(piperazin-1-yl)-3,7-dihydropurine-2,6-dione trifluoroacetate

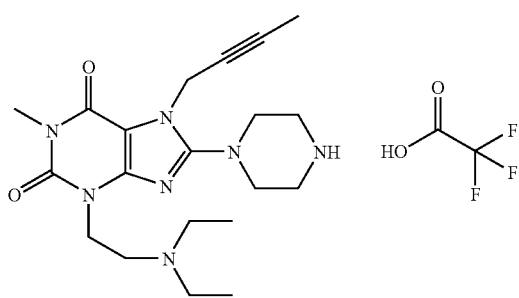

The title compound was obtained using (2-diethylaminoethyl) bromide and steps similar to Example 222.
MS m/e (ESI) 402(MH$^+$—CF$_3$COOH)

EXAMPLE 242

7-(2-Butynyl)-3-allyl-1-methyl-8-(piperazin-1-yl)-3,7-dihydropurine-2,6-dione trifluoroacetate

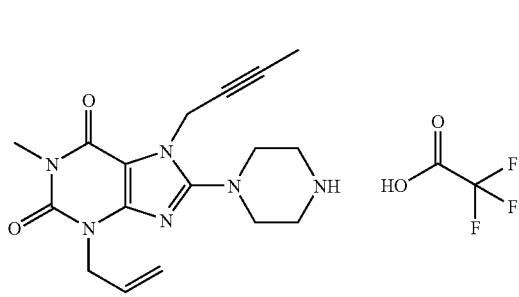

The title compound was obtained using allyl bromide and steps similar to Example 222.
MS m/e (ESI) 343(MH$^+$—CF$_3$COOH)

EXAMPLE 243

7-(2-Butynyl)-3-propyl-1-methyl-8-(piperazin-1-yl)-3,7-dihydropurine-2,6-dione trifluoroacetate

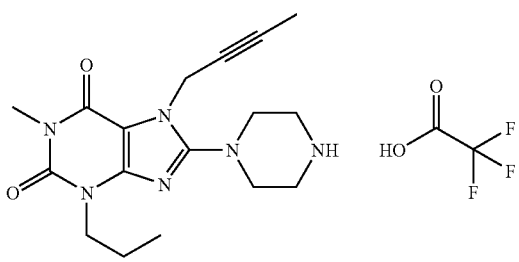

The title compound was obtained using Iodopropane and steps similar to Example 222.
MS m/e (ESI) 345(MH$^+$—CF$_3$COOH)

EXAMPLE 244

7-(2-Butynyl)-3-butyl-1-methyl-8-(piperazin-1-yl)-3,7-dihydropurine-2,6-dione trifluoroacetate

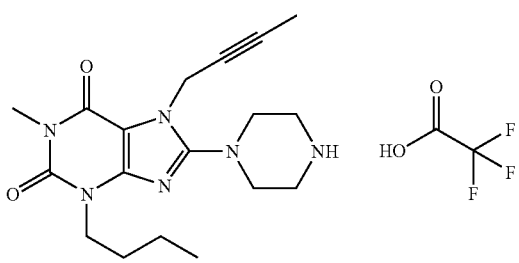

The title compound was obtained using iodobutane and steps similar to Example 222.
MS m/e (ESI) 359(MH$^+$—CF$_3$COOH)

EXAMPLE 245

7-(2-Butynyl)-3-cyclohexyl-1-methyl-8-(piperazin-1-yl)-3,7-dihydropurine-2,6-dione trifluoroacetate

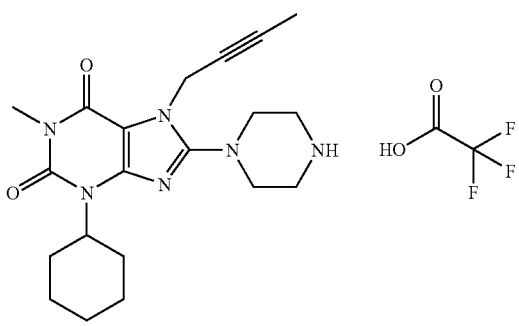

The title compound was obtained using iodocyclohexane and steps similar to Example 222.
MS m/e (ESI) 385(MH$^+$—CF$_3$COOH)

EXAMPLE 246

7-(2-Butynyl)-3-(2-butenyl)-1-methyl-8-(piperazin-1-yl)-3,7-dihydropurine-2,6-dione trifluoroacetate

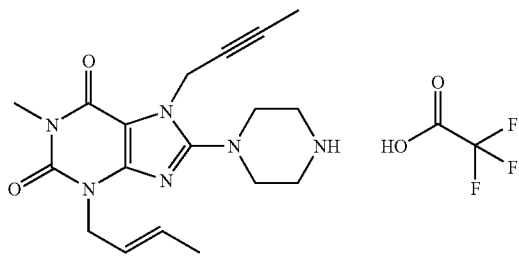

The title compound was obtained using 1-iodo-2-butene and steps similar to Example 222.
MS m/e (ESI) 357(MH$^+$—CF$_3$COOH)

EXAMPLE 247

7-(2-Butynyl)-3-(2-methylbutyl)-1-methyl-8-(piperazin-1-yl)-3,7-dihydropurine-2,6-dione trifluoroacetate

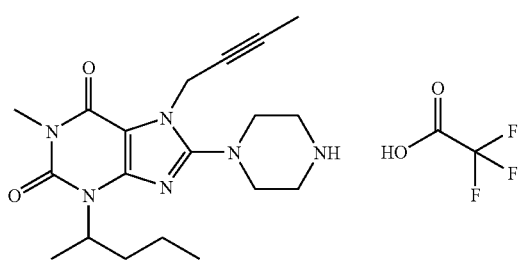

The title compound was obtained using 2-iodopentane and steps similar to Example 222.
MS m/e (ESI) 373(MH$^+$—CF$_3$COOH)

EXAMPLE 248

7-(2-Butynyl)-3-(3-cyanopropyl)-1-methyl-8-(piperazin-1-yl)-3,7-dihydropurine-2,6-dione trifluoroacetate

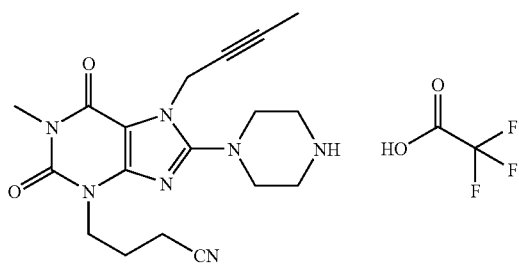

The title compound was obtained using 4-bromobutyronitrile and steps similar to Example 222.
MS m/e (ESI) 370(MH$^+$—CF$_3$COOH)

EXAMPLE 249

7-(2-Butynyl)-3-(2-phenoxyethyl)-1-methyl-8-(piperazin-1-yl)-3,7-dihydropurine-2,6-dione trifluoroacetate

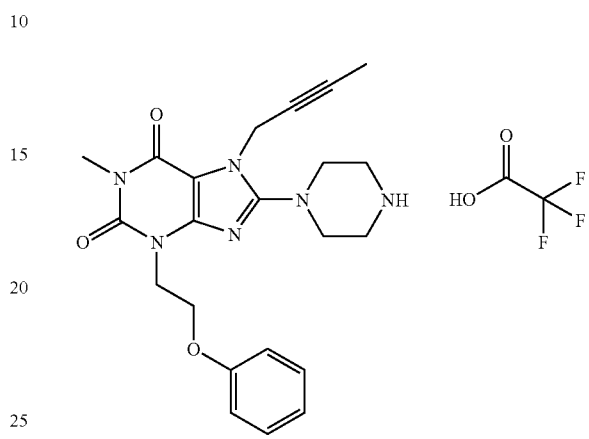

The title compound was obtained using 2-phenoxyethyl bromide and steps similar to Example 222.
$^1$H-NMR(CDCl$_3$) δ: 1.84 (t, J=2.4 Hz, 3H) 3.01–3.04 (m, 4H) 3.35–3.37 (m, 4H) 3.40 (s, 3H) 4.32 (t, J=6.4 Hz, 2H) 4.46 (t, J=6.0 Hz, 2H) 4.85 (q, J=2.4 Hz, 2H) 6.91–6.95 (m, 3H) 7.23–7.27 (m, 2H)
MS m/e (ESI) 423(MH$^+$—CF$_3$COOH)

EXAMPLE 250

7-(2-Butynyl)-3-(2-hydroxypropyl)-1-methyl-8-(piperazin-1-yl)-3,7-dihydropurine-2,6-dione trifluoroacetate

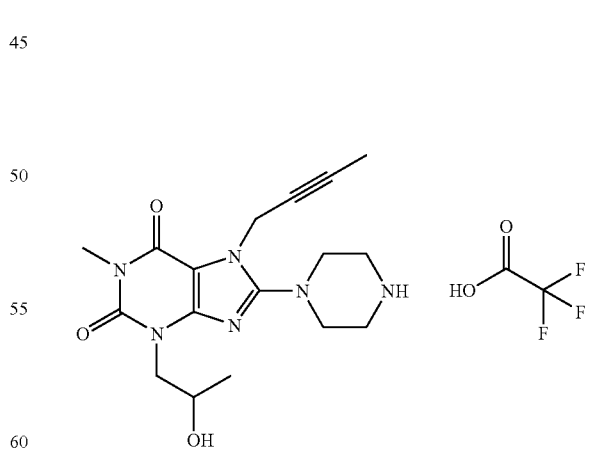

The title compound was obtained using 1-bromo-2-propanol and steps similar to Example 222.
MS m/e (ESI) 361(MH$^+$—CF$_3$COOH)

EXAMPLE 251

7-(2-Butynyl)-3-(3-chlorobenzyl)-1-methyl-8-(piperazin-1-yl)-3,7-dihydropurine-2,6-dione trifluoroacetate

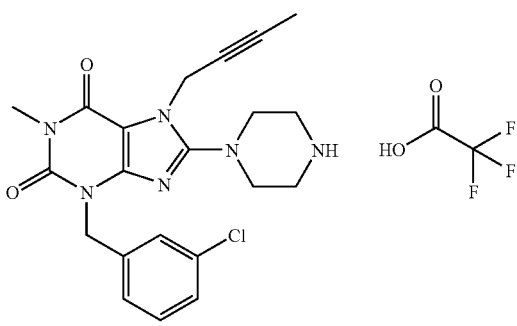

The title compound was obtained using 3-chlorobenzyl bromide and steps similar to Example 222.
MS m/e (ESI) 427(MH$^+$—CF$_3$COOH)

EXAMPLE 252

7-(2-Butynyl)-3-(1-methylpropyl)-1-methyl-8-(piperazin-1-yl)-3,7-dihydropurine-2,6-dione trifluoroacetate

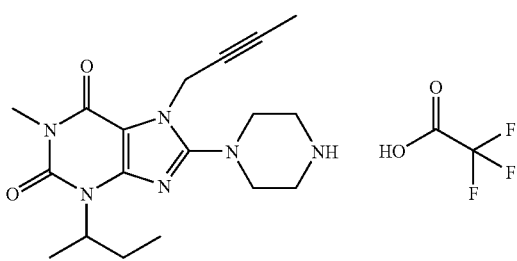

The title compound was obtained using 2-bromobutane and steps similar to Example 222.
MS m/e (ESI) 359(MH$^+$—CF$_3$COOH)

EXAMPLE 253

7-(2-Butynyl)-3-cyclopentyl-1-methyl-8-(piperazin-1-yl)-3,7-dihydropurine-2,6-dione trifluoroacetate

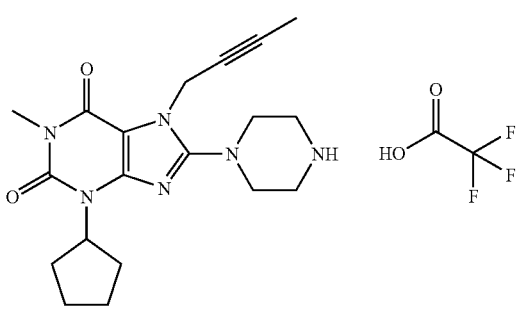

The title compound was obtained using bromocyclopentane and steps similar to Example 222.
MS m/e (ESI) 371(MH$^+$—CF$_3$COOH)

EXAMPLE 254

7-(2-Butynyl)-3-(2-propynyl)-1-methyl-8-(piperazin-1-yl)-3,7-dihydropurine-2,6-dione trifluoroacetate

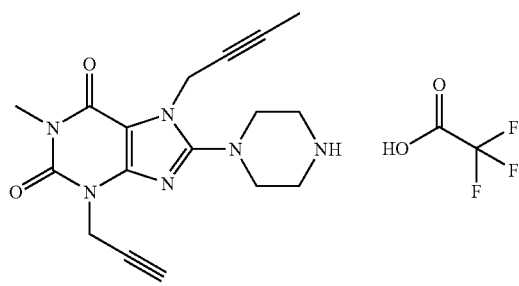

The title compound was obtained using propargyl bromide and steps similar to Example 222.
MS m/e (ESI) 341(MH$^+$—CF$_3$COOH)

EXAMPLE 255

7-(2-Butynyl)-3-(2-chlorobenzyl)-1-methyl-8-(piperazin-1-yl)-3,7-dihydropurine-2,6-dione trifluoroacetate

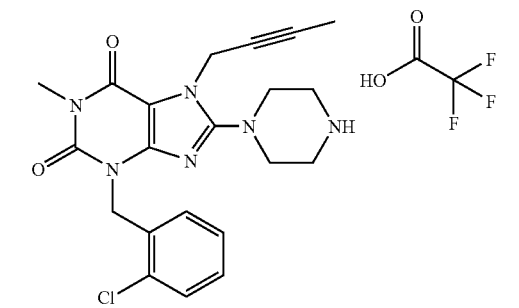

The title compound was obtained using 2-chlorobenzyl bromide and steps similar to Example 222.
MS m/e (ESI) 427(MH$^+$—CF$_3$COOH)

EXAMPLE 256

7-(2-Butynyl)-3-(2-oxo-2-phenethyl)-1-methyl-8-(piperazin-1-yl)-3,7-dihydropurine-2,6-dione trifluoroacetate

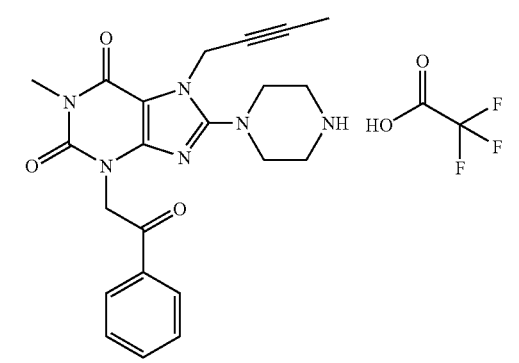

The title compound was obtained using phenacyl bromide and steps similar to Example 222.

$^1$H-NMR(CDCl$_3$) δ: 1.85 (t, J=2.4 Hz, 3H) 2.96–2.99 (m, 4H) 3.28–3.31 (m, 4H) 3.41 (s, 3H) 4.85 (q, J=2.4 Hz, 2H) 5.48 (s, 2H) 7.50–7.54 (m, 2H) 7.61–7:65 (m, 1H) 8.02–8.05 (m, 2H)

MS m/e (ESI) 421(MH$^+$—CF$_3$COOH)

EXAMPLE 257

2-[7-(2-Butynyl)-1-methyl-2,6-dioxo-8-(piperazin-1-yl)-1,2,6,7-tetrahydropurin-3-yl]propionic acid ethyl ester trifluoroacetate

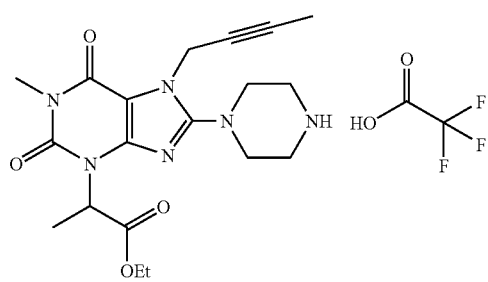

The title compound was obtained using ethyl 2-bromopropionate and steps similar to Example 222.

$^1$H-NMR(CDCl$_3$) δ: 1.23 (t, J=7.2 Hz, 3H) 1.70 (d, J=7.2 Hz, 3H) 1.84 (t, J=2.4 Hz, 3H) 3.00–3.03 (m, 4H) 3.33–3.37 (m, 4H) 3.38 (s, 3H) 4.15–4.25 (m, 2H) 4.85 (q, J=2.4 Hz, 2H) 5.43 (q, J=7.2 Hz, 1H)

MS m/e (ESI) 403(MH$^+$—CF$_3$COOH)

EXAMPLE 258

7-(2-Butynyl)-3-(3-butenyl)-1-methyl-8-(piperazin-1-yl)-3,7-dihydropurine-2,6-dione trifluoroacetate

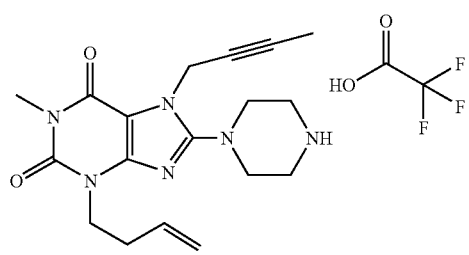

The title compound was obtained using 1-bromo-3-butene and steps similar to Example 222.

MS m/e (ESI) 357(MH$^+$—CF$_3$COOH)

EXAMPLE 259

7-(2-Butynyl)-3-cyclohexylmethyl-1-methyl-8-(piperazin-1-yl)-3,7-dihydropurine-2,6-dione trifluoroacetate

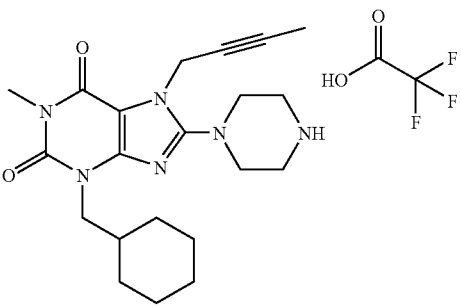

The title compound was obtained using iodomethylcyclohexane and steps similar to Example 222.

MS m/e (ESI) 399(MH$^+$—CF$_3$COOH)

EXAMPLE 260

7-(2-Butynyl)-3-(3-cyclohexenyl)-1-methyl-8-(piperazin-1-yl)-3,7-dihydropurine-2,6-dione trifluoroacetate

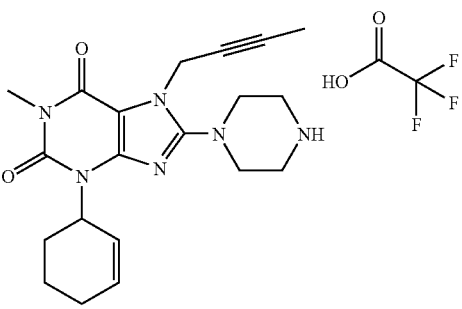

The title compound was obtained using 3-bromocyclohexene and steps similar to Example 222.

MS m/e (ESI) 383(MH$^+$—CF$_3$COOH)

EXAMPLE 261

2-[7-(2-Butynyl)-1-methyl-2,6-dioxo-8-(piperazin-1-yl)-1,2,6,7-tetrahydropurin-3-yl] butyric acid ethyl ester trifluoroacetate

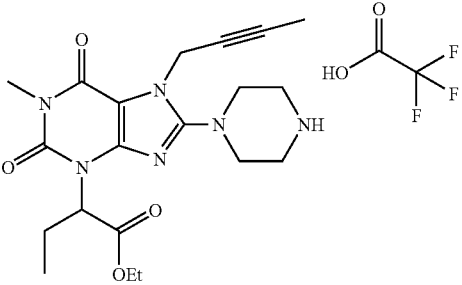

The title compound was obtained using 2-bromobutanoic acid ethyl ester and steps similar to Example 222.

MS m/e (ESI) 417(MH$^+$—CF$_3$COOH)

EXAMPLE 262

7-(2-Butynyl)-3-(2-methoxyethyl)-1-methyl-8-(piperazin-1-yl)-3,7-dihydropurine-2,6-dione trifluoroacetate

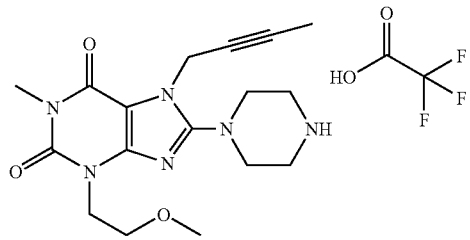

The title compound was obtained using 2-methoxyethyl bromide and steps similar to Example 222.

MS m/e (ESI) 361(MH$^+$—CF$_3$COOH)

EXAMPLE 263

7-(2-Butynyl)-3-(2-oxo-tetrahydrofuran-3-yl)-1-methyl-8-(piperazin-1-yl)-3,7-dihydropurine-2,6-dione trifluoroacetate

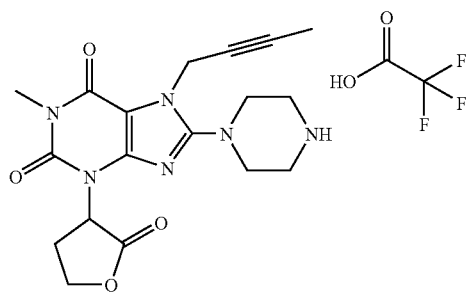

The title compound was obtained using α-bromo-γ-butyrolactone and steps similar to Example 222.

$^1$H-NMR(CDCl$_3$) δ: 1.84 (t, J=2.4 Hz, 3H) 2.59–2.68 (m, 1H) 2.69–2.91 (m, 1H) 3.01–3.03 (m, 4H) 3.34–3.37 (m, 5H) 3.38 (s, 3H) 4.39–4.45 (m, 1H) 4.68 (dt, J=2.8, 9.2 Hz, 2H) 4.84 (br, 2H)

MS m/e (ESI) 387(MH$^+$—CF$_3$COOH)

EXAMPLE 264

7-(2-Butynyl)-3-(1-phenethyl)-1-methyl-8-(piperazin-1-yl)-3,7-dihydropurine-2,6-dione trifluoroacetate

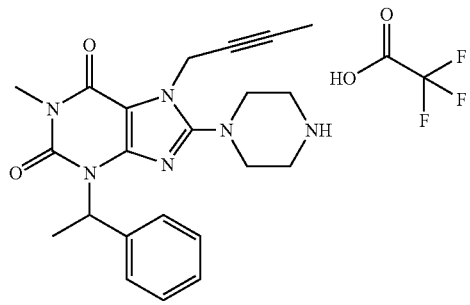

The title compound was obtained using 1-phenethyl bromide and steps similar to Example 222.

MS m/e (ESI) 407(MH$^+$—CF$_3$COOH)

EXAMPLE 265

7-(2-Butynyl)-3-(2,3-dihydroxypropyl)-1-methyl-8-(piperazin-1-yl)-3,7-dihydropurine-2,6-dione trifluoroacetate

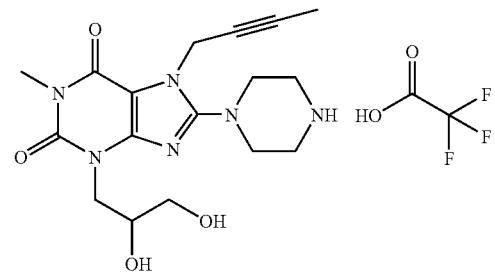

The title compound was obtained using 1-bromopropane-2,3-diol and steps similar to Example 222.

MS m/e (ESI) 377(MH$^+$—CF$_3$COOH)

EXAMPLE 266

7-(2-Butynyl)-3-(2-ethoxyethyl)-1-methyl-8-(piperazin-1-yl)-3,7-dihydropurine-2,6-dione trifluoroacetate

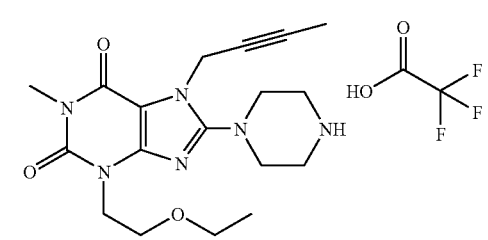

The title compound was obtained using 2-ethoxyethyl bromide and steps similar to Example 222.

$^1$H-NMR(CDCl$_3$) δ: 1.16 (t, J=7.2 Hz, 3H) 1.83 (t, J=2.4 Hz, 3H) 3.01–3.06 (m, 4H) 3.33–3.46 (m, 4H) 3.39 (s, 3H) 3.58 (q, J=7.2 Hz, 2H) 3.77 (t, J=6.0 Hz, 2H) 4.26 (t, J=6.0 Hz, 2H) 4.85 (q, J=2.4 Hz, 2H)

MS m/e (ESI) 375(MH$^+$—CF$_3$COOH)

EXAMPLE 267

7-(2-Butynyl)-3-(2-methyl-2-propenyl)-1-methyl-8-(piperazin-1-yl)-3,7-dihydropurine-2,6-dione trifluoroacetate

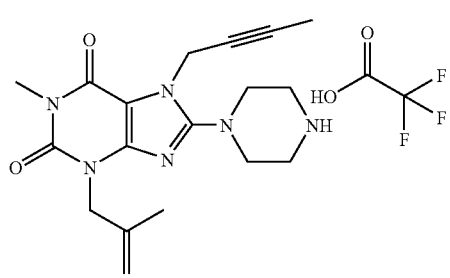

The title compound was obtained using 2-methyl-2-propenyl bromide and steps similar to Example 222.

MS m/e (ESI) 357(MH$^+$—CF$_3$COOH)

EXAMPLE 268

7-(2-Butynyl)-3-(2-ethylbutyl)-1-methyl-8-(piper-azin-1-yl)-3,7-dihydropurine-2,6-dione trifluoroacetate

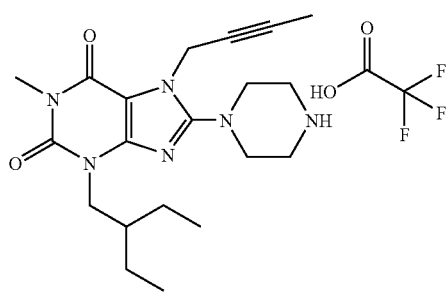

The title compound was obtained using 2-ethylbutyl bromide and steps similar to Example 222.
MS m/e (ESI) 387(MH⁺—CF₃COOH)

EXAMPLE 269

4-[7-(2-Butynyl)-1-methyl-2,6-dioxo-8-(piperazin-1-yl)-1,2,6,7-tetrahydropurin-3-yl]-2-butenoic acid ethyl ester trifluoroacetate

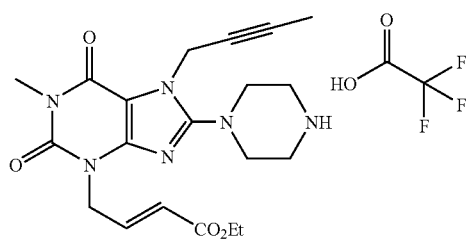

The title compound was obtained using 4-bromo-2-butenoic acid ethyl ester and steps similar to Example 222.
MS m/e (ESI) 415(MH⁺—CF₃COOH)

EXAMPLE 270

7-(2-Butynyl)-3-isopropyl-1-methyl-8-(piperazin-1-yl)-3,7-dihydropurine-2,6-dione trifluoroacetate

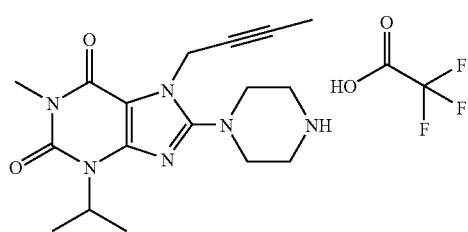

The title compound was obtained using 2-iodopropane and steps similar to Example 222.
MS m/e (ESI) 345(MH⁺—CF₃COOH)

EXAMPLE 271

7-(2-Butynyl)-3-(3-methyl-2-butenyl)-1-methyl-8-(piperazin-1-yl)-3,7-dihydropurine-2,6-dione trifluoroacetate

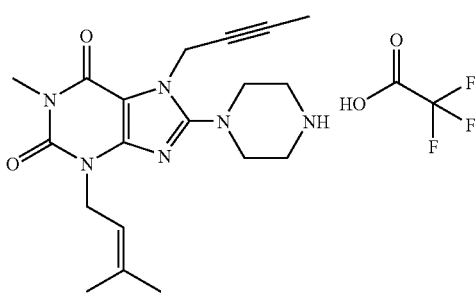

The title compound was obtained using 1-bromo-3-methyl-2-butene and steps similar to Example 222.
MS m/e (ESI) 371 (MH⁺—CF₃COOH)

EXAMPLE 272

7-(2-Butynyl)-3-[2-(2-methoxyphenyl)-2-oxoethyl]-1-methyl-8-(piperazin-1-yl)-3,7-dihydropurine-2,6-dione trifluoroacetate

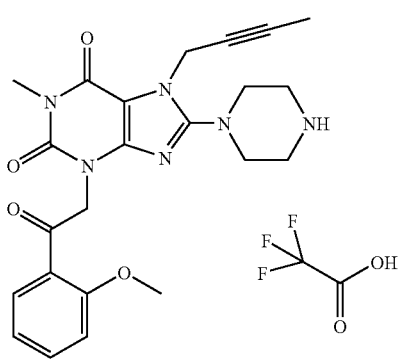

The title compound was obtained using 2-bromo-2'-methoxyacetophenone and steps similar to Example 222.
MS m/e (ESI) 451(MH⁺—CF₃COOH)

EXAMPLE 273

3-(3-Benzyloxypropyl)-7-(2-butynyl)-1-methyl-8-(piperazin-1-yl)-3,7-dihydropurine-2,6-dione trifluoroacetate

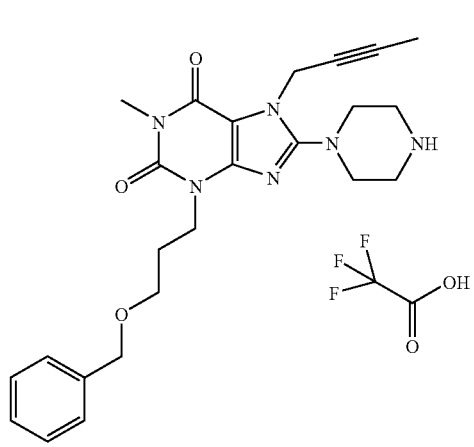

The title compound was obtained using benzyl 3-bromopropyl ether and steps similar to Example 222.
MS m/e (ESI) 451(MH$^+$—CF$_3$COOH)

EXAMPLE 274

7-(2-Butynyl)-3-(3,3-dimethyl-2-oxobutyl)-1-methyl-8-(piperazin-1-yl)-3,7-dihydropurine-2,6-dione trifluoroacetate

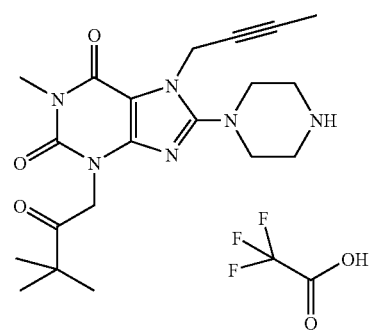

The title compound was obtained using 1-bromopinacolone and steps similar to Example 222.
MS m/e (ESI) 401(MH$^+$—CF$_3$COOH)

EXAMPLE 275

2-[7-(2-Butynyl)-1-methyl-2,6-dioxo-8-(piperazin-1-yl)-1,2,6,7-tetrahydropurine-3-ylmethyl]benzonitrile trifluoroacetate

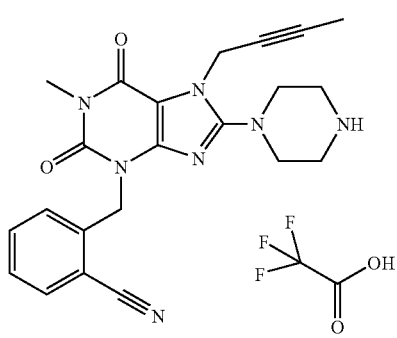

The title compound was obtained using α-bromo-o-tolunitrile and steps similar to Example 222.
MS m/e (ESI) 418(MH$^+$—CF$_3$COOH)

EXAMPLE 276

[7-(2-Butynyl)-1-methyl-2,6-dioxo-8-(piperazin-1-yl)-1,2,6,7-tetrahydropurin-3-yl]acetic acid tert-butyl ester trifluoroacetate

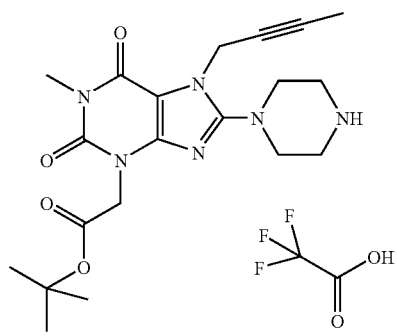

The title compound was obtained using bromoacetic acid tert-butyl ester and steps similar to Example 222.
MS m/e (ESI) 417(MH$^+$—CF$_3$COOH)

EXAMPLE 277

7-(2-Butynyl)-3-[2-(3-methoxyphenyl)-2-oxoethyl]-1-methyl-8-(piperazin-1-yl)-3,7-dihydropurine-2,6-dione trifluoroacetate

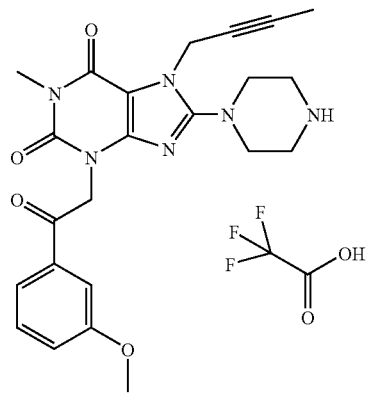

The title compound was obtained using 2-bromo-3'-methoxyacetophenone and steps similar to Example 222.
MS m/e (ESI) 451(MH$^+$—CF$_3$COOH)

EXAMPLE 278

7-(2-Butynyl)-3-(2-chloroethyl)-1-methyl-8-(piperazin-1-yl)-3,7-dihydropurine-2,6-dione trifluoroacetate

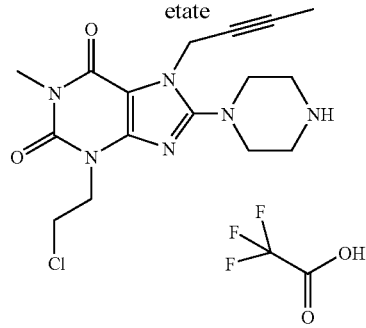

The title compound was obtained using 1-bromo-2-chloroethane and steps similar to Example 222.
MS m/e (ESI) 365(MH$^+$—CF$_3$COOH)

EXAMPLE 279

[7-(2-Butynyl)-1-methyl-2,6-dioxo-8-(piperazin-1-yl)-1,2,6,7-tetrahydropurin-3-yl]acetic acid ethyl ester trifluoroacetate

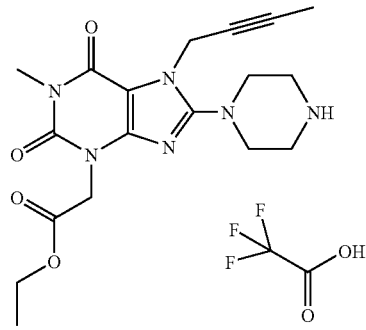

The title compound was obtained using bromoacetic acid ethyl ester and steps similar to Example 222.
MS m/e (ESI) 389(MH$^+$—CF$_3$COOH)

EXAMPLE 280

7-(2-Butynyl)-3-(3-hydroxy-2,2-dimethylpropyl)-1-methyl-8-(piperazin-1-yl)-3,7-dihydropurine-2,6-dione trifluoroacetate

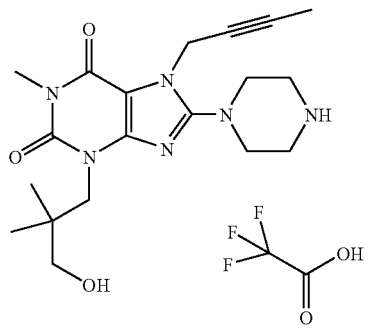

The title compound was obtained using 3-bromo-2,2-dimethyl-1-propanol and steps similar to Example 222.
MS m/e (ESI) 389(MH$^+$—CF$_3$COOH)

EXAMPLE 281

7-(2-Butynyl)-1-methyl-8-(piperazin-1-yl)-3-[2-(pyrrol-1-yl)ethyl]-3,7-dihydropurine-2,6-dione trifluoroacetate

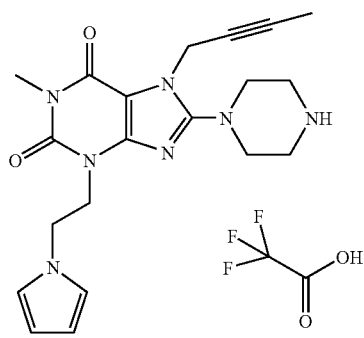

The title compound was obtained using 1-(2-bromoethyl)pyrrole and steps similar to Example 222.
MS m/e (ESI) 396(MH$^+$—CF$_3$COOH)

EXAMPLE 282

[7-(2-Butynyl)-1-methyl-2,6-dioxo-8-(piperazin-1-yl)-1,2,6,7-tetrahydropurin-3-yl]acetic acid benzyl ester trifluoroacetate

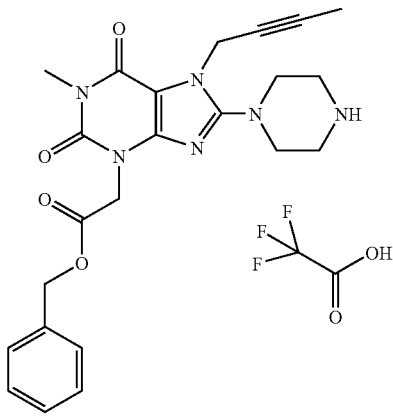

The title compound was obtained using bromoacetic acid benzyl ester and steps similar to Example 222.
MS m/e (ESI) 451(MH$^+$—CF$_3$COOH)

EXAMPLE 283

7-(2-Butynyl)-3-(2,6-dichloropyridin-4-ylmethyl)-1-methyl-8-(piperazin-1-yl)-3,7-dihydropurine-2,6-dione trifluoroacetate

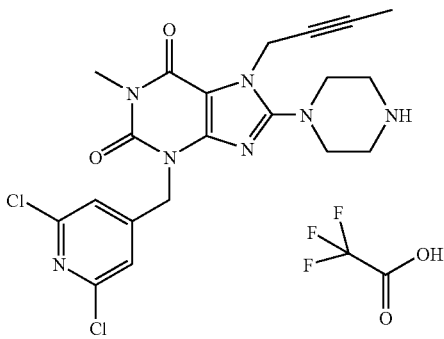

The title compound was obtained using 4-(bromomethyl)-2,6-dichloropyridine and steps similar to Example 222.
MS m/e (ESI) 463(MH$^+$—CF$_3$COOH)

EXAMPLE 284

7-(2-Butynyl)-1-methyl-3-(2-oxopyrrolidin-3-yl)-8-(piperazin-1-yl)-3,7-dihydropurine-2,6-dione hydrochloride

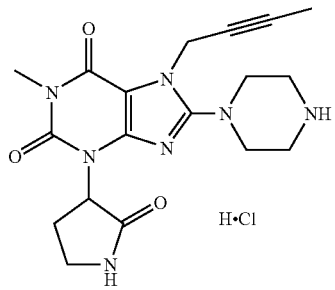

The title compound was synthesized using 3-bromo-2-oxopyrrolidine and steps similar to Example 222.
$^1$H-NMR(d6-DMSO)
δ: 1.80 (t, J=2 Hz, 3H) 2.32–2.48 (m, 2H) 3.17 (s, 3H) 3.20–3.55 (m, 10H) 4.96 (q, J=2 Hz, 2H) 5.14 (t, J=10 Hz) 7.94 (brs, 1H) 9.04 (brs, 2H)

EXAMPLE 285

7-(2-Butynyl)-1-methyl-3-(1-methyl-2-oxopyrrolidin-3-yl)-8-(piperazin-1-yl)-3,7-dihydropurine-2,6-dione hydrochloride

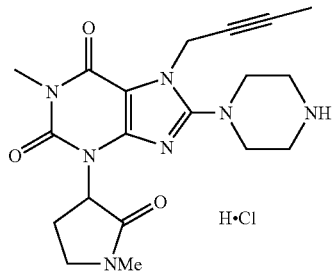

The title compound was synthesized using 3-bromo-1-methyl-2-oxopyrrolidine and steps similar to Example 222.
$^1$H-NMR(d6-DMSO) δ: 1.81 (t, J=2 Hz, 3H) 2.28–2.36 (m, 2H) 2.77 (s, 3H) 3.16 (s, 3H) 3.20–3.54 (m, 10H) 4.96 (brs, 2H) 5.21 (t, J=9 Hz, 1H) 9.04 (brs, 2H)

EXAMPLE 286

7-(2-Butynyl)-3-phenyl-1-methyl-8-(piperazin-1-yl)-3,7-dihydropurine-2,6-dione trifluoroacetate

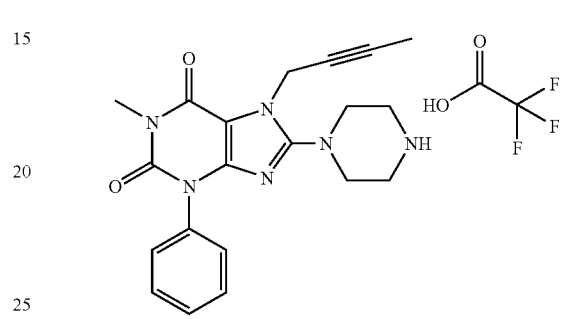

4-[7-(2-Butynyl)-1-methyl-2,6-dioxo-2,3,6,7-tetrahydro-1H-purin-8-yl]piperazine-1-carboxylic acid tert-butyl ester (12 mg), phenylboronic acid (10 mg), copper(II) acetate (10 mg), and pyridine (0.02 ml) were suspended in N,N-dimethylformamide (0.2 ml), and the suspension was stirred at room temperature for 3 days. The reaction mixture was passed through a short column filled with NH silica gel, the filtrate was diluted with ethyl acetate, and was washed with water and 1 N hydrochloric acid. The solvent was concentrated, the residue was dissolved in trifluoroacetic acid, and was concentrated. The residue was purified by reversed phase high performance liquid chromatography to give 2.16 mg of the title compound.
MS m/e (ESI) 379 (MH$^+$—CF$_3$COOH)

EXAMPLE 287

7-(2-Butynyl)-3-(2-methylphenyl)-1-methyl-8-(piperazin-1-yl)-3,7-dihydropurine-2,6-dione trifluoroacetate

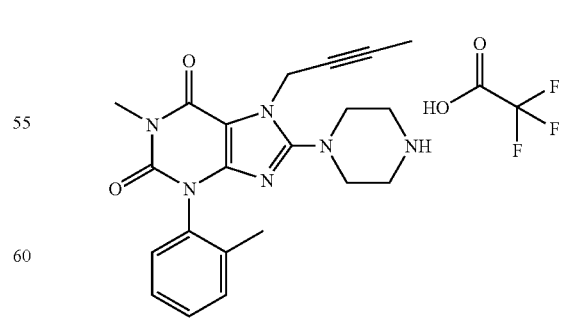

1.74 mg of the title compound was obtained using 2-methylphenylboronic acid and steps similar to Example 286.
MS m/e (ESI) 393(MH$^+$—CF$_3$COOH)

EXAMPLE 288

7-(2-Butynyl)-3-(3-methylphenyl)-1-methyl-8-(piperazin-1-yl)-3,7-dihydropurine-2,6-dione trifluoroacetate

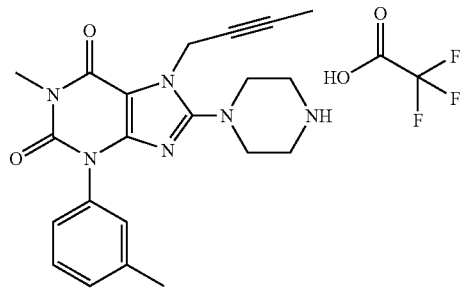

3.11 mg of the title compound was obtained using 3-methylphenylboronic acid and steps similar to Example 286.
MS m/e (ESI) 393(MH$^+$—CF$_3$COOH)

EXAMPLE 289

7-(2-Butynyl)-3-(4-methylphenyl)-1-methyl-8-(piperazin-1-yl)-3,7-dihydropurine-2,6-dione trifluoroacetate

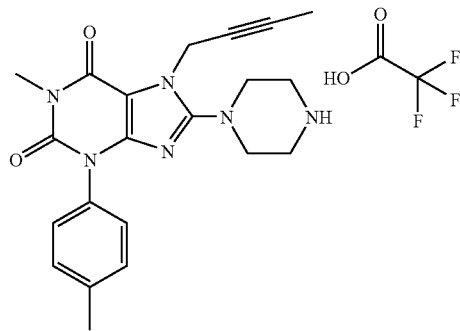

5.96 mg of the title compound was obtained using 4-methylphenylboronic acid and steps similar to Example 286.
MS m/e (ESI) 393(MH$^+$—CF$_3$COOH)

EXAMPLE 290

7-(2-Butynyl)-3-(2,3-dimethylphenyl)-1-methyl-8-(piperazin-1-yl)-3,7-dihydropurine-2,6-dione trifluoroacetate

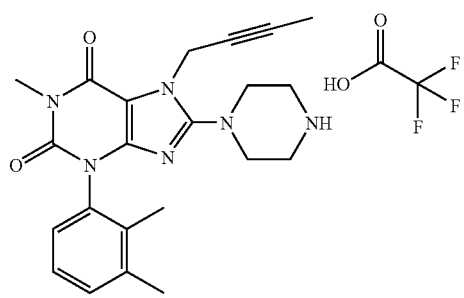

0.93 mg of the title compound was obtained using 2,3-dimethylphenylboronic acid and steps similar to Example 286.
MS m/e (ESI) 407(MH$^+$—CF$_3$COOH)

EXAMPLE 291

7-(2-Butynyl)-3-(2,5-dimethylphenyl)-1-methyl-8-(piperazin-1-yl)-3,7-dihydropurine-2,6-dione trifluoroacetate

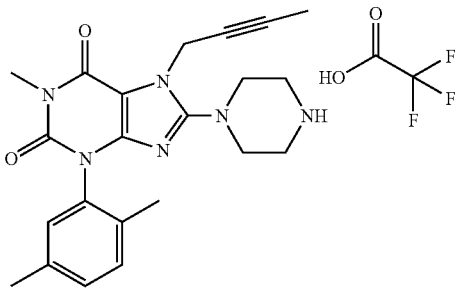

1.21 mg of the title compound was obtained using 2,5-dimethylphenylboronic acid and steps similar to Example 286.
MS m/e (ESI) 407(MH$^+$—CF$_3$COOH)

EXAMPLE 292

7-(2-Butynyl)-3-(3,4-dimethylphenyl)-1-methyl-8-(piperazin-1-yl)-3,7-dihydropurine-2,6-dione trifluoroacetate

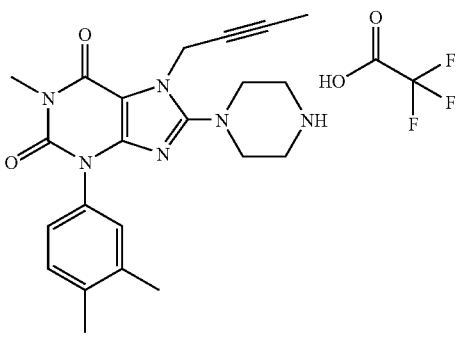

5.88 mg of the title compound was obtained using 3,4-dimethylphenylboronic acid and steps similar to Example 286.
MS m/e (ESI) 407(MH$^+$—CF$_3$COOH)

EXAMPLE 293

7-(2-Butynyl)-3-(3,5-dimethylphenyl)-1-methyl-8-(piperazin-1-yl)-3,7-dihydropurine-2,6-dione trifluoroacetate

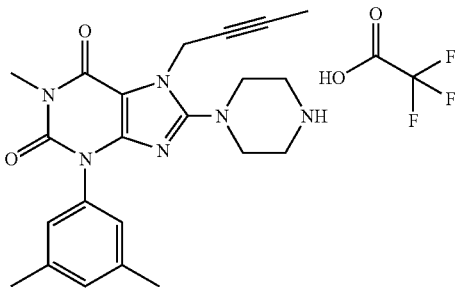

8.09 mg of the title compound was obtained using 3,5-dimethylphenylboronic acid and steps similar to Example 286.
MS m/e (ESI) 407(MH$^+$—CF$_3$COOH)

EXAMPLE 294

7-(2-Butynyl)-3-(2-acetylphenyl)-1-methyl-8-(piperazin-1-yl)-3,7-dihydropurine-2,6-dione trifluoroacetate

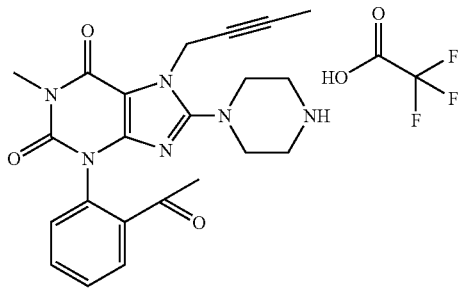

0.52 mg of the title compound was obtained using 2-acetylphenylboronic acid and steps similar to Example 286.

MS m/e (ESI) 421(MH$^+$—CF$_3$COOH)

EXAMPLE 295

7-(2-Butynyl)-3-(3-acetylphenyl)-1-methyl-8-(piperazin-1-yl)-3,7-dihydropurine-2,6-dione trifluoroacetate

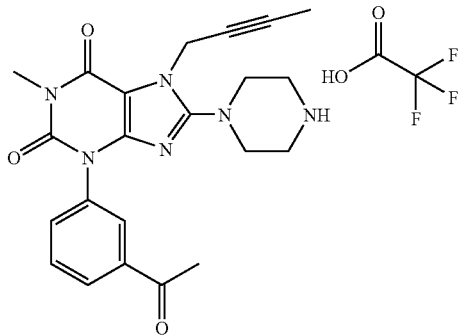

3.70 mg of the title compound was obtained using 3-acetylphenylboronic acid and steps similar to Example 286.

MS m/e (ESI) 421(MH$^+$—CF$_3$COOH)

EXAMPLE 296

7-(2-Butynyl)-3-(4-acetylphenyl)-1-methyl-8-(piperazin-1-yl)-3,7-dihydropurine-2,6-dione trifluoroacetate

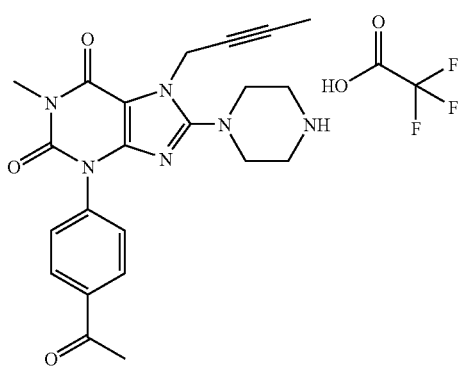

3.71 mg of the title compound was obtained using 4-acetylphenylboronic acid and steps similar to Example 286.

MS m/e (ESI) 421(MH$^+$—CF$_3$COOH)

EXAMPLE 297

7-(2-Butynyl)-3-(3-trifluoromethylphenyl)-1-methyl-8-(piperazin-1-yl)-3,7-dihydropurine-2,6-dione trifluoroacetate

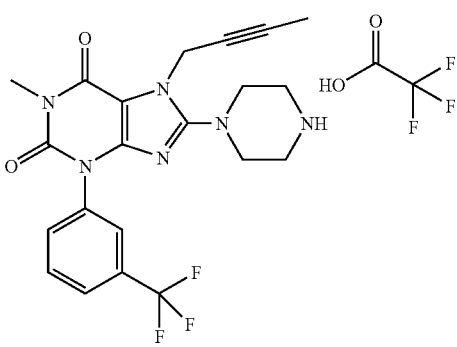

6.79 mg of the title compound was obtained using 3-trifluoromethylphenylboronic acid and steps similar to Example 286.

MS m/e (ESI) 447(MH$^+$—CF$_3$COOH)

EXAMPLE 298

7-(2-Butynyl)-3-(4-trifluoromethylphenyl)-1-methyl-8-(piperazin-1-yl)-3,7-dihydropurine-2,6-dione trifluoroacetate

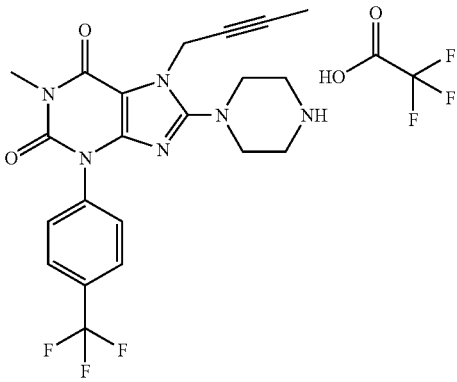

6.79 mg of the title compound was obtained using 4-trifluoromethylphenylboronic acid and steps similar to Example 286.

MS m/e (ESI) 447(MH$^+$—CF$_3$COOH)

EXAMPLE 299

7-(2-Butynyl)-3-(3,5-bis-trifluoromethylphenyl)-1-methyl-8-(piperazin-1-yl)-3,7-dihydropurine-2,6-dione trifluoroacetate

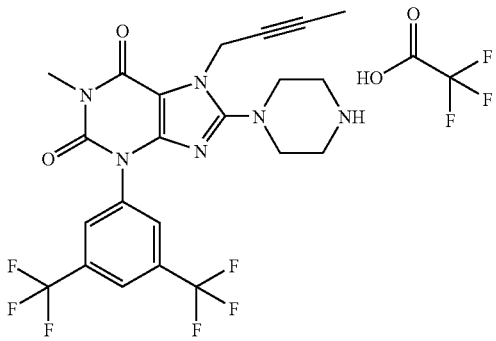

3.72 mg of the title compound was obtained using 3,5-bis-trifluoromethylphenylboronic acid and steps similar to Example 286.

MS m/e (ESI) 515(MH$^+$—CF$_3$COOH)

EXAMPLE 300

7-(2-Butynyl)-3-(2-ethoxyphenyl)-1-methyl-8-(piperazin-1-yl)-3,7-dihydropurine-2,6-dione trifluoroacetate

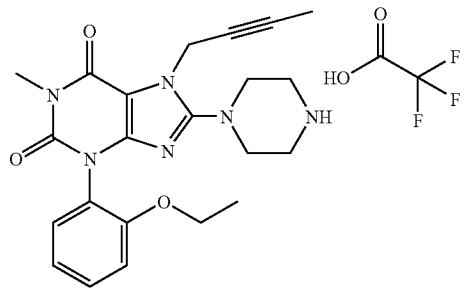

1.12 mg of the title compound was obtained using 2-ethoxyphenylboronic acid and steps similar to Example 286.

MS m/e (ESI) 423(MH$^+$—CF$_3$COOH)

EXAMPLE 301

7-(2-Butynyl)-3-(3-ethoxyphenyl)-1-methyl-8-(piperazin-1-yl)-3,7-dihydropurine-2,6-dione trifluoroacetate

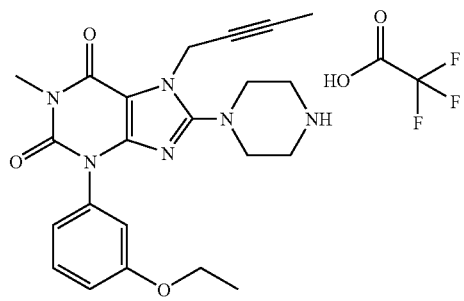

3.83 mg of the title compound was obtained using 3-ethoxyphenylboronic acid and steps similar to Example 286.

MS m/e (ESI) 423(MH$^+$—CF$_3$COOH)

EXAMPLE 302

7-(2-Butynyl)-3-(benzo[1,3]dioxol-5-yl)-1-methyl-8-(piperazin-1-yl)-3,7-dihydropurine-2,6-dione trifluoroacetate

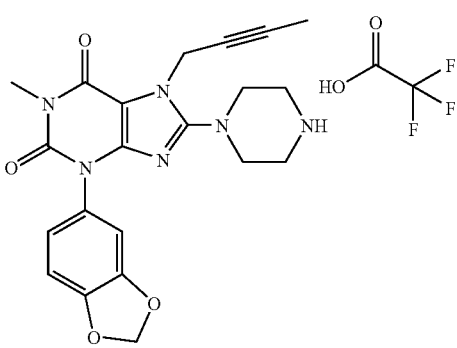

5.09 mg of the title compound was obtained using benzo[1,3]dioxol-5-ylboronic acid and steps similar to Example 286.

MS m/e (ESI) 423(MH$^+$—CF$_3$COOH)

EXAMPLE 303

7-(2-Butynyl)-3-(3-trifluoromethoxyphenyl)-1-methyl-8-(piperazin-1-yl)-3,7-dihydropurine-2,6-dione trifluoroacetate

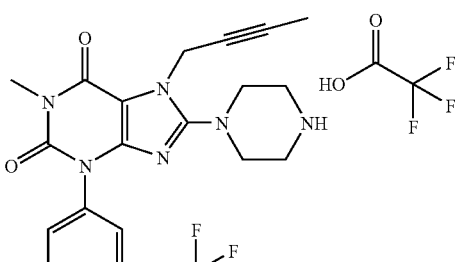

5.08 mg of the title compound was obtained using 3-trifluoromethoxyphenylboronic acid and steps similar to Example 286.

MS m/e (ESI) 463(MH$^+$—CF$_3$COOH)

EXAMPLE 304

7-(2-Butynyl)-3-(4-trifluoromethoxyphenyl)-1-methyl-8-(piperazin-1-yl)-3,7-dihydropurine-2,6-dione trifluoroacetate

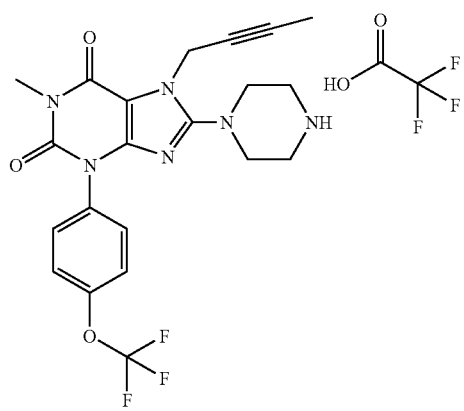

4.58 mg of the title compound was obtained using 4-trifluoromethoxyphenylboronic acid and steps similar to Example 286.
MS m/e (ESI) 463(MH$^+$—CF$_3$COOH)

EXAMPLE 305

7-(2-Butynyl)-3-(3-biphenyl)-1-methyl-8-(piperazin-1-yl)-3,7-dihydropurine-2,6-dione trifluoroacetate

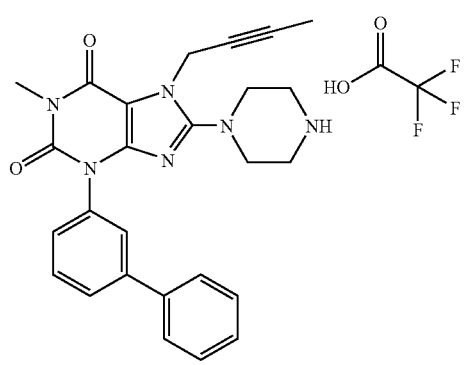

3.74 mg of the title compound was obtained using 3-biphenylboronic acid and steps similar to Example 286.
MS m/e (ESI) 455(MH$^+$—CF$_3$COOH)

EXAMPLE 306

7-(2-Butynyl)-3-(4-biphenyl)-1-methyl-8-(piperazin-1-yl)-3,7-dihydropurine-2,6-dione trifluoroacetate

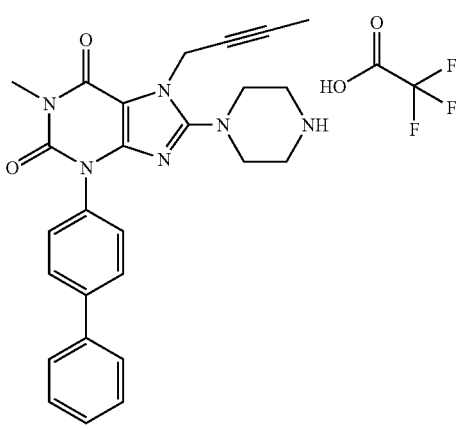

4.28 mg of the title compound was obtained using 4-biphenylboronic acid and steps similar to Example 286.
MS m/e (ESI) 455(MH$^+$—CF$_3$COOH)

EXAMPLE 307

7-(2-Butynyl)-3-(3-furyl)-1-methyl-8-(piperazin-1-yl)-3,7-dihydropurine-2,6-dione trifluoroacetate

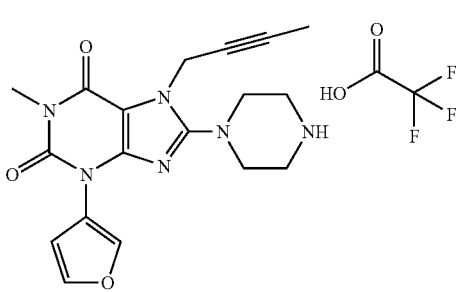

1.81 mg of the title compound was obtained using 3-furylboronic acid and steps similar to Example 286.
MS m/e (ESI) 369(MH$^+$—CF$_3$COOH)

EXAMPLE 308

7-(2-Butynyl)-3-(3-thienyl)-1-methyl-8-(piperazin-1-yl)-3,7-dihydropurine-2,6-dione trifluoroacetate

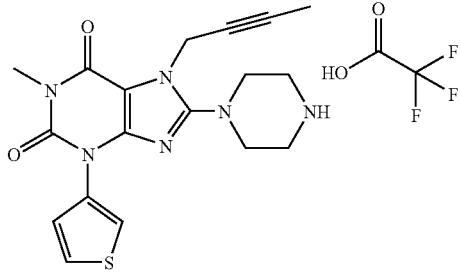

8.39 mg of the title compound was obtained using 3-thienylboronic acid and steps similar to Example 286.
MS m/e (ESI) 385(MH$^+$—CF$_3$COOH)

EXAMPLE 309

7-(2-Butynyl)-3-methyl-1-(4-methylphenyl)-8-(piperazin-1-yl)-3,7-dihydropurine-2,6-dione trifluoroacetate

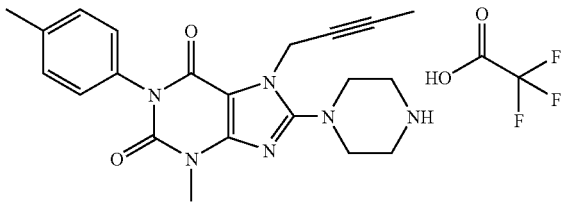

2.00 mg of the title compound was obtained using 4-[7-(2-butynyl)-3-methyl-2,6-dioxo-2,3,6,7-tetrahydro-1H-purin-8-yl]piperazine-1-carboxylic acid tert-butyl ester and 4-methylphenylboronic acid, and steps similar to Example 286.
MS m/e (ESI) 393(MH$^+$—CF$_3$COOH)

EXAMPLE 310

[7-(3-Methylbut-2-enyl)-2,6-dioxo-1-(2-oxo-2-phenylethyl)-8-(piperazin-1-yl)-1,2,6,7-tetrahydropurin-3-yl] acetic acid ethyl ester trifluoroacetate a) 2,2-Dimethylpropionic acid [8-chloro-3-(2,2-dimethylpropionyloxymethyl)-2,6-dioxo-2,3,6,7-tetrahydropurine-1-yl]methyl ester

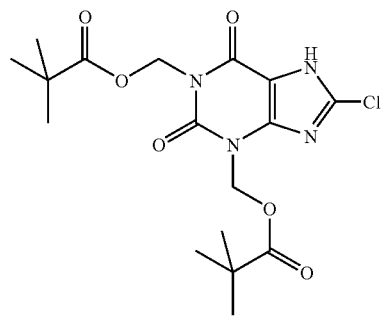

2,2-Dimethylpropionic acid [3-(2,2-dimethylpropionyloxymethyl)-2,6-dioxo-2,3,6,7-tetrahydropurin-1-yl]methyl ester (2.31 g) was dissolved in N,N-dimethylformamide (18 ml), and N-chlorosuccinimide (973 mg) was added to the solution while cooling on ice. Then, the mixture was stirred for 10 minutes on ice, and then at room temperature for 20 hours. The obtained reaction mixture was diluted with ethyl acetate, washed with water, and dried over anhydrous magnesium sulfate. After removing the solvent by distillation from the organic layer, the residue was purified by silica gel column chromatography to give 1.61 g of the title compound from the elution fraction of hexane-ethyl acetate (1:1).
$^1$H-NMR(CDCl$_3$) δ: 1.19 (s, 9H) 1.20 (s, 9H) 6.04 (s, 2H) 6.05 (s, 2H)

b) 2,2-Dimethylpropionic acid [8-chloro-3-(2,2-dimethylpropionyloxymethyl)-7-(3-methylbut-2-enyl)-2,6-dioxo-2,3,6,7-tetrahydropurin-1-yl]methyl ester

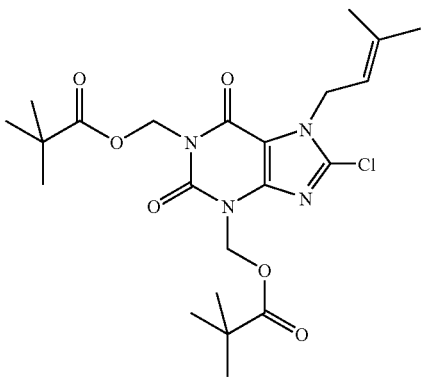

2,2-Dimethylpropionic acid [8-chloro-3-(2,2-dimethylpropionyloxymethyl)-2,6-dioxo-2,3,6,7-tetrahydropurin-1-yl]methyl ester (600 mg) and potassium carbonate (630 mg) were suspended in N,N-dimethylformamide (10 ml), and 4-bromo-2-methyl-2-butene (183 μl) was added to the suspension at room temperature. After the reaction mixture was stirred at room temperature for 24 hours, the mixture was diluted with ethyl acetate, washed with water, and dried over anhydrous magnesium sulfate. After the solvent was removed by distillation from the organic layer, the residue was purified by silica gel column chromatography to give 470 mg of the title compound from the elution fraction of hexane-ethyl acetate (3:1).
$^1$H-NMR(CDCl$_3$) δ: 1.18 (s, 9H) 1.19 (s, 9H) 1.58 (s, 6H) 4.95 (d, J=7.2 Hz, 2H) 5.32 (t, J=7.0 Hz, 1H) 6.03 (s, 2H) 6.04 (s, 2H)

c) 4-[1,3-Bis(2,2-dimethylpropionyloxymethyl)-7-(3-methylbut-2-enyl)-2,6-dioxo-2,3,6,7-tetrahydro-1H-purin-8-yl]piperazine-1-carboxylic acid tert-butyl ester

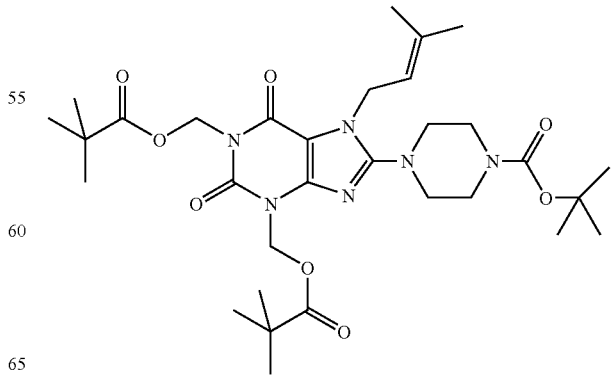

2,2-Dimethylpropionic acid [8-chloro-3-(2,2-dimethyl-propionyloxymethyl)-7-(3-methylbut-2-enyl)-2,6-dioxo-2,3,6,7-tetrahydropurin-1-yl]methyl ester (470 mg) and 1-piperazinecarboxylic acid tert-butyl ester (218 mg) were dissolved in N-methylpyrrolidone (4 ml), and diazabicyclo [5.4.0]undecene (160 µl) was added to the solution. The mixture was stirred at 150° C. for 6.5 hours. The reaction mixture was filtered through Celite, diluted with chloroform, washed with water, and dried over anhydrous magnesium sulfate. After the solvent was removed by distillation from the organic layer, the residue was purified by silica gel column chromatography to give 277 mg of the title compound from the elution fraction of hexane-ethyl acetate (2:1)

$^1$H-NMR(CDCl$_3$) δ: 1.18 (s, 9H) 1.19 (s, 9H) 1.48 (s, 9H) 1.75 (s, 6H) 3.19 (t, J=5.0 Hz, 4H) 3.56 (t, J=5.0 Hz, 1H) 4.72 (d, J=6.4 Hz, 2H) 5.38–5.44 (m, 1H) 6.03 (s, 2H) 6.04 (s, 2H)

d) 4-[1-(2,2-Dimethylpropionyloxymethyl)-7-(3-methylbut-2-enyl)-2,6-dioxo-2,3,6,7-tetrahydro-1H-purin-8-yl]piperazine-1-carboxylic acid tert-butyl ester

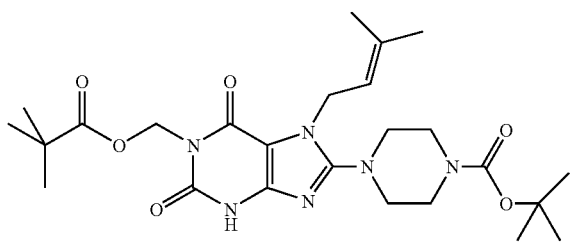

4-[1,3-Bis(2,2-dimethylpropionyloxymethyl)-7-(3-methylbut-2-enyl)-2,6-dioxo-2,3,6,7-tetrahydro-1H-purin-8-yl]piperazine-1-carboxylic acid tert-butyl ester (277 mg) was dissolved in a solvent mixture of tetrahydrofuran (3 ml) and methanol (6 ml), sodium hydride (21 mg) was added to the solution, and the mixture was stirred at room temperature for 1 hour and 10 minutes. The reaction mixture was diluted with ethyl acetate, washed with water, and dried over anhydrous magnesium sulfate. The solvent was removed by distillation from the organic layer to give 214 mg of the title compound.

$^1$H-NMR(CDCl$_3$) δ: 1.19 (s, 9H) 1.48 (s, 9H) 1.75 (s, 6H) 3.15–3.21 (m; 4H) 3.53–3.59 (m, 4H) 4.67–4.73 (m, 2H) 5.37–5.42 (m, 1H) 6.00 (s, 2H)

e) 4-[1–(2,2-Dimethylpropionyloxymethyl)-3-ethoxycarbonylmethyl-7-(3-methylbut-2-enyl)-2,6-dioxo-2,3,6,7-tetrahydro-1H-purin-8-yl]piperazine-1-carboxylic acid tert-butyl ester

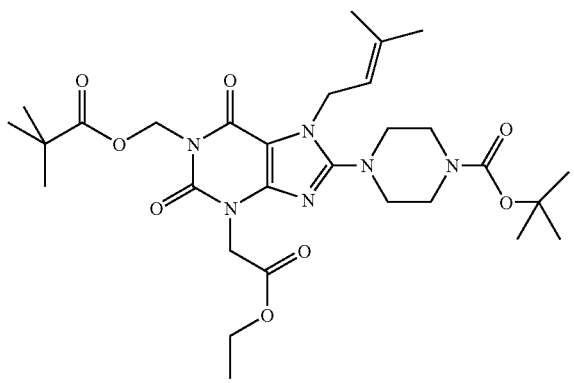

4-[1-(2,2-Dimethylpropionyloxymethyl)-7-(3-methylbut-2-enyl)-2,6-dioxo-2,3,6,7-tetrahydro-1H-purin-8-yl]piperazine-1-carboxylic acid tert-butyl ester (43 mg) and potassium carbonate (13 mg) were suspended in N,N-dimethylformamide (1 ml), and ethyl bromoacetate (9.6 µl) was added to the suspension. After the reaction mixture was stirred at room temperature for 13 hours, the mixture was diluted with ethyl acetate, washed with water, and dried over anhydrous magnesium sulfate. The solvent was removed by distillation from the organic layer to give 44 mg of the title compound. δ: 1.19 (s, 9H) 1.23–1.51 (m, 3H) 1.48 (s, 9H) 1.74 (s, 6H) 3.14–3.20 (m, 4H) 3.52–3.58 (m, 4H) 4.17–4.27 (m, 2H) 4.68–4.72 (m, 2H) 4.75 (s, 2H) 5.37–5.42 (m, 1H) 6.03 (s, 2H)

f) 4-[3-Ethoxycarbonylmethyl-7-(3-methylbut-2-enyl)-2,6-dioxo-2,3,6,7-tetrahydro-1H-purin-8-yl]piperazine-1-carboxylic acid tert-butyl ester

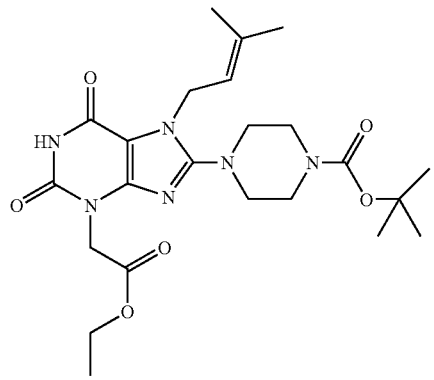

4-[1-(2,2-Dimethylpropionyloxymethyl)-3-ethoxycarbonylmethyl-1-7-(3-methylbut-2-enyl)-2,6-dioxo-2,3,6,7-tetrahydro-1H-purin-8-yl]piperazine-1-carboxylic acid tert-butyl ester (44 mg) was dissolved in a solvent mixture of tetrahydrofuran (1 ml) and methanol (2 ml), and sodium hydride (4 mg) was added to the solution at room temperature. The reaction mixture was stirred at room temperature for 16 hours, diluted with ethyl acetate, washed with water, and dried over anhydrous magnesium sulfate. After the solvent was removed by distillation from the reaction mixture at reduced pressure, the residue was purified by HPLC with a reversed phase system column using water-acetonitrile-trifluoroacetic acid system as elution solvent to give the title compound.

MS m/e (ESI) 491(MH$^+$—CF$_3$COOH)

g) [7-(3-Methylbut-2-enyl)-2,6-dioxo-1-(2-oxo-2-phenylethyl)-8-(piperazin-1-yl)-1,2,6,7-tetrahydropurin-3-yl] acetic acid ethyl ester trifluoroacetate

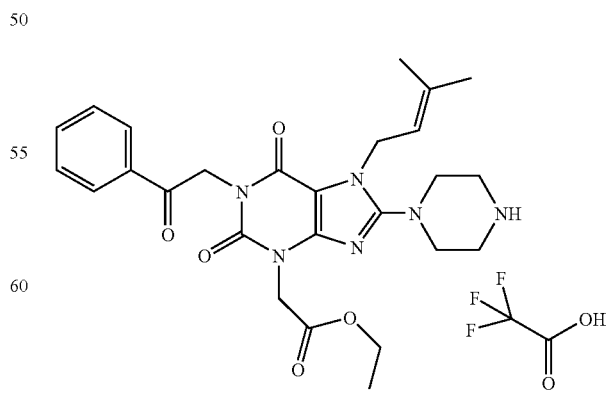

boxylic acid tert-butyl ester (10 mg) and potassium carbonate (4 mg) were suspended in N,N-dimethylformamide, and 2-bromoacetophenone (5 mg) was added to the suspension. The reaction mixture was stirred at 60° C. for 5 hours, and was diluted with ethyl acetate. The mixture was then washed with water, and dried over anhydrous magnesium sulfate. The solvent was removed by distillation from the organic layer, and a quarter of the resultant 4-[3-ethoxycarbonylmethyl-7-(3-methylbut-2-enyl)-2,6-dioxo-1-(2-oxo-2-phenylethyl)-2,3,6,7-tetrahydro-1H-purin-8-yl]piperazine-1-carboxylic acid tert-butyl ester was dissolved in trifluoroacetic acid (0.5 ml). Then, the solution was stirred at room temperature for 30 minutes. After the solvent was removed by distillation from the reaction mixture, the residue was purified by HPLC with a reversed phase column using water-acetonitrile-trifluoroacetic acid system as elution solvent to give 0.23 mg of the title compound.

MS m/e (ESI) 509(MH$^+$—CF$_3$COOH)

EXAMPLE 311

2-[7-(3-Methylbut-2-enyl)-2,6-dioxo-1-(2-oxo-2-phenylethyl)-8-(piperazin-1-yl)-1,2,6,7-tetrahydropurin-3-yl] acetamide trifluoroacetate

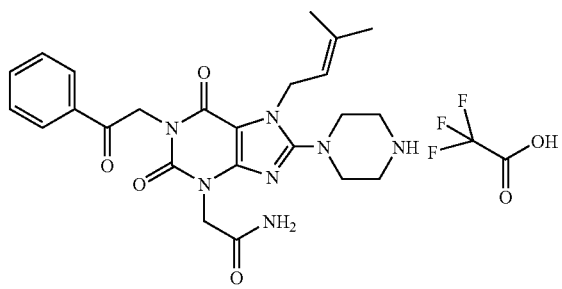

The title compound was obtained using 2-bromoacetamide and 2-bromoacetophenone, and steps similar to Example 310.

MS m/e (ESI) 480(MH$^+$—CF$_3$COOH)

EXAMPLE 312

2-[7-(3-Methylbut-2-enyl) 2,6-dioxo-1-(2-phenylethyl)-8-(piperazin-1-yl)-1,2,6,7-tetrahydropurin-3-yl] acetamide trifluoroacetate

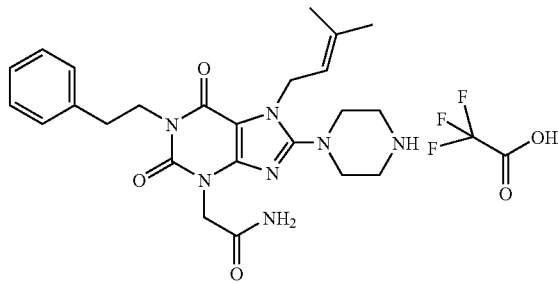

The title compound was obtained using 2-bromoacetamide and (2-bromoethyl)benzene, and steps similar to Example 310.

MS m/e (ESI) 466(MH$^+$—CF$_3$COOH)

EXAMPLE 313

7-(3-Methylbut-2-enyl)-1-(2-oxo-2-phenylethyl)-8-(piperazin-1-yl)-3-(tetrahydrofuran-2-ylmethyl)-3,7-dihydropurine-2,6-dione trifluoroacetate

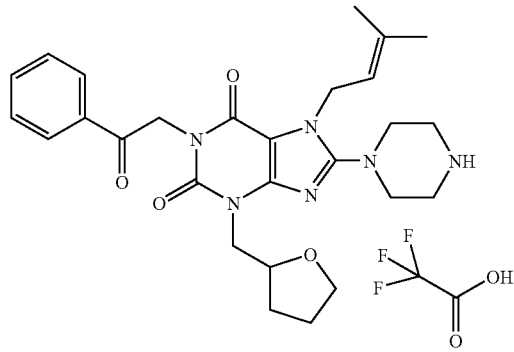

The title compound was obtained using tetrahydrofurfuryl bromide and 2-bromoacetophenone, and steps similar to Example 310.

MS m/e (ESI) 507(MH$^+$—CF$_3$COOH)

EXAMPLE 314

7-(3-Methylbut-2-enyl)-1-(2-phenylethyl)-8-(piperazin-1-yl)-3-(tetrahydrofuran-2-ylmethyl)-3,7-dihydropurine-2,6-dione trifluoroacetate

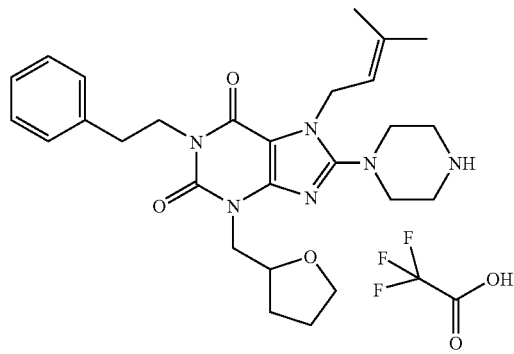

The title compound was obtained using tetrahydrofurfuryl bromide and (2-bromoethyl)benzene, and steps similar to Example 310.

MS m/e (ESI) 493(MH$^+$—CF$_3$COOH)

EXAMPLE 315

1-Methyl-7-(3-methylbut-2-enyl)-8-(piperazin-1-yl)-3-(tetrahydrofuran-2-ylmethyl)-3,7-dihydropurine-2,6-dione trifluoroacetate

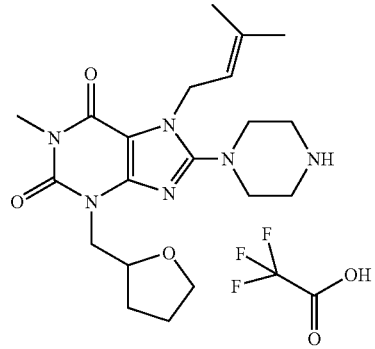

The title compound was obtained using tetrahydrofurfuryl bromide and methyl iodide, and steps similar to Example 310.

MS m/e (ESI) 403(MH$^+$—CF$_3$COOH)

EXAMPLE 316

3-(3,3-Dimethyl-2-oxobutyl)-7-(3-methylbut-2-enyl)-1-(2-oxo-2-phenylethyl)-8-(piperazin-1-yl)-3,7-dihydropurine-2,6-dione trifluoroacetate

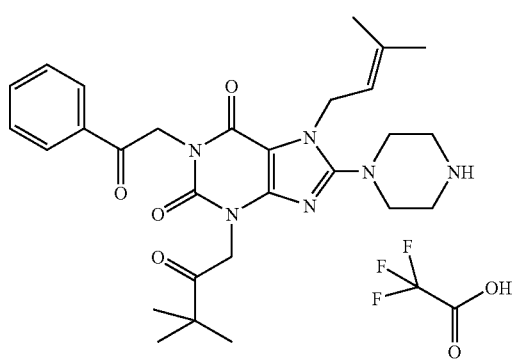

The title compound was obtained using 1-bromo-3,3-dimethyl-2-butanone and 2-bromoacetophenone, and steps similar to Example 310.

MS m/e (ESI) 521(MH$^+$—CF$_3$COOH)

EXAMPLE 317

3-(3,3-Dimethyl-2-oxobutyl)-7-(3-methylbut-2-enyl)-1-(2-phenylethyl)-8-(piperazin-1-yl)-3,7-dihydropurine-2,6-dione trifluoroacetate

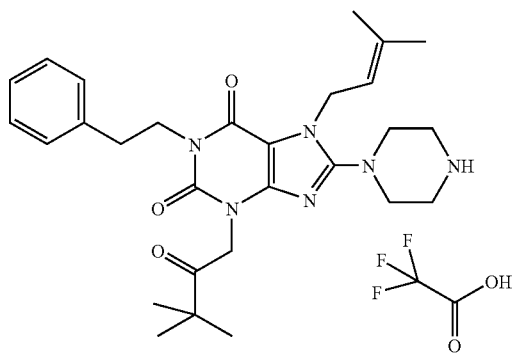

The title compound was obtained using 1-bromo-3,3-dimethyl-2-butanone and (2-bromoethyl)benzene, and steps similar to Example 310.

MS m/e (ESI) 507(MH$^+$—CF$_3$COOH)

EXAMPLE 318

[7-(2-Butynyl)-3-methoxycarbonylmethyl-2,6-dioxo-8-(piperazin-1-yl)-2,3,6,7-tetrahydropurin-1-yl] acetic acid methyl ester trifluoroacetate a) 4-[7-(2-Butynyl)-1,3-bis-(2,2-dimethylpropionyloxymethyl)-2,6-dioxo-2,3,6,7-tetrahydro-1H-purin-8-yl]piperazine-1-carboxylic acid tert-butyl ester The title compound was obtained using 2,2-dimethylpropionic acid 1-(2,2-dimethylpropionyloxymethyl)-2,6-dioxo-1,2,6,7-tetrahydro-1H-purin-3-ylmethyl ester and steps similar to Example 14-a).

$^1$H-NMR(CDCl$_3$) δ: 1.18 (s, 18H) 1.49 (s, 9H) 1.83 (t, J=2.4 Hz, 3H) 3.35–3.37 (m, 4H) 3.57–3.59 (m, 4H) 4.85 (q, J=2.4 Hz, 2H) 6.02 (s, 2H) 6.03 (s, 2H)

b) 4-[7-(2-Butynyl)-2,6-dioxo-2,3,6,7-tetrahydro-1H-purin-8-yl]piperazine-1-carboxylic acid tert-butyl ester 4-[7-(2-Butynyl)-1,3-bis-(2,2-dimethylpropionyloxymethyl)-2,6-dioxo 2,3,6,7-tetrahydro-1H-purin-8-yl]piperazine-1-carboxylic acid tert-butyl ester (1.9 g) was dissolved in a solvent mixture of tetrahydrofuran (20 ml) and methanol (10 ml), and sodium hydride (0.31 g) was added to the solution. The mixture was stirred at room temperature for 1 hour. The reaction mixture was neutralized with 2 N hydrochloric acid and extracted with ethyl acetate. The organic layer was concentrated by distillation to give 1.2 g of the title compound.

$^1$H-NMR(CDCl$_3$) δ: 1.49 (s, 9H) 1.83 (t, J=2.4 Hz, 3H) 3.37–3.40 (m, 4H) 3.58–3.60 (m, 4H) 4.85 (q, J=2.4 Hz, 2H) 8.00 (s, 1H) 9.33 (s, 1H)

c) [7-(2-Butynyl)-3-methoxycarbonylmethyl-2,6-dioxo-8-(piperazin-1-yl)-2,3,6,7-tetrahydropurin-1-yl] acetic acid methyl ester trifluoroacetate

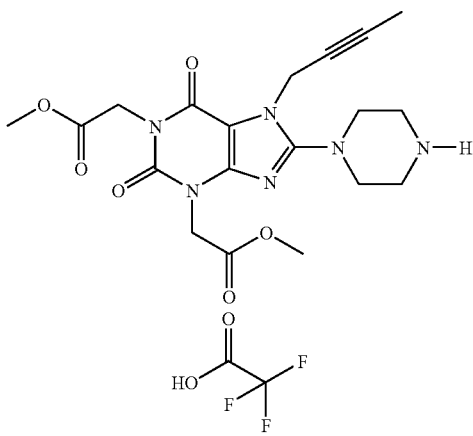

4-[7-(2-Butynyl)-2,6-dioxo-2,3,6,7-tetrahydro-1H-purin-8-yl]piperazine-1-carboxylic acid tert-butyl ester (20 mg) and potassium carbonate (21 mg) were dissolved in N,N-dimethylformamide (1 ml), and methyl bromoacetate (15 μl) was added to the solution. After the reaction mixture was stirred at room temperature overnight, the mixture was diluted with ethyl acetate, washed with water, and dried over anhydrous magnesium sulfate. After the organic layer was concentrated by distillation, the residue was dissolved in trifluoroacetic acid (0.5 ml). The mixture was stirred at room temperature for 30 minutes. After the solvent was removed by distillation, a half of the residue was purified by HPLC with a reversed phase column using water-acetonitrile-trifluoroacetic acid system as elution solvent to give 2.2 mg of the title compound.

MS m/e (ESI) 433(MH$^+$—CF$_3$COOH)

EXAMPLE 319

7-(2-Butynyl)-1,3-bis-(2-ethoxyethyl)-8-(piperazin-1-yl)-3,7-dihydropurine-2,6-dione trifluoroacetate

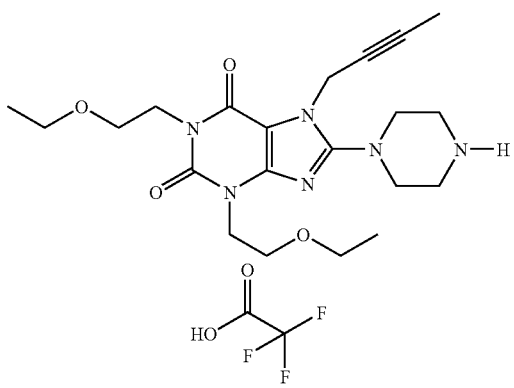

The title compound was obtained using, 2-bromoethyl-ethyl ether and steps similar to Example 318-c).

MS m/e (ESI) 433(MH$^+$—CF$_3$COOH)

EXAMPLE 320

[7-(2-Butynyl)-2,6-dioxo-8-(piperazin-1-yl)-1,2,6,7-tetrahydropurin-3-yl] acetic acid methyl ester trifluoroacetate a) 4-[7-(2-Butynyl)-3-methoxycarbonylmethyl-2,6-dioxo-2,3,6,7-tetrahydro-1H-purin-8-yl]piperazine-1-carboxylic acid tert-butyl ester

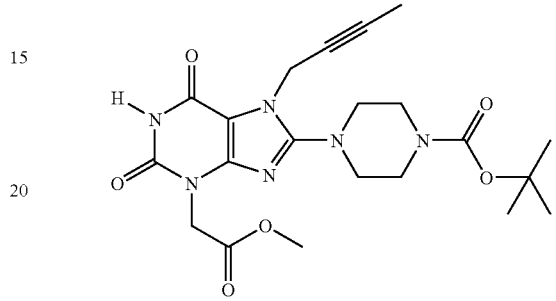

4-[7-(2-Butynyl)-2,6-dioxo-2,3,6,7-tetrahydro-1H-purin-8-yl]piperazine-1-carboxylic acid tert-butyl ester (50 mg) and potassium carbonate (20 mg) were dissolved in N,N-dimethylformamide (1.5 ml) and methyl bromoacetate (14 μl) was added to the solution while cooling on ice. After the mixture was stirred at room temperature overnight, the mixture was diluted with ethyl acetate, washed with water, and dried over anhydrous magnesium sulfate. After the organic layer was concentrated by distillation, the residue was purified by silica gel column chromatography to give 26 mg of the title compound from the elution fraction of hexane-ethyl acetate (1:1).

$^1$H-NMR(CDCl$_3$) δ: 1.48 (s, 9H) 1.83 (t, J=2.4 Hz, 3H) 3.32–3.35 (m, 4H) 3.56–3.58 (m, 4H) 3.78 (s, 3H) 4.73 (s, 2H) 4.84 (q, J=2.4 Hz, 2H) 7.80 (s, 2H)

b) [7-(2-Butynyl)-2,6-dioxo-8-(piperazin-1-yl)-1,2,6,7-tetrahydropurin-3-yl] acetic acid methyl ester trifluoroacetate

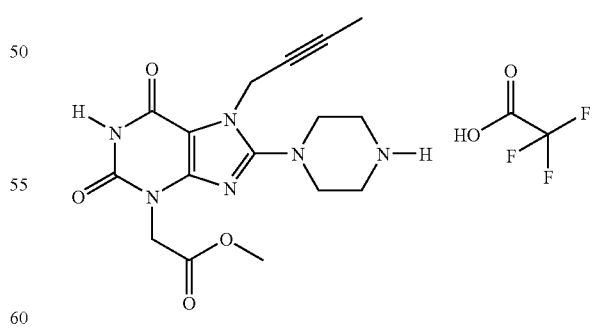

4-[7-(2-Butynyl)-3-methoxycarbonylmethyl-2,6-dioxo-2,3,6,7-tetrahydro-1H-purin-8-yl]piperazine-1-carboxylic acid tert-butyl ester (13 mg) was dissolved in trifluoroacetic acid (0.5 ml), and the solution was stirred at room temperature for 30 minutes. After the solvent was removed by distillation, a half of the residue was purified by HPLC with

EXAMPLE 321

7-(2-Butynyl)-3-(2-ethoxyethyl)-8-(piperazin-1-yl)-3,7-dihydropurine-2,6-dione trifluoroacetate a) 4-[7-(2-Butynyl)-1,3-bis-(2,2-dimethylpropionyloxymethyl)-2,6-dioxo-2,3,6,7-tetrahydro-1H-purin-8-yl]piperazine-1-carboxylic acid tert-butyl ester

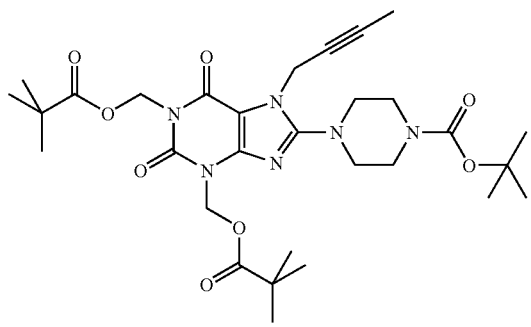

A mixture of 2,2-dimethylpropionic acid [3-(2,2-dimethylpropionyloxymethyl)-2,6-dioxo-2,3,6,7-tetrahydropurin-1-yl]methyl ester (1.0 g), 1-bromo-2-butyne (0.28 ml), anhydrous potassium carbonate (0.73 g), and N,N-dimethylformamide (15 ml) was stirred at room temperature for 2 hours. The reaction mixture was extracted with ethyl acetate-water, and the organic layer was washed with water and saturated brine. The organic layer was dried over anhydrous magnesium sulfate, the mixture was concentrated under reduced pressure. The residue was purified by silica gel column chromatography using 20–30% ethyl acetate/hexane to give 1.06 g of 2,2-dimethylpropionic acid [7-(2-butynyl)-3-(2,2-dimethylpropionyloxymethyl)-2,6-dioxo-2,3,6,7-tetrahydropurin-1-yl]methyl ester.

A mixture of the whole amount of the product, N-chlorosuccinimide (390 mg), and N,N-dimethylformamide (5 ml) was stirred at room temperature for 1 hour. The reaction mixture was extracted with ethyl acetate-water, and the organic layer was washed with water and saturated brine. After the organic layer was dried over anhydrous magnesium sulfate, the mixture was concentrated under reduced pressure. The residue was purified by silica gel column chromatography using 20–30% ethyl acetate/hexane to give 1.18 g of 2,2-dimethylpropionic acid [7-(2-butynyl)-8-chloro-3-(2,2-dimethylpropionyloxymethyl)-2,6-dioxo-2,3,6,7-tetrahydropurin-1-yl]methyl ester.

A mixture of the whole amount of the product and piperazine-1-carboxylic acid tert-butyl ester (1.4 g) was heated and stirred in an oil bath at 150° C. for 30 minutes. The reaction mixture was purified by silica gel column chromatography using 20–30% ethyl acetate/hexane to give 1.34 g of the title compound.

$^1$H-NMR(CDCl$_3$) δ: 1.18 (s, 18H) 1.49 (s, 9H) 1.84 (t, J=2 Hz, 3H) 3.36 (t, J=5 Hz, 4H) 3.58 (t, J=5 Hz) 4.86 (q, J=2 Hz, 2H) 6.02 (s, 2H), 6.03 (s, 2H)

b) 4-[7-(2-Butynyl)-1-(2,2-dimethylpropionyloxymethyl)-2,6-dioxo-2,3,6,7-tetrahydro-1H-purin-8-yl]piperazine-1-carboxylic acid tert-butyl ester

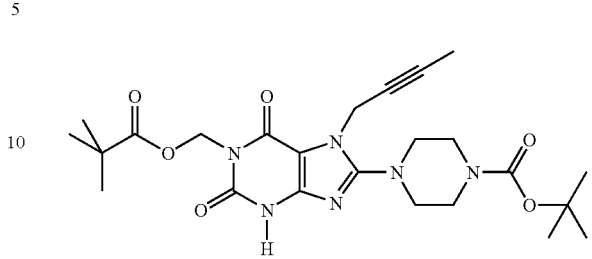

4-[7-(2-Butynyl)-1,3-bis-(2,2-dimethylpropionyloxymethyl)-2,6-dioxo-2,3,6,7-tetrahydro-1H-purin-8-yl]piperazine-1-carboxylic acid tert-butyl ester (0.63 g) was dissolved in a solvent mixture of tetrahydrofuran (4 ml) and methanol (2 ml), and diazabicyclo[5.4.0]undecene (0.18 ml) was added to the solution. The mixture was stirred at room temperature overnight. The reaction mixture was concentrated, and the residue was purified by silica gel column chromatography to give 0.29 g of the title compound from the elution fraction of hexane-ethyl acetate (1:5).

$^1$H-NMR(CDCl$_3$) δ: 1.19 (s, 9H) 1.48 (s, 9H) 1.83 (t, J=2.4 Hz, 3H) 3.37–3.39 (m, 4H) 3.58–3.60 (m, 4H) 4.86 (q, J=2.4 Hz, 2H) 6.00 (s, 2H) 9.08 (s, 1H)

c) 7-(2-Butynyl)-3-(2-ethoxyethyl)-8-(piperazin-1-yl)-3,7-dihydropurine-2,6-dione trifluoroacetate

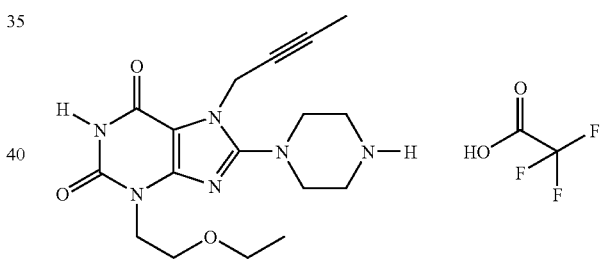

4-[7-(2-Butynyl)-1-(2,2-dimethylpropionyloxymethyl)-2,6-dioxo-2,3,6,7-tetrahydro-1H-purin-8-yl]piperazine-1-carboxylic acid tert-butyl ester (50 mg) and potassium carbonate (15 mg) were dissolved in N,N-dimethylformamide (1.2 ml), and 2-bromoethylethyl ether (12 µl) was added to the solution. The mixture was stirred at 60° C. for 2 hours, diluted with ethyl acetate, washed with water, and dried over anhydrous magnesium sulfate. After the organic layer was concentrated by distillation, the residue was purified by silica gel column chromatography to give 4-[7-(2-butynyl)-1-(2,2-dimethylpropionyloxymethyl)-3-(2-ethoxyethyl)-2,6-dioxo-2,3,6,7-tetrahydro-1H-purin-8-yl]piperazine-1-carboxylic acid tert-butyl ester from the elution fraction of hexane-ethyl acetate (2:1). The obtained 4-[7-(2-butynyl)-1-(2,2-dimethylpropionyloxymethyl)-3-(2-ethoxyethyl)-2,6-dioxo-2,3,6,7-tetrahydro-1H-purin-8-yl]piperazine-1-carboxylic acid tert-butyl ester was dissolved in a solvent mixture of tetrahydrofuran (1.0 ml) and methanol (0.5 ml), sodium hydride (5 mg) was added to the solution, and the mixture was stirred at room temperature for 1 hour. After the reaction mixture was neutralized with 2N hydrochloric acid and extracted with ethyl acetate, the organic layer was dried over anhydrous magnesium sulfate. The solvent was removed by distillation to give 4-[7-(2-butynyl)-3-(2-ethoxyethyl)-2,6-dioxo-2,3,6,7-tetrahydro-1H-purin-8-yl]piperazine-1-carboxylic acid tert-butyl ester. A quarter of the obtained 4-[7-(2-butynyl)-3-(2-ethoxyethyl)-2,6-dioxo-2,3,6,7-tetrahydro-1H-purin-8-yl]piperazine-1-carboxylic acid tert-butyl ester was dissolved in trifluoroacetic acid (0.5 ml), and the solution was stirred at room temperature for 30 minutes. After the solvent was removed by distillation, a half of the residue was purified by HPLC with a reversed phase column using water-acetonitrile-trifluoroacetic acid system as elution solvent to give 3.2 mg of the title compound.
MS m/e (ESI) 361(MH⁺—CF₃COOH)

EXAMPLE 322

[7-(2-Butynyl)-3-(2-ethoxyethyl)-2,6-dioxo-8-(piperazin-1-yl)-2,3,6,7-tetrahydropurin-1-yl] acetic acid methyl ester trifluoroacetate

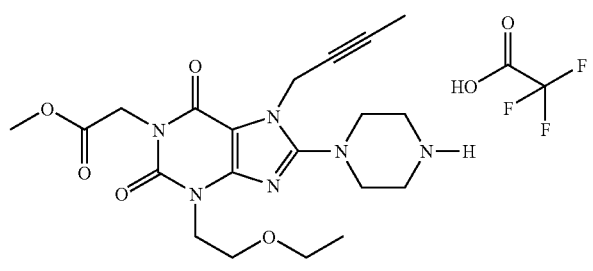

A quarter of 4-[7-(2-butynyl)-3-(2-ethoxyethyl)-2,6-dioxo-2,3,6,7-tetrahydro-1H-purin-8-yl]piperazine-1-carboxylic acid tert-butyl ester obtained in Example 321-c) and potassium carbonate (7 mg) were dissolved in N,N-dimethylformamide (0.8 ml), and methyl bromoacetate (10 μl) was added to the solution. After the mixture was stirred at room temperature overnight, the mixture was diluted with ethyl acetate, washed with water, and dried over anhydrous magnesium sulfate. After the organic layer was concentrated by distillation, the residue was dissolved in trifluoroacetic acid (0.5 ml), and the mixture was stirred at room temperature for 30 minutes. After the solvent was removed by distillation, a half of the residue was purified by HPLC with a reversed phase column using water-acetonitrile-trifluoroacetic acid system as elution solvent to give 3.2 mg of the title compound.
MS m/e (ESI) 433(MH⁺—CF₃COOH)

EXAMPLE 323

7-(2-Butynyl)-3-(2-ethoxyethyl)-1-(2-oxo-2-phenylethyl-8-(piperazin-1-yl)-3,7-dihydropurine-2,6-dione trifluoroacetate

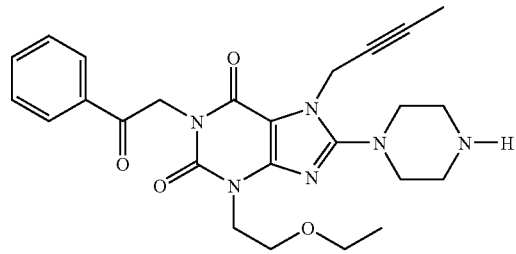

-continued

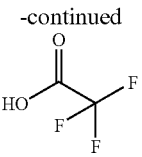

The title compound was obtained using 2-bromoacetophenone and steps similar to Example 322.
MS m/e (ESI) 479(MH⁺—CF₃COOH)

EXAMPLE 324

[7-(2-Butynyl)-1-(2-ethoxyethyl)-2,6-dioxo-8-(piperazin-1-yl)-1,2,6,7-tetrahydropurin-3-yl] acetic acid methyl ester trifluoroacetate a) 4-[7-(2-Butynyl)-3-(2,2-dimethylpropionyloxymethyl)-2,6-dioxo-2,3,6,7-tetrahydro-1H-purin-8-yl]piperazine-1-carboxylic acid tert-butyl ester

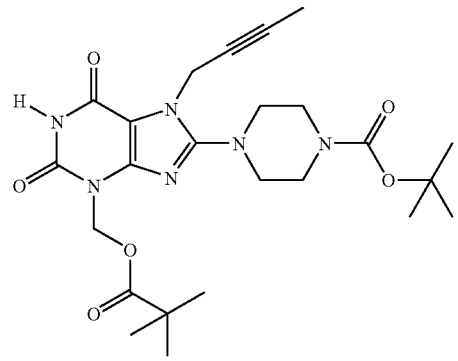

4-[7-(2-Butynyl)-2,6-dioxo-2,3,6,7-tetrahydro-1H-purin-8-yl]piperazine-1-carboxylic acid tert-butyl ester (1.1 g) and potassium carbonate (0.43 g) were dissolved in N,N-dimethylformamide (15 ml), and chloromethyl pivalate (0.60 ml) was added to the solution while cooling on ice. After the mixture was stirred at room temperature overnight, the reaction mixture was diluted with ethyl acetate and washed with water. Insoluble white solid was collected by filtration, and washed with a mixture of hexane-ethyl acetate (1:1) to give 0.57 g of the title compound.
¹H-NMR(CDCl₃) δ: 1.18 (s, 9H) 1.49 (s, 9H) 1.83 (t, J=2.4 Hz, 3H) 3.33–3.36 (m, 4H) 3.57–3.59 (m, 4H) 4.84 (q, J=2.4 Hz, 2H) 5.99 (s, 2H) 7.72 (s, 1H)

b) [7-(2-Butynyl)-1-(2-ethoxyethyl)-2,6-dioxo-8-(piperazin-1-yl)-1,2,6,7-tetrahydropurin-3-yl] acetic acid methyl ester trifluoroacetate

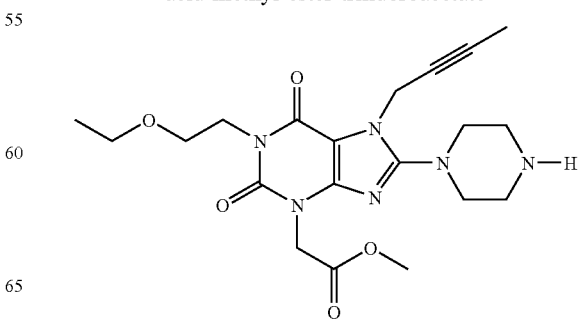

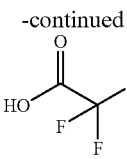

4-[7-(2-Butynyl)-3-(2,2-dimethylpropionyloxymethyl)-2,6-dioxo-2,3,6,7-tetrahydro-1H-purin-8-yl]piperazine-1-carboxylic acid tert-butyl ester (40 mg) and potassium carbonate (17 mg) were dissolved in N,N-dimethylformamide (1.5 ml), and 2-bromoethylethyl ether (14 µl) was added to the solution. The mixture was stirred at 60° C. for 5 hours, diluted with ethyl acetate, washed with water, and dried over anhydrous magnesium sulfate. After removing the solvent by distillation, the residue was purified by silica gel column chromatography to give 4-[7-(2-butynyl)-3-(2,2-dimethylpropionyloxymethyl)-1-(2-ethoxyethyl)-2,6-dioxo-2,3,6,7-tetrahydro-1H-purin-8-yl]piperazine-1-carboxylic acid tert-butyl ester from the elution fraction of hexane-ethyl acetate (1:1). The obtained 4-[7-(2-butynyl)-3-(2,2-dimethylpropionyloxymethyl)-1-(2-ethoxyethyl)-2,6-dioxo-2,3,6,7-tetrahydro-1H-purin-8-yl]piperazine-1-carboxylic acid tert-butyl ester was dissolved in a solvent mixture of tetrahydrofuran (1.0 ml) and methanol (0.5 ml), sodium hydride (5 mg) was added to the solution, and the mixture was stirred at room temperature for 1 hour. The reaction mixture was neutralized with 2 N hydrochloric acid, and extracted with ethyl acetate. Then, the organic layer was dried over anhydrous magnesium sulfate and the solvent was removed by distillation. The obtained residue was dissolved in N,N-dimethylformamide (1 ml), and potassium carbonate (10 mg) and methyl bromoacetate (10 µl) were added to the solution. The mixture was stirred at room temperature for 2 hours, diluted with ethyl acetate, and washed with water. After the organic layer was concentrated by distillation, the residue was dissolved in trifluoroacetic acid (0.5 ml), and the solution was stirred at room temperature for 30 minutes. After removing the solvent by distillation, a half of the residue was purified by HPLC with a reversed phase column using water-acetonitrile-trifluoroacetic acid system as elution solvent to give 6.2 mg of the title compound.

MS m/e (ESI) 433(MH$^+$—CF$_3$COOH)

EXAMPLE 325

[7-(2-Butynyl)-2,6-dioxo-1-(2-oxo-2-phenylethyl)-8-(piperazin-1-yl)-1,2,6,7-tetrahydropurin-3-yl] acetic acid methyl ester trifluoroacetate

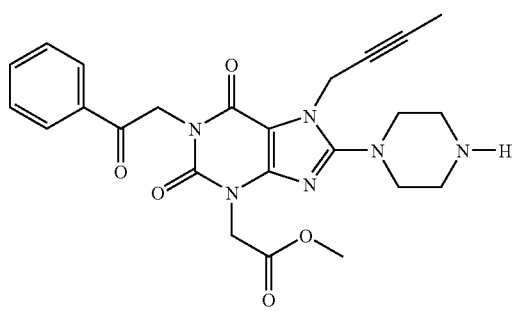

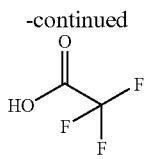

The title compound was obtained using 2-bromoacetophenone and steps similar to Example 324.

MS m/e (ESI) 479(MH$^+$—CF$_3$COOH)

EXAMPLE 326

[7-(2-Butynyl)-2,6-dioxo-1-(2-phenethyl)-8-(piperazin-1-yl)-1,2,6,7-tetrahydropurin-3-yl]acetic acid ethyl ester hydrochloride a) (7-Benzyl-2,6-dioxo-1,2,6,7-tetrahydropurin-3-yl) acetic acid ethyl ester

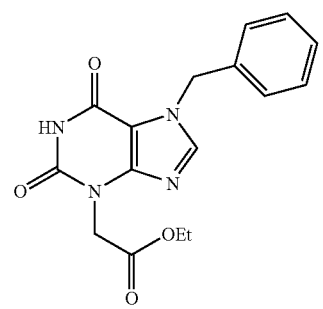

A mixture of 7-benzyl-3,7-dihydropurine-2,6-dione (3.0 g), anhydrous potassium carbonate (2.0 g), and N,N-dimethylformamide (60 ml) was stirred with heating in an oil bath of 40° C., and ethyl bromoacetate (1.5 g) was added thereto. The mixture was stirred by heating at the same temperature for 4 hours. The reaction mixture was diluted with ethyl acetate and water, and extracted with ethyl acetate. The organic layer was washed with water and saturated brine, dried over anhydrous magnesium sulfate, and concentrated under reduced pressure. The residue was purified by silica gel column chromatography using 20–40% (20% 2-propanol/ethyl acetate)/hexane to give 1.3 g of the title compound.

$^1$H-NMR(CDCl$_3$) δ: 1.28 (t, J=7 Hz, 3H) 4.23 (q, J=7 Hz, 2H) 4.78 (s, 2H) 5.04 (s, 2H) 7.31–7.39 (m, 5H) 7.51 (s, 1H) 8.01 (br.s, 1H)

b) [7-Benzyl-1-(2-phenylethyl)-2,6-dioxo-1,2,6,7-tetrahydropurin-3-yl]acetic acid ethyl ester

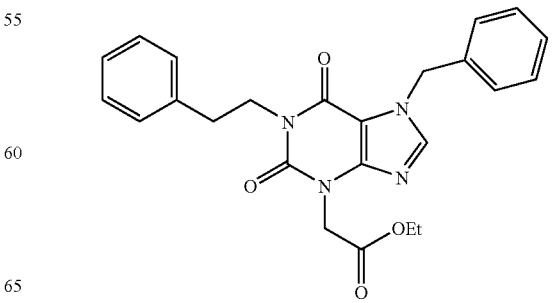

A mixture of (7-benzyl-2,6-dioxo-1,2,6,7-tetrahydropurin-3-yl)acetic acid ethyl ester (300 mg), anhydrous potassium carbonate (250 mg), 2-bromoethylbenzene (0.25 ml), and N,N-dimethylformamide (5 ml) was stirred with heating in an oil bath of 50° C. for 2 hours. The reaction mixture was diluted with ethyl acetate and water, and extracted with ethyl acetate. The organic layer was washed with water and saturated brine, dried over anhydrous magnesium sulfate, and concentrated under reduced pressure. The residue was purified by silica gel column chromatography using 10–20% (20% 2-propanol/ethyl acetate)/hexane to give 366 mg of the title compound.

$^1$H-NMR(CDCl$_3$) δ: 1.29 (t, J=7 Hz, 3H) 2.95 (t, J=8 Hz, 2H) 4.22 (t, J=8 Hz, 2H) 4.24 (q, J=7 Hz, 2H) 4.83 (s, 2H) 5.48 (s, 2H) 7.17–7.39 (m, 10H) 7.49 (s, 1H)

c) [7-(2-Butynyl)-8-chloro-1-(2-phenylethyl)-2,6-dioxo-1,2,6,7-tetrahydropurin-3-yl]acetic acid ethyl ester

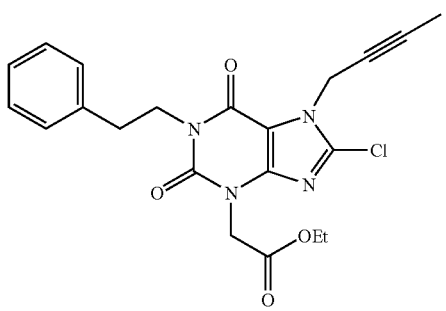

A catalytic amount of 10% palladium-carbon was added to a mixture of [7-benzyl-1-(2-phenylethyl)-2,6-dioxo-1,2,6,7-tetrahydropurin-3-yl]acetic acid ethyl ester (366 mg) and acetic acid (10 ml), and the resulting mixture was stirred at room temperature under hydrogen atmosphere overnight. The catalyst was removed by filtration, and the filtrate was concentrated under reduced pressure to give 320 mg of the residue. A mixture of the whole amount of the concentrated residue, anhydrous potassium carbonate (260 mg), 1-bromo-2-butyne (0.1 ml), and N,N-dimethylformamide (5 ml) was stirred at room temperature for 2 hours. The reaction mixture was diluted with ethyl acetate and water, and extracted with ethyl acetate. The organic layer was washed with water and saturated brine, dried over anhydrous magnesium sulfate, and concentrated under reduced pressure. The residue was purified by silica gel column chromatography using 20–30% ethyl acetate/hexane to give 290 mg of oil. A mixture of the whole amount of the oil, N,N-dimethylformamide (3 ml), and N-chlorosuccinimide (120 mg) was stirred at room temperature for 1 hour. The reaction mixture was extracted with ethyl acetate and water. The organic layer was washed with water and saturated brine, dried over anhydrous magnesium sulfate, and concentrated under reduced pressure. The residue was purified by silica gel column chromatography using 20–30% ethyl acetate/hexane to give 273 mg of the title compound.

$^1$H-NMR(CDCl$_3$) δ: 1.31 (t, J=7 Hz, 3H) 1.82 (t, J=2 Hz, 3H) 2.94 (t, J=8 Hz, 2H) 4.21 (t, J=8 Hz, 2H) 4.25 (q, J=7 Hz, 2H) 4.78 (s, 2H) 5.09 (q, J=2 Hz, 2H) 7.19–7.24 (m, 1H), 7.26–7.33 (m, 4H)

d) 4-[7-(2-Butynyl)-3-ethoxycarbonylmethyl-1-(2-phenylethyl)-2,6-dioxo-1,2,6,7-tetrahydropurin-8-yl]piperazine-1-carboxylic acid tert-butyl ester

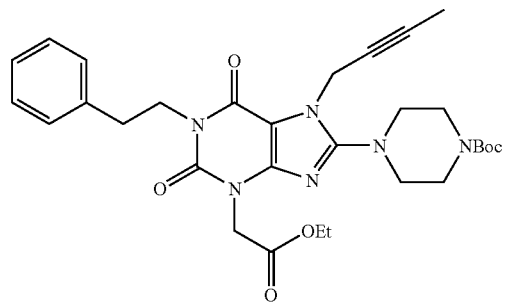

A mixture of [7-(2-butynyl)-8-chloro-1-(2-phenylethyl)-2,6-dioxo-1,2,6,7-tetrahydropurin-3-yl]acetic acid ethyl ester (273 mg) and piperazine-1-carboxylic acid tert-butyl ester (360 mg) was heated in an oil bath of 150° C. for 30 minutes. The reaction mixture was purified by silica gel column chromatography using 20–30% ethyl acetate/hexane to give 320 mg of the title compound.

$^1$H-NMR(CDCl$_3$) δ: 1.30 (t, J=7 Hz, 3H) 1.49 (s, 9H) 1.84 (t, J=2 Hz, 3H) 2.93 (t, J=8 Hz, 2H) 3.33 (t, J=5 Hz, 4H) 3.57 (t, J=5 Hz, 4H) 4.19 (t, J=8 Hz, 2H) 4.25 (q, J=7 Hz, 2H) 4.76 (s, 2H) 4.86 (q, J=2 Hz, 2H) 7.19 (t, J=7 Hz, 1H) 7.25–7.34 (m, 4H)

e) [7-(2-Butynyl)-2,6-dioxo-1-(2-phenethyl)-8-(piperazin-1-yl)-1,2,6,7-tetrahydropurin-3-yl]acetic acid ethyl ester hydrochloride

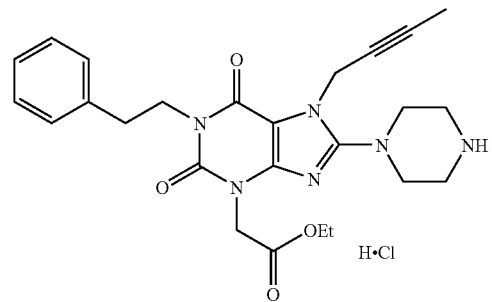

A mixture of 4-[7-(2-butynyl)-3-ethoxycarbonylmethyl-1-(2-phenylethyl)-2,6-dioxo-1,2,6,7-tetrahydropurin-8-yl]piperazine-1-carboxylic acid tert-butyl ester (27 mg) and trifluoroacetic acid (0.25 ml) was stirred at room temperature for 30 minutes. The reaction mixture was concentrated and the residue was purified by reversed phase column chromatography using 20–80% methanol/water (containing 0.1% conc. hydrochloric acid) to give 17 mg of the title compound.

$^1$H-NMR(d6-DMSO) δ: 1.22 (t, J=7 Hz, 3H) 1.82 (t, J=2 Hz, 3H) 2.80 (t, J=8 Hz, 2H) 3.22–3.28 (m, 4H) 3.46–3.51 (m, 4H) 4.05 (t, J=8 Hz, 2H) 4.17 (q, J=7 Hz, 2H) 4.69(s, 2H) 4.96(q, J=2 Hz, 2H) 7.19–7.24 (m, 3H) 7.30 (t, J=7 Hz, 2H)

EXAMPLE 327

[7-(2-Butynyl)-2,6-dioxo-1-(2-phenethyl)-8-(piperazin-1-yl)-1,2,6,7-tetrahydropurin-3-yl]acetic acid hydrochloride a) 4-[7-(2-Butynyl)-3-carboxymethyl-1-(2-phenylethyl)-2,6-dioxo-1,2,6,7-tetrahydropurin-8-yl]piperazine-1-carboxylic acid tert-butyl ester

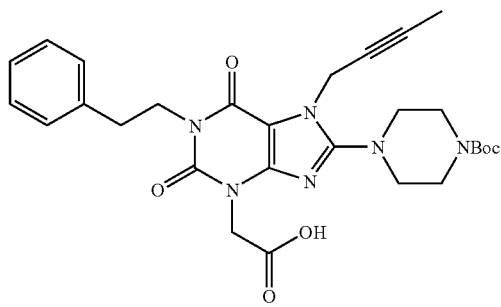

A mixture of 4-[7-(2-butynyl)-3-ethoxycarbonylmethyl-1-(2-phenylethyl)-2,6-dioxo-1,2,6,7-tetrahydropurin-8-yl]piperazine-1-carboxylic acid tert-butyl ester (190 mg), ethanol (3 ml), and 1N aqueous sodium hydroxide solution (0.5 ml) was stirred with heating in an oil bath of 50° C. for 2 hours. 1N aqueous hydrochloric acid solution (0.55 ml) was added to the reaction mixture, and the mixture was extracted with ethyl acetate and water. The organic layer was washed with water and saturated brine, dried over anhydrous magnesium sulfate, concentrated under reduced pressure, and crystallized from ethyl acetate-hexane to give 166 mg of the title compound.
$^1$H-NMR(CDCl$_3$) δ: 1.49 (s, 9H) 1.84 (t, J=2 Hz, 3H) 2.93 (t, J=8 Hz, 2H) 3.34 (t, J=5 Hz, 4H) 3.58 (t, J=5 Hz, 4H) 4.19 (t, J=8 Hz, 2H) 4.82 (s, 2H) 4.85 (q, J=2 Hz, 2H) 7.19 (t, J=7 Hz, 1H) 7.24–7.33 (m, 4H)

b) [7-(2-Butynyl)-2,6-dioxo-1-(2-phenethyl)-8-(piperazin-1-yl)-1,2,6,7-tetrahydropurin-3-yl]acetic acid hydrochloride

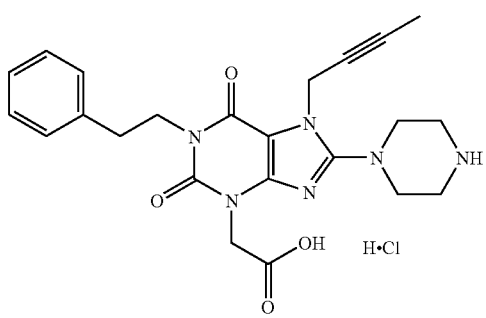

2.2 mg of the title compound was obtained using 22 mg 4-[7-(2-butynyl)-3-carboxymethyl-1-(2-phenylethyl)-2,6-dioxo-1,2,6,7-tetrahydropurin-8-yl]piperazine-1-carboxylic acid tert-butyl ester and steps similar to Example 326 e).
$^1$H-NMR(d6-DMSO) δ: 1.82 (t, J=2 Hz, 3H) 2.80 (t, J=8 Hz, 2H) 3.23–3.28 (m, 4H) 3.46–3.53(m, 4H) 4.05 (t, J=8 Hz, 2H) 4.59 (s, 2H) 4.96 (q, J=2 Hz, 2H) 7.19–7.25 (m, 3H) 7.30 (t, J=7 Hz, 2H)

EXAMPLE 328

7-(2-Butynyl)-3-[2-oxo-2-(pyrrolidin-1-yl)ethyl]-1-(2-phenethyl)-8-piperazin-1-yl)-3,7-dihydropurine-2,6-dione hydrochloride

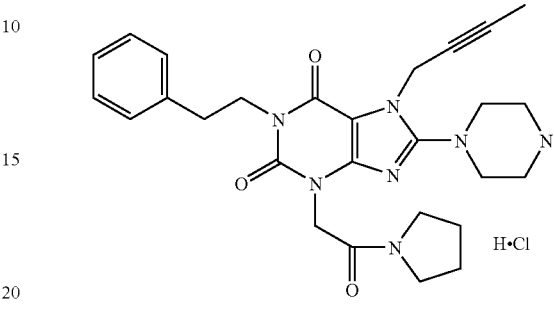

A mixture of 4-[7-(2-butynyl)-3-carboxymethyl-1-(2-phenylethyl)-2,6-dioxo-1,2,6,7-tetrahydropurin-8-yl]piperazine-1-carboxylic acid tert-butyl ester (20 mg), diethyl phosphorcyanide (8 μl), triethylamine (10 μl) pyrrolidine (20 μl), and N,N-dimethylformamide (0.3 ml) was left standing at room temperature for 3 days. The reaction mixture was diluted with ethyl acetate and water, and extracted with ethyl acetate. The organic layer was washed with water and saturated brine, and concentrated. Trifluoroacetic acid (0.5 ml) was added to the residue, and the mixture was reacted at room temperature for 30 minutes. The reaction mixture was concentrated, and the residue was purified by reversed phase column chromatography using 20–80% methanol/water (containing 0.1% conc. hydrochloric acid) to give 3.2 mg of the title compound.
$^1$H-NMR(d6-DMSO) δ: 1.76–1.84 (m, 5H) 1.95 (quint. J=7 Hz, 2H), 2.79 (t, J=8 Hz, 2H) 3.22–3.34 (m, 6H) 3.45–3.52 (m, 4H) 3.55 (t, J=7 Hz, 2H) 4.03 (t, J=8 Hz, 2H) 4.68 (s, 2H) 4.96 (q, J=2 Hz, 2H) 7.18–7.26 (m, 3H) 7.31 (t, J=8 Hz, 2H)

EXAMPLE 329

2-[7-(2-Butynyl)-2,6-dioxo-1-(2-phenethyl)-8-(piperazin-1-yl)-1,2,6,7-tetrahydropurin-3-yl]-N-methylacetamide hydrochloride

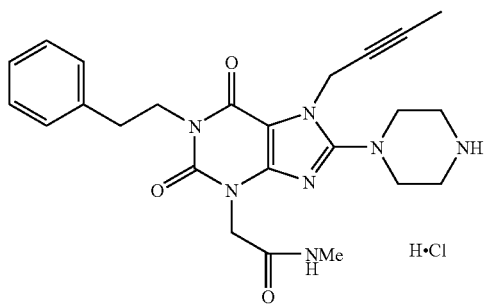

The title compound was synthesized using aqueous methylamine solution and steps similar to Example 328.

¹H-NMR(d6-DMSO) δ: 1.82 (t, J=2 Hz, 3H) 2.61 (d, J=5 Hz, 3H) 2.79 (t, J=8 Hz, 2H) 3.20–3.28 (m, 4H) 3.44–3.52 (m, 4H) 4.03 (t, J=8 Hz, 2H) 4.48 (s, 2H) 4.96 (q, J=2 Hz, 2H) 7.19–7.26 (m, 3H) 7.31 (t, J=7 Hz, 2H) 8.09 (brd, J=5 Hz, 1H)

EXAMPLE 330

2-[7-(2-Butynyl)-2,6-dioxo-1-(2-phenethyl)-8-(piperazin-1-yl)-1,2,6,7-tetrahydropurin-3-yl]-N-cyclopropylacetamide hydrochloride

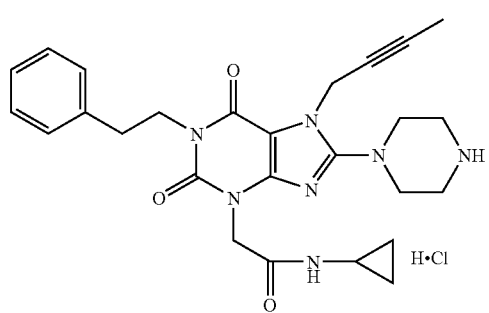

The title compound was synthesized using cyclopropylamine and steps similar to Example 328.

¹H-NMR(d6-DMSO) δ: 0.39–0.44 (m, 2H) 0.60–0.66 (m, 2H) 1.82 (t, J=2 Hz, 3H) 2.60–2.68 (m, 1H) 2.79 (t, J=8 Hz, 2H) 3.20–3.30 (m, 4H) 3.44–3.54 (m, 4H) 4.03 (t, J=8 Hz, 2H) 4.44 (s, 2H) 4.96 (q, J=2 Hz, 2H) 7.19–7.27 (m, 3H) 7.31 (t, J=8 Hz, 2H) 8.27 (d, J=4 Hz, 1H)

EXAMPLE 331

2-[7-(2-Butynyl)-2,6-dioxo-1-(2-phenethyl)-8-(piperazin-1-yl)-1,2,6,7-tetrahydropurin-3-yl]-N-phenylacetamide hydrochloride

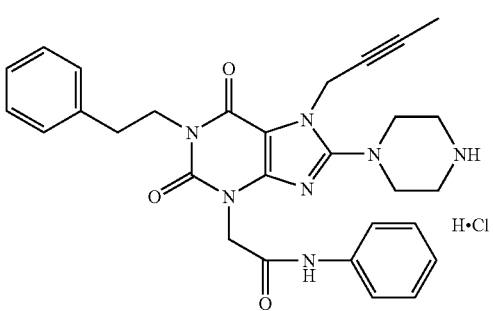

The title compound was synthesized using aniline and steps similar to Example 328.

¹H-NMR(d6-DMSO) δ: 1.83 (t, J=2 Hz, 3H) 2.81 (t, J=8 Hz, 2H) 3.20–3.30 (m, 4H) 3.44–3.54 (m, 4H) 4.05 (t, J=8 Hz, 2H) 4.74 (s, 2H), 4.98 (q, J=2 Hz, 2H) 7.06 (t, J=8 Hz, 1H) 7.18–7.35 (m, 7H) 7.56 (d, J=8 Hz, 2H) 9.01 (brs, 2H) 10.39 (s, 1H)

EXAMPLE 332

2-[7-(2-Butynyl)-2,6-dioxo-1-(2-phenethyl)-8-(piperazin-1-yl)-1,2,6,7-tetrahydropurin-3-yl]-N-(2-propynyl)acetamide hydrochloride

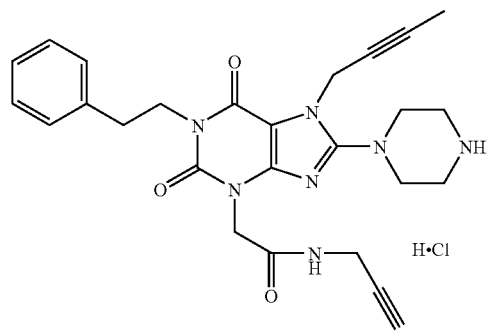

The title compound was synthesized using propargylamine and steps similar to Example 328.

¹H-NMR(d6-DMSO) δ: 1.81 (t, J=3 Hz) 2.80 (t, J=8 Hz, 2H) 3.18 (t, J=2 Hz 1H), 3.22–3.32 (m, 4H) 3.44–3.54 (m, 4H) 3.90 (dd, J=2 Hz, 5 Hz, 2H) 4.03 (t, J=8 Hz, 2H) 4.51 (s, 2H) 4.96 (q, J=2 Hz, 2H) 7.16–7.34 (m, 5H) 8.66 (t, J=5 Hz, 1H) 8.96 (br.s, 2H)

EXAMPLE 333

[7-(2-Butynyl)-2,6-dioxo-1-(2-phenoxyethyl)-8-(piperazin-1-yl)-1,2,6,7-tetrahydropurin-3-yl]acetic acid ethyl ester hydrochloride

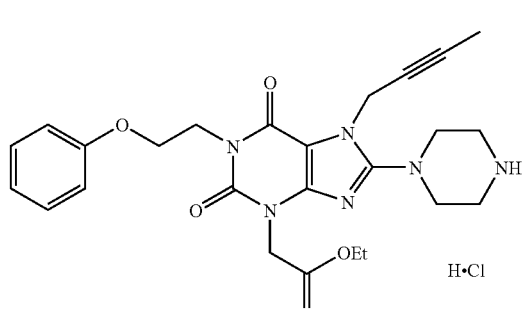

The title compound was synthesized using 2-bromoethyl phenyl ether and steps similar to Example 326.

¹H-NMR(d6-DMSO) δ: 1.20 (t, J=7 Hz, 3H) 1.81 (s, 3H) 3.22–3.28 (m, 4H) 3.46–3.53 (m, 4H) 4.06–4.19 (m, 4H) 4.25 (t, J=6 Hz, 2H) 4.69 (s, 2H) 4.97 (s, 2H) 6.88–6.96 (m, 3H) 7.26 (t, J=7 Hz, 2H) 8.96 (brs, 2H)

EXAMPLE 334

[7-(2-Butynyl)-2,6-dioxo-1-[2-(4-chlorophenoxy)ethyl]-8-(piperazin-1-yl)-1,2,6,7-tetrahydropurin-3-yl]acetic acid ethyl ester hydrochloride

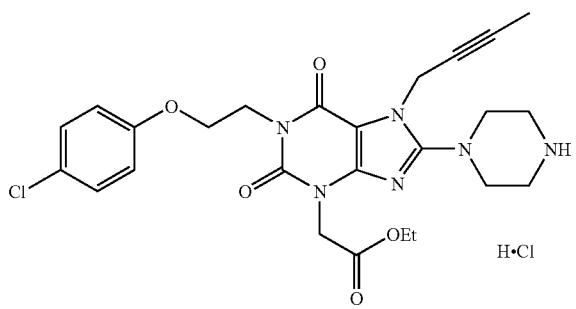

The title compound was synthesized using 2-bromoethyl (4-chlorophenyl) ether and steps similar to Example 326.

$^1$H-NMR(d6-DMSO) δ: 1.20 (t, J=7 Hz, 3H) 1.81 (s, 3H) 3.26 (br.s, 4H) 3.46–3.54 (m, 4H) 4.10–4.20 (m, 4H) 4.23 (t, J=6 Hz, 2H) 4.68 (s, 2H) 4.96 (s, 2H) 6.93 (d, J=9 Hz, 2H) 7.30 (d, J=9 Hz, 2H) 9.00 (brs, 2H)

EXAMPLE 335

N-[2-[7-(2-Butynyl)-3-methyl-2,6-dioxo-8-(piperazin-1-yl)-2,3,6,7-tetrahydropurin-1-yl]-ethyl]acetamide trifluoroacetate a) 4-[1-(2-Azidoethyl)-7-(2-butynyl)-3-methyl-2,6-dioxo-2,3,6,7-tetrahydro-1H-purin-8-yl]piperazine-1-carboxylic acid tert-butyl ester

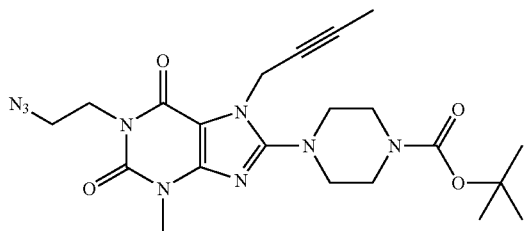

4-[7-(2-Butynyl)-1-(2-hydroxyethyl)-3-methyl-2,6-dioxo-2,3,6,7-tetrahydro-1H-purin-8-yl]piperazine-1-carboxylic acid tert-butyl ester (0.28 g) was dissolved in pyridine (4 ml), and methanesulfonyl chloride (73 μl) was added to the solution while cooling on ice. The mixture was stirred at room temperature for 1 hour, diluted with ethyl acetate, washed with 2N hydrochloric acid, and dried over anhydrous magnesium sulfate. The organic layer was concentrated by distillation at reduced pressure, and the obtained residue was dissolved in N,N-dimethylformamide (10 ml). Then, sodium azide (47 mg) was added to the solution, and the mixture was stirred at 50° C. for 3 hours. The mixture was diluted with ethyl acetate, washed with water, and dried over anhydrous magnesium sulfate. The organic layer was concentrated by distillation at reduced pressure, and the residue was purified by silica gel column chromatography to give 0.17 g of the title compound from the elution fraction of hexane-ethyl acetate (1:2).

$^1$H-NMR(CDCl$_3$) δ: 1.49 (s, 9H) 1.82 (t, J=2.4 Hz, 3H) 3.34–3.36 (m, 4H) 3.50 (s, 3H) 3.56 (t, J=6.0 Hz, 2H) 3.57–3.60 (m, 4H) 4.24 (t, J=6.0 Hz, 2H) 4.86 (q, J=2.4 Hz, 2H)

b) 4-[1-(2-Aminoethyl)-7-(2-butynyl)-3-methyl-2,6-dioxo-2,3,6,7-tetrahydro-1H-purin-8-yl]piperazine-1-carboxylic acid tert-butyl ester

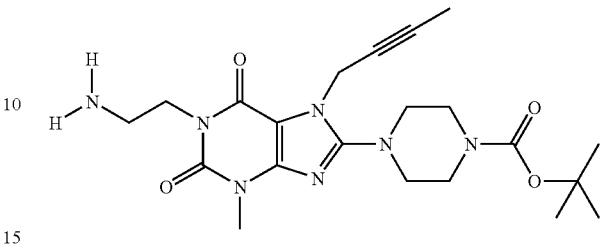

4-[1-(2-Azidoethyl)-7-(2-butynyl)-3-methyl-2,6-dioxo-2,3,6,7-tetrahydro-1H-purin-8-yl]piperazine-1-carboxylic acid tert-butyl ester (0.17 g) was dissolved in tetrahydrofuran (3.5 ml), and water (0.23 ml) and triphenylphosphine (0.13 g) were added to the solution. After the mixture was stirred at room temperature overnight, the solvent was removed by distillation at reduced pressure. The residue was purified by silica gel column chromatography to give 0.12 g of the title compound from the elution fraction of ethyl acetate-methanol (10:1).

$^1$H-NMR(CDCl$_3$) δ: 1.49 (s, 9H) 1.82 (t, J=2.4 Hz, 3H) 2.99 (t, J=6.4 Hz, 2H) 3.33–3.36 (m, 4H) 3.51 (s, 3H) 3.58–3.61 (m, 4H) 4.10 (t, J=6.4 Hz, 2H) 4.86 (q, J=2.4 Hz, 2H)

c) N-[2-[7-(2-Butynyl)-3-methyl-2,6-dioxo-8-(piperazin-1-yl)-2,3,6,7-tetrahydropurin-1-yl]-ethyl]acetamide trifluoroacetate

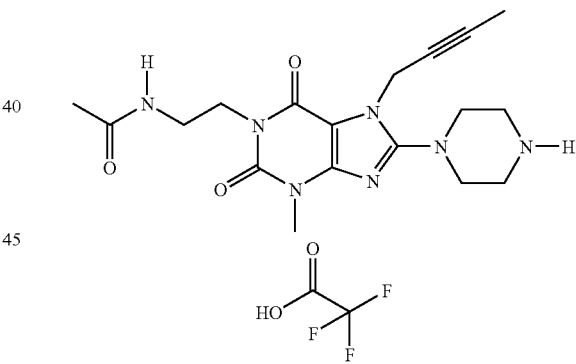

4-[1-(2-Aminoethyl)-7-(2-butynyl)-3-methyl-2,6-dioxo-2,3,6,7-tetrahydro-1H-purin-8-yl]piperazine-1-carboxylic acid tert-butyl ester (20 mg) was dissolved in dichloromethane (1 ml), and triethylamine (14 μl) and acetyl chloride (4 μl) were added to the solution while cooling on ice. Then, the mixture was stirred at room temperature for 2 hours. The reaction mixture was diluted with ethyl acetate, washed with water, and dried over anhydrous magnesium sulfate. The organic layer was concentrated by distillation. The residue was dissolved in trifluoroacetic acid (0.5 ml), and the mixture was stirred at room temperature for 30 minutes. After the organic layer was concentrated by distillation, a half of the residue was purified by HPLC with a reversed phase system column using water-acetonitrile-trifluoroacetic acid system as elution solvent to give 12 mg of the title compound.

MS m/e (ESI) 388(MH$^+$—CF$_3$COOH)

EXAMPLE 336

N-[2-[7-(2-Butynyl)-3-methyl-2,6-dioxo-8-(piperazin-1-yl)-2,3,6,7-tetrahydropurin-1-yl]-ethyl]benzamide trifluoroacetate

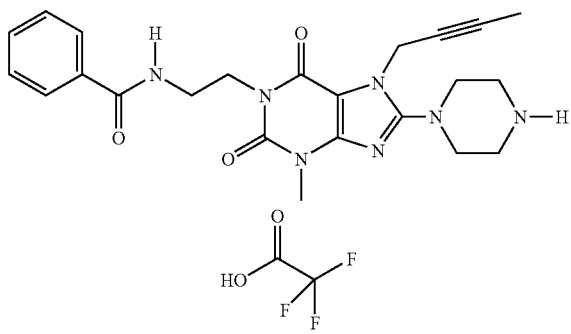

The title compound was obtained using benzoyl chloride and steps similar to Example 335-c).
MS m/e (ESI) 450(MH$^+$—CF$_3$COOH)

EXAMPLE 337

N-[2-[7-(2-Butynyl)-3-methyl-2,6-dioxo-8-(piperazin-1-yl)-2,3,6,7-tetrahydropurin-1-yl]-ethyl]methanesulfonamide trifluoroacetate

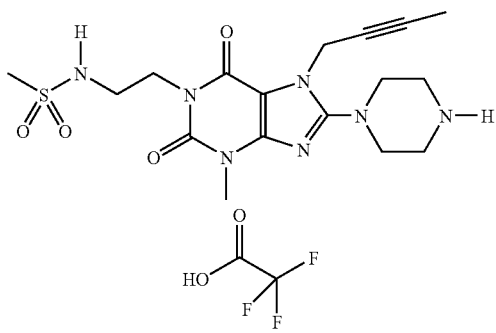

The title compound was obtained using methanesulfonyl chloride and steps similar to Example 335-c).
MS m/e (ESI) 424(MH$^+$—CF$_3$COOH)

EXAMPLE 338

N-[2-[7-(2-Butynyl)-3-methyl-2,6-dioxo-8-(piperazin-1-yl)-2,3,6,7-tetrahydropurin-1-yl]-ethyl]benzenesulfonamide trifluoroacetate

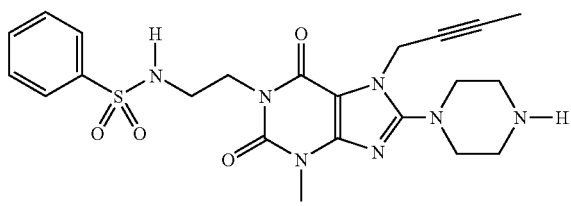

-continued

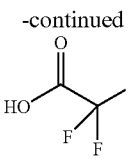

The title compound was obtained using benzenesulfonyl chloride and steps similar to Example 335-c).
MS m/e (ESI) 486(MH$^+$—CF$_3$COOH)

EXAMPLE 339

1,3-Dimethyl-9,9a,10,11,12,13-hexahydro-1H-1,3,4b,11,13a,14-hexaazatribenzo[a,e,h]azulene-2,4-dione trifluoroacetate a) 7-(2-Bromophenyl)-1,3-dimethyl-3,7-dihydropurine-2,6-dione

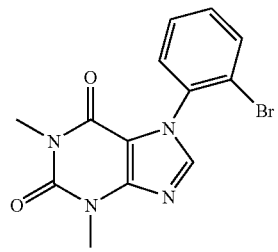

7.32 g of the title compound was obtained using theophylline (13.42 g) and 2-bromophenylboronic acid (30.07 g), and steps similar to Example 153a).
$^1$H-NMR(CDCl$_3$) δ: 3.38 (s, 3H) 3.67 (s, 3H) 7.39–7.52 (m, 3H) 7.66 (s, 1H) 7.76 (d, J=7.0 Hz, 1H)

b) 2-[[2-(1,3-Dimethyl-2,6-dioxo-1,2,3,6-tetrahydropurin-7-yl)phenyl]hydroxymethyl]piperazine-1,4-dicarboxylic acid di-tert-butyl ester

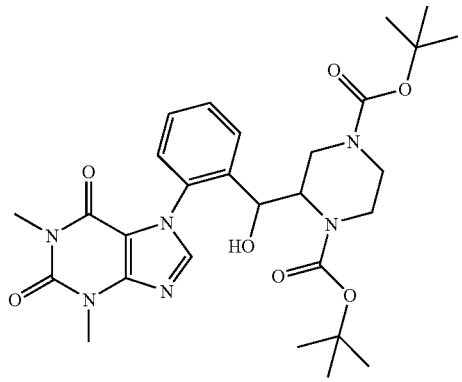

1.7 M solution of t-butyl lithium in pentane (1.8 ml) was dropwise added to a solution of 7-(2-bromophenyl)-1,3-dimethyl-3,7-dihydropurine-2,6-dione (0.908 g) in tetrahydrofuran (40 ml) at −70° C. under nitrogen atmosphere. After the mixture was stirred for 10 minutes, a solution of 2-formylpiperazine-1,4-dicarboxylic acid di-tert-butyl ester (0.989 g) in tetrahydrofuran (10 ml) was dropwise added thereto. After raising the temperature of the reaction mixture to room temperature, saturated aqueous ammonium chloride solution (100 ml) was added to the reaction mixture, and the mixture was extracted with ethyl acetate (300 ml). The organic layer was dried over anhydrous magnesium sulfate, and the solvent was removed by distillation at reduced pressure. The residue was purified by silica gel column chromatography to give 0.214 g and 0.128 g of the two isomers of the title compound, respectively, in the order eluted from the elution fraction of hexane-ethyl acetate (7:3 to 1:1).

$^1$H-NMR(CDCl$_3$) δ: 1.38 (s, 9H) 1.50 (s, 9H) 2.74–2.81 (m, 1H) 2.85–2.97 (m, 1H) 3.10–3.19 (m, 1H) 3.38 (s, 3H) 3.56 (s, 3H) 3.76–3.83 (m, 4H) 4.49 (t, J=9.7 Hz, 1H) 7.38–7.45 (m, 5H)

MS m/e (ESI) 571(MH$^+$)

$^1$H-NMR(CDCl$_3$) δ: 1.18(s, 9H) 1.36(s, 9H) 2.68–2.90 (m, 3H) 3.28 (s, 3H) 3.52–3.70 (m, 4H) 3.60 (s, 3H) 4.39 (m, 1H) 7.24 (m, 1H) 7.39–7.52 (m, 5H)

MS m/e (ESI) 571(MH$^+$)

c) 2-[1-[2-(1,3-Dimethyl-2,6-dioxo-1,2,3,6-tetrahydropurin-7-yl)phenyl]-1-methylsulfanylthiocarbonyloxymethyl]piperazine-1,4-dicarboxylic acid di-tert-butyl ester

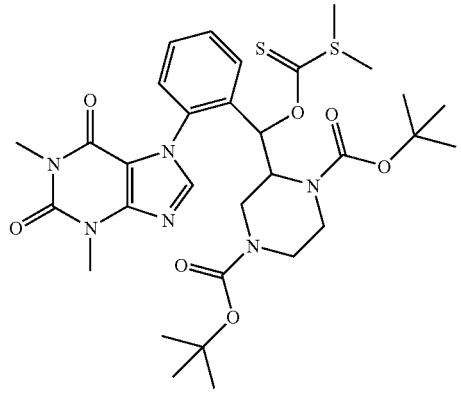

Sodium hydride (60% oleaginous) was added to a solution of 2-[[2-(1,3-dimethyl-2,6-dioxo-1,2,3,6-tetrahydropurin-7-yl)-phenyl]hydroxymethyl]piperazine-1,4-dicarboxylic acid di-tert-butyl ester (low polarity) (0.214 g) in tetrahydrofuran (10 ml) at 0° C. under nitrogen atmosphere, and the mixture was stirred at room temperature for 20 minutes. The temperature of the mixture was returned to 0° C., carbon disulfide (0.045 ml) was added thereto, and the mixture was stirred for 1 hour. Then, methyl iodide (0.047 ml) was added to the reaction mixture, and the mixture was further stirred at room temperature for 2 hours. The reaction mixture was poured into 50 ml of ethyl acetate and 20 ml of water, the organic layer was dried over anhydrous magnesium sulfate, and the solvent was removed by distillation at reduced pressure. The residue was purified by silica gel column chromatography to give 0.175 g of the title compound from the elution fraction of hexane-ethyl acetate (3:7).

$^1$H-NMR(CDCl$_3$) δ: 1.40 (s, 9H) 1.46 (s, 9H) 2.44 (s, 3H) 2.76–2.90 (m, 1H) 3.02–3.14 (m, 1H) 3.20–3.25 (m, 1H) 3.38 (s, 3H) 3.62 (s, 3H) 3.71–4.01 (m, 4H) 6.80 (m, 1H) 7.26–7.55 (m, 5H)

0.086 g of the other isomer was similarly obtained from 2-[[2-(1,3-dimethyl-2,6-dioxo-1,2,3,6-tetrahydropurin-7-yl) phenyl]hydroxymethyl]piperazine-1,4-dicarboxylic acid di-tert-butyl ester of high polarity (0.128 g).

$^1$H-NMR(CDCl$_3$) δ: 1.24 (s, 9H) 1.40 (s, 9H) 2.24 (s, 3H) 2.55–2.62 (m, 1H) 2.70–2.82 (m, 1H) 2.84–3.01 (m, 1H) 3.34 (s, 3H) 3.63 (s, 3H) 3–61–3.83 (m, 3H) 4.08–4.20 (m, 1H) 6.40 (m, 1H) 7.20 (s, 1H) 7.39–7.58 (m, 4H)

d) 2-[2-(1,3-Dimethyl-2,6-dioxo-1,2,3,6-tetrahydropurin-7-yl)benzyl]piperazine-1,4-dicarboxylic acid di-tert-butyl ester

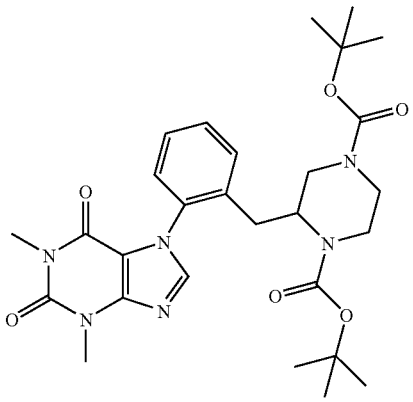

2-[1-[2-(1,3-Dimethyl-2,6-dioxo-1,2,3,6-tetrahydropurin-7-yl)-phenyl]-1-methylsulfanylthiocarbonyloxymethyl] piperazine-1,4-dicarboxylic acid di-tert-butyl ester (low polarity) (0.175 g), tributyltin hydride (0.25 g), and 2,2'-azobis(isobutyronitrile) (0.010 g) were dissolved in toluene (5 ml) under nitrogen atmosphere, and the mixture was heated to reflux for 2 hours. The reaction mixture was cooled and the solvent was removed by distillation at reduced pressure. The residue was purified by silica gel column chromatography to give 0.123 g of the title compound from the elution fraction of hexane-ethyl acetate (1:1).

0.055 g of the title compound was similarly obtained from the high polar isomer of 2-[1-[2-(1,3-dimethyl-2,6-dioxo-1, 2,3,6-tetrahydropurin-7-yl)-phenyl]-1-methylsulfanylthiocarbonyloxymethyl]piperazine-1,4-dicarboxylic acid di-tert-butyl ester (0.086 g).

$^1$H-NMR(CDCl$_3$) δ: 1.31 (s, 9H) 1.44 (s, 9H) 2.45–3.02 (m, 5H) 3.34(s, 3H) 3.62 (s, 3H) 3.75–4.04 (m, 4H) 7.33 (m, 1H) 7.53 (s, 4H)

MS m/e (ESI) 555(MH$^+$)

e) 1,3-Dimethyl-9,9a,10,11,12,13-hexahydro-1H-1, 3,4b,11,13a,14-hexaazatribenzo[a,e,h]azulene-2,4-dione trifluoroacetate

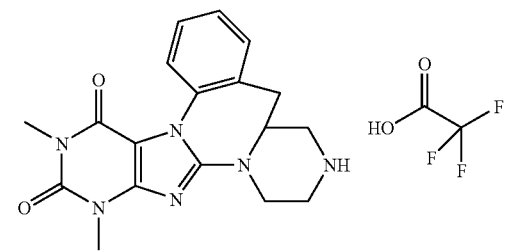

2-[2-(1,3-dimethyl-2,6-dioxo-1,2,3,6-tetrahydropurin-7-yl)benzyl]piperazine-1,4-dicarboxylic acid di-tert-butyl ester (0.055 g) was dissolved in trifluoroacetic acid (0.5 ml), the mixture was stirred for 30 minutes, and the solvent was removed by distillation at reduced pressure. The residue was dissolved in N,N-dimethylformamide, and N-chlorosuccinimide (0.025 g) was added to the solution. The mixture was stirred at room temperature for 14 hours, 1,8-diazabicyclo-[5,4,0]-7-undecene (0.050 ml) was added thereto, and was further stirred for 1 hour. After removing the solvent by distillation at reduced pressure, the residue was purified by HPLC with a reversed phase column using water-acetonitrile-trifluoroacetic acid system as elution solvent to give 0.0079 g of the title compound.

$^1$H-NMR(CD$_3$OD) δ: 2.45–2.56 (m, 2H) 3.09–3.96 (m, 7H) 3.35 (s, 3H) 3.64 (s, 3H) 7.44–7.52 (m, 2H) 7.53–7.63 (m, 2H)

MS m/e (ESI) 353(MH$^+$)

EXAMPLE 340

[1-Methyl-2,6-dioxo-8-(piperazin-1-yl)-7-(2-vinylphenyl)-1,2,6,7-tetrahydropurin-3-yl]acetic acid ethyl ester trifluoroacetate a) 2,2-Dimethylpropionic acid [1–(2,2-dimethylpropionyloxymethyl)-7-(2-formylphenyl)-2,6-dioxo-1,2,6,7-tetrahydropurin-3-yl]methyl ester

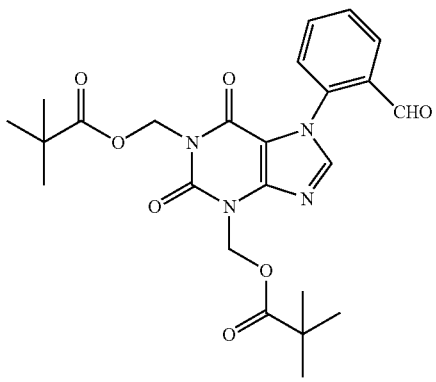

2,2-Dimethylpropionic acid [3-(2,2-dimethylpropionyloxymethyl)-2,6-dioxo-2,3,6,7-tetrahydropurin-1-yl]methyl ester (10.2 g), 2-formylphenylboronic acid (8.04 g), and copper(II) acetate (7.30 g) were suspended in N,N-dimethylformamide (50 ml), pyridine (4.34 ml) was added thereto, and the mixture was stirred at room temperature for 37 hours. The reaction mixture was diluted with ethyl acetate; and washed with water. The organic layer was dried over anhydrous magnesium sulfate and filtered. The filtrate was concentrated under reduced pressure and the residue was purified by silica gel column chromatography to give 4.12 g of the title compound from the elution fraction of hexane-ethyl acetate (1:2).

$^1$H-NMR(CDCl$_3$) δ: 1.16 (s, 9H) 1.23 (s, 9H) 5.95 (s, 2H) 6.20 (s, 2H) 7.46–7.48 (m, 1H) 7.42–7.78 (m, 2H) 7.75 (s, 1H) 8.03–8.06 (m, 1H) 9.92 (s, 1H)

b) 2,2-Dimethylpropionic acid [8-chloro-1-(2,2-dimethylpropionyloxymethyl)-7-(2-formylphenyl)-2,6-dioxo-1,2,6,7-tetrahydropurin-3-yl]methyl ester

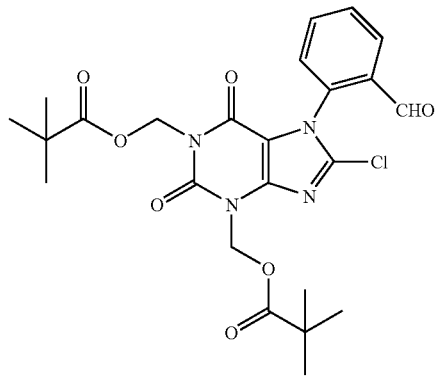

2,2-Dimethylpropionic acid [1-(2,2-dimethylpropionyloxymethyl)-7-(2-formylphenyl)-2,6-dioxo-1,2,6,7-tetrahydropurin-3-yl]methyl ester (2.50 g) and N-chlorosuccinimide (896 mg) were dissolved in N,N-dimethylformamide (25 ml), and the mixture was stirred at room temperature for 8 hours. The reaction mixture was diluted with ethyl acetate and washed with water. The organic layer was dried over anhydrous magnesium sulfate and filtered. The filtrate was concentrated under reduced pressure and the residue was purified by silica gel column chromatography to give 2.0 g of the title compound from the elution fraction of hexane-ethyl acetate (2:1).

$^1$H-NMR(CDCl$_3$) δ: 1.15 (s, 9H) 1.24 (s, 9H) 5.91 (s, 2H) 6.14 (s, 2H) 7.49–7.51 (m, 1H) 7.81–7.83 (m, 2H) 8.03–8.06 (m, 1H) 9.92 (s, 1H)

c) 4-[1,3-Bis(2,2-dimethylpropionyloxymethyl)-7-(2-formylphenyl)-2,6-dioxo-2,3,6,7-tetrahydro-1H-purin-8-yl]piperazine-1-carboxylic acid tert-butyl ester

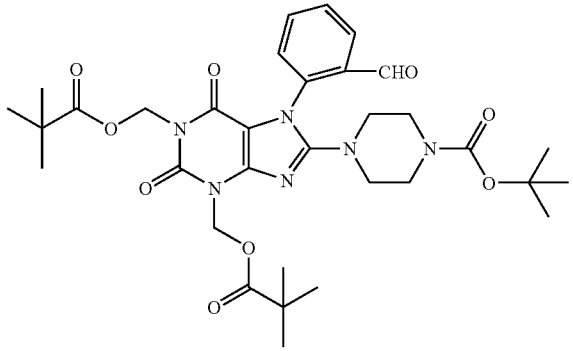

2,2-Dimethylpropionic acid [8-chloro-1-(2,2-dimethylpropionyloxymethyl)-7-(2-formylphenyl)-2,6-dioxo-1,2,6,7-tetrahydropurin-3-yl]methyl ester (2.0 g) and piperazine-1-carboxylic acid tert-butyl ester (2.15 g) were mixed, and the mixture was stirred at 150° C. for 1 hour and 10 minutes. The reaction mixture was diluted with chloroform and purified by silica gel column chromatography to give 1.94 g of the title compound from the elution fraction of hexane-ethyl acetate (1:1).

d) 4-[1,3-Bis(2,2-dimethylpropionyloxymethyl)-2,6-dioxo 7-(2-vinylphenyl)-2,3,6,7-tetrahydro-1H-purin-8-yl]piperazine-1-carboxylic acid tert-butyl ester

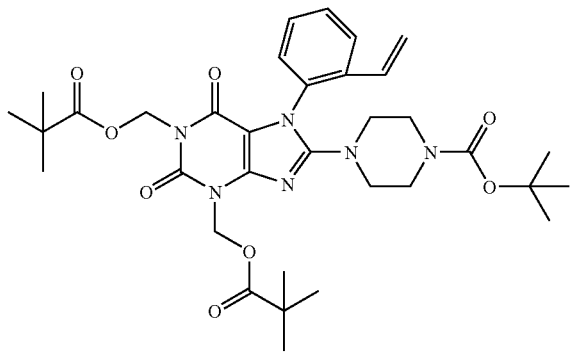

Methyltriphenylphosphonium bromide (3.52 g) was dissolved in tetrahydrofuran (20 ml), potassium tert-butoxide (948 mg) was added to the solution, and the mixture was stirred at room temperature for 1 hour. A solution of 4-[1,3-bis(2,2-dimethylpropionyloxymethyl)-7-(2-formylphenyl)-2,6-dioxo-2,3,6,7-tetrahydro-1H-purin-8-yl]piperazine-1-carboxylic acid tert-butyl ester (1.94 g) in tetrahydrofuran (20 ml) was added to the obtained reaction mixture at room temperature, and the mixture was stirred at room temperature for 3 hours and 50 minutes. The reaction mixture was diluted with ethyl acetate and washed with water. The organic layer was dried over anhydrous magnesium sulfate and filtered. The filtrate was concentrated under reduced pressure and the residue was purified by silica gel column chromatography to give 704 mg of the title compound from the elution fraction of hexane-ethyl acetate (2:1).

e) 4-[1-(2,2-Dimethylpropionyloxymethyl)-2,6-dioxo-7-(2-vinylphenyl)-2,3,6,7-tetrahydro-1H-purin-8-yl]piperazine-1-carboxylic acid tert-butyl ester

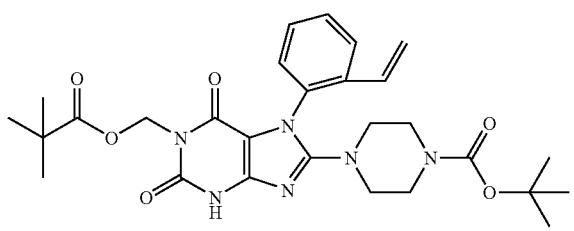

4-[1,3-Bis(2,2-dimethylpropionyloxymethyl)-2,6-dioxo-7-(2-vinylphenyl)-2,3,6,7-tetrahydro-1H-purin-8-yl]piperazine-1-carboxylic acid tert-butyl ester (704 mg) was dissolved in tetrahydrofuran (7 ml) and methanol (14 ml), sodium hydride (51 mg) was added to the solution, and the mixture was stirred at room temperature for 17 minutes. The reaction mixture was diluted with chloroform and washed with saturated brine. The organic layer was dried over anhydrous magnesium sulfate and filtered. The filtrate was concentrated under reduced pressure and the residue was purified by silica gel column chromatography to give 510 mg of the title compound from the elution fraction of hexane-ethyl acetate (2:3).

f) 4-[1-(2,2-Dimethylpropionyloxymethyl)-3-ethoxycarbonylmethyl-2,6-dioxo-7-(2-vinylphenyl)-2,3,6,7-tetrahydro-1H-purin-8-yl]piperazine-1-carboxylic acid tert-butyl ester

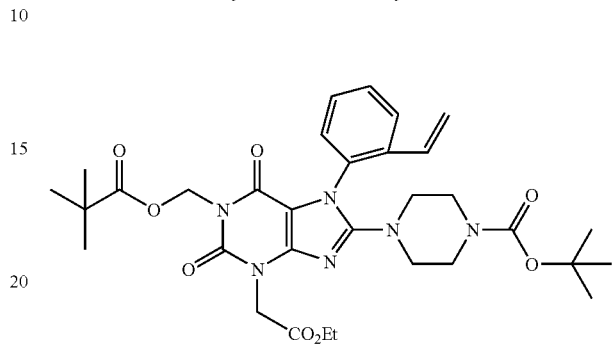

4-[1-(2,2-Dimethylpropionyloxymethyl)-2,6-dioxo-7-(2-vinylphenyl)-2,3,6,7-tetrahydro-1H-purin-8-yl]piperazine-1-carboxylic acid tert-butyl ester (80 mg) was dissolved in N,N-dimethylformamide (2 ml), ethyl bromoacetate (19 µl) and potassium carbonate (22 mg) were added to the solution, and the mixture was stirred at room temperature for 14 hours. The reaction mixture was diluted with ethyl acetate and washed with water. The organic layer was dried over anhydrous magnesium sulfate and filtered. The filtrate was concentrated under reduced pressure to give 89 mg of the title compound g) 4-[3-Ethoxycarbonylmethyl-2,6-dioxo-7-(2-vinylphenyl)-2,3,6,7-tetrahydro-1H-purin-8-yl]piperazine-1-carboxylic acid tert-butyl ester

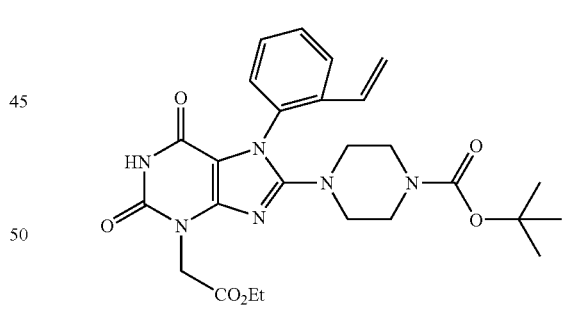

4-[1-(2,2-Dimethylpropionyloxymethyl)-3-ethoxycarbonylmethyl-2,6-dioxo-7-(2-vinylphenyl)-2,3,6,7-tetrahydro-1H-purin-8-yl]piperazine-1-carboxylic acid tert-butyl ester (89 mg) was dissolved in tetrahydrofuran (1 ml) and methanol (2 ml), sodium hydride (7 mg) was added to the solution, and the mixture was stirred at room temperature for 3.5 hours. The reaction mixture was diluted with ethyl acetate and washed with water. The organic layer was dried over anhydrous magnesium sulfate and filtered, followed by concentration of the filtrate under reduced pressure. The residue was purified by silica gel column chromatography to give 60 mg of the title compound from the elution fraction of hexane-ethyl acetate (1:2).

h) 4-[3-Ethoxycarbonylmethyl-1-methyl-2,6-dioxo-7-(2-vinylphenyl)-2,3,6,7-tetrahydro-1H-purin-8-yl]piperazine-1-carboxylic acid tert-butyl ester

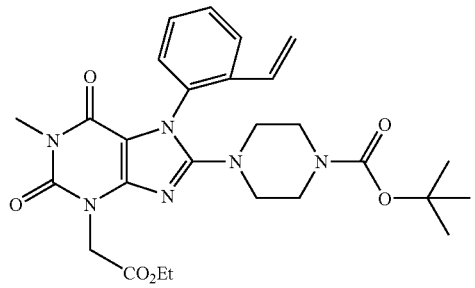

4-[3-Ethoxycarbonylmethyl-2,6-dioxo-7-(2-vinylphenyl)-2,3,6,7-tetrahydro-1H-purin-8-yl]piperazine-1-carboxylic acid tert-butyl ester (60 mg) was dissolved in N,N-dimethylformamide (2 ml), methyl iodide (17 μl) and potassium carbonate (17 mg) were added to the solution, and the mixture was stirred at room temperature for 13 hours. The reaction mixture was diluted with ethyl acetate and washed with water. The organic layer was dried over anhydrous magnesium sulfate and filtered. The filtrate was concentrated under reduced pressure to give 48 mg of the title compound.

i) [1-Methyl-2,6-dioxo-8-(piperazin-1-yl)-7-(2-vinylphenyl)-1,2,6,7-tetrahydropurin-3-yl]acetic acid ethyl ester trifluoroacetate

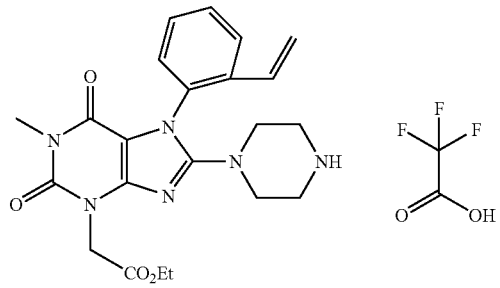

4-[3-Ethoxycarbonylmethyl-1-methyl-2,6-dioxo-7-(2-vinylphenyl)-2,3,6,7-tetrahydro-1H-purin-8-yl]piperazine-1-carboxylic acid tert-butyl ester (8 mg) was dissolved in trifluoroacetic acid and the solution was concentrated. The residue was purified by reversed phase high performance liquid chromatography to give 2.68 mg of the title compound.

MS m/e (ESI) 439(MH$^+$—CF$_3$COOH)

EXAMPLE 341

[1-Methyl-2,6-dioxo-8-(piperazin-1-yl)-7-(2-vinylphenyl)-1,2,6,7-tetrahydropurin-3-yl]acetic acid trifluoroacetate

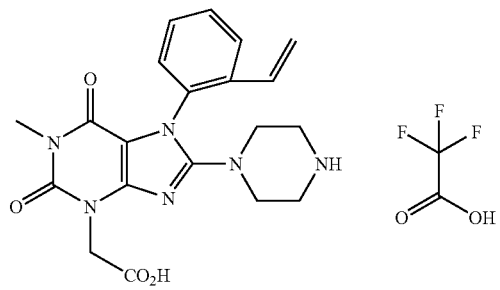

4-[3-Ethoxycarbonylmethyl-1-methyl-2,6-dioxo-7-(2-vinylphenyl)-2,3,6,7-tetrahydro-1H-purin-8-yl]piperazine-1-carboxylic acid tert-butyl ester (40 mg) was dissolved in tetrahydrofuran (4 ml), 2N sodium hydroxide (1 ml) was added to the solution, and the mixture was stirred at 90° C. for 4 hours. The reaction mixture was concentrated under reduced pressure, and then was subjected to azeotropic distillation with toluene. The residue was dissolved in trifluoroacetic acid and concentrated. The residue was purified by reversed phase high performance liquid chromatography to give 29.5 mg of the title compound.

MS m/e (ESI) 411(MH$^+$—CF$_3$COOH)

EXAMPLE 342

2-[2,6-Dioxo-8-(piperazin-1-yl)-7-(2-vinylphenyl)-1,2,6,7-tetrahydropurin-3-yl]acetamide trifluoroacetate

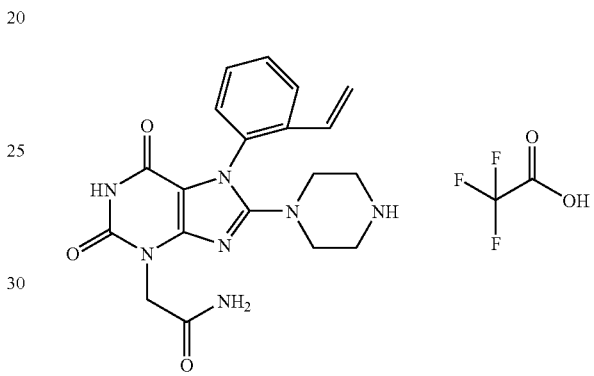

18.2 mg of the title compound was obtained using 2-bromoacetamide, and steps similar to Example 340 f), g), and i).

MS m/e (ESI) 396(MH$^+$—CF$_3$COOH)

EXAMPLE 343

2-[1-Methyl-2,6-dioxo-8-(piperazin-1-yl)-7-(2-vinylphenyl)-1,2,6,7-tetrahydropurin-3-yl]acetamide trifluoroacetate

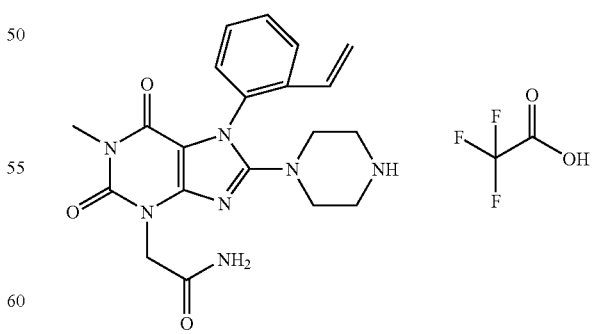

13 mg of the title compound was obtained using 2-bromoacetamide, and steps similar to Example 340 f), g), h), and i).

MS m/e (ESI) 410(MH$^+$—CF$_3$COOH)

Test Example 1

In Vitro Test

Control Compound 1

A compound which was considered to have the strongest activity among the compounds of Examples described in the pamphlet of WO 02/02560 was synthesized according to Examples.

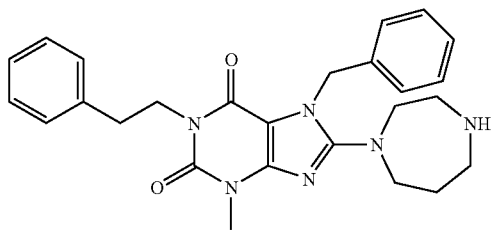

Control Compound 2 (NVP DPP728)

The compound described in the specification of U.S. Pat. No. 6,011,155 was synthesized according to Example.

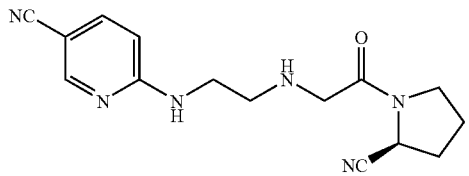

Determination of the Inhibition Action of DPPIV

DPP-IV obtained from swine kidney was dissolved in reaction buffer (50 mM Tris-HCl pH 7.4, 0.1% BSA) at a concentration of 10 mU/mL, and 110 μl of the solution was added. Then, medicament (15 μl) was added thereto, and the mixture was incubated at room temperature for 20 minutes. Gly-Pro-p-nitroanilide (25 μl, final concentration: 0.33 mM) dissolved to 2 mM was added to the mixture to start enzymatic reaction. The reaction time was 20 minutes, and 1N phosphoric acid solution (25 μl) was added to the mixture to quench the reaction. The absorbance at 405 nm was measured and the enzymatic reaction inhibition rate was determined to calculate $IC_{50}$.

TABLE 41

| Test sample | $IC_{50}$ (nM) | Test sample | $IC_{50}$ (nM) |
|---|---|---|---|
| Example 30 | 0.654 | Example 39 | 9.48 |
| Example 42 | 4.56 | Example 160 | 8.77 |
| Example 162 | 9.52 | Example 168 | 6.97 |
| Example 169 | 7.18 | Example 213 | 1.20 |
| Example 214 | 2.16 | Example 323 | 1.95 |
| Example 325 | 1.81 | Example 326 | 4.02 |
| Example 327 | 0.864 | Example 328 | 1.14 |
| Example 329 | 1.55 | Example 330 | 1.7 |
| Example 331 | 3.37 | Example 332 | 0.472 |
| Control compound 1 | 24.1 | Control compound 2 | 226 |

Test Example 2

In-vivo Test

Effect on Glucose Tolerance of Normal Mouse

Animal:

male C57BL/6N mouse (purchased from CHARLES RIVER JAPAN, INC.)

Method:

Preparation and Administration of Test Compounds

Compounds to be tested were suspended in 0.5% methylcellulose (MC) solution at an amount shown in the following Table. A suspension of the test compound and NVP DPP728 or 0.5% MC solution (solvent control group) were orally administered at a dose of 10 mL/kg, and after 30 minutes, glucose solution was orally administered at a dose of 10 mL/kg. Glucose was orally administered at a dose of 2 g/kg.

Blood Collection and Measurement of Blood Glucose Level:

Immediately before the administration of the test substance and NVP DPP728, immediately before the administration of the glucose solution and at 30 minutes, 60 minutes, and 120 minutes after the administration, a tail vein of the mouse was injured to slightly bleed by a razor under no anesthesia. 10 μl of blood was collected and was immediately mixed with 0.6M perchloric acid (140 μl). Glucose in the supernatant obtained by centrifugation (1500 g, 10 minutes, 4° C., refrigerated centrifuge GS-6KR, Beckman Instruments, Inc.) was measured using Glucose CII-Test Wako (Wako Pure Chemical Industries, Ltd.).

Result:

Area under the curve of blood glucose level-time ($AUC_{0-120}$; Area Under the Curve) from the time of administration of glucose to 120 minutes after administration was calculated for respective administration groups, i.e., 0.5% MC solution, NVP DPP728, and the test compounds. Taking the $AUC_{0-120}$ of the 0.5% MC solution administration group as 100% and the $AUC_{0-120}$ of NVP DPP728 (10 mg/kg) administration group as 0%, the improvement degree of the glucose tolerance of a test compound was calculated using the following formula:

Improvement degree of the glucose tolerance (%)= ($AUC_{0-120}$ of the test compound–$AUC_{0-120}$ of the NVP DPP728 (10 mg/kg) administration group)/($AUC_{0-120}$ of the 0.5% MC solution administration group–$AUC_{0-120}$ of the NVP DPP728 (10 mg/kg) administration group)×100.

The lower the % value, the greater the improvement degree of the glucose tolerance will be.

TABLE 5

| Test sample (mg/kg) | Improvement degree of glucose tolerance (%) | Test sample (mg/kg) | Improvement degree of glucose tolerance (%) |
|---|---|---|---|
| Example 10(3) | 0.5 | Example 14(1) | 41.9 |
| Example 15(3) | −17.2 | Example 18(3) | 9.5 |
| Example 19(3) | −13.1 | Example 20(3) | 5.0 |
| Example 21(3) | 4.8 | Example 30(1) | −14.3 |
| Example 30(0.3) | 49.4. | Example 39(1) | 45.5 |
| Example 123(3) | 17.9 | Example 147(3) | 13.0 |
| Example 156(3) | 0.9 | Example 166(3) | 16.1 |
| Example 174(3) | −9.1 | Example 174(1) | 24.3 |

TABLE 5-continued

| Test sample (mg/kg) | Improvement degree of glucose tolerance (%) | Test sample (mg/kg) | Improvement degree of glucose tolerance (%) |
|---|---|---|---|
| Example 194(3) | 9.9 | Example 216(3) | −5.0 |
| Example 218(3) | 16.8 | Example 219(3) | −1.4 |
| Example 226(3) | −5.2 | Example 240(3) | −2.8 |
| Example 243(3) | 8.4 | Example 256(3) | 2.4 |
| Example 257(3) | 10.5 | Example 263(3) | 16.4 |
| Example 266(3) | −2.3 | Example 270(3) | 7.3 |
| Example 274(3) | 1.9 | Example 284(3) | 11.3 |
| Example 321(3) | 16.9 | Example 323(3) | 0.5 |
| Example 326(3) | −30.6 | Example 326(1) | −19.2 |
| Control compound 1(3) | 49.2 | | |

Test Example 3

Administration Timing Tolerance in In-vivo Test

An equal improvement effect on the high blood sugar level after eating is ideally required for a medicament for treating hyperglycemia after eating either by taking the medicament just before eating or one hour before eating. If this is realized, an excellent medicament which has an extensive tolerance for medicine-administration timing and a reliable medical effect is provided.

Method:

In combination with the in-vivo medical effect test (administered 0.5 hour earlier) shown in Test example 2, the following tests were conducted.
1. The test compound was-administered at the same time as glucose loading (2 g/kg) (the test compound was suspended in 0.5% aqueous methyl cellulose solution, mixed with an equal volume of glucose solution, and orally administered at a dose of 10 ml/kg).
2. The test compound was administered one hour before the glucose loading (2 g/kg) (the test compound was suspended in 0.5% aqueous methyl cellulose solution was orally administered one hour before the oral administration of the glucose solution; the oral administration at a dose of 10 ml/kg in any case). The level of tolerance for variation in timing of administration can be judged by calculating the degree of improvement in glucose tolerance for each test, and judging whether an equal degree of improvement is achieved by the amounts administered, with a difference of preferably within three times, and most preferably an equal degree of improvement being obtained by administration of the same amount.

Compounds with the above administration timing tolerance could be found among the compounds of the present invention.

What is claimed is:

1. A compound represented by the formula (I):

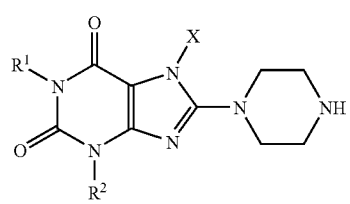

(I)

wherein,
$R^1$ stands for a hydrogen atom, a substituted or unsubstituted $C_{1-6}$ alkyl group, a substituted or unsubstituted $C_{1-6}$ alkoxy $C_{1-6}$ alkyl group, a substituted or unsubstituted $C_{3-6}$ alkynyl group, a substituted or unsubstituted $C_{2-7}$ cyanoalkyl group, a substituted or unsubstituted $C_{6-12}$ aryl $C_{1-6}$ alkyl group, a substituted or unsubstituted $C_{1-12}$ aryloxy $C_{1-6}$ alkyl group, or a group represented by the formula:

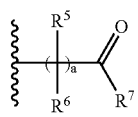

wherein,
a denotes 1;
$R^5$ and $R^6$ both denote a hydrogen atom; and,
$R^7$ denotes a hydroxyl group, a substituted or unsubstituted $C_{1-6}$ alkoxy group, a substituted or unsubstituted phenyl group, or a group represented by the formula —N($R^3$)$R^4$,
wherein, $R^3$ and $R^4$ are identical to or different from each other and individually denote a hydrogen atom, or a substituted or unsubstituted $C_{1-6}$ alkyl group;
$R^2$ stands for a hydrogen atom, a substituted or unsubstituted $C_{1-6}$ alkyl group, a substituted or unsubstituted $C_{1-6}$ alkoxy $C_{1-6}$ alkyl group, a substituted or unsubstituted 3 to 10-membered heterocyclic $C_{1-6}$ alkyl group, a substituted or unsubstituted $C_{6-12}$ aryl $C_{1-6}$ alkyl group, a group represented by the formula:

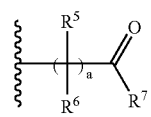

wherein,
a denotes 1;
$R^5$ and $R^6$ are identical to or different from each other and individually denote a hydrogen atom, $C_{1-6}$ alkyl group, or phenyl group; and,
$R^7$ denotes a hydroxyl group, $C_{1-6}$ alkyl group, $C_{1-6}$ alkoxy group, a substituted or unsubstituted phenyl group, or a group represented by —N($R^3$)$R^4$,
wherein,
$R^3$ and $R^4$ are identical to or different from each other and individually denote a hydrogen atom, $C_{1-6}$ alkyl group, $C_{3-7}$ cycloalkyl group, $C_{3-6}$ alkynyl group, or $C_{6-12}$ aryl group; or,
$R^3$ and $R^4$ may be linked to each other to form a ring containing one or more heteroatoms,
or a group represented by the formula:

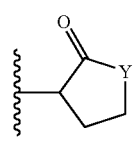

wherein Y denotes an oxygen atom, or a group represented by —NR$^8$, wherein R$^8$ denotes a hydrogen atom, or $C_{1-6}$ alkyl group; and X stands for a phenyl group wherein position 2 may have a substituent selected from the group consisting of a hydrogen atom, hydroxyl group, fluorine atom, chlorine atom, methyl group, ethyl group, fluoromethyl group, ethenyl group, methoxy group, ethoxy group, acetyl group, cyano group, formyl group, and $C_{2-7}$ aliphaticailcoxy carbonyl group, or a salt thereof.

2. The compound of claim 1, or a salt thereof, wherein $R^1$ stands for a hydrogen atom, $C_{1-6}$ alkyl group, C alkynyl group, cyanomethyl group, a substituted or unsubstituted benzyl group, a substituted or unsubstituted phenethyl group, a substituted or unsubstituted phenoxyethyl group, or a group represented by the formula:

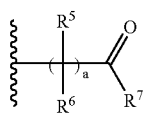

wherein, a denotes 1;
$R^5$ and $R^6$ both denote a hydrogen atom; and,
$R^7$ denotes a hydroxyl group, $C_{1-6}$ alkoxy group, or a substituted or unsubstituted phenyl group.

3. The compound of claim 1, or a salt thereof, wherein $R^1$ stands for a hydrogen atom, methyl group, 2-propynyl group, 2-butynyl group, cyanometbyl group, phenethyl group, phenoxyethyl group, or a group represented by the formula:

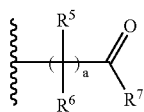

wherein, a denotes 1;
$R^5$ and $R^6$ both denote a hydrogen atom; and,
$R^7$ denotes a hydroxyl group, $C_{1-6}$ alkoxy group, or phenyl group.

4. The compound of claim 1, or a salt thereof, wherein $R^2$ stands for a substituted or unsubstituted $C_{1-6}$ alkoxy $C_{1-6}$ alkyl group, a substituted or unsubstituted 3 to 10-membered heterocyclic $C_{1-6}$ alkyl group, a substituted or unsubstituted $C_{6-12}$ aryl $C_{1-6}$ alkyl group, a group represented by the formula:

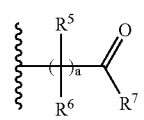

wherein,
a denotes 1;
$R^5$ and $R^6$ are identical to or different from each other and individually denote a hydrogen atom, $C_{1-6}$ alkyl group, or a phenyl group; $R^7$ denotes a hydroxyl group, $C_{1-6}$ alkyl group, $C_{1-6}$ alkoxy group, a substituted or unsubstituted phenyl group, or a group represented by the formula —N($R^3$)$R^4$,
wherein,
$R^3$ and $R^4$ are identical to or different from each other and individually denote a hydrogen atom, $C_{1-6}$ alkyl group, $C_{3-7}$ cycloalkyl group, $C_{3-6}$ alkynyl group, or $C_{6-12}$ aryl group; or, $R^3$ and $R^4$ may be linked to each other to form a ring containing one or more heteroatoms, or a group represented by the formula:

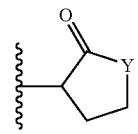

wherein Y denotes an oxygen atom, or a group represented by —$NR^8$, wherein $R^8$ denotes a hydrogen atom, or a $C_{1-6}$ alkyl group.

5. The compound of claim 1, or a salt thereof, wherein $R^2$ stands for a hydrogen atom, $C_{1-6}$ alkyl group, $C_{1-6}$ alkoxy $C_{1-6}$ alkyl group, tetrahydrofuranylmethyl group, a substituted or unsubstituted benzyl group, a group represented by the formula:

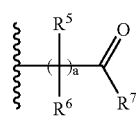

wherein,
a denotes 1;
$R^5$ and $R^6$ are identical to or different from each other and individually denote a hydrogen atom, $C_{1-6}$ alkyl group, or a phenyl group; and,
$R^7$ denotes a hydroxyl group, $C_{1-6}$ alkyl group, $C_{1-6}$ alkoxy group, a substituted or unsubstituted phenyl group, or a group represented by the formula —N($R^3$) $R^4$,
wherein,
$R^3$ and $R^4$ are identical to or different from each other and individually denote a hydrogen atom, or a $C_{1-6}$ alkyl group,
or a group represented by the formula:

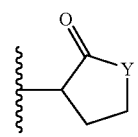

wherein Y denotes an oxygen atom, or —$NR^8$, wherein $R^8$ denotes a hydrogen atom, or $C_{1-6}$ alkyl group.

6. The compound of claim 1, or a salt thereof, wherein $R^2$ stands for a $C_{1-6}$ alkoxy $C_{1-6}$ alkyl group, tetrahydrofuranylmethyl group, a substituted or unsubstituted benzyl group, a group represented by the formula:

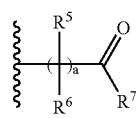

wherein,
a denotes 1; and,
$R^5$ and $R^6$ are identical to or different from each other and individually denote a hydrogen atom, $C_{1-6}$ alkyl group, or a phenyl group; $R^7$ denotes a hydroxyl group, $C_{1-6}$ alkyl group, $C_{1-6}$ alkoxy group, a substituted or unsubstituted phenyl group, or a group represented by the formula $-N(R^3)R^4$, wherein, $R^3$ and $R^4$ are identical to or different from each other and individually denote a hydrogen atom, or $C_{1-6}$ alkyl group, or a group represented by the formula:

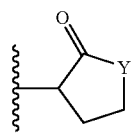

wherein Y denotes an oxygen atom, or $-NR^8$, wherein $R^8$ denotes a hydrogen atom, or $C_{1-6}$ alkyl group.

7. The compound of claim 1, or a salt thereof, wherein $R^2$ stands for a hydrogen atom, $C_{1-6}$ alkyl group, ethoxyethyl group, tetrahydrofuranylmethyl group, a group represented by the formula:

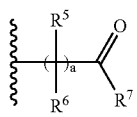

wherein, a denotes 1;

$R^5$ and $R^6$ are identical to or different from each other and individually denote a hydrogen atom, methyl group, or phenyl group; and, $R^7$ denotes a hydroxyl group, $C_{1-6}$ alkoxy group, or phenyl group, or a group represented by the formula:

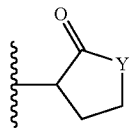

wherein Y denotes $-NR^8$ wherein $R^8$ denotes a hydrogen atom.

8. The compound of claim 1, or a salt thereof, wherein $R^2$ stands for an ethoxyethyl group, tetrahydrofuranylmethyl group, a group represented by the formula:

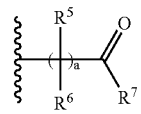

wherein, a denotes 1;

$R^5$ and $R^6$ are identical to or different from each other and individually denote a hydrogen atom, methyl group, or phenyl group; and, $R^7$ denotes a hydroxyl group, $C_{1-6}$ alkoxy group, or phenyl group, or a group represented by the formula:

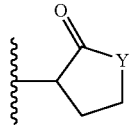

wherein Y denotes $-NR^8$, wherein $R^8$ denotes a hydrogen atom.

9. A pharmaceutical composition comprising a compound of claim 1, or a salt thereof, and a pharmaceutically acceptable excipient.

* * * * *